(12) United States Patent
Walder et al.

(10) Patent No.: US 10,596,387 B2
(45) Date of Patent: Mar. 24, 2020

(54) TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES

(71) Applicants: IMMUNOLIGHT, LLC., Detroit, MI (US); DUKE UNIVERSITY, Durham, NC (US)

(72) Inventors: Harold Walder, Belville, NC (US); Frederic A. Bourke, Greenwich, CT (US); Zakaryae Fathi, Raleigh, NC (US); Wayne F. Beyer, Bahama, NC (US); Mark W. Dewhirst, Durham, NC (US); Mark Oldham, Durham, NC (US); Justus Adamson, Durham, NC (US); Michael Nolan, Raleigh, NC (US)

(73) Assignees: IMMUNOLIGHT, LLC., Detroit, MI (US); DUKE UNIVERSITY, Durham, NC (US)

( * ) Notice: Subject to any disclaimer, the term of this patent is extended or adjusted under 35 U.S.C. 154(b) by 397 days.

(21) Appl. No.: 15/307,766

(22) PCT Filed: Apr. 22, 2015

(86) PCT No.: PCT/US2015/027058
§ 371 (c)(1),
(2) Date: Oct. 28, 2016

(87) PCT Pub. No.: WO2015/164485
PCT Pub. Date: Oct. 29, 2015

(65) Prior Publication Data
US 2017/0050046 A1 Feb. 23, 2017

Related U.S. Application Data

(60) Provisional application No. 62/147,390, filed on Apr. 14, 2015, provisional application No. 62/132,270, (Continued)

(51) Int. Cl.
*A61N 5/06* (2006.01)
*A61N 5/10* (2006.01)
(Continued)

(52) U.S. Cl.
CPC .......... *A61N 5/062* (2013.01); *A61K 39/0011* (2013.01); *A61K 41/0066* (2013.01);
(Continued)

(58) Field of Classification Search
CPC ............ A61K 39/0011; A61K 41/0019; A61K 41/0066; A61K 49/0423; A61K 2039/585;
(Continued)

(56) References Cited

U.S. PATENT DOCUMENTS

| 6,218,100 B1 | 4/2001 | Wollowitz et al. |
| 6,716,525 B1 * | 4/2004 | Yadav .................... A61L 27/06 428/402 |

(Continued)

FOREIGN PATENT DOCUMENTS

| EP | 0986401 A1 * | 3/2000 | ........... A61K 31/702 |
| EP | 0 986 401 B1 | 2/2004 | |

(Continued)

OTHER PUBLICATIONS

Sugie, H., et al. "Carbon nanotubes as electron source in an x-ray tube." 2001. American Institute of Physics: Applied Physics Letters. vol. 78 No. 17. 2578-2580. (Year: 2001).*

(Continued)

*Primary Examiner* — Amanda K Hulbert
*Assistant Examiner* — Phillip C Edwards
(74) *Attorney, Agent, or Firm* — Oblon, McClelland, Maier & Neustadt, L.L.P.

(57) ABSTRACT

A system and method for imaging or treating a disease in a human or animal body. The system provides to the human or animal body a pharmaceutical carrier including one or more (Continued)

phosphors which are capable of emitting ultraviolet or visible light into the body and which provide x-ray contrast. The system includes one or more devices which infuse a diseased site with a photoactivatable drug and the pharmaceutical carrier, an initiation energy source comprising an x-ray or high energy source which irradiates the diseased site with at least one of x-rays, gamma rays, or electrons to thereby initiate emission of said ultraviolet or visible light into the body, and a processor programmed to at least one of 1) produce images of the diseased site or 2) control a dose of said x-rays, gamma rays, or electrons to the diseased site for production of said ultraviolet or visible light at the diseased site to activate the photoactivatable drug.

108 Claims, 69 Drawing Sheets

Related U.S. Application Data filed on Mar. 12, 2015, provisional application No. 62/096,773, filed on Dec. 24, 2014, provisional application No. 61/982,585, filed on Apr. 22, 2014.

(51) Int. Cl.
*A61N 5/02* (2006.01)
*A61K 49/04* (2006.01)
*A61K 41/00* (2020.01)
*A61K 39/00* (2006.01)

(52) U.S. Cl.
CPC .......... *A61K 49/0423* (2013.01); *A61N 5/022* (2013.01); *A61N 5/10* (2013.01); *A61N 5/1081* (2013.01); *A61K 2039/585* (2013.01); *A61N 2005/0627* (2013.01); *A61N 2005/0659* (2013.01); *A61N 2005/0661* (2013.01); *A61N 2005/0662* (2013.01); *A61N 2005/1089* (2013.01); *A61N 2005/1098* (2013.01)

(58) Field of Classification Search
CPC .......... A61N 5/022; A61N 5/062; A61N 5/10; A61N 5/1081; A61N 2005/0627; A61N 2005/0659; A61N 2005/0661; A61N 2005/0662; A61N 2005/1089; A61N 2005/1098
USPC .......................................................... 600/431
See application file for complete search history.

(56) References Cited

U.S. PATENT DOCUMENTS

| | | | |
|---|---|---|---|
| 2004/0062754 A1* | 4/2004 | O'Brien | A61M 1/3681 424/93.7 |
| 2009/0104212 A1 | 4/2009 | Bourke | |
| 2010/0016783 A1 | 1/2010 | Bourke, Jr. et al. | |
| 2010/0241058 A1 | 9/2010 | Ahmed et al. | |
| 2011/0021970 A1* | 1/2011 | Vo-Dinh | A61K 49/0039 604/20 |
| 2012/0184495 A1* | 7/2012 | Koyakutty | A61K 49/0019 514/19.3 |
| 2012/0259268 A1* | 10/2012 | Gerrans | A61K 41/00 604/21 |
| 2016/0325111 A1 | 11/2016 | Bourke, Jr. et al. | |

FOREIGN PATENT DOCUMENTS

WO 2013/009688 A1 1/2013
WO WO-2013009688 A1 * 1/2013 ......... A61K 41/0085

OTHER PUBLICATIONS

Plazas, M.C., et al. "Opical Fiber Detectors as In-Vivo Dosimetry Method of Quality Assurance in Radiation Therapy." Jan. 2005 . Revista Colombiana de Fisica. vol. 37 No. 1. 307-313. (Year: 2005).*
H. Sugie, et al., "Carbon nanotubes as electron source in an x-ray tube," Applied Physics Letters, vol. 78, No. 17, Apr. 23, 2001, 4 pages.
M. C. Plazas, et al., "Optical Fiber Detectors as In-Vivo Dosimetry Method of Quality Assurance in Radiation Therapy," Revista Colombiana de Fisica, vol. 37, No. 1, 2005, pp. 307-313.
M. B. Paiva, et al., "Update on Laser Photochemotherapy: An Alternative for Cancer Treatment," Anti-Cancer Agents in Medicinal Chemistry, vol. 11, 2011, 9 pages.
"Smartbeam™ IMRT: Patient Information and Frequently Asked Questions", Varian Medical Systems, Dec. 18, 2011, URL: http://www.nicancer.com/pdf/IMRT.pdf, 5 pages.
International Search Report dated Jul. 29, 2015 in PCT/US2015/027058 filed Apr. 22, 2015.
Extended European Search Report dated Nov. 20, 2017 in Patent Application No. 15783728.7.
Communication pursuant to Article 94(3) EPC dated Jul. 25, 2018 in European Patent Application No. 15 783 728.7.
Office Action dated Mar. 14, 2019 in the corresponding European Application No. 15 783 728.7.

* cited by examiner

FIG. 8
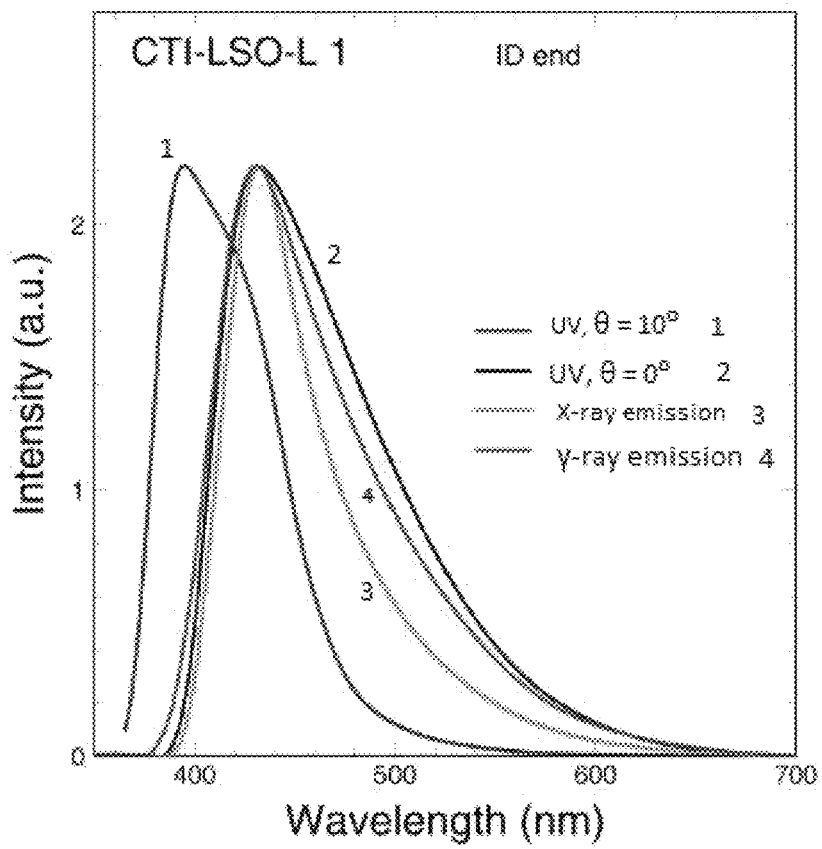
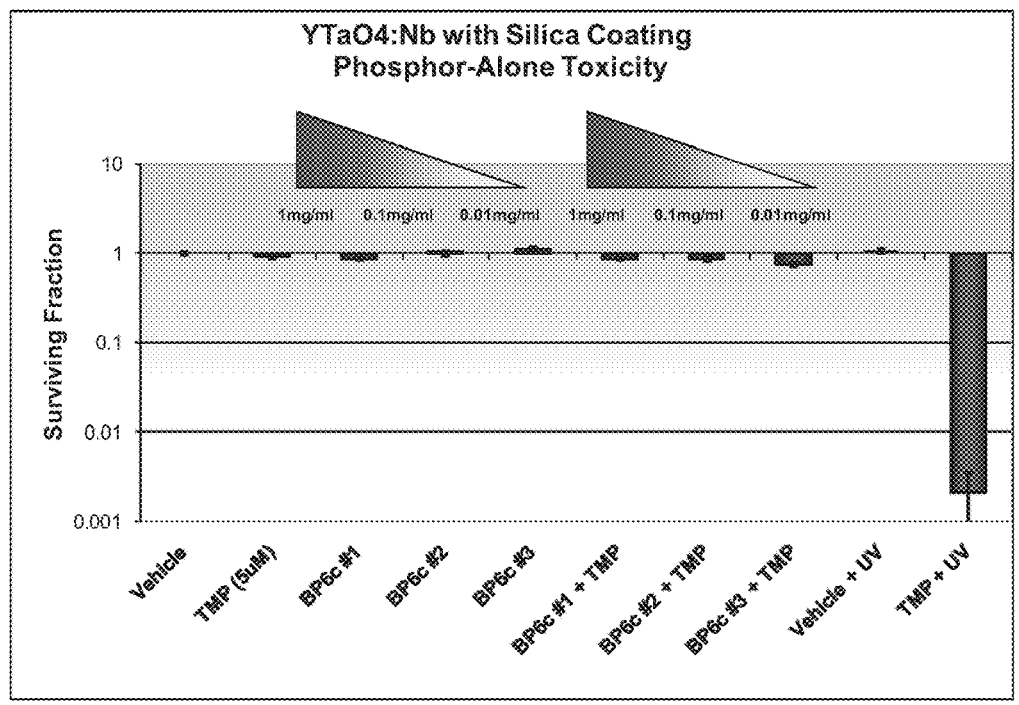
FIG. 9A

FIG. 10A
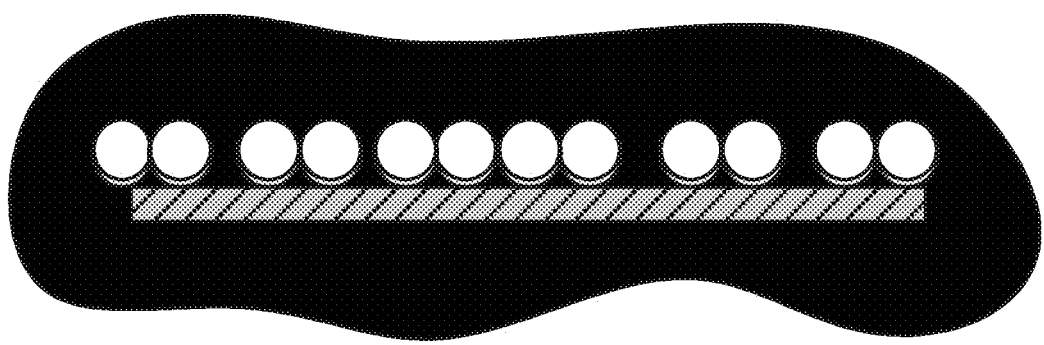
FIG. 10B
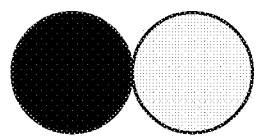
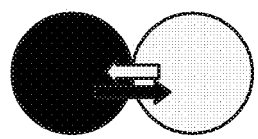 Mass transport and necking between particles
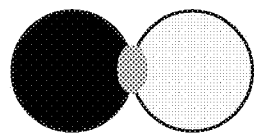

Clustered   Rings and closed lines   Dendrite

FIG. 18

| ENDOGENOUS FLUOROPHORES | EXCITATION MAX. (nm) | EMISSION MAX. (nm) |
|---|---|---|
| Amino acids: | | |
| Tryptophan | 280 | 350 |
| Tyrosine | 275 | 300 |
| Phenylalanine | 260 | 280 |
| Structured Proteins: | | |
| Collagen | 325, 360 | 400 |
| Elastin | 290, 325 | 405 |
| Enzymes and Coenzymes: | | |
| flavine adenine dinucleatide | 450 | 535 |
| reduced nicotinamidedinucleotide | 290, 351 | 440, 460 |
| reduced nicotinamide dinucleotide phosphate | 336 | 464 |
| Vitamins: | | |
| Vitamin A | 327 | 510 |
| Vitamin K | 335 | 480 |
| Vitamin D | 390 | 480 |
| Vitamins $B_2$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 | emission wavelength (nm)

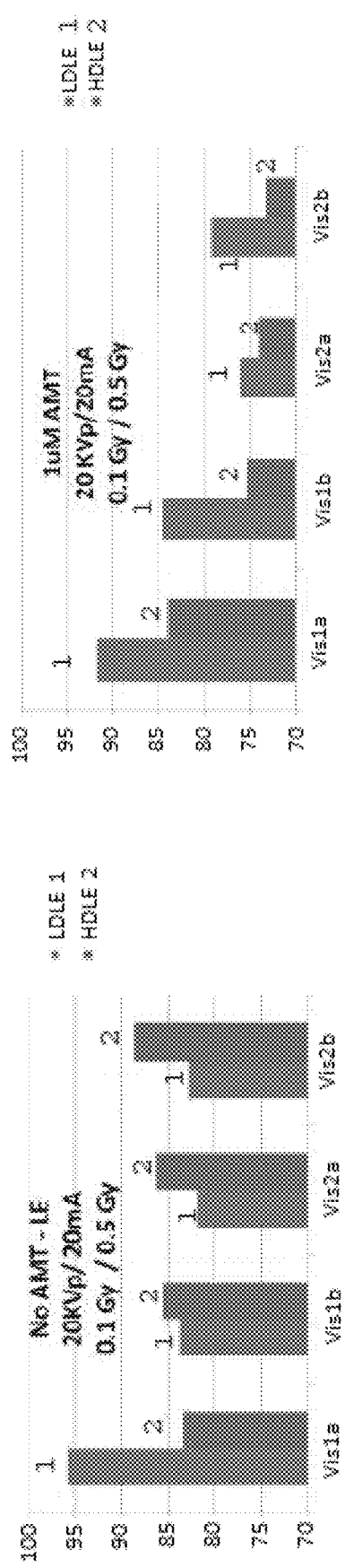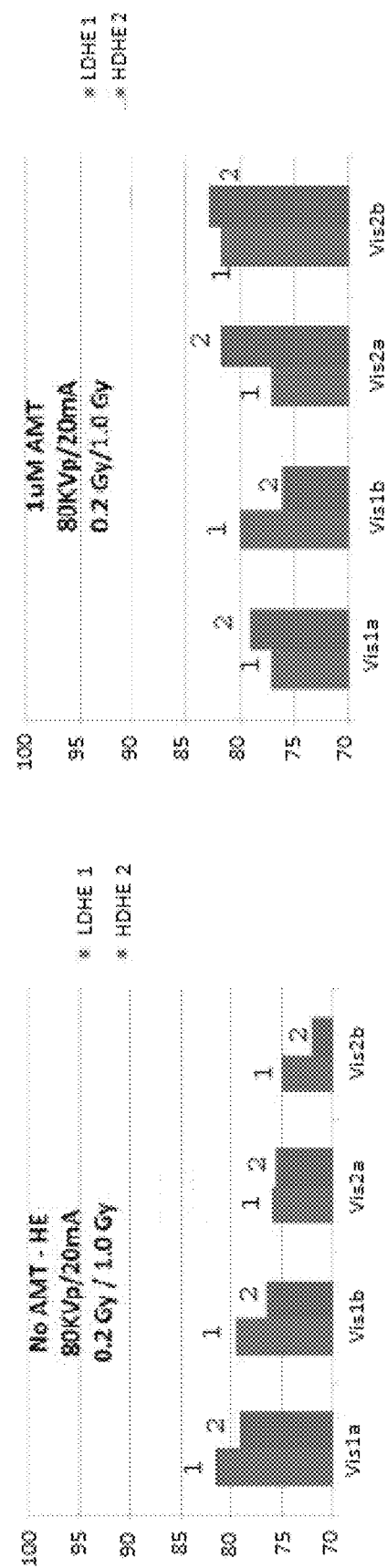
Fig. 34A  Fig. 34B  Fig. 35A  Fig. 35B

*Fig. 79*
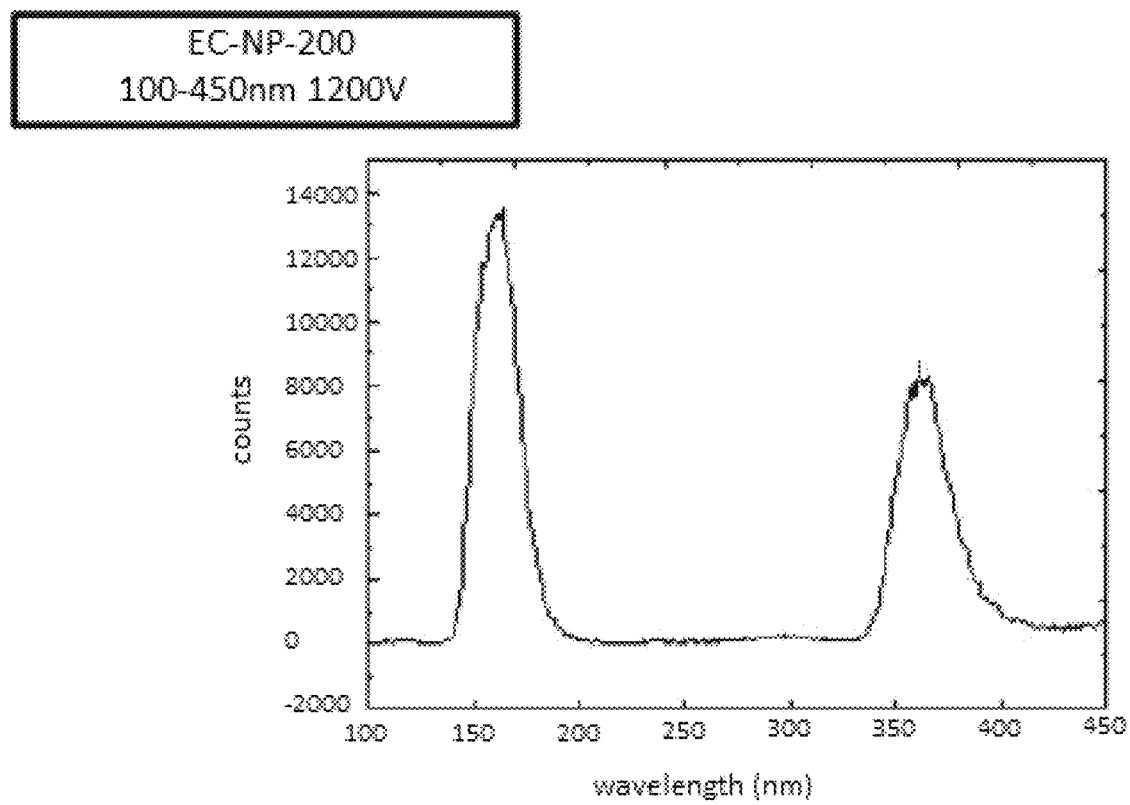
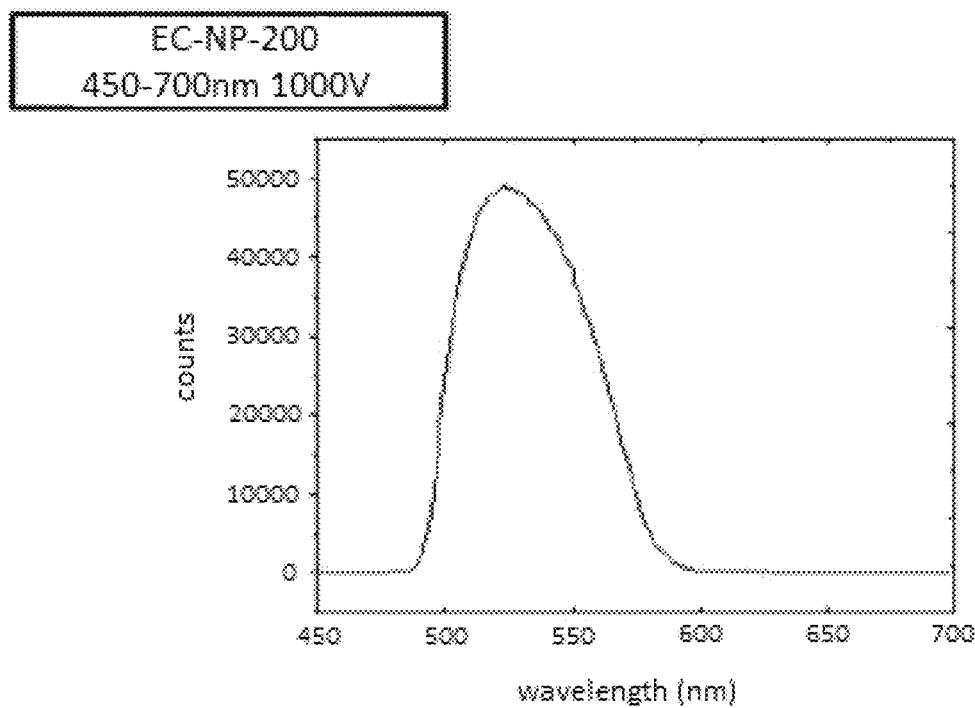

*Fig. 80*
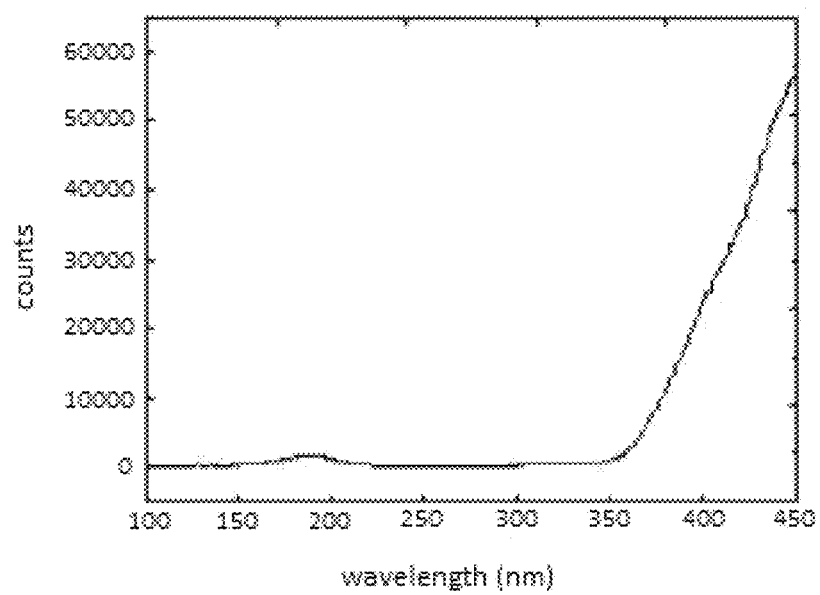
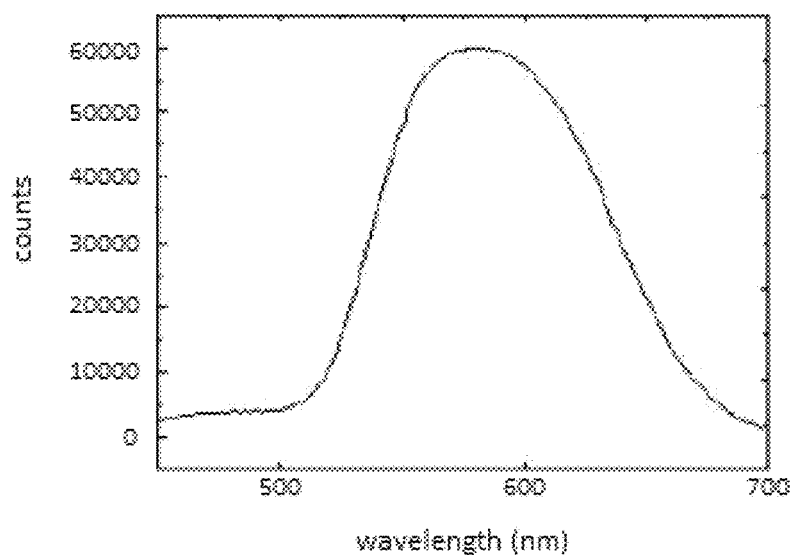

Fig. 82
Longer times: 10-100 μs
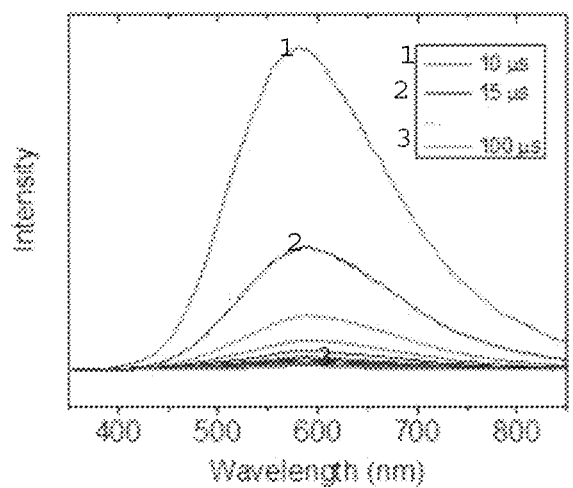
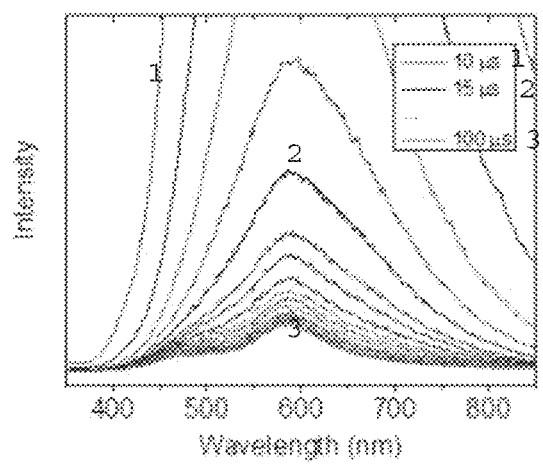
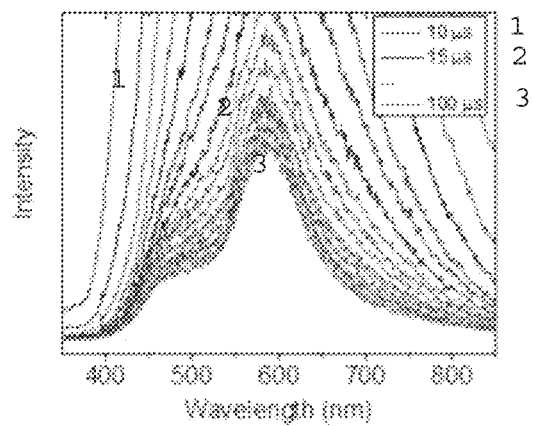

*Fig. 83*
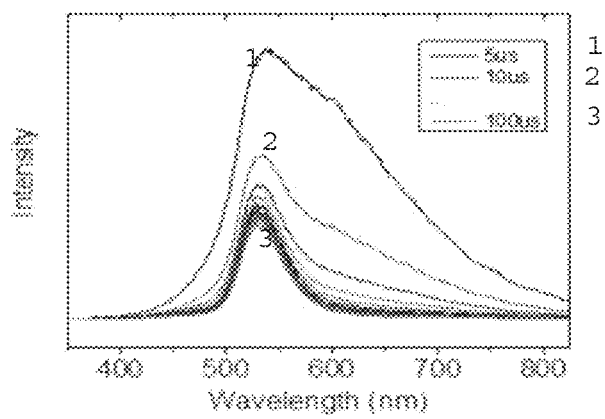
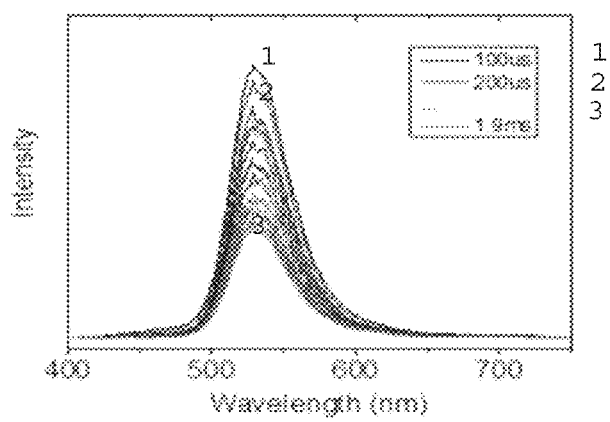
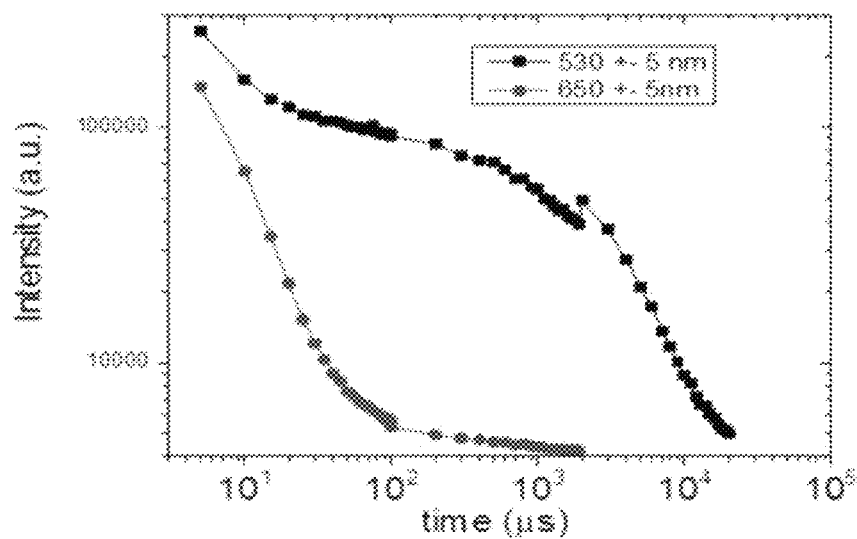

TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES

CROSS REFERENCE TO RELATED APPLICATIONS

This application is related to and claims priority to U.S. provisional Ser. No. 61/982,585, filed Apr. 22, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE", the entire contents of which are hereby incorporated by references. This application is related to provisional Ser. No. 62/096,773, filed: Dec. 24, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of each of which is incorporated herein by reference. This application is related to U.S. provisional Ser. No. 62/132,270, filed Mar. 12, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references. This application is related to U.S. provisional Ser. No. 62/147,390, filed Apr. 14, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by references.

This application is related to provisional U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to U.S. Ser. No. 13/102,277 entitled "ADHESIVE BONDING COMPOSITION AND METHOD OF USE," filed May 6, 2011, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 12/389,946, filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655, filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is also related to provisional Ser. No. 61/792,125, filed Mar. 15, 2013, entitled "INTERIOR ENERGY-ACTIVATION OF PHOTO-REACTIVE SPECIES INSIDE A MEDIUM OR BODY," the entire contents of which are hereby incorporated herein by reference. This application is further related to provisional Ser. No. 61/505,849 filed Jul. 8, 2011, and U.S. application Ser. No. 14/131,564, filed Jan. 8, 2014, each entitled "PHOSPHORS AND SCINTILLATORS FOR LIGHT STIMULATION WITHIN A MEDIUM," the entire contents of each of which is incorporated herein by reference. This application is related to and U.S. application Ser. No. 14/206,337, filed Mar. 12, 2014, entitled "INTERIOR ENERGY-ACTIVATION OF PHOTO-REACTIVE SPECIES INSIDE A MEDIUM OR BODY," the entire contents of which are hereby incorporated herein by reference.

BACKGROUND OF THE INVENTION

Field of Invention

The invention relates to methods and systems for generating in the interior of a medium or body radiant energy for producing a change in the properties of a medium or body by exposure to the radiation. The invention also relates to a method for performing such treatments using for example an initiation energy source such as an X-ray source, and limiting any negative effects imparted by the initiation energy source.

Discussion of the Background

Presently, light (i.e., electromagnetic radiation from the radio frequency through the visible to the X-ray and gamma ray wavelength range) activated processing is used in a number of industrial processes ranging from photoresist curing, to on-demand ozone production, to sterilization, to the promotion of polymer cross-linking activation (e.g. in adhesive and surface coatings) and others. Today, light activated processing is seen in these areas to have distinct advantages over more conventional approaches.

Light modulation from a deeply penetrating radiation like X-ray to a photo-catalytic radiation like UV, opens the possibility for activating bio-therapeutic agents of various kinds within mammalian bodies. Other possibilities include the activation of photo-catalysts in mediums for cross-linking reactions in polymeric chains and polymer based adhesives.

These examples are but two examples of a number of possibilities that can be more generally described as the use of a conversion material to convert an initiating radiation that is deeply penetrating to another useful radiation possessing the capability of promoting photo-based chemical reactions. The photo-chemistry is driven inside mediums of far ranging kinds including organic, inorganic or composited from organic and inorganic materials.

The photo-activation with no line of site required can be done in-vivo and ex-vivo such as those carried out in cell cultures. In turn, the photo activation of select bio-therapeutic agent, and conceivably more than one agent at a time, can lead to the onset of a desirable chemical reaction, or a cascade of reactions, that in turn lead to a beneficial therapeutic outcome. As an example, the binding of psoralen to DNA through the formation of monoadducts is well known to engender an immune response if done properly. An in-depth treatise of the subject is available in the open literature. Psoralen under the correct photo-catalytic light gains the aptitude to bind to DNA. Psoralen has been reported to react to other sites that have a suitable reactivity including and not limited to cell walls. If this reaction is of the correct kind, as is the case for psoralen-DNA monoadducts formation, the binding leads to a programmable cell death referred to as Apoptosis. Such programmable cell death, if accomplished over a sufficiently large cell population, can signal the body to mount an immune response enabling target specific cell kill throughout the body. Such immune response is of the upmost importance for various medical treatments including cancer cure.

In particular, in U.S. Ser. No. 11/935,655, entitled "METHODS AND SYSTEMS FOR TREATING CELL PROLIFERATION DISORDERS," the use of a phosphorescent emitting source was described with the advantage of phosphorescent emitting molecules or other source may be electroactivated or photoactivated prior to insertion into the tumor either by systemic administration or direct insertion into the region of the tumor. Phosphorescent materials have longer relaxation times than fluorescent materials. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In particular, in U.S. Ser. No. 12/401,478, entitled "PLASMONIC ASSISTED SYSTEMS AND METHODS FOR INTERIOR ENERGY-ACTIVATION FROM AN EXTERIOR SOURCE," the use of phosphorescent materials as energy modulation agents was described. The '478 application details a number of modulation agents some having a very short energy retention time (on the order of fs-ns, e.g. fluorescent molecules) whereas others having a very long half-life (on the order of seconds to hours, e.g. luminescent inorganic molecules or phosphorescent molecules). Specific types of energy modulation agents described in the '478 application included $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er3^+$; ZnS:$Mn^{2+}$; ZnS:Mn,$Er^{3+}$.

SUMMARY OF THE INVENTION

In one embodiment, there is provided a system for imaging or treating a tumor in a human or animal body. The system includes a pharmaceutical carrier including one or more phosphors which are capable of emitting light into the tumor or the body upon interaction and which provide x-ray contrast, one or more devices which infuse the tumor with a photoactivatable drug and the pharmaceutical carrier, an x-ray or high energy electron source, and a processor programmed to at least one of 1) produce images of the tumor or 2) control a dose of x-rays or electrons to the tumor for production of light inside the tumor to activate the photoactivatable drug.

In one embodiment, there is provided a method for imaging or treating a tumor in a human or animal body. The method includes injecting into a vicinity of and inside the tumor a pharmaceutical carrier including one or more phosphors which are capable of emitting light into the tumor or the body upon interaction and which provide x-ray contrast, infusing the tumor with a photoactivatable drug and the pharmaceutical carrier, applying x-ray or high energy electrons to the tumor, and at least one of obtaining images of the tumor and producing the light inside the tumor to activate the photoactivatable drug.

In one embodiment, there is provided a system or method for imaging or treating a tumor in a human or animal body. The method includes injecting into a vicinity of and inside the tumor a pharmaceutical carrier including one or more phosphors which are capable of emitting light into the tumor or the body upon interaction and which provide imaging contrast, infusing the tumor with a photoactivatable drug and the pharmaceutical carrier, applying x-ray or high energy electrons to the tumor, and at least one of obtaining images of the tumor and producing the light inside the tumor to activate the photoactivatable drug.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 6M is a schematic of the emission spectra for the $CaWO_4$ and $YTaO_4$ mixture under different excitation X-Ray excitation energies;

FIG. 8 is a schematic of emission spectra of lutetium oxyorthosilicate LSO under different excitation sources;

FIG. 9A is a schematic of the results from a clonogenic assay for an $YTaO_4$:Nb phosphor with and without a silica coating;

FIG. 10A is a schematic of the half coated phosphor particles disposed around a metallic nano rod and heated to sufficient temperatures to alloy the metallic coating with the metallic nano rod;

FIG. 10B is a schematic of mass transport being used to form a neck between particles;

FIG. 18 is a table providing a list of possible, but not comprehensive, photoactivatable agents;

FIGS. 34A and 34B are plotted cell kill comparisons (shown here as the number of surviving colonies) between cancer cells treated with and without Psoralen (AMT) with different phosphor mixtures;

FIGS. 35A and 35B are plotted cell kill comparisons similar to FIGS. 33A and 33B at higher kVp x-ray conditions;

FIG. 79 is a plot of cathode luminescence for phosphor NP200;

FIG. 80 is a plot of cathode luminescence for phosphor GTP 4300;

FIG. 8 is a transient photoluminescent (PL) Spectra-GTP 4300 using a 365 nm LASER as an excitation source;

FIG. 82 is a transient PL spectra showing that, after ~40 μs, the broad peak starts to turn into two sharper peaks at 480 and 585 nm; and FIG. 83 are transient PL spectra for phosphor NP200.

DETAILED DESCRIPTION OF THE INVENTION

Figure 1:
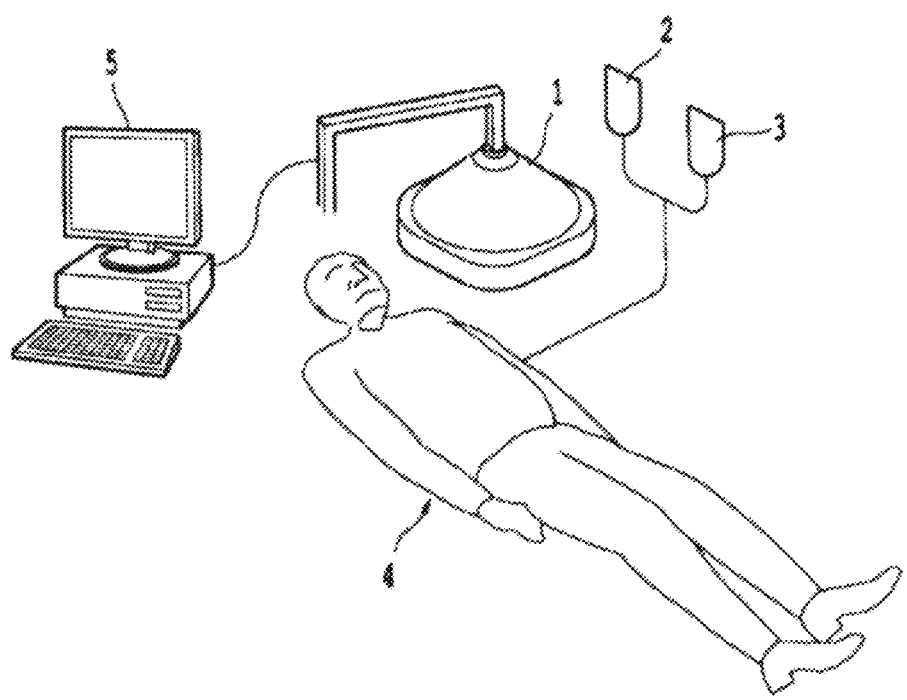
FIG. 1 is a schematic illustration of a system according to one exemplary embodiment of the invention.

The invention sets forth a novel method for causing a change in activity in a medium or body that is effective, specific, and able to produce a change to the medium or body. The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

Reference will now be made in detail to the present preferred embodiments of the invention, an example of which are illustrated in the accompanying drawings (including color drawings), in which like reference characters refer to corresponding elements.

FIG. 1 illustrates a system according to one exemplary embodiment of the invention. Referring to FIG. 1, an exemplary system according to one embodiment of the invention may have an initiation energy source 1 directed at the subject 4. An activatable pharmaceutical agent 2 and an energy modulation agent 3 can be administered to the subject 4. The initiation energy source may additionally be controlled by a computer system 5 that is capable of directing the delivery of the initiation energy (e.g., X-rays).

In further embodiments, dose calculation and robotic manipulation devices (such as the CYBER-KNIFE robotic radiosurgery system, available from Accuray, or similar types of devices) may also be included in the system to adjust the distance between the initiation energy source 1 and the subject 4 and/or to adjust the energy and/or dose (e.g., kVp or filtering) of the initiation energy source such that the x-rays incident on the target site are within an energy band bounded by a lower energy threshold capable of inducing desirable reactions and an upper energy threshold leading to denaturization of the medium. Results described below show the range of X-ray kVp. Further refinements in the x-ray energy and dose can be had by adjusting the distance to the subject 5 or the intervening materials between the target site and the initiation energy source 1. The X-ray sources described later can also provide images of the target area being treated.

In yet another embodiment, there is also provided a computer implemented system for designing and selecting suitable combinations of initiation energy source, energy transfer agent, and activatable pharmaceutical agent, comprising:

a central processing unit (CPU) having a storage medium on which is provided:

a database of excitable compounds;

a first computation module for identifying and designing an excitable compound (e.g., a photoactivatable drug) that is capable of binding with a target cellular structure or component; and a second computation module predicting the absorption energy of the excitable compound, wherein the system, upon selection of a target cellular structure or component, computes an excitable compound that is capable of interacting with the target structure.

The computer-implemented system according to one embodiment of the invention may have a central processing unit (CPU) connected to a memory unit, configured such that the CPU is capable of processing user inputs and selecting a combination of initiation source (or initiation energies or distances), activatable pharmaceutical agent, and energy modulation or energy transfer agents for use in a method of the invention.

The computer-implemented system according to one embodiment of the invention includes (or is programmed to act as) an x-ray source (or high energy source such as an electron beam) control device configured to calculate an x-ray (radiation) exposure condition including a distance between the initiation energy source 1 and the subject 4 and the energy band bounded by the above-noted lower energy threshold capable of inducing desirable reactions and the above-noted upper energy threshold leading to denaturization of the medium. The control device operates the x-ray or high energy source (the initiation energy source 1) within the exposure condition to provide a requisite energy and/or dose of x-rays to the subject or a target site of the subject.

In one aspect of the invention, a system (and corresponding method) is provided for imaging or treating a tumor in a human or animal body. The system includes a pharmaceutical carrier including one or more phosphors which are capable of emitting light into the tumor or the body upon interaction and which provide x-ray contrast, one or more devices which infuse the tumor with a photoactivatable drug and the pharmaceutical carrier, an x-ray or high energy electron source, and a processor programmed to 1) produce images of the tumor and/or 2) control a dose of x-rays or electrons to the tumor for production of light inside the tumor to activate the photoactivatable drug.

The method hereby includes injecting into a vicinity of and inside the tumor a pharmaceutical carrier including the one or more phosphors which are capable of emitting light into the tumor or the body upon interaction and which provide x-ray contrast, infusing the tumor with the photoactivatable drug and the pharmaceutical carrier, applying x-ray or high energy electrons to the tumor, and obtaining images of the tumor and/or producing the light inside the tumor to activate the photoactivatable drug.

While described with respect to phosphors (i.e., energy modulation agents), the invention is not so limited and can utilize down conversion media, combinations of different down conversion media, upconversion media, combinations of different up conversion media, and/or combinations of different up and down conversion media. These different media are detailed below in the various embodiments.

Excitation of the energy modulation agents can be provided by a reduced-voltage x-ray source configured to generate x-rays from a peak applied cathode voltage at or below 200 kVp. The energy modulation agents can be included in the medium to be radiated as a first plurality of energy-converting particles which, upon radiation from the x-ray source, radiate at a first lower energy than the x-ray source to interact with the medium or with at least one photoactivatable agent in the medium. (The energy-converting particles of the present invention are alternatively called "energy modulation agents" herein, and the terms may be used interchangeably herein). Radiation from the first plurality of energy-converting particles can alter the biological activity of the medium, as described in more detail below.

Accordingly, as noted above, in one embodiment of this invention, there is provided a system or method for light stimulation within a medium. The system has a reduced-voltage x-ray source configured to generate x-rays from a peak applied cathode voltage at or below 200 kVp, and a first plurality of energy-converting particles in the medium which, upon radiation from the x-ray source, radiate at a first lower energy than the x-ray source to interact with photoactivatable agent(s) in the medium. The method accordingly introduces a first plurality of energy-converting particles into the medium, radiates the first plurality of energy-converting particles in the medium with x-rays generated from a peak applied cathode voltage at or below 200 kVp, and emits a first lower energy than the x-ray source to interact with photoactivatable agent(s) in the medium. In various aspects to the invention the peak applied cathode voltage is at or below 160 kVp, is at or below 120 kVp, is at or below 105 kVp, is at or below 70 kVp, is at or below 60 kVp, is at or below 50 kVp, is at or below 40 kVp, is at or below 30 kVp, or is at or below 20 kVp, or is at or below 10 kVp or is at or below 5 kVp. In one aspect of the invention, the distance to the target is utilized to also alter the effect of varying the incident energy of the X-rays incident on the medium. The distance can be set to a value of less than 5 mm, less than 10 mm, less than 15 mm, or less than 20 mm. In other embodiments, the x-ray source can be positioned farther away from the target being irradiated.

"kVp" is peak accelerating voltage applied in an X-ray tube between the cathode and anode. The term and its definition derive from the fact that in some systems the accelerating potential is not constant, but varies over time (i.e., has a voltage ripple). The kVp (in units of kilovolts) is the kinetic energy (in keV) of the most energetic electrons arriving at the anode, and also the energy of the most energetic X-ray photon produced by bremsstrahlung. The strength of x-rays in the invention may be referred to herein as X-rays of a particular kVp energy. This indicates that the X-rays are generated from a peak applied cathode voltage of the stated amount.

The initiation energy source can be any energy source capable of providing energy at a level sufficient to activate the activatable agent directly, or to provide the energy modulation agent with the input needed to emit the activation energy for the activatable agent (indirect activation). In preferred embodiments, the initiation energy source is a source of low energy X-rays, preferably X-rays generated from a peak-applied cathode voltage of 200 kVp or less. Suitable preferred low energy X-ray sources include, but are not limited to, a CT scanner, alone or in combination with a second therapy beam, a fluoroscope, a radiography with programmable radiation dose, a system with low energy imaging X-Ray function along with higher energy X-Ray function for delivering the required dose with the adequate kv and mA. It also possible to enhance the activation by X-Ray by adding a second form of incident electromagnetic energy having a deeply penetrating characteristic (such as in the radio frequency or microwave realm) applied to the desirable target area to improve the success ratio of X-Ray activation. In a particularly preferred embodiment, the initiation energy source is a computed tomography scanner (better known as a CT scanner or CAT scan), which is conventionally used in medicine for non-invasive diagnostic imaging of part or all of a body, using low energy x-rays. In one embodiment of the invention, these low energy x-rays can be used as a non-invasive method of activating the activatable agent (whether an activatable pharmaceutical agent or in a non-medical embodiment such as activating polymerization or curing), while exposing the subject to only low levels of radiation. In a particularly preferred embodiment, the CT scanner can be used to simultaneously image and treat a subject to cause photobiomodulation, or for treatment of a cell proliferation disorder, such as cancer.

In certain embodiments of the invention, it is preferred to target the tissue such that radiation dose can be maximized in the target area, while being minimized in skin and superficial dose, particularly to below state regulations for the particular state in which treatment occurs. Such targeting can be preferably done with appropriate collimation, using as an associated imaging system, a fan beam or cone beam x-ray system, or combinations thereof. Other targeting mechanisms include axial and angular mA modulation of the CT system, and spectrum shaping through k-edge or crystalline filtering to "tune" the x-ray energy precisely where the energy-converting or energy modulation agent shows maximum sensitivity, while otherwise lowering the bulk radiation dose.

In one embodiment, the initiation energy is capable of penetrating completely through the medium. Within the context of the invention, the phrase "capable of penetrating completely through the medium" is used to refer to energy capable of penetrating a container to any distance necessary to activate the activatable agent within the medium. It is not required that the energy applied actually pass completely through the medium, merely that it be capable of doing so in order to permit penetration to any desired distance to activate the activatable agent, such as by targeting the focus of the x-ray beam and thus the desired x-ray dose in the desired tissue. The type of energy source chosen will depend on the medium itself.

The efficiency of X-ray production by bremsstrahlung increases with increasing kVp, and so therefore does X-ray tube output. If the kVp (in kilovolts) is higher than the binding energy of an electron shell of the X-ray tube target material, it is possible for the electron to ionize that shell and for characteristic radiation to be produced.

For any given kVp, the X-ray spectrum contains a spread of energies, the highest of which is proportional to the kVp. However, the number of photons in lower energy ranges is greater than at the very highest energies, and the average energy of the X-ray beam is lower than the kVp. Nonetheless, the average energy increases with increasing kVp and the beam becomes more penetrating.

The energy distribution of x-rays as a function of kVp shows a progressive reduction in the peak x-ray energy and a reduction in the number of x-rays as kVp is reduced. Accordingly, the computer system 5 shown in FIG. 1 (or another x-ray source controller) controlling the initiation energy source can control the kVp setting to change the dose and average x-ray energies incident on a target of subject 4. While the x-ray energy used in the experimental results below were obtained without an aluminum filter on the x-ray source, an aluminum or other filter can be used to truncate a portion of the x-ray spectrum and selectively provide different x-ray doses and x-ray energies to the target.

Regardless of method of treatment, psoralen and psoralen derivatives are of interest for many of the biological applications of this invention. The absorption of psoralen was measured in different solvents including toluene, tetrahydrofuran (THF), ethanol, and dimethyl sulfoxide (DMSO). In particular, the absorption spectrum of psoralen measured in different solvents and over a broad range extending from the UVB, the UVA and part of the visible shows shifts depending on the particular solvent.

In one aspect of the invention, the UV light emitted inside a cell or inside an organ depends on the light conversion capability of the utilized particle and on the number of particles residing close to the point of measurement. The higher the number of particles the higher the net intensity according to the superposition principles applicable to light in particular and to electromagnetic waves in general. The nano-particle conversion material can be selected to have a high probability of interaction with X-ray and strong emission in UV range with as much intensity as possible. Alternatively, the nano-particle conversion material can be a scintillator selected to have a high probability of interaction with an ionizing particle and strong emission in UV range with as much intensity as possible. A scintillator is a material which exhibits luminescence when excited by ionizing radiation, such as for example an incoming particle (electron or ion), absorb its energy and reemit the absorbed energy in the form of light.

Some phosphors can be doped with ionic species such that the material formed can exhibit fluorescence and phosphorescence at the same time. The materials can be formed in single crystal or poly-crystalline forms, in powders or monoliths.

However, once the conversion material selection is done, further improvement of intensity depends for example on the size, the number, and the distribution of the nano-particles that are close to target or to the measurement point. The delivery of particles inside an organ can be gated by the organ's vasculature. The delivery of particles inside a cell can also be gated by the ion channels residing in the cell walls. Organs can accept larger particles than cells, since the openings gated by the organ's vasculature is much larger than ion channels in the cell walls.

One embodiment of this invention deals with the delivery of phosphors or scintillators or a combination thereof having particle sizes below 40 nm and that can pass through the ion channels of cells. Once inside the cell, the phosphors of this invention are trapped in sufficient concentration. The entrapment of the phosphors of this invention can be facilitated by the combination of applying a magnetic coating to the particles and using magnetic fields that are imposed externally to a given mammalian body (or external to an artificial medium). In addition to entrapment of phosphors or scintillators or a combination thereof inside cells or organs, the phosphors of this invention can be made to assemble in patterns that increase their net UV light output under X-Ray excitation.

In one embodiment, there is provided a system for light stimulation within a medium. The system has a first plurality of light-emitting particles which upon encountering an appropriate initiating excitation of light energy or particle beam energy radiate an output energy having photocatalysis potential to activate phtoactivatable agents with minimized impact on the medium. The system further has a second plurality of light-emitting particles which, upon encountering the same appropriate initiating excitation of light energy or particle beam energy, radiate an output energy complementary to the output of the first set of particles A combination of energy emission from the first and second plurality of energy emitting particles produces a combined energy capable of activating chemical agents inside the medium more effectively than the first set of particles alone. The two sets of particles are interoperably complimentary to one another. The energy outputs can be of different natures. The first set of particles can output light energy and the second set of particles can output chemical energy.

The energy spectrum of the first set of particles has an energy distribution having a peak position in common with a peak in an absorption spectrum of the photoactivatable agent(s) and having a bandwidth overlapping the absorption spectrum of the photoactivatable chemical agents. The second energy potentiates the photoactivation by predisposing reactive sites to the photoactivatable chemical agent(s). The second energy can also be a light energy of different spectrum or a chemical energy resulting in the favorable alteration of the reaction potential of select reactive sites. For instance, light can cause excitation of photosensitizers, in the presence of oxygen, to produce various toxic species, such as singlet oxygen and hydroxyl radicals. Meanwhile, microwave and RF energy leads to dipolar alignment of molecular species having an asymmetrical charge distribution over their length.

More specific methods by which chemical pathways of photoactivatable chemistries can be altered is described below in at least the photo-treatment section and the photobiomodulation section.

Accordingly, in one embodiment of the invention, there is provided a method for light stimulation within a medium. The method includes introducing a first plurality of light-emitting particles into the medium, introducing a second plurality of light-emitting particles into the medium, exposing the first plurality of light-emitting particles to an initiating excitation of light energy or particle beam energy to produce from the first plurality of light-emitting particles a first output energy having photocatalysis potential to activate phtoactivatable agents in the medium, and exposing the second plurality of light-emitting particles to an initiating excitation of light energy or particle beam energy to produce from the second plurality of light-emitting particles a second output energy complementary to the first output. A combination of energy emission from the first and second plurality of energy emitting particles produces a combined energy capable of activating chemical agents inside the medium.

One attribute of this invention is to provide phosphor materials capable of specific light outputs under X-ray excitation in the absence of line-of-sight access to the external energy source.

A further attribute of this invention is to provide a set of phosphor or scintillator particles or a combination thereof that has a combined light output spectrum closely matching the absorption of a photoactivatable agent.

Another attribute of this invention is to provide phosphor or scintillator particles or a combination thereof capable of being oriented under an applied magnetic field.

Another attribute of this invention is to provide phosphor or scintillator particles or a combination thereof capable of being oriented under an applied electric field.

Another attribute of this invention is to provide self-assembly of nanoparticles under an applied magnetic or electric field. In this attribute, the assembly of phosphor or scintillator or a combination thereof particles can form simple geometrical patterns such as dendrites, spherical clusters and rings.

Another attribute of this invention is to provide a method by which a set amount of phosphor or scintillator particles or a combination thereof yield more intensity at a targeted site than would occur the same amount of randomly distributed phosphor particles.

Another attribute of this invention is to provide a method by which two or more phosphors or scintillators or a combination thereof each emitting an intrinsic spectral signature, can be mixed or alloyed to form a particle mixture yielding a specific emission spectral signature.

Another attribute of this invention is to provide a method by which a particle mixture has a specific spectral signature matching a specific absorption of a photoactivatable agent, e.g., a photo-catalyst agent or bio therapeutic agent.

Another attribute of this invention is to provide a method by which a particle mixture has a specific spectral signature to activate two photo catalysts or two bio-therapeutic agents.

Another attribute of this invention is to provide a method by which a particle mixture acts as the carrier for the photo-catalyst of a bio-therapeutic agent.

Another attribute of this invention is to provide a method by which phosphor or scintillator particles or a combination thereof can be made to emit a single specific wavelength to actuate specific biological functions or can be used to assist or block intracellular communication.

Another attribute of this invention is to provide a method by which phosphor particles or scintillator particles of a sufficiently small size are delivered to an organ, to a cell, or to an inside of the cell nucleus and then are trapped inside the target using magnetic fields.

A further attribute of the invention is the ability to optimize the x-ray spectrum for maximum effectiveness.

Another attribute of the invention is to provide targeted delivery of x-ray activation for optimum spatial distribution of activation intensity, via spatial and temporal modulations.

Another attribute of the invention is to provide the ability to monitor the x-ray irradiation via an associated supplemental imaging apparatus (such as a CT system).

DNA Crosslinking

Light intensity plays a substantial role in photo-activation or photo-catalysis. The more light intensity that is available, the higher the chance of activating reactions that are suitable for photo-activation. Conversely, the lower the intensity, the lower the chance of activating chemical reactions. In other words, usually, photonic flux at a sufficient intensity (number of photons per unit time) is necessary to trigger reactions.

Besides light intensity, a minimum level of spectral matching between the radiation(s) emanating from the conversion media and the radiation that can be absorbed by the photo-catalyst being targeted is desirable not necessarily required. In other words, the emitted radiation would preferably be suitable or matched to the absorption of the chemical species under consideration.

As described herein, the effect of psoralen on crosslinking DNA was used to determine the effectiveness of light modulating particles (phosphors, scintillators and combinations thereof) under X-Ray irradiation. Of particular interest were the crosslinking signals associated with DNA and in particular having a minimization effect of denaturing DNA while maximizing the density of desirable crosslinks such as those engendering an immune response.

Gel electrophoresis is method for qualitatively analyzing DNA crosslinking. If no denaturing conditions are applied, then an observable pattern consisting of an aggregation of double stranded genomic DNA (or ds genomic DNA) are present. On the other hand, if denaturing conditions are applied, then an observable signal represented by a smear pattern is observed since a distribution of species is present, not just a single stranded DNA.

DNA was incubated with psoralen then exposed to X-Ray energy in the presence of nano particles and a biotherapeutic agent. Denaturing conditions were then applied in the form of heat, formamide. Agarose gel having an electric field gradient was used to force DNA to travel through its pores by a diffusion process. The signals resulting from the ds DNA and ss DNA are then recorded using the fluorescent dye technique described above. The intensity of the gel is directly related to the mass loading.

A DNA crosslinking test plan utilizes X-ray radiation as the initiating crosslinking radiation. The experimental space was mapped out, and variables were altered as part of the experimental plan. Surprising results were observed in that more ssDNA was generated at higher X-Ray intensity. The solutions were prepared using a total volume per glass vial (2 mL DNA solution+AMT or phosphors). Dissolved stock lyophilized DNA (2 mg) in 20 mL of 1×PBS. The drug concentrations of AMT were kept at a fixed concentration of 0.1 ΦM. The phosphors were added to the solution as follows: 0.1 mg/mL final concentration in DNA. This was obtained by creating a suspension of 1 mg/mL BP7c suspension in PBS, adding 200 ΦL suspension to vial of 2 mL DNA+TMPS solution and finally adding 200 ΦL suspension to vial of 2 mL DNA+AMT solution. After treatment, all the vials were transferred to ice, covered from the light, and stored in cold room on wet ice prior to the gel electrophoresis measurements.

The gel electrophoresis results post DNA crosslinking attempts under X-Ray radiation and using temperature and distance from the source as variables are described below. The experimental conditions are provided in Table 1 below from the BP7c (phosphor) suspension in PBS under different high energy X-Ray exposures.

TABLE 1

| 320 kVp, 10 mA | | |
| --- | --- | --- |
| Phosphor | Distance from the source (cm) | Temperature (C.) |
| S1 | 26.5 | 15 C. |
| S2 | 26.5 | 21 C. |
| S3 | 26.5 | 33 C. |
| S4 | 35 | 25 C. |

TABLE 1-continued 320 kVp, 10 mA

| Phosphor | Distance from the source (cm) | Temperature (C.) |
|---|---|---|
| S5 | 40.5 | 25 C. |
| S6 | 0.1 | 25 C. |

All the experiments were conducted using a constant source voltage and amperage. Sample S6 had the most energy input from the irradiator. Sample condition S6 revealed that more X-Ray intensity yielded more ssDNA than other conditions of lesser energy inputs. Production of ssDNA is considered to be the less desirable result. The generation of more ssDNA at higher X-Ray intensity was an unexpected result.

The results from gel electrophoresis post DNA crosslinking evaluations using various experimental conditions are described below. Table 2 provides the experimental conditions for evaluating the effect of total delivered energy (some conditions had constant power and some conditions had constant flux).

TABLE 2

|  | Constant Power ||||||  Constant Flux/Different kVp ||||||
|---|---|---|---|---|---|---|---|---|---|---|---|---|
|  | 10 mA || 20 mA || 30 mA || 30 mA || 30 mA || 30 mA ||
|  | 320 kvp || 160 kvp || 105 kvp || 105 kvp || 80 kvp || 40 kvp ||
| [Phosphor] | 2 min | 6 min | 2 min | 6 min | 2 min | 6 min | 2 min | 6 min | 2 min | 6 min | 2 min | 6 min |
| S1 | XX |  |  |  |  |  |  |  |  |  |  |  |
| S2 |  | XX |  |  |  |  |  |  |  |  |  |  |
| S3 |  |  | XX |  |  |  |  |  |  |  |  |  |
| S4 |  |  |  | XX |  |  |  |  |  |  |  |  |
| S5 |  |  |  |  | XX |  | XX |  |  |  |  |  |
| S6 |  |  |  |  |  | XX |  | XX |  |  |  |  |
| S7 |  |  |  |  |  |  |  |  | XX |  |  |  |
| S8 |  |  |  |  |  |  |  |  |  | XX |  |  |
| S9 |  |  |  |  |  |  |  |  |  |  | XX |  |
| S10 |  |  |  |  |  |  |  |  |  |  |  | XX |
| S11* |  |  | XX |  |  |  |  |  |  |  |  |  |
| S12* |  |  |  | XX |  |  |  |  |  |  |  |  |

The total delivered energy was an experimentally designed variable. The power was maintained constant by varying kVp (peak voltage on the x-ray cathode) and filament current accordingly. The impact of a constant flux was tested. For each of these conditions, time was fixed in two major intervals: e.g., a two minute duration or a six minute duration. As shown in Table 2, all of the two minute runs (regardless of the flux and kVp conditions) showed a strong ds DNA signal. On the other hand, all of the six minute runs (regardless of the flux and kVp conditions) showed a strong ss-DNA signal. In effect, the total energy delivered to the system makes a substantial difference in the formation of ss-DNA versus ds-DNA. Though the DNA crosslinking test is qualitative rather than quantitative, the exhibited trend is clear. More energy leads to the formation of smaller molecular weight species from the original DNA.

A visual ranking of brightness from the electrophoresis technique was adopted to rank the various conditions. The results are tabulated in Table 3 below showing for respective sampler S1 to S12 the luminosity results from the dsDNA and the ssDNA, with the higher the number the higher brightness.

TABLE 3

|  | ds DNA | ss DNA |
|---|---|---|
| S1 | 2 | 0 |
| S2 | 0 | 1 |
| S3 | 2 | 0 |
| S4 | 0 | 3 |
| S5 | 1 | 1 |
| S6 | 0 | 4 |
| S7 | 3 | 0 |
| S8 | 0 | 4 |
| S9 | 3 | 0 |
| S10 | 1 | 1 |
| S11 | 1 | 1 |
| S12 | 0 | 4 |

The sum total of all the brightness results in the "ds" column and the sum total of all the brightness in the "ss" column for the duration periods applied during the test show that the two minute duration X-ray irradiation treatments lead to more ds-DNA, and the six minute duration X-ray irradiation treatments lead to more ss-DNA.

The total energy delivered to the X-ray cathode tube during the X-Ray treatments was calculated by integrating the power delivery over the time period by multiplying the voltage and the amperage, as illustrated in Table 4 shown below.

TABLE 4

| Power Condition | Time (sec) | kV | m-A | Total Energy (joules) |
|---|---|---|---|---|
| S1 | 120 | 320 | 10 | 384,000 |
| S2 | 360 | 320 | 10 | 1,152,000 |
| S3 | 120 | 160 | 20 | 384,000 |
| S4 | 360 | 160 | 20 | 1,152,000 |
| S5 | 120 | 105 | 30 | 378,000 |
| S6 | 360 | 105 | 30 | 1,134,000 |
| S7 | 120 | 80 | 30 | 288,000 |
| S8 | 360 | 80 | 30 | 864,000 |
| S9 | 120 | 40 | 30 | 144,000 |
| S10 | 360 | 40 | 30 | 432,000 |
| S11 * | 120 | 160 | 20 | 384,000 |
| S12 * | 360 | 160 | 20 | 1,152,000 |

In order to test the impact of phosphor loading, a series of phosphor loadings were prepared for testing. The X-ray treatment was kept at two minutes for the conditions in this experiment (for the sake of confirming the repeatability of the fact that the lower level of energy delivery leads to ds-DNA signal). The phosphor concentration was varied from 0.1 mg/ml to 0.15 mg/ml and 0.18 mg/ml.

The results from gel electrophoresis post DNA crosslinking attempts using varying phosphor concentrations at kVp values at or below 80 kVp are described below. The ds-DNA signal can be observed across the entire series of samples treated according to the experimental conditions, as seen in Table 5 showing experimental conditions for testing the effect of phosphor concentration variation. This reinforces the effects of lower incident energy levels to avoid generating ssDNA.

TABLE 5

| [Phosphor] | Samples | Constant flux different KVP | | | |
| --- | --- | --- | --- | --- | --- |
| | | 30 mA | | | |
| | | 80 kvp | 40 kvp | 20 kvp | 10 kvp* |
| | | 2 min | 2 min | 2 min | 2 min |
| 0.1 mg/ml | S1 | XX | | | |
| | S2 | | XX | | |
| | S3 | | | XX | |
| | S4 | | | | XX |
| repeat | S5 | | | | |
| | S6 | | | | |
| 0.15 mg/ml | S7 | XX | | | |
| | S8 | | XX | | |
| | S9 | | | XX | |
| | S10 | | | | XX |
| 0.18 mg/ml | S11 | | XX | | |
| | S12 | | | XX | |
| | S13 | | | | XX |
| | S14** | $2^{nd}$ XX | | $1^{st}$ XX | |
| | S15 | | | | |
| | S16*** | $1^{st}$ XX | | $2^{nd}$ XX | |
| repeat | S17 | | | | |

XX Strong ds DNA signal

Furthermore, sample S4 treated using 10 kVp exhibits a relatively stronger ds-DNA signal than S1 which was treated using 80 kVp. The lower the kVp results in stronger observable ds-DNA signal for the phosphor in 0.1 mg/mL final concentration in DNA. The comparison of S1, S2, S3 and S4 conditions further reinforces that lower kVp values are helpful to the crosslinking process.

The condition that led to most crosslinking was sample S11. The phosphor loading in this case is 0.18 mg/mL final concentration in DNA which crosslinks best at 40 kVp. Besides the positive results at 80 kVp and below, positive results at 105 kVp have been obtained.

Figure 2:
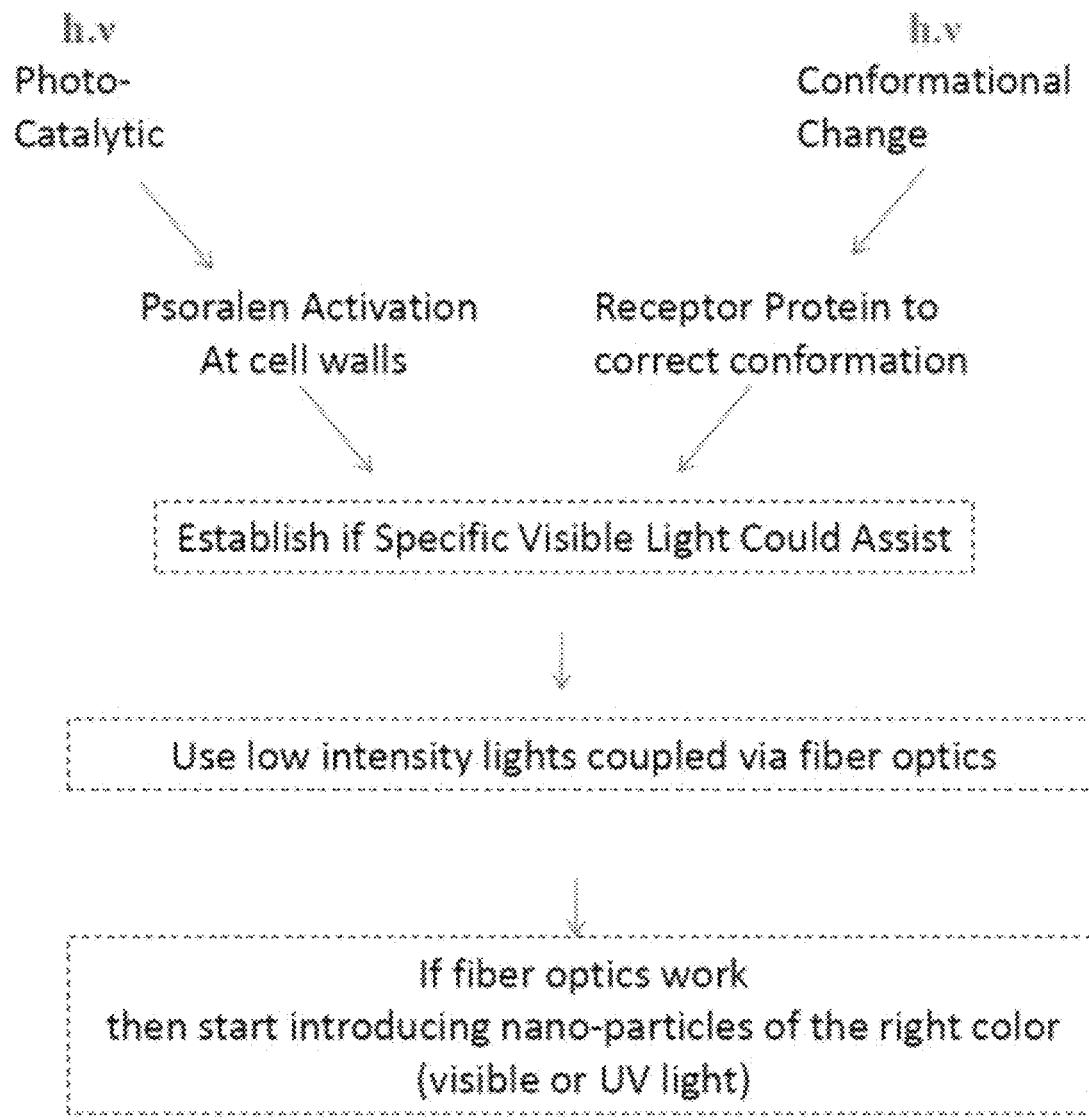
FIG. 2 is a schematic illustration of how photo-catalytic light works cooperatively with non-ionizing radiation to potentiate the activation of bio-therapeutics.
Figure 3:
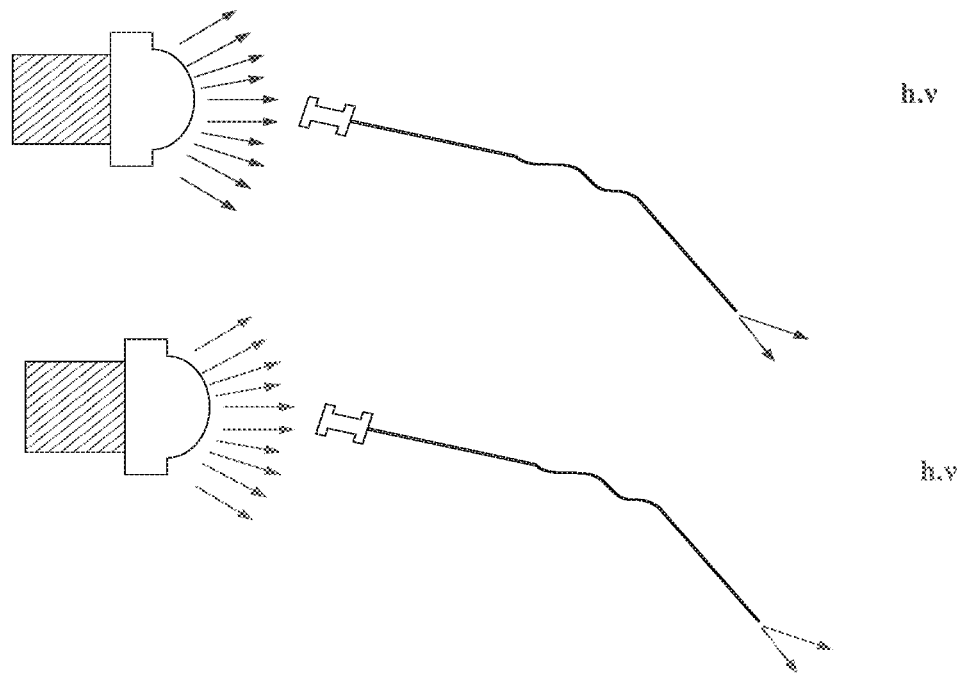
FIG. 3 is a schematic of a test set up devised to channel an external radiation source into the x-ray radiation system.
Figure 4:
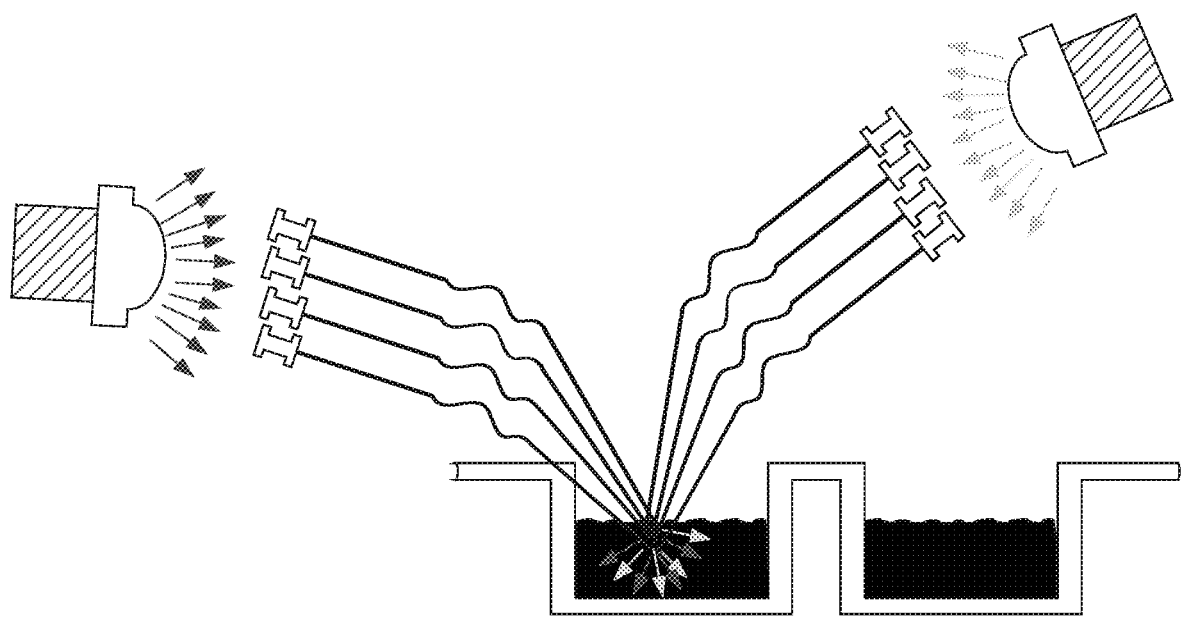
FIG. 4 is a schematic of a weakly coupled fiber bundle for combining different wavelengths of ionizing and non-ionizing radiation.

A non-limiting illustration of how photo-catalytic light can work cooperatively with non-ionizing radiation to potentiate the activation of bio-therapeutics is provided in FIG. 2. A test set up was devised to permit channeling of external radiation source into the x-ray radiation system as illustrated in FIG. 3. The weakly coupled fibers coupled red light and white light, UV light, and LASER light (from outside the irradiator) to the inside of the irradiator where the X-Ray energy was turned on. FIG. 4 provides an illustration of the weakly coupled fiber permitting different wavelengths of ionizing and non-ionizing radiation to be applied in conjunction with X-Ray. While the sample depicted in FIG. 4 is inside a petri dish, the concept relates to any sample regardless of the environment where the activation occurs.

Figure 5A:
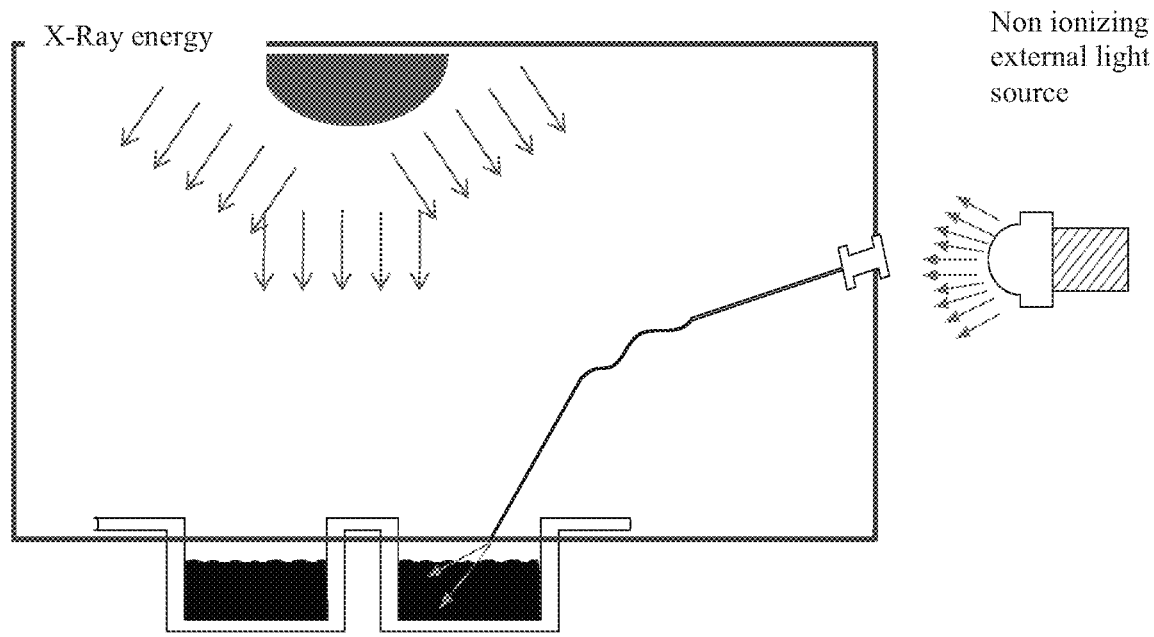
FIG. 5A is a schematic of the combination of X-Ray and a fiber optic for simultaneous use of X-Ray energy with external light sources having potentiating effects.
Figure 5B:
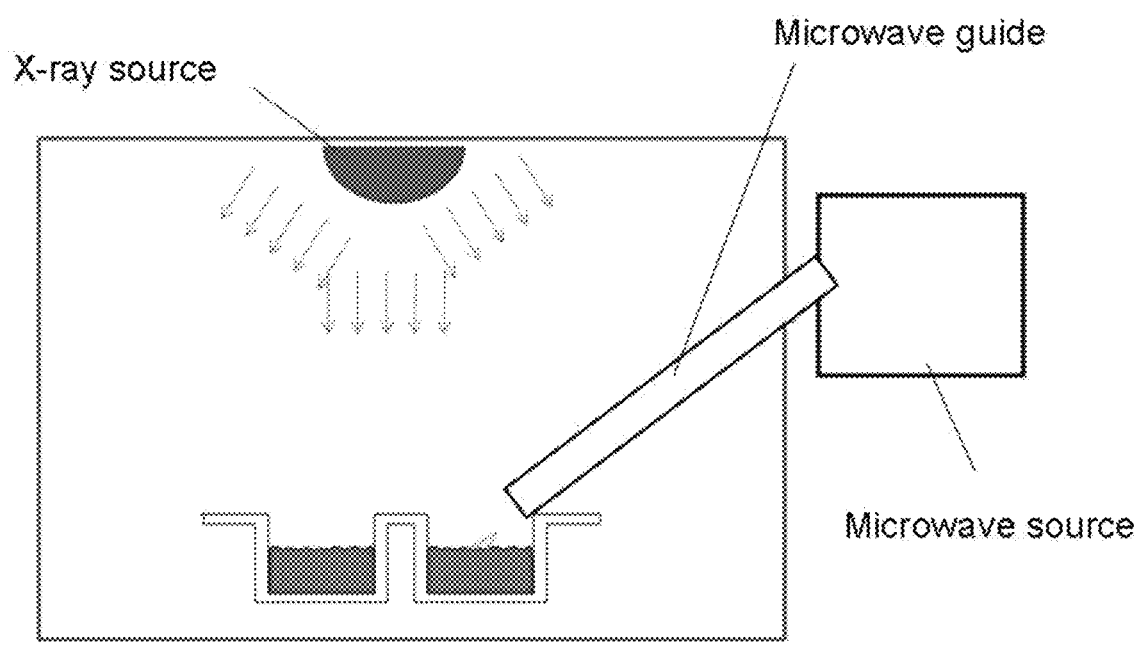
FIG. 5B is a schematic of the combination of X-Ray and a microwave guide allowing the simultaneous use of X-Ray energy and microwave energy to interact with a target or reactive site.

In one embodiment of this invention, various colors can be used to optimize an X-ray irradiation treatment. For example, the application of photo-catalytic energy can be done in conjunction with energy able to induce conformational changes in certain reactive site (i.e., a target site). FIG. 5A illustrates the combination of X-Ray and a fiber optic allowing the simultaneous use of X-Ray energy with external light sources having potentiating effects. FIG. 5A shows that various colors can be used to optimize the X-ray irradiation treatment. For example, the application of photo-catalytic energy can be done in conjunction with energy able to induce conformational changes in certain reactive site(s). FIG. 5B illustrates the combination of X-Ray and a microwave guide allowing the simultaneous use of X-Ray energy and microwave energy to interact with a target or reactive site.

Energy Modulators

The phosphors or scintillator particles of this invention can be synthesized from known material chemistries that possess the capability of fluorescence (caused by the instantaneous decay of electrons from a high energetic state to a lower one) or phosphorescence (delayed decay of electrons from a high energetic state). A comprehensive set of chemistries is provided.

The phosphors or scintillator particles of this invention can be further prepared using additive processes (i.e., coatings) to gain the self-assembly capability inside cells when exposed to electrical field or magnetic fields stimulation. Externally imposed electrical field or magnetic fields can be applied in a cyclic manner of specific frequencies and magnitudes that promote the assembly into patterned configurations.

Besides phosphors and scintillator particles, this invention can also use other light emitting particles such as fluorescent particles and up-converting particles. In those cases, the techniques described here for improving the efficiency of delivering light to a target or for spectrally matching the emitted light to a photoactivatable substance still apply. Various fluorescent particles and up-converting particles are described in the related applications listed above. Moreover, the light emitters of the invention can utilize plasmonic metallic shell structures to increase the efficiency of absorption and light emission, as described in the related applications listed above.

Some of the materials of interest include phosphors such as YTaO4, YVO$_4$, YNbO$_4$ and CaWO$_4$. Each of these lattice structures is an effective X-Ray absorber and a strong UV emitter. The absorption spectra exhibit strong and broad bands in the UV. The transition involved in these lattices is typically the result of a charge transfer from the oxygen to the d0 ion. An electron can be excited from a non-bonding orbital on the oxygen to an anti-bonding orbital (d on the metal ion). Another lattice structure of interest is Y$_2$O$_3$. All of these materials have been doped using ionic species to create color centers. Y$_2$O$_3$ can be doped with Gd and YTaO$_4$ can be doped with Nb. The specific influence of the host lattice on the luminescent center is different for different materials. The influence of the lattice on optical centers is relatively well known for some materials such as YF$_3$:E$^{3+}$ and Y$_2$O$_3$:Eu$^{3+}$.

One factor for the influence of the lattice on the optical properties of an ion is covalency. A high covalency translates to reduced interactions between electrons since they spread out over wider orbitals. Electronic transitions between energy levels are set by the difference in these energy levels which are in turn gated by electronic interactions. The difference in energy levels is lower for increasing covalency.

Another factor for the influence of the lattice on the optical properties of an ion is the crystal field. Certain optical transitions are determined by the strength of the crystal field. This explains why $Cr_2O_3$ is green but $Al_2O_3$:$Cr^{3+}$ is red even though both materials have the same crystalline structure.

ability of interaction between X-ray and phosphors. These interrelated terms include the coupling efficiency, and emission effectiveness between the X-ray and the phosphor. A list of some of the X-ray phosphors emitting in the VIS range is reported in Table 6 below.

TABLE 6

| # | Phosphor | Emission Spectrum Peak Emission (nm) | X-Ray Absorption | | | Microstructure | | Hygroscopic |
|---|---|---|---|---|---|---|---|---|
| | | | Emiss Eff (%) | Eff (Z) | K-edge (keV) | Specific Gravity | Crystal Structure | |
| 1 | BaFCl:Eu2+ | 380 | 13 | 49.3 | 37.38 | 4.7 | Tetragonal | N |
| 2 | BaSO4–:Eu2+ | 390 | 6 | 45.5 | 37.38 | 4.5 | Rhombic | N |
| 3 | LaOBr:Tm3+ | 360, 460 | 14 | 49.3 | 38.92 | 6.3 | Tetragonal | N |
| 4 | YTaO4 | 337 | | 59.8 | 67.42 | 7.5 | Monolithic | N |
| 5 | YTaO4:Nb (*) | 410 | 11 | 59.8 | 67.42 | 7.5 | Monolithic | N |
| 6 | CaWO4 | 420 | 5 | 61.8 | 69.48 | 6.1 | Tetragonal | N |
| 7 | LaOBr:Tb3+ | 420 | 20 | 49.3 | 38.92 | 6.3 | Tetragonal | N |
| 8 | Y2O2S:Tb3+ | 420 | 18 | 34.9 | 17.04 | 4.9 | Hexagonal | N |
| 9 | ZnS:Ag | 450 | 17 | 26.7 | 9.66 | 3.9 | Hexagonal | N |
| 10 | (Zn, Cd)S:Ag | 530 | 19 | 38.4 | 9.66/26.7 | 4.8 | Hexagonal | N |
| 11 | Gd2O2S:Tb3+ | 545 | 13 | 59.5 | 50.22 | 7.3 | Hexagonal | N |
| 12 | La2O2S:Tb3+ | 545 | 12.5 | 52.6 | 38.92 | 6.5 | Hexgonal | N |

The $Cr^{3+}$ ions occupy the smaller $Al^{3+}$ sites and as a result feel a stronger crystal filed in $Al_2O_3$ than in $Cr_2O_3$. The synthesis of the materials influences the emission of the color centers. The defects as well as the particle size and particle size distribution all play a role.

Controllable and repeatable processes that can be utilized to produce nano-particles, and use thereof, have emerged as an area of science and engineering of considerable interest in recent years. The use of electric or magnetic field-assisted transport offers an approach for manipulating millimeter, micrometer and nanometer particles in a repeatable and controllable manner. The use of such electric fields is generally referred to as dielectro-phoresis (DEP).

The application of a field gradient gives rise to translation and orientation of particles exhibiting dipolar characteristics. The net asymmetrical distribution of charge along the dimension of a particle dictates the magnitude of the resultant dipole which has units of unit charge per unit length or Coulomb/meter. The same is true for magnetic fields as well as electric fields. In magnetic fields, this effect is characterized by the susceptibility of the material forming the particle. The net magnetization per unit length will define the strength of the magnetic dipole.

Phosphor or scintillator particles, such as those made of oxide materials, do not have a net dielectric dipole or magnetic dipole. However, according to one embodiment of the invention, phosphor or scintillator particles can be made to act in a dipolar fashion.

Phosphor selection criterions for this invention are based on peak intensity of the emission, peak position with UV of the emission, the need to have a workable phosphor with minimal storage requirements, handling and packaging, the ability of the phosphor to couple to X-ray energy, the control over its particle size and particle size distribution; surface chemistry; and other factors.

In one embodiment of the invention, the peak emission target is between 310 nm and 800 nm, or alternatively the peak emission target is simply the UVA spectrum. It is desirable to have the maximum conversion of X-ray intensity into UVA intensity and visible light. This conversion can be characterized in various interrelated terms. Sometimes the conversion is referred to as the quantum yield or prob- As noted above, a variety of scintillator materials can also be used in the invention including organic scintillators, plastic scintillators, and inorganic crystals.

Organic scintillators are usually aromatic hydrocarbon compounds which contain benzene ring structures interlinked in various ways. Their luminescence typically decays within a few nanoseconds. Some organic scintillators are pure crystals. The most common types are anthracene ($C_{14}H_{10}$, decay time≈30 ns), stilbene ($C_{14}H_{12}$, few ns decay time), and naphthalene ($C_{10}H_8$, few ns decay time). These organic crystal scintillators are very durable, but their response is anisotropic.

Anthracene has the highest light output of all organic scintillators Plastic scintillators are solutions of organic scintillators in a solvent which is subsequently polymerized to form a solid. Some of the common solutes are p-Terphenyl, PBD, b-PBD, PBO, POPOP. The most widely used plastic solvents are polyvinyltoluene and polystyrene. Plastics scintillators give a fast signal (a few ns) and a high light output. The number of emitted scintillation photons is best described by the convolution of an exponential decay and a Gaussian (rather than the exponential decay alone).

Plastics by their nature can very easily be shaped and machined to the forms (cylinders, rods, flat sheets, fibers, microspheres and thin films) and are relatively inexpensive. Plastics scintillators, while generally resistant, can be scratched and attacked by organic solvents (e.g. acetone). Also, bodily acids can cause cracking over time. Nonetheless, in one embodiment of the invention, plastic sheet scintillators can be inserted around or near a tumor site to provide light emission upon exposure to an electron beam.

Inorganic scintillator crystals include materials such as tungstates and alkali metal halides, often with a small amount of activator impurity. One of the most widely used inorganic scintillator crystal is NaI(Tl) (sodium iodide doped with thallium). Other inorganic alkali halide crystals are: CsI(Tl), CsI(Na), CsI(pure), CsF, KI(Tl), LiI(Eu). Some non-alkali crystals include: $BaF_2$, $CaF_2$(Eu), ZnS(Ag), $CaWO_4$, $CdWO_4$, YAG(Ce) ($Y_3Al_5O_{12}$(Ce)), BGO bismuth germanate, GSO, LSO, $LaCl_3$(Ce), $LaBr_3$(Ce), $LaPO_4$; Ce, Tb (doped), and $Zn_2SiO_4$:Mn with Mn doped between 0.05-10%.

In one embodiment of this invention, the following phosphors with visible emissions can be used: $CaWO_4:Pb^{2+}$, $CaWO_4:W$, $Sr_3(PO_4)_2:Eu^{2+}$, $Ba_3(PO_4)_2:Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4:Mn^{2+}$, $Y_3(Al,Ga)_5O_{12}:Ce^{3+}$, $BaMg_2Al_{14}O_{24}:Mn^{2+}$, $BaMgAl_{14}O_{23}:Mn^{2+}$, $SrAl_{12}SiO_{19}:Mn^{2+}$, $ZnAl_{12}O_{19}:Mn^{2+}$, $CaAl_{12}O_{19}:Mn^{2+}$, $YBO_3:Tb^{3+}$, $Sr_4Si_3O_8Cl_4:Eu^{3+}$, $Y_2O_3:Eu^{3+}$, $Y_2SiO_5:Eu^{3+}$, $Y_3Al_5O_{12}:Eu^{3+}$, $CaSiO_3:Mn^{2+}$, $YVO_4:Eu^{3+}$, $Zn_2SiO_4:Mn^{2+}$, and combinations thereof.

A disadvantage of some inorganic crystals, e.g., NaI, is their hygroscopicity, a property which requires them typically to be housed in an air-tight enclosure to protect them from moisture. CsI(Tl) and $BaF_2$ are only slightly hygroscopic and do not usually need protection. CsF, NaI(Tl), $LaC_{13}(Ce)$, $LaBr_3(Ce)$ are hygroscopic, while BGO, $CaF_2$(Eu), LYSO, and YAG(Ce) are not. The hygroscopic inorganic crystals for application in this invention would typically be encapsulated with a silica or plastic.

Like the phosphors above, scintillators show typical emission peaks. $BaF_2$ or barium fluoride is reported to emit in the UV band (220 nm) and at longer wavelengths (310 nm) and has a 630 ns decay time. $BaF_2$ is not hygroscopic. CaF has a reported emission at 390 nm. $CaF_2(Eu)$ or calcium fluoride doped with europium is not hygroscopic, has a 940 ns decay time, and has been reported to have an emission centered at 435 nm. BGO or bismuth germanate has a higher stopping power, but a lower optical yield than NaI(Tl). BGO has emission centered at 480 nm. $CdWO_4$ or cadmium tungstate has a relatively high light output (about ⅓ of that of NaI(Tl)). $CdWO_4$ has been reported to have an emission centered at 475 nm. $CaWO_4$ or calcium tungstate has been reported to have emission at centered at 420 nm. CsI(Tl) or cesium iodide doped with thallium crystals have been reported as one of the brightest scintillators. The maximum wavelength of light emission is centered at 550 nm. CsI(Tl) is only slightly hygroscopic. CsI(Na) or cesium iodide doped with sodium is less bright than CsI(Tl), but comparable in light output to NaI(Tl). The wavelength of maximum emission is at 420 nm. CsI(Na) is hygroscopic. CsI undoped cesium iodide emits predominantly at 315 nm, and is only slightly hygroscopic. The light output is relatively low. $LaBr_3(Ce)$ (or lanthanum bromide doped with cerium is an alternative to NaI(Tl). $LaBr_3(Ce)$ has been reported to have emission at centered at 370 nm. It is hygroscopic. $LaCl_3(Ce)$ (or lanthanum chloride doped with cerium) is an alternative to $LaBr_3(Ce)$. It is hygroscopic. It has been reported to have emissions centered at 350 and 390 nm.

U.S. Pat. No. 7,084,403 (the entire contents of which are incorporated herein by reference) shows a variety of emission from lanthanum halides.

$PbWO_4$ or lead tungstate has a high stopping power. It has emission at 420 nm. $LuI_3$ or lutetium iodide has emission at 420 nm. LSO or lutetium oxyorthosilicate ($Lu_2SiO_5$) has emission around 420 nm. GSO or gadolinium oxyorthosilicate ($Gd_2SiO_5$) has emission around 430 nm. However, as reported by Mao et al, in "Emission Spectra of LSO and LYSO Crystals Excited by UV Light, X-Ray and (-ray," in IEEE TRANSACTIONS ON NUCLEAR SCIENCE, VOL. 55, NO. 3, JUNE 2008, the emission spectrum shifts depending on the source of excitation. Accordingly, in one embodiment of this invention, the choice of phosphor emission as a light activation source can be used to peak match to a particular photoactivatable substance such as to match the peak in the psoralen absorption.

LYSO ($Lu_{1.8}Y_{0.2}SiO_5(Ce)$) has a broad emission around 425 nm. LYSO is non-hygroscopic. NaI(Tl) or sodium iodide doped with thallium. NaI(Tl) is the most widely used scintillator material. It has an emission around 410 nm. NaI(Tl) is hygroscopic. YAG(Ce) or yttrium aluminum garnet: YAG(Ce) is non-hygroscopic. The wavelength of maximum emission is around 550 nm. Its light output is about ⅓ of that of NaI(Tl). ZnS(Ag) or zinc sulfide has emission at 450 nm. $ZnWO_4$ or zinc tungstate has a peak emission at 480 nm (with emission range between 380-660 nm).

In one embodiment of the invention, mixtures of these scintillators (or phosphors or down conversion media or upconversion media noted herein, separately or in combination) can provide a spectral output for photoactivation of photoactivatable agent(s) such as psoralen. In one embodiment of the invention, the amounts of each particular scintillator (or phosphors or down conversion media or upconversion media noted herein, separately or in combination) mixed into the composition is a weighted sum where the product of the emission intensity of each scintillator and the weight composition percentage provides at each emission wavelength a predetermined component of a spectral emission band. In one embodiment of the invention, light from the composition of scintillators (or phosphors or down conversion media or upconversion media noted herein, separately or in combination) simulates at least a part of an absorption spectrum of the photoactivatable agents. For example, a wavelength distribution of the light from the composition of scintillators (or phosphors or down conversion media or upconversion media noted herein, separately or in combination) can have a peak position in common with one of the peaks in the absorption spectra of the psoralens in different media. Further, the wavelength distribution of the light from the composition of scintillators (or phosphors or down conversion media or upconversion media noted herein, separately or in combination) can simulate an absorption edge of the absorption spectrum of the photoactivatable agents, such as for example the absorption edge to the higher wavelength side of the peaks. Further, the wavelength distribution of the light from the composition of scintillators (or phosphors or down conversion media or upconversion media noted herein, separately or in combination) can overlap the absorption spectrum of the photoactivatable agents in part or in whole as if a replicating the absorption spectra.

UVA/UVB Emissions:

In some applications, the desirable incident or initiation energy is different than X-ray (such as EUV) while the desirable down-converted output intensity remains in the UVA and the visible. In other applications, the desirable incident or initiation energy is X-ray but the desirable down-converted energy output of the phosphor is in the UVB. Yet, in other cases, the desirable incident or initiation energy is X-ray but the desirable down-converted energy output of the phosphor is in the UVA and the UVB or the UV and the visible.

According to one embodiment of the invention, phosphors were selected to work with excitation sources including X-ray, Extreme UV and e-beam. Within the X-ray regime, the selected phosphors can couple to a flux of X-ray photons emanating from commercially available equipment sources used for therapeutic tumor treatments, medical imaging and semiconductor inspection.

One example of a material that emits in the UVA regime is $YTaO_4$ reported to have a peak emission at 337 nm under X-ray excitation. However, emission at 327 nm was observed.

One example of a material having an output in the UVB is LaOBr:$Tm_3^+$ reported to have a peak emission at 280 nm under X-ray excitation. However, emission at 300 nm was observed.

One example of a material having an output in the UVA, UVB and the visible is $CaWO_4$.

Impact of X-Ray on UV Output Intensity:

The initiation energy (X-ray in this example) influences the UV output of the phosphor. Both the intensity of X-Ray and the energy of the X-Ray photon excitation influence the UV light output. The following examples are provided to illustrate how modifying the photonic energy and intensity of X-Ray can modulate the light output of the UV and Visible light. These examples were made using three different voltages between the filament and the tungsten target of the X-ray generator. In each case, the emission peak and intensity of the phosphor emission was dependent on the voltage between the filament and the target (i.e., dependent on the intensity of X-ray and the energy of the X-ray photon excitation).

In these examples, various phosphors were weighed to 12 grams and placed in UV transparent containers. These phosphors were activated under X-ray generated using different voltages (50 kVp, 90 kVp and 130 kVp). A photo-spectrometer was placed in the same position vis-à-vis the various containers.

Figure 6A:
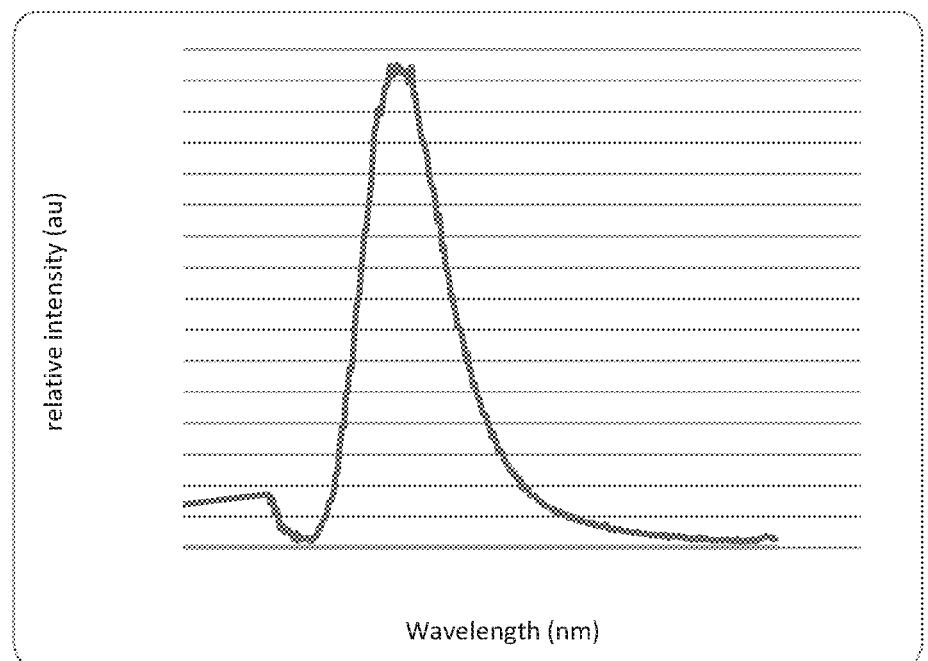
FIG. 6A is a schematic of the spectral emission of $YTaO_4$ (reported to have a peak emission at 337 nm under X-Ray excitation) showing emission at 327 nm.
Figure 6B:
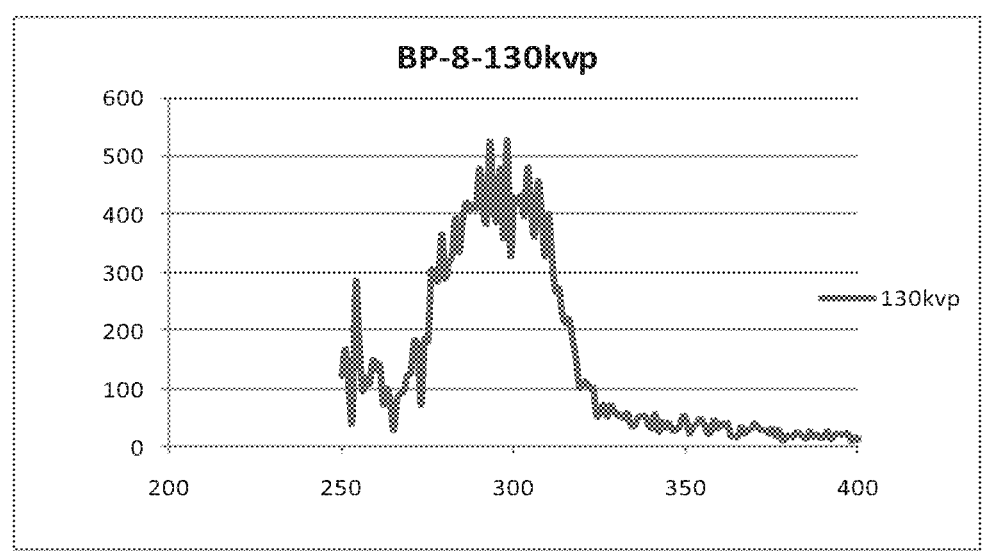
FIG. 6B is a schematic of the spectral emission of $LaF_3$:Ce (reported to have a peak emission at 337 nm under X-Ray excitation) showing emission at 300 nm.
Figure 6C:
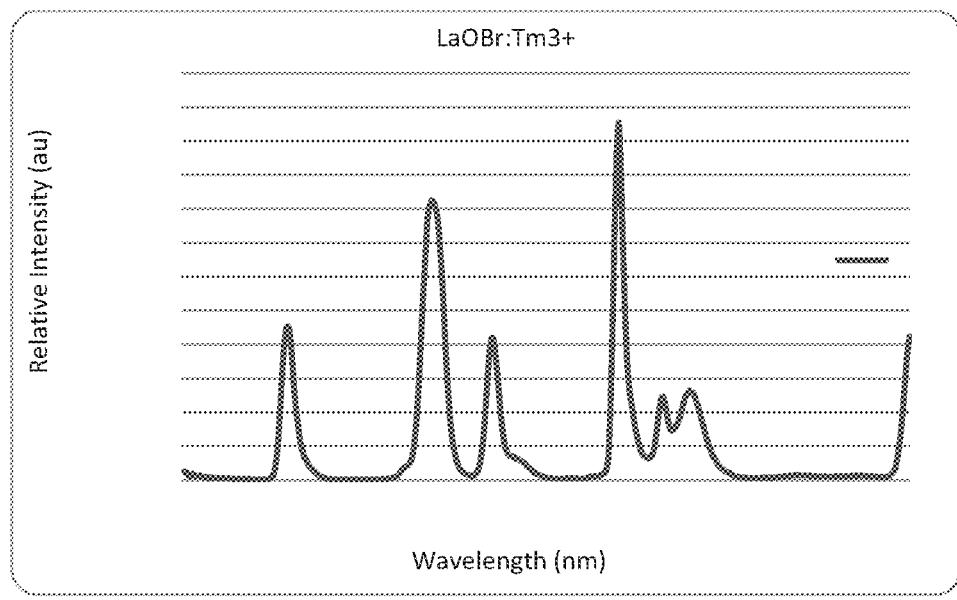
FIG. 6C is a schematic of the spectral emission of LaOBr:$Tm_3^+$ coated with silica suitable for phosphor chemistry capable of emission in the UVB, UVA and the visible light regions.
Figure 6D:
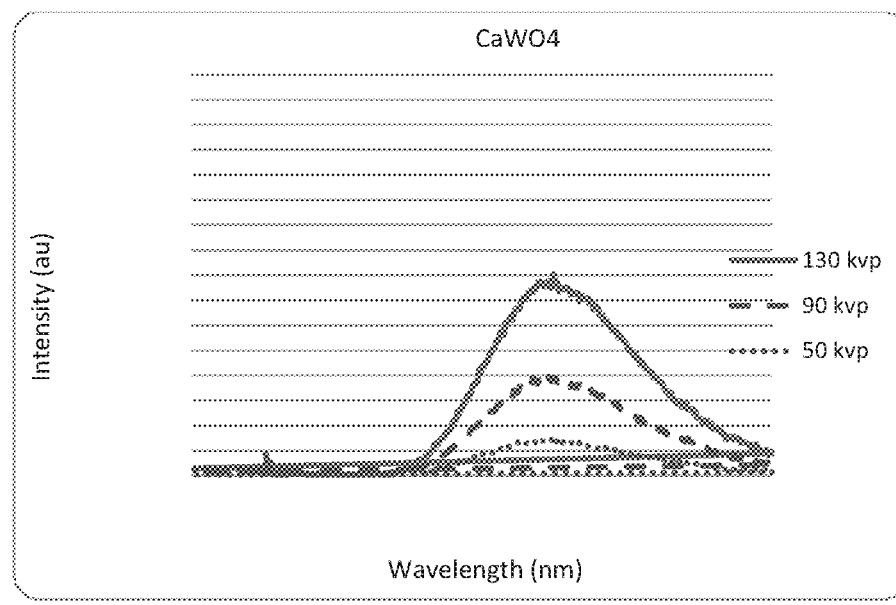
FIG. 6D is a schematic of the spectral output of a visible $CaWO_4$ phosphor under X-Ray excitation from different energy level and different flux x-rays.
Figure 6E:
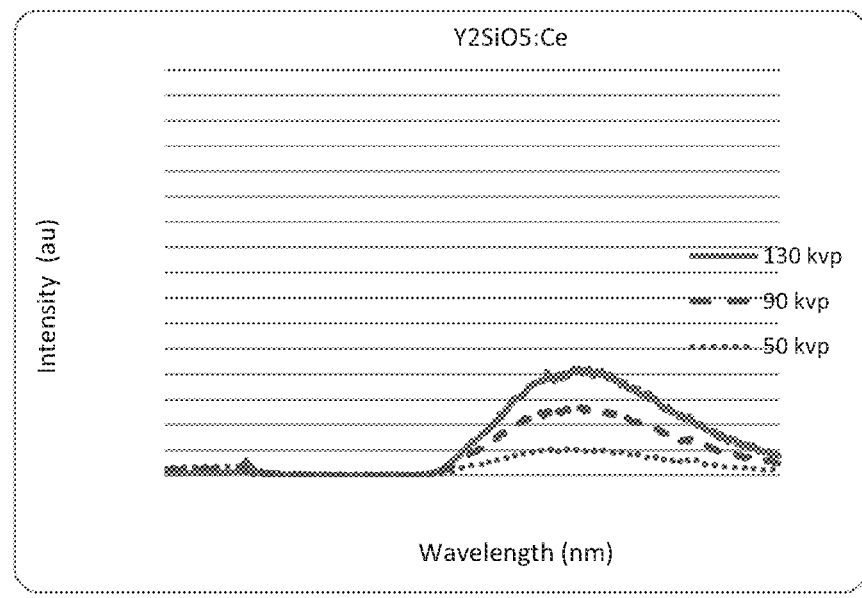
FIG. 6E is a schematic of the spectral output of a visible $Y_2SiO_5$:Ce phosphor under X-Ray excitation from different energy level and different flux x-rays.
Figure 6F:
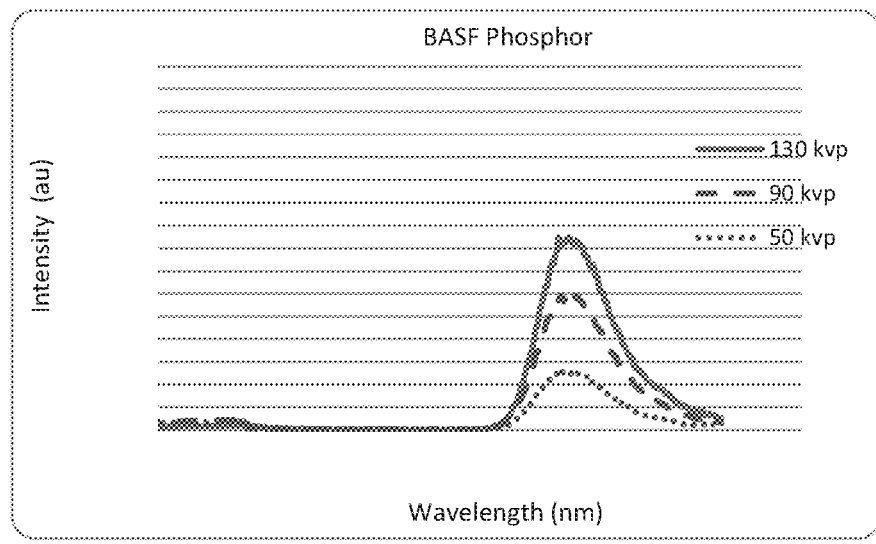
FIG. 6F is a schematic of the spectral output of a visible phosphor (BASF commercial phosphor XYMARA MARKER BLUE LF2A) under X-Ray excitation from different energy level and different flux x-rays.
Figure 6G:
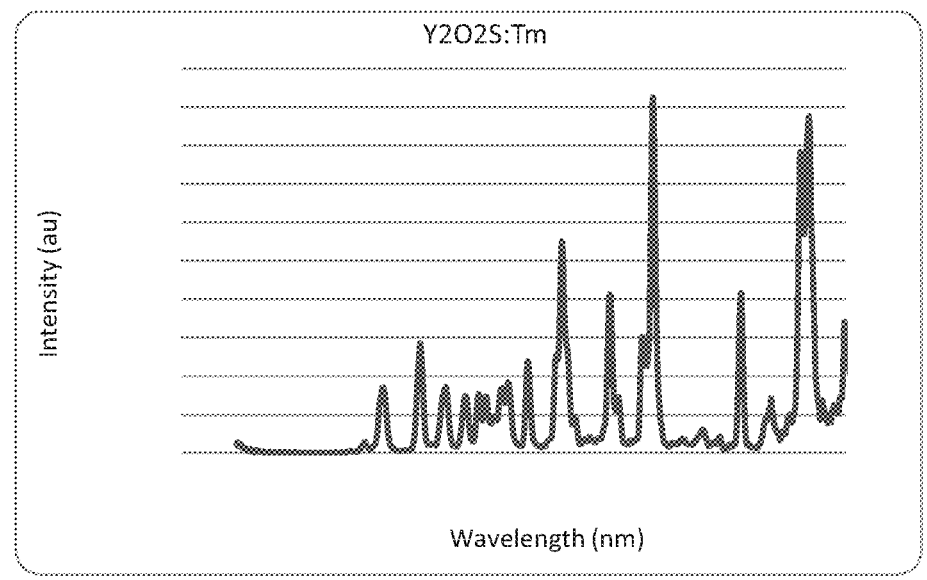
FIG. 6G is a schematic of the spectral output of an $Y_2O_2S$:Tm phosphor capable of emission in the UVA and in the visible light regions.
Figure 6H:
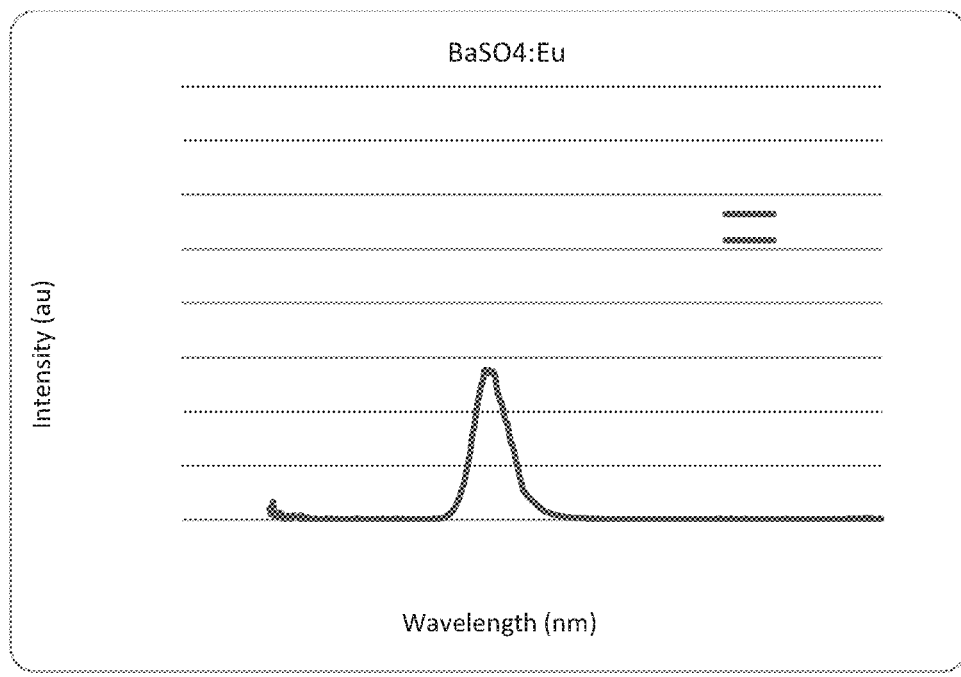
FIG. 6H is a schematic of the spectral output of a BaSO4:Eu phosphor capable of emission in the UVA and in the visible light regions.
Figure 6I:
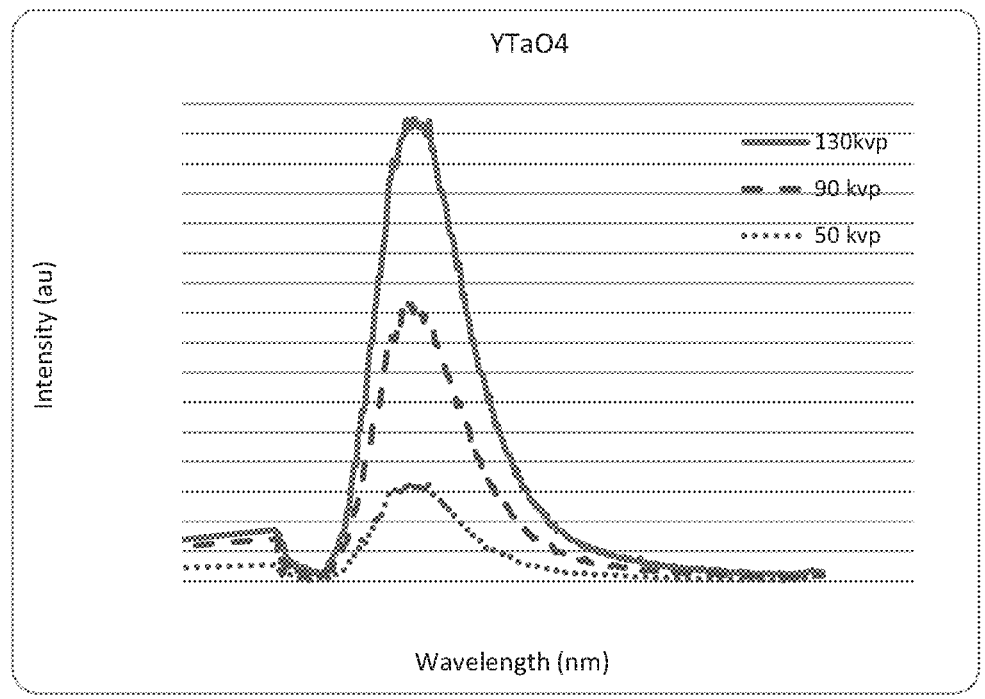
FIG. 6I is a schematic of the spectral output of a $YTaO_4$ phosphor capable of emission in the UVA and in the visible light regions.
Figure 6J:
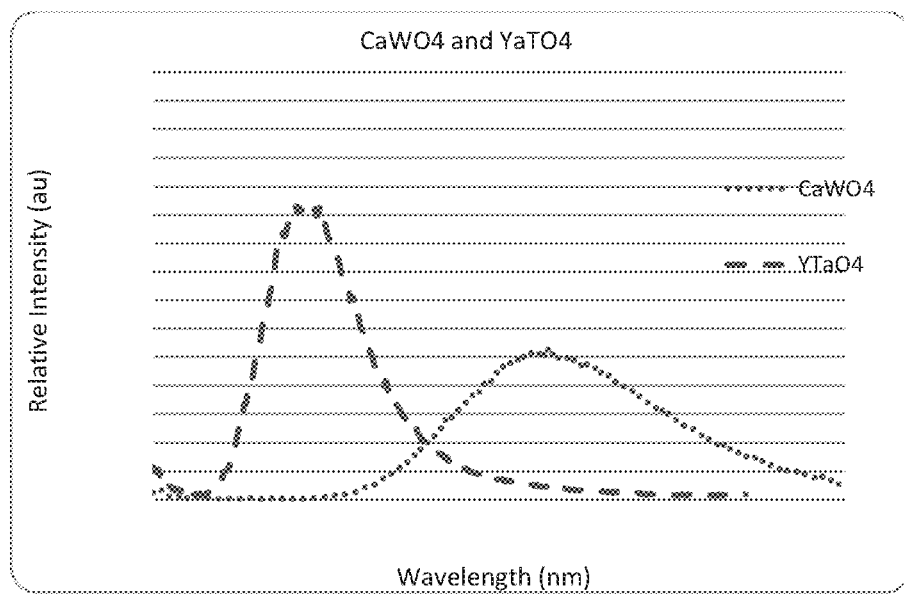
FIG. 6J is a schematic of the spectral output of a $YTaO_4$ phosphor chemistry capable of emission in the UVA and $CaWO_4$ capable of emitting in the UVA and in the visible.

FIG. 6A is the spectral output from a visible phosphor $Y_2SiO_5$:Ce under X-ray excitation using three different voltages between the filament and the target. FIG. 6B is a schematic of the spectral emission of LaF3:Ce (reported to have a peak emission at 337 nm under X-Ray excitation) showing emission at 300 nm. FIG. 6C is a schematic of the spectral emission of LaOBr:Tm3+ coated with silica suitable for phosphor chemistry capable of emission in the UVB, UVA and the visible light regions. FIG. 6D is a schematic of the spectral output of a visible CaWO4 phosphor under X-Ray excitation from different energy level and different flux x-rays. FIG. 6E is a schematic of the spectral output of a visible $Y_2SiO_5$:Ce phosphor under X-Ray excitation from different energy level and different flux x-rays. FIG. 6F is the spectral output of a visible phosphor (BASF commercial phosphor XYMARA MARKER BLUE LF2A) under X-Ray using three different voltages between the filament and the target of the X-ray generator. FIG. 6G is the spectral output of a visible phosphor $Y_2O_2S$:Tm. FIG. 6H is the spectral output of a $BaSO_4$:Eu phosphor capable of emission in the UVA and in the visible. FIG. 6I is the spectral output of a $YTaO_4$ phosphor capable of emission in the UVA and in the visible. FIG. 6J is a schematic of the spectral output of a $YTaO_4$ phosphor chemistry capable of emission in the UVA and $CaWO_4$ capable of emitting in the UVA and in the visible.

A Mixed or Alloyed Configuration of the Invention

According to another embodiment of the invention, at least two phosphors (or scintillators or down conversion media or upconversion media noted herein, separately or in combination) are mixed to broaden the output of the mixture as compared to the individual starting phosphors. According to this embodiment, multi-peak output phosphors can be obtained from one phosphor chemistry or by combining multiple phosphor chemistries. All or any of the phosphor chemistries listed in Table 7 can be combined with one another to form multiple wavelengths of interest. These phosphors in Table 7 (for mixing) are listed in an ascending order of wavelength emissions.

In one embodiment of the invention, the amounts of each particular phosphor (or scintillators or down conversion media) mixed into the composition is a weighted sum where the product of the emission intensity of each phosphor and the weight composition percentage provides at each emission wavelength a predetermined component of a spectral emission band. In one embodiment of the invention, light from the composition of phosphors (or scintillators or down conversion media or upconversion media noted herein, separately or in combination) simulates at least a part of an absorption spectrum of the photoactivatable agents. For example, a wavelength distribution of the light from the composition of phosphors can have a peak position in common with one of the peaks in the absorption spectra of the psoralens in different media Further, the wavelength distribution of the light from the composition of phosphors can simulate an absorption edge of the absorption spectrum of the photoactivatable agents. Further, the wavelength distribution of the light from the composition of phosphors can overlap the absorption spectrum of the photoactivatable agents in part or in whole as if a replicating the absorption spectra.

TABLE 7

| Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2:Tl+ | 310 | | | | | | N |
| BaF2 | 310 | | | | | | Slightly |
| CsI | 315 | | | | | | N |
| Ca3(PO4)2:Tl+ | 330 | | | | | | N |
| YTaO4 | 337 | | | | | | N |
| CsI:Na | 338 | | | | | | Y |
| BaSi2O5:Pb2+ | 350 | | | | | | N |
| Borosilicate | 350 | | 59.8 | 67.42 | 7.5 | Monolithic | N |
| LaCl3(Ce) | 350 | | | | | | Y |
| SrB4O7F:Eu2+ | 360 | | | | | | N |
| RbBr:Tl+ | 360 | | | | | | ? |
| (Ba, Sr, Mg)3Si2O7:Pb2+ | 370 | | | | | | N |
| YAlO3:Ce3+ | 370 | | | | | | N |
| BC-422 | 370 | | | | | Organic | ? |
| BaFCl:Eu2+ | 380 | 13 | 49.3 | 37.38 | 4.7 | Tetragonal | N |
| BaSO4-:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |

TABLE 7-continued

| Phosphor | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| SrMgP2O7:Eu2+ | 394 | | | | | | N |
| BaBr2:Eu2+ | 400 | | | | | | N |
| (Sr, Ba)Al2Si2O8:Eu2+ | 400 | | | | | | N |
| YTaO4:Nb (*) | 410 | 11 | 59.8 | 67.42 | 7.5 | Monolithic | N |
| Y2SiO5:Ce3+ | 410 | | | | | | N |
| CaWO4 | 420 | 5 | 61.8 | 69.48 | 6.1 | Tetragonal | N |
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexagonal | N |
| Li2SiO5:Ce3+ | 420 | | | | | | N |
| Lu1.8 Y0.2SiO5:Ce | 420 | | | | | | N |
| ZnS:Ag | 450 | 17 | 26.7 | 9.66 | 3.9 | Hexagonal | N |
| CdWO4 | 475 | | | | | | Slightly |
| Bi4Ge3O12 (BGO) | 480 | | | | | | N |
| (Zn, Cd)S:Ag | 530 | 19 | 38.4 | 9.66/26.7 | 4.8 | Hexagonal | N |
| Gd2O2S:Tb3+ | 545 | 13 | 59.5 | 50.22 | 7.3 | Hexagonal | N |
| La2O2S:Tb3+ | 545 | 12.5 | 52.6 | 38.92 | 6.5 | Hexagonal | N |
| Y3Al5O12 (Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

In one embodiment, the weighted product produces a spectral emission band which simulates a commercial UV light source, which has a broader spectral width than the absorption line of psoralen.

Accordingly, in one embodiment of the invention, the mixed phosphors and scintillators of the invention provide a spectral response of higher UV dose and a closer spectral match to that of commercial UVA sources than for example single fluorescent emitters or single phosphor emitters or single scintillator emitters.

Figure 6K:
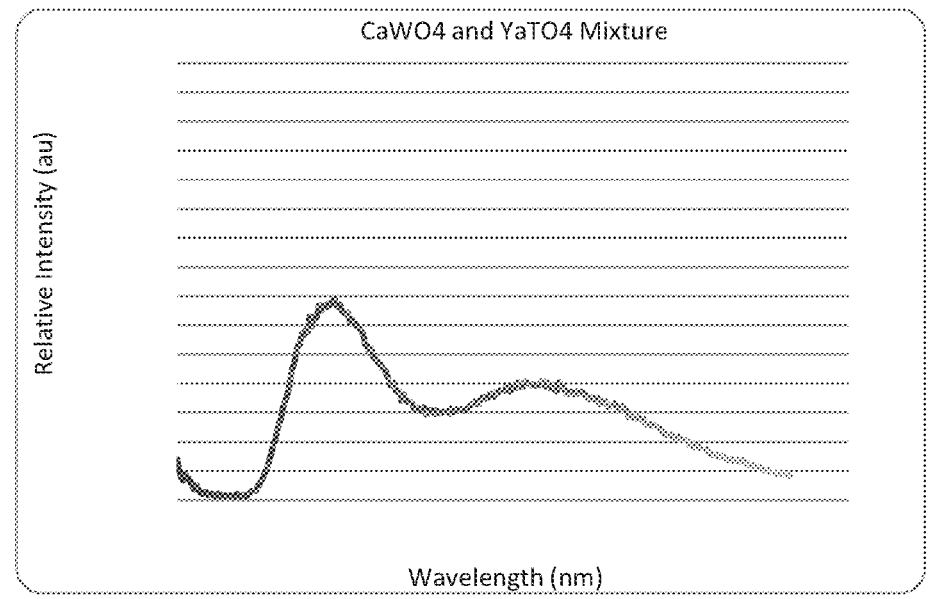
FIG. 6K is a schematic of the emission spectra under X-Ray excitation of CaWO and of $YTaO_4$.
Figure 6L:
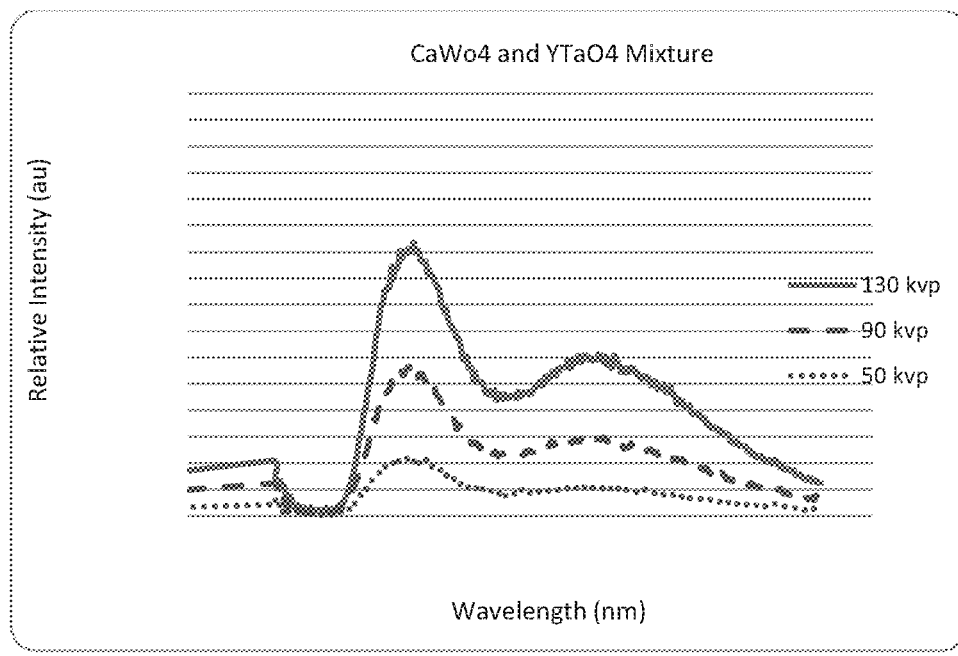
FIG. 6L is a schematic of the emission spectra for the $CaWO_4$ and $YTaO_4$ mixture.

FIG. 6K is the superimposed emission spectra under X-ray excitation for $CaWO_4$ phosphors and $YTaO_4$ phosphors. In the example illustrated in FIG. 6K, the two phosphors each emit in a distinct region. FIGS. 6L and 6M are emission spectra under X-ray excitation (for various voltages between the filament and the target) for the combination of a mixture of $CaWO_4$ and $YTaO_4$ phosphors. The spectral output demonstrates the ability to influence the output intensity of the mixture as compared to the staring materials. The intensity of the initiation energy (X-ray in this case) influences the UV output of the phosphor.

The following examples are provided to illustrate how modifying the intensity of photonic energy of X-ray can modulate the light output of the UV and Visible light. The relative intensity output of a phosphor ($CaOW_4$) was measured as a function of the energy of the X-ray photons. The X-ray energy was intensified by modifying the peak voltages that exist between the filament and the target. The target in this case was Tungsten. The measurements were carried out using the same mass of phosphor under 50 kVp, 90 kVp and 130 kVp. The relative intensity of the emission in arbitrary units is indicative but not conclusive in terms of comparing different materials. However, within the same conditions used to conduct measurements, it is clear that the higher X-ray intensity the higher the relative intensity of the emitted wavelength. In one embodiment, the spectrum of the x-ray is matched with the spectral sensitivity of the phosphor to maximize their interaction. In other words, the higher the match between these two, and the higher the x-ray flux, the higher the energy output that results from the energy modulation agent.

According to one embodiment of the invention, phosphors are synthesized from different chemicals and using different processes to control their morphology, in turn influence their properties and light intensity output, but more importantly their stability in ambient air environments. It is preferred in certain applications to have phosphors that are not hygroscopic. Phosphors are easier to handle and to work with when the phosphors are stable in water and do not contain dopants that are toxic; however, even when phosphors are not stable in water and do contain dopants that are toxic, particles of these phosphors in one embodiment of the invention can be coated using chemistrical synthesis methods to build-up a protective coating which shields the phosphor from the environment (water for example) and which shields the environment from the toxic dopant in the phosphor (Bromide for example).

The protective coating can be silica or can be diamond or diamond-like carbon. Silica can be formed using sol-gel derived techniques. Diamond and diamond-like carbon can be derived from chemical vapor deposition (CVD) techniques based for example on Hydrogen-Methane gas mixtures. The handling and packaging of various phosphors (and phosphor or scintillator or down conversion media mixtures) can be achieved through dispersion in solution or in powder form. It was found that silica coated phosphors do not have a tendency to agglomerate.

Figure 7A:
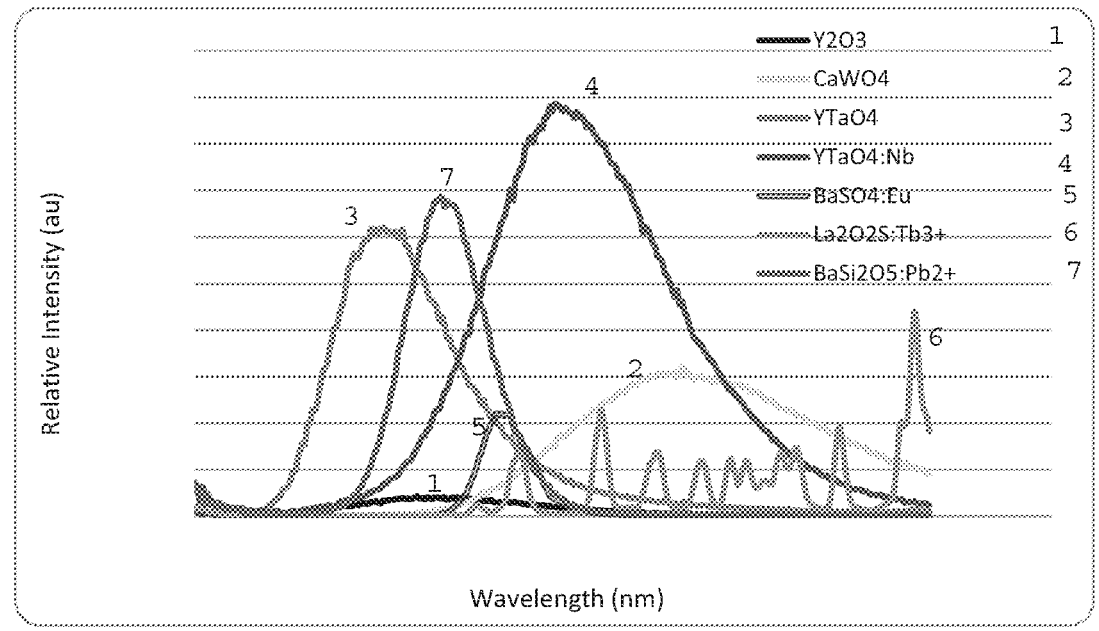
FIG. 7A is a schematic of the emission spectra under X-Ray for various materials including. $Y_2O_3$, $CaWO_4$, $YaTO_4$, $YaTO_4$:Nb, $BaSO_4$:Eu, $La_2O_2S$:Tb, $BaSi_2O_5$:Pb for various voltages between the filament and the target.

FIG. 7A is the emission spectra under X-ray excitation for various materials including $Y_2O_3$, $CaWO_4$, $YaTO_4$, $YaTO_4$:Nb, $BaSO_4$:Eu, $La_2O_2S$:Tb, $BaSi_2O_5$:Pb. These materials yield various peak intensities and wavelengths. As seen from this figure, the phosphor and scintillator materials ($CaWO_4$, $YaTO_4$, $YaTO_4$:Nb, $BaSO_4$:Eu, $La_2O_2S$:Tb, $BaSi_2O_5$:Pb) are considerably brighter than that of $Y_2O_3$ a conventional fluorescent material.

Hence, in one embodiment, there is provided a system and method for energy generation within a medium. The system includes an initiation source configured to provide an initiation energy and a plurality of energy-converting particles in the medium which, upon radiation from the initiation source, radiate at a lower energy than the initiation source to interact with photoactivatable agents in the medium. The energy-converting particles can radiate with an intensity at least two times greater than that of intrinsic (or undoped) $Y_2O_3$, upon exposure of $Y_2O_3$ to the radiation from the initiation source. The method includes introducing a plurality of energy-converting particles into the medium, radiating the plurality of energy-converting particles in the medium with radiation from an initiation energy source, and emitting from the plurality of energy-converting particles a lower energy than the radiation from the initiation energy source to interact with photoactivatable agents in the medium. In various aspects of the invention, the energy-converting particles radiate with an intensity at least 10 times greater than that of intrinsic $Y_2O_3$, at least 50 times greater than that of intrinsic $Y_2O_3$, or at least 100 times greater than that of intrinsic $Y_2O_3$, or at least 500 times greater than that of intrinsic $Y_2O_3$, or at least 1000 times greater than that of intrinsic $Y_2O_3$.

In this and other embodiments, the plurality of energy-converting particles can include at least one of phosphors, scintillators, fluorescent materials, down conversion media, and combinations and agglomerations thereof with or without plasmonic inducing agents. In this and other embodiments, the initiation energy source can be one of an X-ray source, a high energy source, a particle source, and extended UV source, and a radioactive source including at least one of a Cobalt 60 source, a Cesium-137 source, an Iridium-192 source, a Krypton-85 source, a Radium-226 source, and a Strontium-90 source or a combination thereof.

Figure 7B:
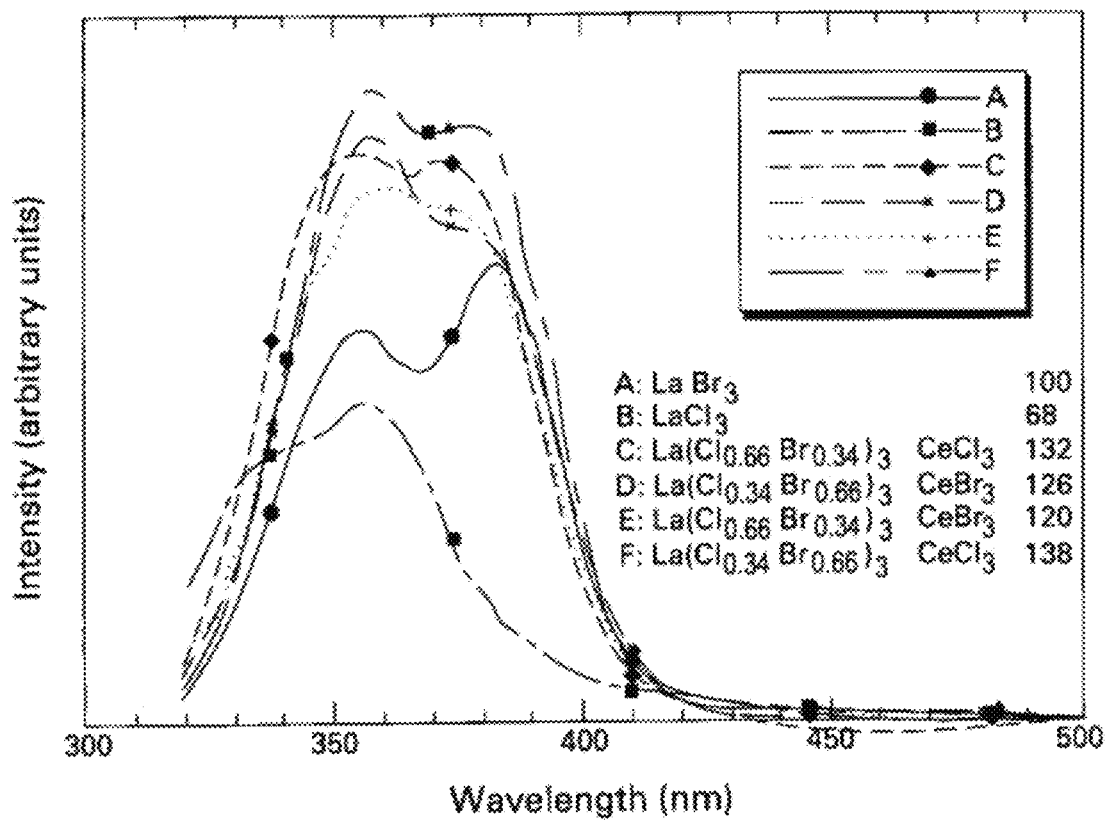
FIG. 7B is a schematic of emission spectra under X-ray excitation for scintillators.

According to one embodiment of the invention, a combination of these materials can yield a spectrum with a specific signature. Phosphor emissions from these materials, as illustrated in FIGS. 7A, 7B, and 8, cover a broad range of the VIS and UV spectrum. Hence, in one embodiment, there is provided a system for light stimulation within a medium. The system includes an initiation source configured to radiate an initiation energy, a first plurality of energy-converting particles in the medium which (upon radiation from the initiation source) radiate at a first lower energy than the initiation source to interact with photoactivatable agents in the medium, and a second plurality of energy-converting particles in the medium which (upon radiation from the initiation source) radiate at a second lower energy than the initiation source to interact with photoactivatable agents in the medium. A combination of emission from the first and second plurality of energy-converting particles produces a spectrum for illumination of the photoactivatable agents in the medium. The spectrum has a wavelength distribution simulating at least a part of an absorption spectrum of the photoactivatable agents or a spectrum of an ultraviolet discharge lamp.

In one aspect of the invention, the wavelength distribution can have a peak position in common with a peak in the absorption spectrum of the photoactivatable agents or can simulates an absorption edge of the absorption spectrum of the photoactivatable agents. In another aspect, the first and second plurality of energy-converting particles can be a weighted composition of a plurality of different light-emitting particles, where light emitted from the weighted composition simulates part of the absorption spectrum of the photoactivatable agents.

In another aspect, the combination of the emission from the first and second plurality of energy-converting particles can be configured about a target site to form a light source illuminating the target site to treat the target site with the photoactivatable agents. In another aspect, an energy distribution emitted from the first and second plurality of energy-converting particles resembles the absorption spectrum of the photoactivatable agents or the spectrum of the ultraviolet discharge lamp. The energy distribution can overlap with the absorption spectrum of the photoactivatable agents or the spectrum of the ultraviolet discharge lamp.

Toxicity Testing:

Clonogenic Survival Assay (Low Density Protocol): In low density clonogenics, multiple cell densities are plated first and then treated. This clonogenic technique minimizes plating effects and pilot errors. In contrast, high density clonogenics have one stock plate of cells that is treated and then trypsinized and plated at different densities. This assay is more labor intensive and more prone to errors (e.g., pilot and plating) as well as contamination. However, this technique may more accurately depict the clinical situation as it allows cells to have more cell-to-cell contact.

The procedures followed for the clonogenic survival assays below are as follows:
1. Label plates (cells, treatments, date, initials).
    a. Plate cells in triplicate at 3 different densities (such as 100, 300, and 1,000 cells/plate).
        i. The # of cells plated depends on:
            1. The cell line (for example HeLa, HT29, B16/F10 and most MEF cell lines, recommend using 100, 300 and 1,000 cells per plate).
            2. Treatments—the higher drug concentrations, higher IR doses or longer hypoxia treatments are usually more toxic compared to less stringent conditions, so use more cells for the more toxic treatments.
2. Calculate the drug concentrations and the amount of media needed for each treatment.
    a. Media:
        i. In 6-well plates, use 3 mL media per well—so total amount of media needed is (3 mL/well)*(total # of plates)*(# of wells/plate)
        ii. In 6-well plates, use 3 mL media per plate—so total amount of media needed is (3 mL/well)*(total # of plates)*(# of wells/plate)
        iii. Also, account for media changes/washes—if using drug treatments, double the amount of media needed in order to add fresh media after the drugs are rinsed, off the cells.
    b. Drugs:
        i. Make fresh drug dilutions for every experiment
        ii. Make drug dilutions beforehand—if adding drugs directly to the media, add greater 3 μL volume per well. Any volume less than 3 μL adds potential error to the experiment.
3. Plating:
    a. Trypsinize cells.
    b. Determine total # of cells for each cell density in a 6-well format:
        i. (# of plates)*(3 well/plate)*(100 cells/well)=Total # of cells needed to give 3 wells 100 cells/well in each plate.
        ii. (# of plates)*(3 well/plate)*(300 cells/well)=Total # of cells needed to give 3 wells 300 cells/well in all plates
        iii. Calculate media needed to plate each density:
            1. (# of plates)*(3 well/plate)*(3 mL/well)=Total # mL of media needed to plate each density.
    c. Pellet cells—centrifuge @ 1,000 rpm/2-3 min/4° C.
    d. Resuspend in media and count.
    e. Make serial dilutions to obtain the number of cells needed to add to total volume of media (step 3iii).
        i. If 1,200,000 cells/ml are counted, plate #100 and #300 cells/well—dilute the total number of cells down to a more manageable volume.

ii. Dilute (1:10) the main stock 1,200,000 cells/ml- to give 120,000 cells/ml—dilute (1:10) again to give 12,000 cells/ml—dilute (1:10) again gives 1,200 cells/ml.
f. Plate 3 ml of media and cells in each well of all plates
g. Put in the incubator and allow cells ~18-24 hr to attach.
4. Treat cells:
   a. Treat cells according to the experimental design
      i. Optional (depends on experiment): Remove media on all plates, rinse with 2 mL 1×PBS and then add fresh 3 mL of media.
   b. Incubate plates under normal conditions (37° C. and 5% $CO_2$) for 7-14 days, or until visually detecting colonies of greater than 50 cells in the cell alone control plates.
   c. Stain plates.
5. Staining (not necessarily performed under sterile conditions):
   a. Decant media off plates.
   b. Rinse plates with ~2 mL 1×PBS.
   c. Add Fixation Solution and leave on for 10 min/RT
      i. Typically, 2-3 mL is enough (i.e. enough to cover the bottom of the plate)
   d. Decant Fixation Solution
   e. Add Crystal Violet Stain (enough to cover bottom of plate) and leave on for 10 min/RT.
   f. Rinse plates with water.
      i. Fill sink with water and drop plates in as upon removing the crystal violet.
      ii. Rinse off plates with water.
   g. Allow plates to dry on bench paper
   h. Count colonies using the Colony Counter.
      i. Count colonies that have >50 cells in them—look at colonies under the microscope if you are unsure.

| Fixation Solution: | Crystal Violet |
|---|---|
| 10% Methanol | 500 mL of working stock: |
| 10% Acetic Acid | 0.4% Crystal Violet (200 mL of the |
| 80% $H_2O$ | 1% stock) |
| | 20% Ethanol (100 mL) |
| | 200 mL $H_2O$ |
| | 1% Stock - made up in $H_2O$ and store at RT. |

6. Data analysis:
   a. Record the number of colonies for each cell density and treatment group.
   b. Correct for cell density (i.e. normalize all plates to 100 cells)
      i. Compare between groups to see if the groups are all corrected to reflect the same number of cells plated.
         1. To compare treatment #1 on 300 cells to control/vehicle on 100 cells—divide the number of colonies from the 300 cell group by 3 since there are 3 times as many cells.
   c. Calculate the plating efficiency (survival of control-plated cells)
      i. Average the # colonies in the control plates
   d. Correct for plating efficiency (this removes effects just from plating your cells)
      i. Divide the surviving fractions normalized for cell density (Step 6B) by the plating efficiency calculated in Step 6C.
   e. Calculate survival fraction, which is the average of the corrected numbers in Step 6D, standard deviation as well as standard error (standard deviation divided by the square root of (n)).
   f. Plot Surviving Fraction (semi-log plot; y-axis) vs. treatments (linear; x-axis).

Solubilization Protocol:
Reference: Bernardi et al (2001) Clinical Cancer Research 7, 4164-73)
1. Add 33% acetic acid to each of 60 mm plates at 24 hr post-staining.
   a. Do not use less than 400 μL.
2. Aliquot 100 μL from each plate (in triplicate) to a 96-well plate.
3. Read the absorbance at 540 nm and average the 3 values.
4. Normalize all values based on the volume solubilized and then follow regular data analysis steps.

The phosphors were tested in two forms, coated and uncoated. All coated phosphors were designated by a "c" at the end for example BP7c (blue phosphor #7 coated). All uncoated phosphors were designated by a "u" at the end for example BP3u (blue phosphor #3 uncoated). Most of the coatings tested in our experiments consisted of silica. All uncoated phosphors were predominantly oxides. The assigned names to the various phosphors are provided in the following Table 8.

TABLE 8

| Code | Phosphor Material Color | Emission Spectrum Peak Emission (nm) | X-Ray Absorption | | | Density | | |
|---|---|---|---|---|---|---|---|---|
| | | | Emiss Eff (%) | Eff (Z) | K-edge (keV) | g/cc Specific Gravity | Xtal Crystal Structure | Hygroscopic |
| BP1 | CaWO4:Pb | 425 | | | | | | N |
| BP2 | Y2SiO5:Ce | 410 | | | | | | N |
| BP3-C | YTaO4 | 337 | 10 | 59.8 | 67.42 | 7.5 | Monolithic | N |
| BP3-C | YTaO4 | 337 | 10 | 59.8 | 67.42 | 7.5 | Monolithic | N |
| BP4 | BASF-1 | 460 | | | | | | |
| BP5 | BASF-2 | 490 | | | | | | |
| BP6 | YTaO4:Nb (*) | 410 | 11 | 59.8 | 67.42 | 7.5 | Monolithic | N |
| BP6-C | YTaO4:Nb (*) | | | | | | | |
| BP7-C | LaOBr:Tm3+ (coated) | 360, 460 | 14 | 49.3 | 38.92 | 6.3 | Tetragonal | N |
| BP8-C | LaF3:Ce | 280 | | | | | | |
| BP9 | Y2O3 | 365 | | | | | | |
| BP-10 | BaSO4–:Eu2+ (coated) | 390 | 6 | 45.5 | 37.38 | 4.5 | Rhombic | N |
| BP10-C | BaSO4–:Eu2+ (coated) | 390 | 6 | 45.5 | 37.38 | 4.5 | Rhombic | N |

Toxicity Testing of YTaO$_4$:Nb

Various phosphors including YTaO$_4$:Nb phosphors were tested for their inherent toxicity using a clonogenic survival assay. Three different doses of YTaO$_4$:Nb were used in this evaluation. The YTaO$_4$:Nb oxide phosphor was coated with a nano-meter size layer of silica in this evaluation.

The clonogenic survival assay was plated using the B16 mouse melanoma cells with TMP (5 μm/ml) and/or silica coated YTaO$_4$:Nb phosphor at three concentrations (1 mg/ml, 100 μg/ml, 10 μg/ml). The mixture sat on the cells for 3 hr, and then the media was removed. YTaO$_4$:Nb was found to be non-toxic up to a dose of 1 mg/ml alone or in combination with TMP. FIG. 9A is a depiction of the results of YTaO$_4$:Nb Phosphor-Alone Toxicity using clonogenic assay. No inherent toxicity was observed. The YTaO$_4$:Nb with silica coating was found to be nontoxic even in high doses.

Figure 9B:
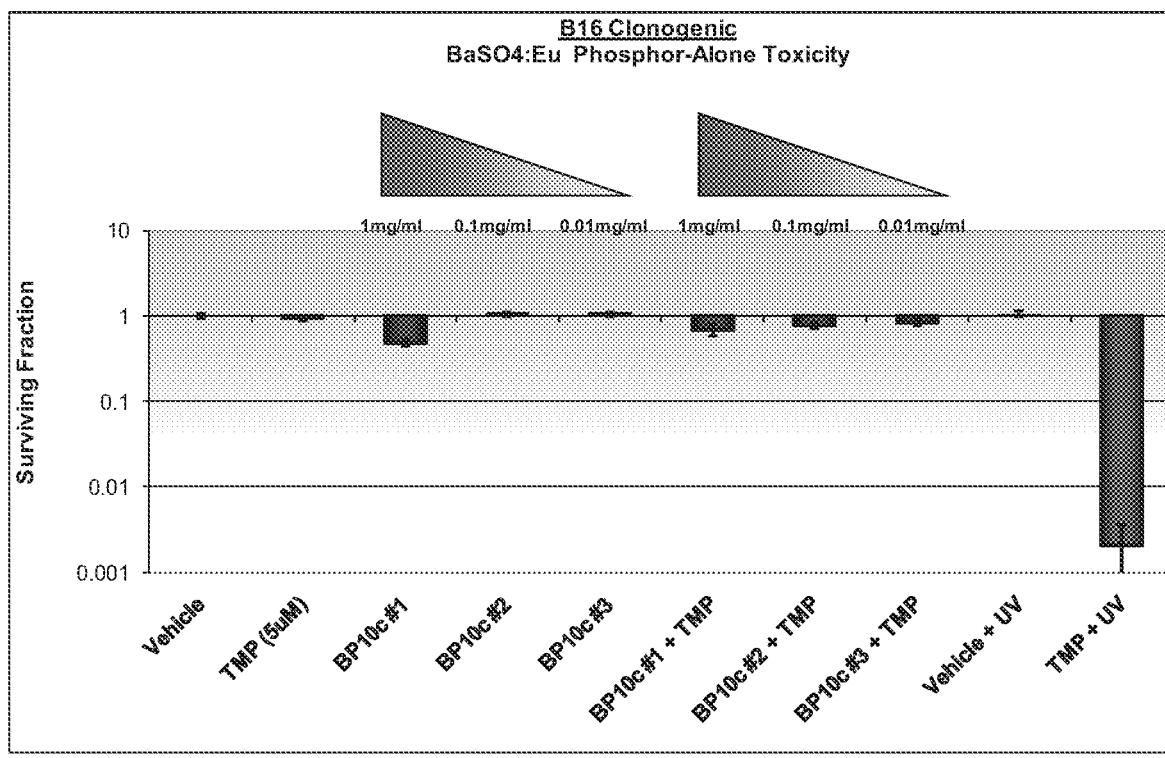
FIG. 9B is a schematic of the results from a clonogenic assay for a $BaSO_4$:Eu phosphor with and without a silica coating.

Toxicity Testing of BaSO$_4$:Eu:

Three doses of BaSO$_4$:Eu were used to look for any inherent toxicity. FIG. 9B is a depiction of the results of BaSO$_4$:Eu phosphor-alone toxicity using the clonogenic assay. BaSO$_4$:Eu with silica coating was added in three different concentrations to B16 mouse melanoma cells with TMP. No inherent toxicity was observed. The clonogenic survival assay was plated using the B16 mouse melanoma cells with TMP (5 μm/ml) and/or BaSO$_4$:Eu phosphor (1 mg/ml, 100 μg/ml, 10 μg/ml) sat on the cells for 3 hr, and then the media was removed. BaSO$_4$:Eu phosphor coated with silica coating was found to be non-toxic at 100 μg/ml and 10 μg/ml. It had moderately toxic at 1 mg/ml.

Figure 9C:
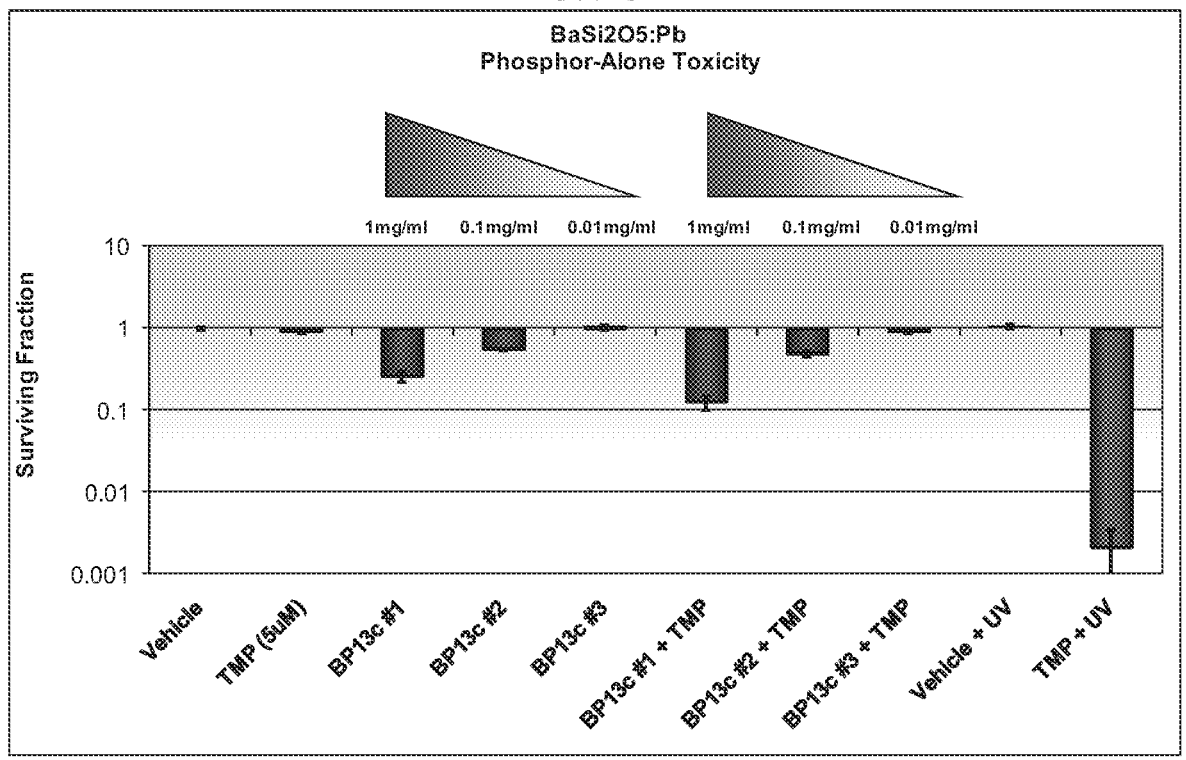
FIG. 9C is a schematic of the results from a clonogenic assay for a $BaSi_2O_5$:Pb phosphor with and without a silica coating.

Toxicity Testing of BaSi$_1$O$_5$:Pb:

Three doses of BaSi$_2$O$_5$:Pb were used to look for any inherent toxicity. FIG. 9C is a depiction of BaSi$_2$O$_5$:Pb phosphor-alone toxicity using the clonogenic assay. A BaSi$_2$O$_5$:Pb phosphor coated in silica containing trace amounts of Pb, is much more toxic at the highest concentration compared to either of the previous phosphors. This clonogenic survival assay was plated using the B16 mouse melanoma cells with TMP (5 μm/ml) and/or BaSi$_2$O$_5$:Pb phosphor (1 mg/ml, 100 μg/ml, 10 μg/ml) sat on the cells for 3 hr, and then the media was removed. BaSi$_2$O$_5$:Pb was found to be non-toxic at 10 μg/ml, moderately toxic at 100 μg/ml, and markedly toxic at 1 mg/ml.

YTaO$_4$ Phosphor Coated with Silica Under X-Ray in the Presence of TMP:

Another clonogenic survival assay was plated using the B16 mouse melanoma cells. The testing was designed to determine if the YTaO$_4$ phosphor plus TMP lead to melanoma cell kill. Two levels of x-ray energy (filament to target voltage) were used. The TMP was added at a concentration of (5 μm/ml) and/or phosphor (1 mg/ml, 100 μg/ml, or 10 μg/ml). The mixture sat on the cells for 3 hr before the cells were exposed to radiation. The radiation was given to the indicated groups using the Orthovoltage machine where the 2 Gy total dose was delivered using 2 different energy levels (135 kVp, 160 kVp).

There is some degree of XRT+phosphor effect even at the lower doses of phosphor at 160 kVp. One effect of the X-ray radiation treatment with the YTaO$_4$ phosphor was observable cell kill although not as pronounced at 135 kVp. The cell kill results indicated a 30-40% 'inherent' toxicity with 1 mg/ml of phosphor (high concentration).

Figure 9D:
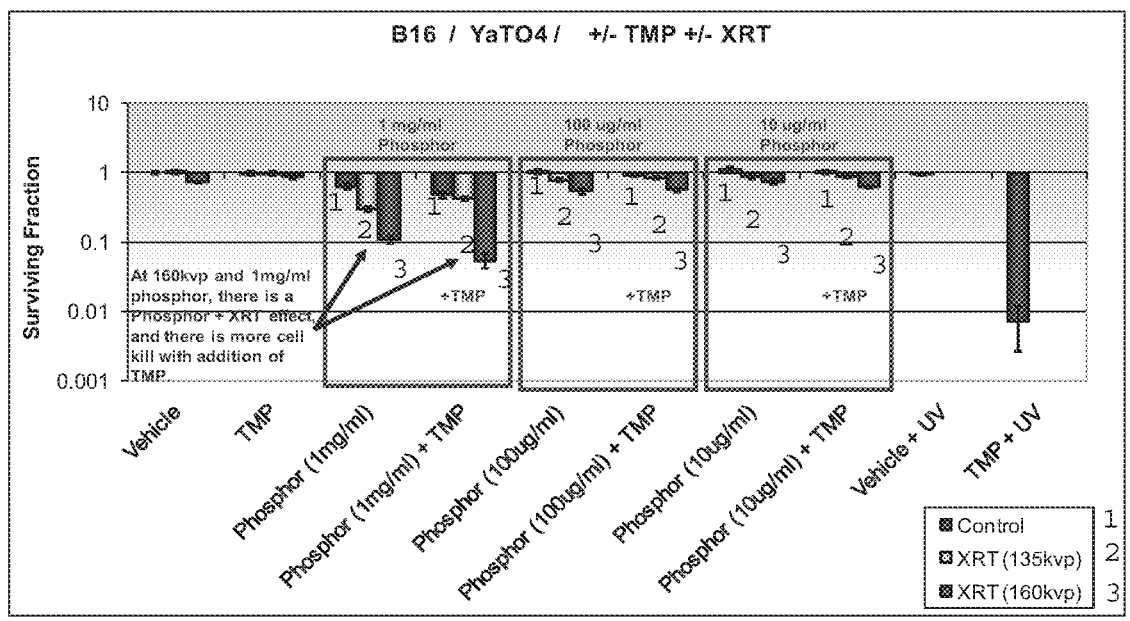
FIG. 9D is a schematic showing the effect of X-ray from a voltage of 160 kVp and 1 mg/ml concentration of the $YTaO_4$ phosphor showing a XRT and Phosphor effect, and further cell kill when adding trimethyl psoralen (TMP)

FIG. 9D is a depiction of the results using a voltage of 160 kVp and 1 mg/ml concentration of the YTaO$_4$ phosphor, which shows a marked XRT and Phosphor effect, and further cell kill when adding TMP.

Based on this data with YTaO$_4$, two concentrations of the YTaO$_4$ phosphors were evaluated to resolve with greater details the combined effect of phosphor plus X-Ray radiation Plus™ at 160 kVp+TMP. This clonogenic survival assay was plated using the B16 mouse melanoma cells with TMP (5 μm/ml) and/or YTaO$_4$ phosphor (1 mg/ml, 500 μg/ml) sat on the cells for 3 hr before the cells were exposed to radiation. The radiation was given to the indicated groups using the Orthovoltage machine with the 2 Gy total dose at 160 kVp.

Figure 9E:
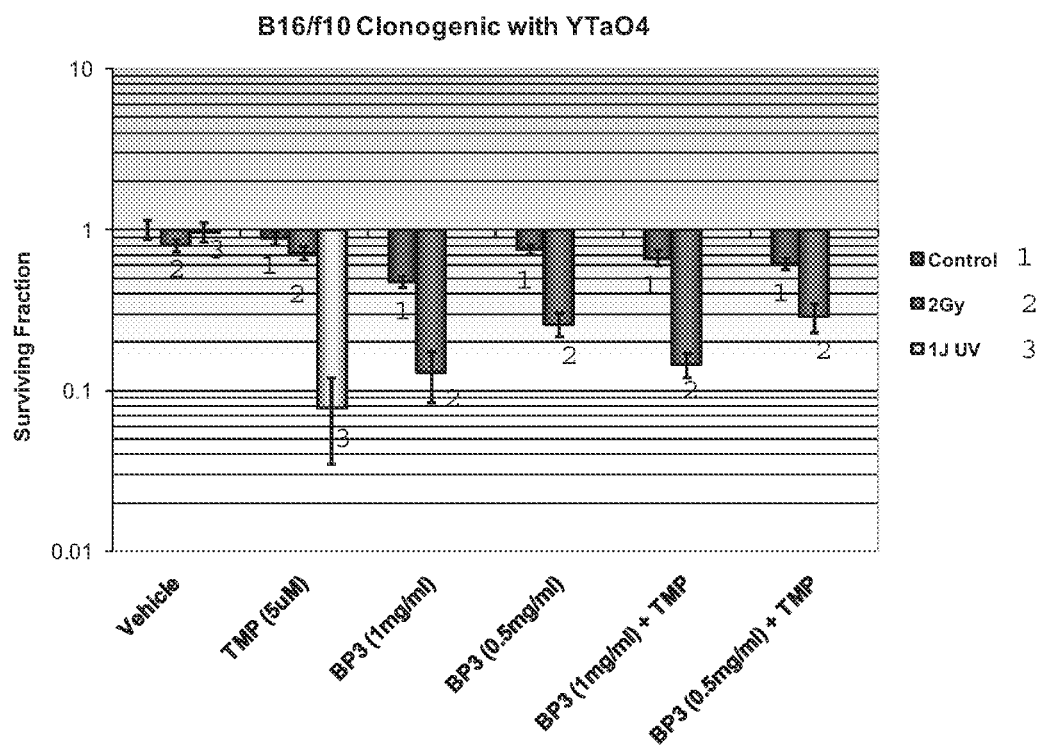
FIG. 9E is a schematic of the results from a clonogenic assay for a $YTaO_4$ phosphor with and without a silica coating for three different concentrations added to a B16 mouse melanoma cells with TMP.

A repeatable and reproducible signal was observed based on the effect of radiation and phosphor. However, no significant benefit of adding TMP was observed. In fact the data showed that (in this case) the addition of TMP lessened the surviving cell fraction. Perhaps, the TMP may have selectively adsorbed on the particle surfaces or the UV intensity was attenuated more in the presence of TMP. In either case, the phosphor effect was observable under X-ray. FIG. 9E is a depiction of the YTaO$_4$ phosphor-alone toxicity—using clonogenic assay with three different concentrations added to B16 mouse melanoma cells with TMP.

Figure 9F:
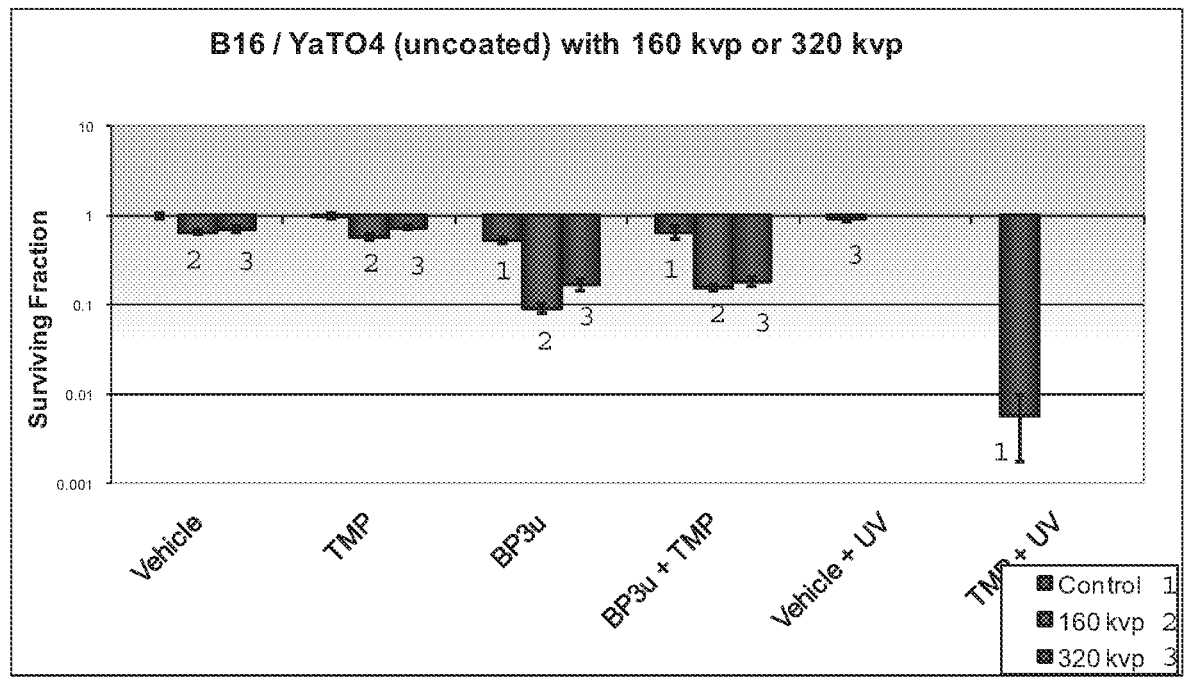
FIG. 9F is a schematic of the results from a clonogenic assay for a $YTaO_4$ phosphor (uncoated) at 0.75 mg/ml+/−2 gray XRT at 160 kVp or 320 kVp.

YTaO$_4$ Phosphor (with No Coating) Under X-Ray in the Presence of TMP:

Another clonogenic test was carried out using an identical YTaO$_4$ (BP3u) without the SiO$_2$. In essence, the innate oxide was tested to resolve the impact of the surface finish of the phosphor. FIG. 9F is a depiction of the results with YTaO$_4$ (uncoated) at 0.75 mg/ml+/−2 gray XRT at 160 kVp or 320 kVp. 30-40% cell kill from radiation alone was observed. There is moderate toxicity with 0.75 mg/ml of YTaO$_4$ uncoated by itself (36-48% kill). There is a markedly enhanced cell kill with YTaO$_4$ plus XRT. However, similarly to the previous result shown in FIG. 9D, there was no observed benefit from XRT+BP3u+TMP.

With YTaO$_4$ (uncoated) at a dose of 0.75 mg/ml, there is moderate toxicity from the phosphor alone. An enhanced cell kill with BP3u+radiation. However, there was observed no added benefit of YTaO$_4$+radiation+TMP at either 160 kVp or 320 kVp.

Figure 9G:
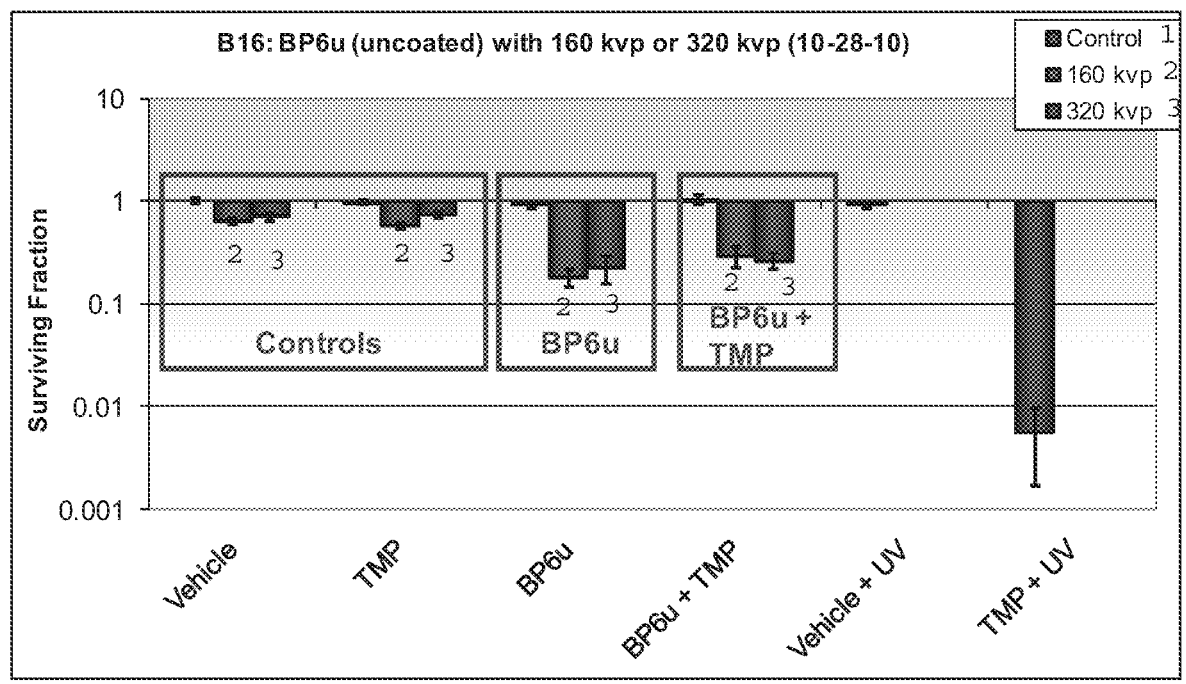
FIG. 9G is a schematic of the results from a clonogenic assay for an $YTaO_4$:Nb phosphor (uncoated) at 0.75 mg/ml, +/−2 gray XRT at 160 kVp and 320 kVp.

YTaO:Nb Phosphor (with No Coating) Under X-Ray in the Presence of TMP:

Another clonogenic test was carried out using the same phosphor base matrix with a doping that shifted the peak emission. This was achieved by adding niobium to the tantalate chemistry to form YTaO$_4$:Nb (BP6u). The evaluated phosphor was without the SiO$_2$ coating. In essence, the innate oxide was tested to resolve the impact of the surface finish of the phosphor. FIG. 9G is a depiction of the results with YTaO$_4$:Nb (uncoated) at 0.75 mg/ml, +/−2 gray XRT at 160 kVp and 320 kVp. 30-40% cell kill from radiation alone was observed. There is minimal toxicity with 0.75 mg/ml of BP6u by itself (0-7% kill). There is markedly enhanced cell kill with YTaO$_4$:Nb plus XRT. However, there is no observed benefit from XRT plus YTaO$_4$:Nb plus TMP at these kVp levels.

LaOBr:Tm$^{3+}$ Phosphor (with SiO$_2$ Coating) Under X-Ray in the Presence of TMP:

Based on the previous data with YTaO4, three doses of LaOBr:Tm$^{3+}$ were evaluated to look for a phosphor plus radiation plus TMP effect. This clonogenic survival assay was plated using the B16 mouse melanoma cells with TMP (5 μm/ml) and/or LaOBr:Tm phosphor (1 mg/ml, 100 :g/ml, 10:g/ml) sat on the cells for 3 hrs before the cells were exposed to radiation. The radiation was given to the indicated groups using the Orthovoltage machine (2 Gy total dose at 160 kVp or 80 kVp).

Figure 9H:
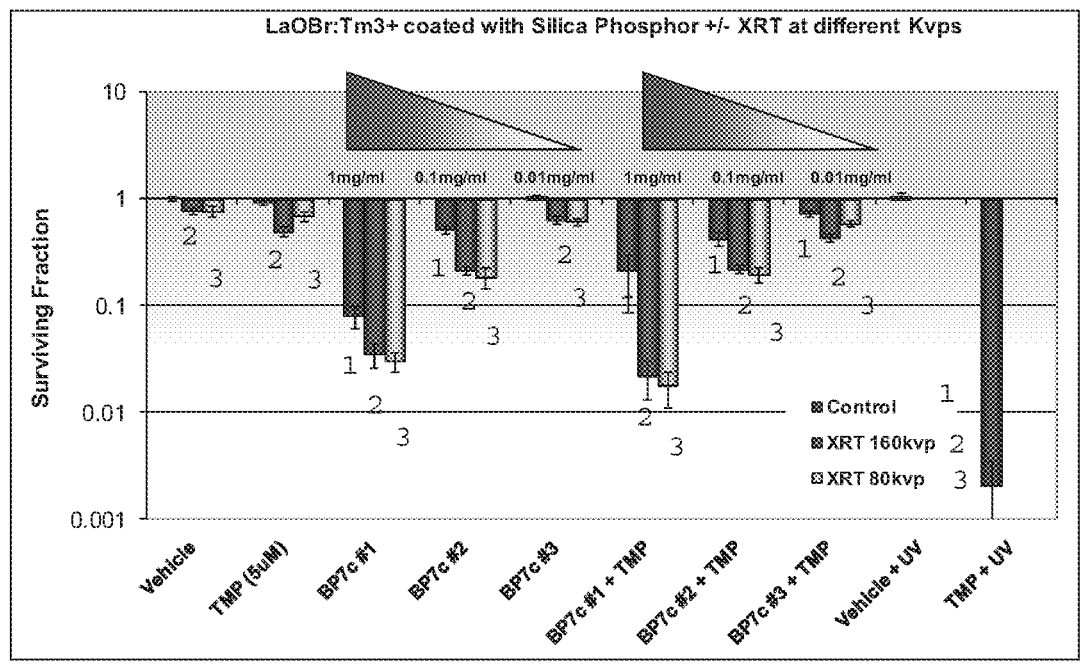
FIG. 9H is a schematic of the results from a clonogenic assay for a LaOBr:Tm phosphor (coated with $SiO_2$)

FIG. 9H is a depiction of the results with LaOBr:Tm (coated with $SiO_2$) phosphor-alone toxicity—using a clonogenic assay with three different concentrations added to B16 mouse melanoma cells with TMP. LaOBr:Tm is toxic by itself (see the blue bars in FIG. 9H). There was no additional benefit of adding TMP at these kVp levels. LaOBr:Tm while the brightest phosphor was found to be toxic by itself. This is not a surprise in the view of the bromine constituent which is toxic. Also, no TMP activation was seen, as with the previous experiment, at either 80 or 160 kVp. However, with this phosphor having a strong UV and visible light intensity, a lower X-Ray dose experiment was carried out. These experiments were carried out at 40 kVp and 80 kVp.

Figure 9I:
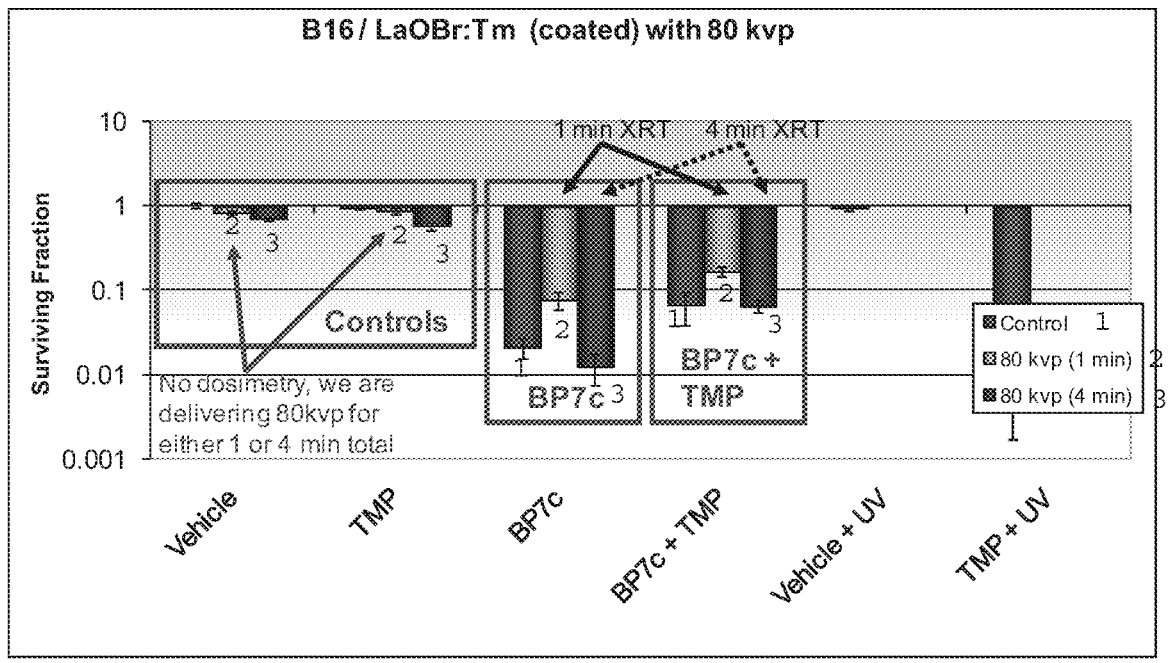
FIG. 9I is a schematic of the results from a clonogenic assay for a LaOBr:Tm phosphor (coated with $SiO_2$) with Phosphor-Alone Toxicity using at 0.75 mg/ml and phosphor plus TMP at 80 kVp XRT for 1 or 4 minutes total.

LaOBr:$Tm^{3+}$ Phosphor (with $SiO_2$ Coating) Under X-Ray Using 80 kVp in the Presence of TMP FIG. 9I is a depiction of the results with a LaOBr:Tm (coated with $SiO_2$) phosphor-(BP7c) toxicity using a concentration of 0.75 mg/ml phosphor plus TMP concentration at 80 kVp for 1 or 4 minutes total. There is marked toxicity with 0.75 mg/ml of LaOBr:Tm by itself resulting in a 93-98% kill. The radiation bars are difficult to interpret in light of the severe, inherent toxicity of these phosphors With BP7c (coated) at a dose of 0.75 mg/ml, there is marked toxicity from the phosphor alone. It was difficult to interpret the radiation data in light of the marked inherent toxicity of this phosphor at the concentration of 0.75 mg/ml. It was not possible from this evaluation to determine if there is a radiation plus phosphor effect, or an added benefit of TMP at 80 kVp for either 1 min or 4 min.

Figure 9J:
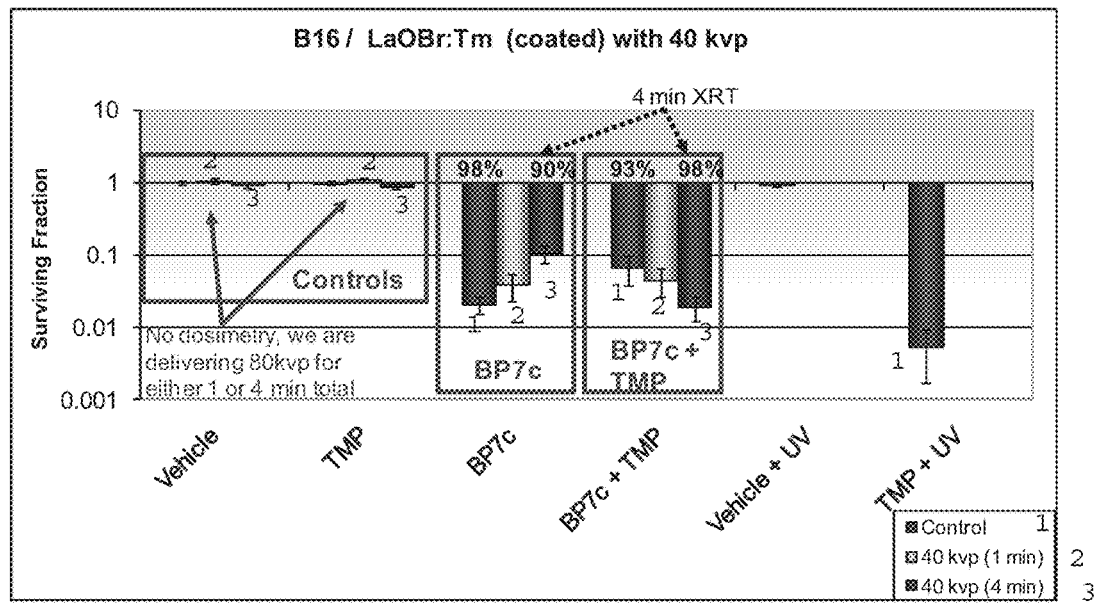
FIG. 9J is a schematic of the results from a clonogenic assay for a LaOBr:Tm phosphor (coated with $SiO_2$) with Phosphor-Alone Toxicity using at 0.75 mg/ml and phosphor plus TMP at 40 kVp XRT for 1 or 4 minutes total.

LaOBr:$Tm^{3+}$ Phosphor (with $SiO_2$ Coating) Under X-Ray Using 40 kVp in the Presence of TMP FIG. 9J is a depiction of the results with a LaOBr:Tm (coated with $SiO_2$) phosphor-alone toxicity using a concentration of 0.75 mg/ml plus TMP at 40 kVp XRT for 1 or 4 minutes total. With LaOBr:Tm (coated) at a dose of 0.75 mg/ml, there is marked toxicity from the phosphor alone. It was difficult to interpret the radiation data in light of the marked inherent toxicity of this phosphor at 0.75 mg/ml. It is not possible from this evaluation to tell if there is a radiation+phosphor effect, or an added benefit of TMP in this study at 40 kVp for either 1 min or 4 min.

There is marked toxicity with 0.75 mg/ml of LaOBr:Tm by itself 93-98% kill. The plus radiation LaOBr:Tm radiation bars are difficult to interpret in light of the inherent toxicity. Though the brown bars (40 kVp for 4 min) may appear to be different, there is only an 8% difference between those bars. The LaOBr:Tm plus TMP plus XRT bar is not different from the toxicity of LaOBr:Tm alone.

Figure 9K:
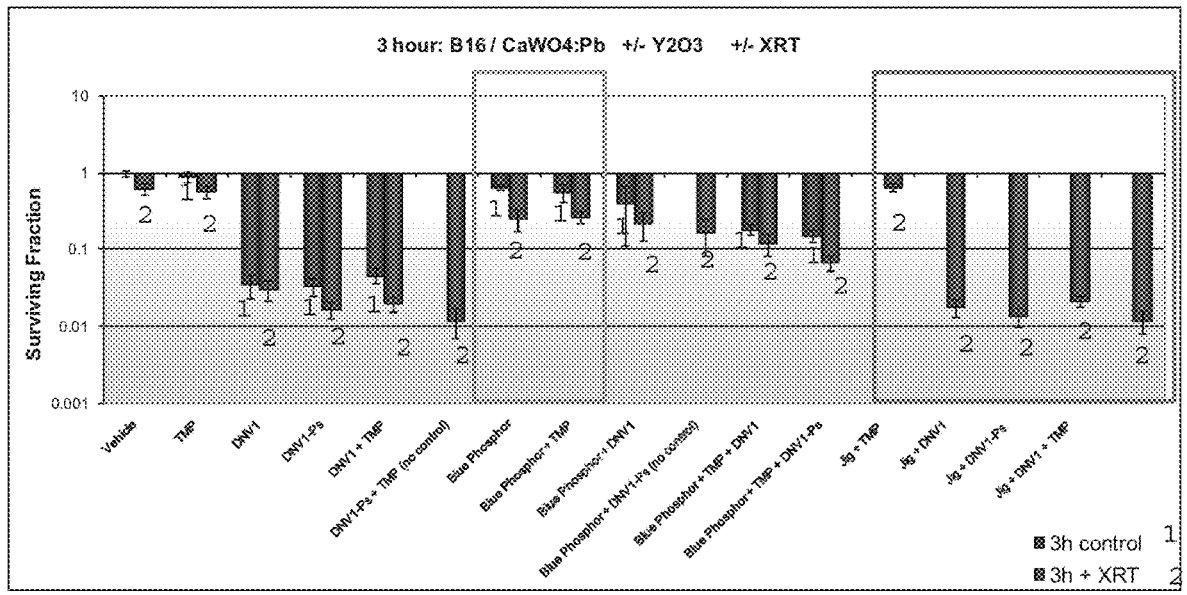
FIG. 9K is a schematic of a cell kill assay performed with a $CaWO_4$ phosphor combined with the $Y_2O_3$ particles.

$CaWO_4$ Phosphor (with No Coating) with Surface Modified $Y_2O_3$ Under X-Ray in the Presence of TMP:

In this experiment, B16 mouse melanoma cells were plated in a 6-well format for a clonogenic survival assay. Cells were treated with combinations of TMP, downconverting nanoparticles, phosphor fixture used for processing in the irradiator or phosphor powder mixed into the media. FIG. 9K is a depiction of the results of the cell kill assay performed with $CaWO_4$ combined with the $Y_2O_3$ particles in some cases. $CaWO_4$ plus TMP show an enhanced cell kill with radiation.

The cells were incubated with or without down-converting yttrium nanoparticles for 3 hours. These particles were either tethered to a tat-peptide or a tat-peptide conjugated with psoralen. X-ray exposure of the blue phosphor fixture results in UV emission which should activate TMP in the cell media. For the radiation set with $CaWO_4$ phosphor in the media, the cells were exposed to the phosphor and/or TMP and/or nanoparticles for 3 hours. The nanoparticle preparation was so toxic that an interpretation of enhanced cell kill with this nanoparticle combination was not possible.

Figure 9L:
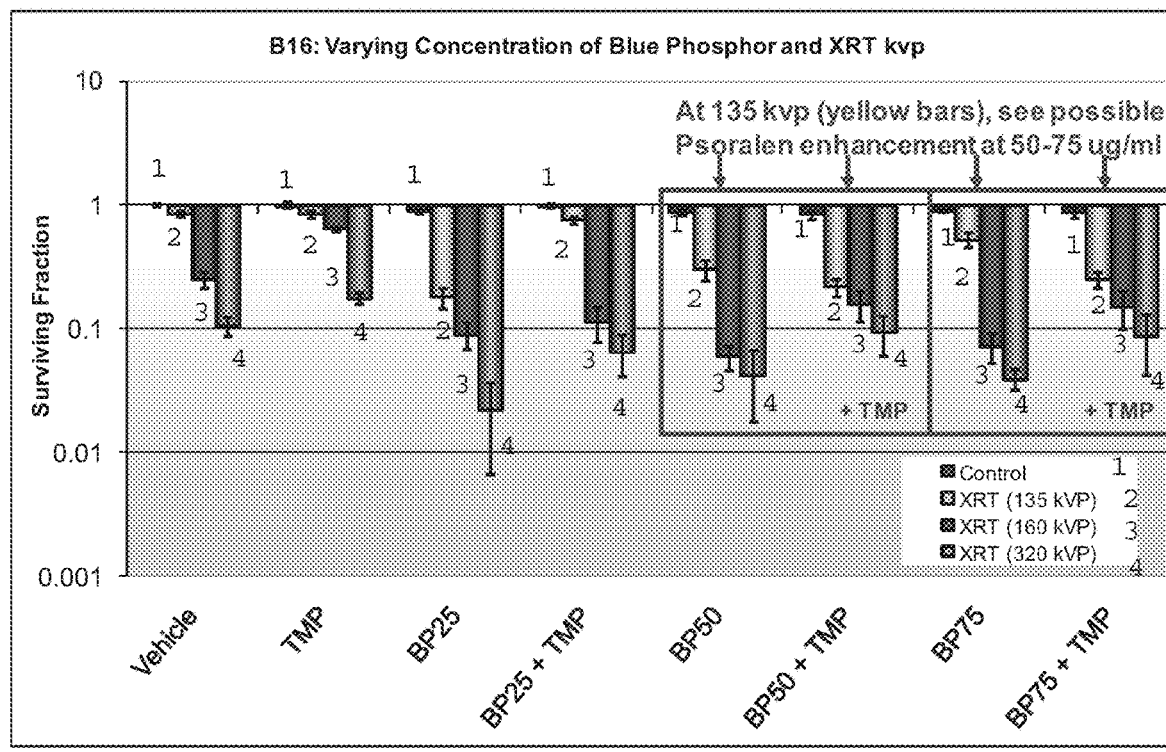
FIG. 9L is a schematic of the results from a clonogenic assay for B16 mouse melanoma cells treated with a $CaWO_4$ phosphor.

Another clonogenic survival assay was plated using the B16 mouse melanoma cells to test if the $CaWO_4$ phosphor at 3 intermediate concentrations can activate TMP to kill melanoma cells using 3 different energy levels of radiation. The cells were plated and allowed to attach to the plates overnight. The next day, $CaWO_4$ powder was suspended in water to give a 100 mg/ml stock and then added directly to the cells to give final concentrations of 0.25 mg/ml, 0.5 mg/ml and 0.75 mg/ml. TMP, previously dissolved in DMSO, was also added to the cells at the same time to give a final concentration of 5:M. The drug and phosphor sat on the cells for 3 hr before the cells were exposed to radiation. The radiation was given to the indicated groups using the Orthovoltage machine where the 2 Gy total dose was delivered using three different energy levels (135 kVp, 160 kVp and 320 kVp). FIG. 9L is a depiction of the results with B16 clonogenic assay for the $CaWO_4$ phosphor by varying the X-ray voltage (135 kVp, 160 kVp and 320 kVp) and phosphor doses 0.25 mg/ml, 0.5 mg/ml and 0.75 mg/ml. A signal of psoralen enhancement at 50 and 75 mg/ml was observed.

Figure 9M:
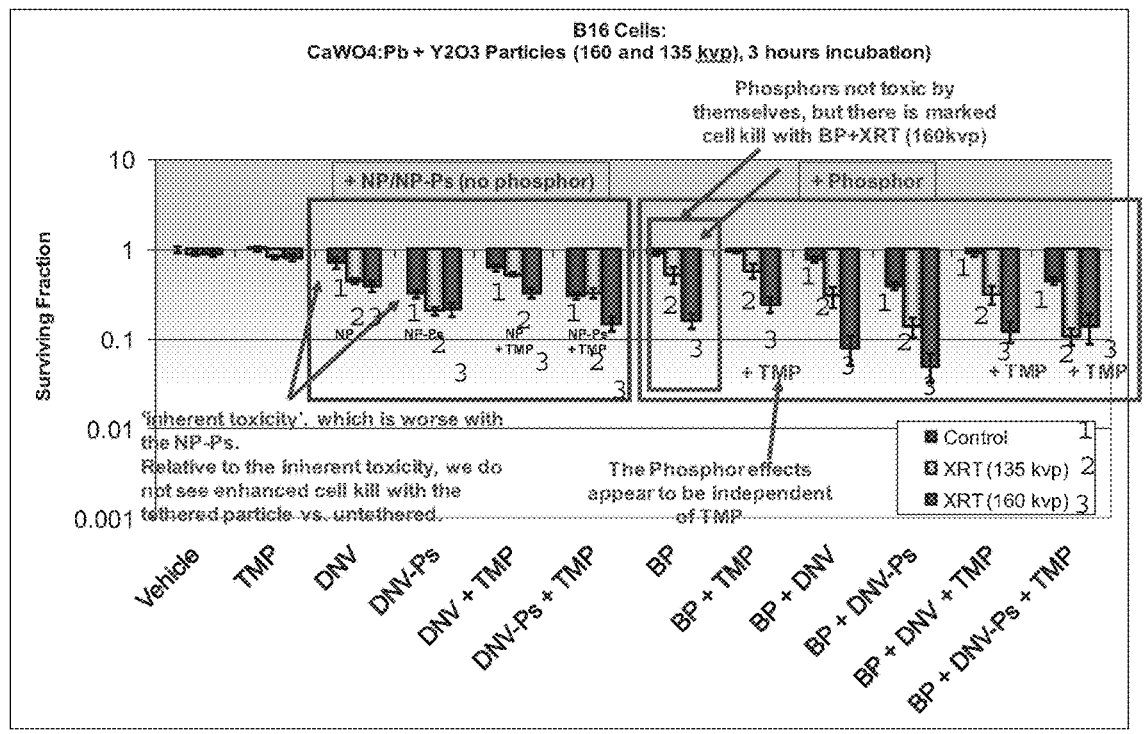
FIG. 9M is a schematic of the results from a clonogenic assay for B16 mouse melanoma cells treated with a CaWO4 phosphor by varying the X-Ray voltage.

Another clonogenic survival assay was plated using the B16 mouse melanoma cells testing if the $CaWO_4$ phosphor plus TMP to kill melanoma cells using two different energy levels of radiation, to determine whether adding nanoparticles provides a benefit. The drug, particles, and phosphor sat on the cells for 3 hr before the cells were exposed to radiation. The radiation was given to the indicated groups using the Orthovoltage machine where the 2 Gy total dose was delivered using two different energy levels (135 kVp and 160 kVp). FIG. 9M is a depiction of the results of a B16 clonogenic assay using the $CaWO_4$ phosphor and varying the X-ray voltage (135 kVp and 160 kVp).

There was significant toxicity from the nanoparticles, especially with the psoralen-tethered particles. The phosphor was not toxic by itself, but provided enhanced cell kill in the present of radiation. This phosphor+radiation effect was independent of TMP. The $CaWO_4$ phosphors have a very pronounced cell kill when treated with X-ray radiation. This effect does not seem to rely on TMP.

Energy Modulation Agent Modifications:

In one embodiment of the invention, a phosphor production process for producing novel phosphor configurations is provided. The following describes this process and the resultant phosphor configurations. US2014/0323946 (the entire contents of which are incorporated herein by reference) describes this process.

A container including a solution containing nano-particles provides solution containing the nano particles to a quartz wafer through the process of spin coating. The quartz wafer once dried has a thin layer of the nanoparticles dispersed across the surface of the wafer.

The nano particle dispersion is taken to a physical vapor deposition system. The wafer with the nano particle dispersion is lower onto a biased and heated stage, and inserted into the physical vapor deposition system for applying a coating on half of the nanoparticles. The coating applied in the PVD system is applied to a top half the particles.

The half coated phosphor particles placed back in a solution inside a container that has a biased stage. The biased stage contains metallic nano rods.

In an alternative process, the solution containing phosphors with a metallic coating is placed in a micro-electrode structure having a RF feed energizing the electrodes. The electrodes are disposed to form various gaps ranging from the micron to submicron levels.

FIG. 10A is a schematic depicting the half coated phosphor particles disposed around a metallic nano rod and heated to sufficient temperatures to alloy the metallic coating with the metallic nano rod. Subsequently, a silica gel coating process is applied to coat the composite structure using silica.

Figure 11:
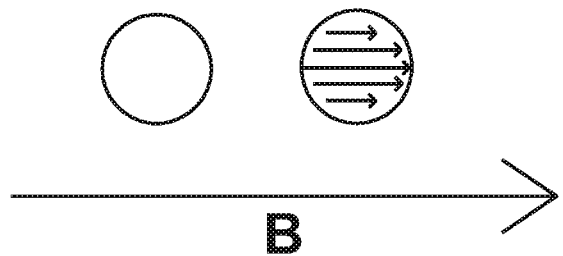
FIG. 11 is a schematic showing alignment of a magnetic particle under a magnetic field and followed by joining the phosphor and the magnetic particles with a lateral field configuration.

FIG. 10B is a schematic depicting a mass transport process, necking the region between particles. FIG. 11 is a schematic depicting alignment of a magnetic particle under a magnetic field and followed by joining the phosphor and the magnetic particles (lateral field configuration).

Figure 12:
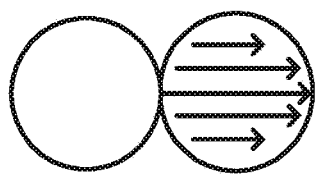
FIG. 12 is a schematic showing the joining of a magnetic particle and phosphor through a necking process.
Figure 13:
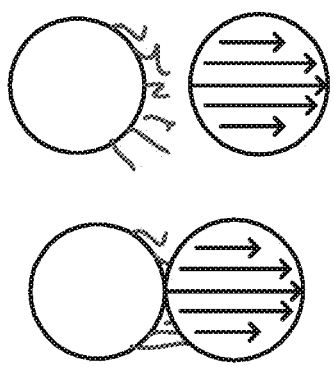
FIG. 13 is a schematic showing the joining of a magnetic particle and phosphor through an adhesion process by surface modification of at least one of the particles.

FIG. 12 is a schematic depicting the joining of a magnetic particle and phosphor through a necking process. FIG. 13 is a schematic depicting the joining of a magnetic particle and phosphor through an adhesion process by surface modification of at least one of the particles.

Figure 14:
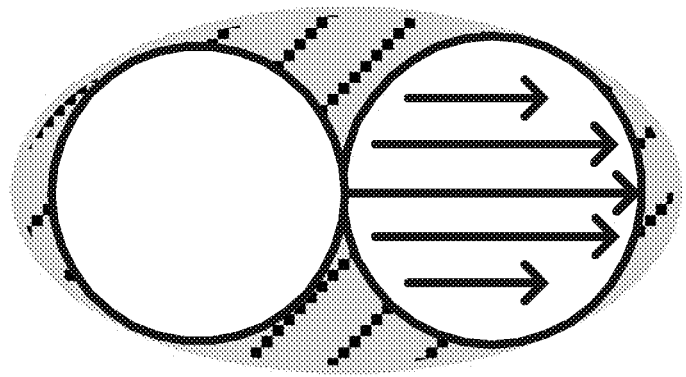
FIG. 14 is a schematic showing a lipid envelop around the adhered phosphor and nano magnetic particle.
Figure 15:
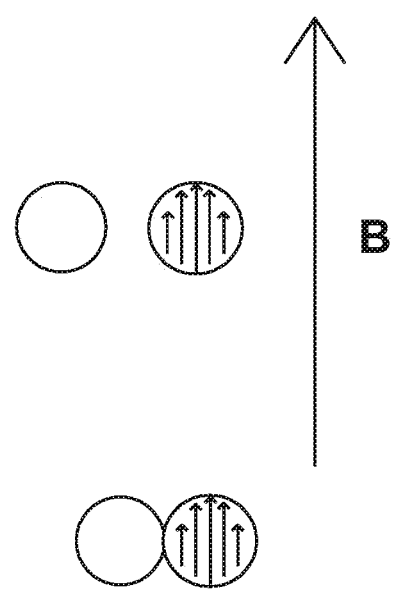
FIG. 15 is a schematic showing the alignment of a magnetic particle under a magnetic field and followed by joining the phosphor and the magnetic particles (orthogonal field configuration)

FIG. 14 is a schematic depicting a lipid envelop around the adhered phosphor and nano magnetic particle. FIG. 15 is a schematic depicting alignment of a magnetic particle under a magnetic field and followed by joining the phosphor and the magnetic particles (orthogonal field configuration).

Figure 16:
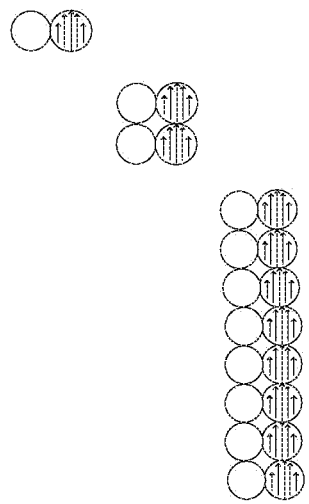
FIG. 16 is a schematic showing that, after joining the particles in an orthogonal field configuration, the particles would have a tendency to self-assemble in a recto-linear fashion.
Figure 17:
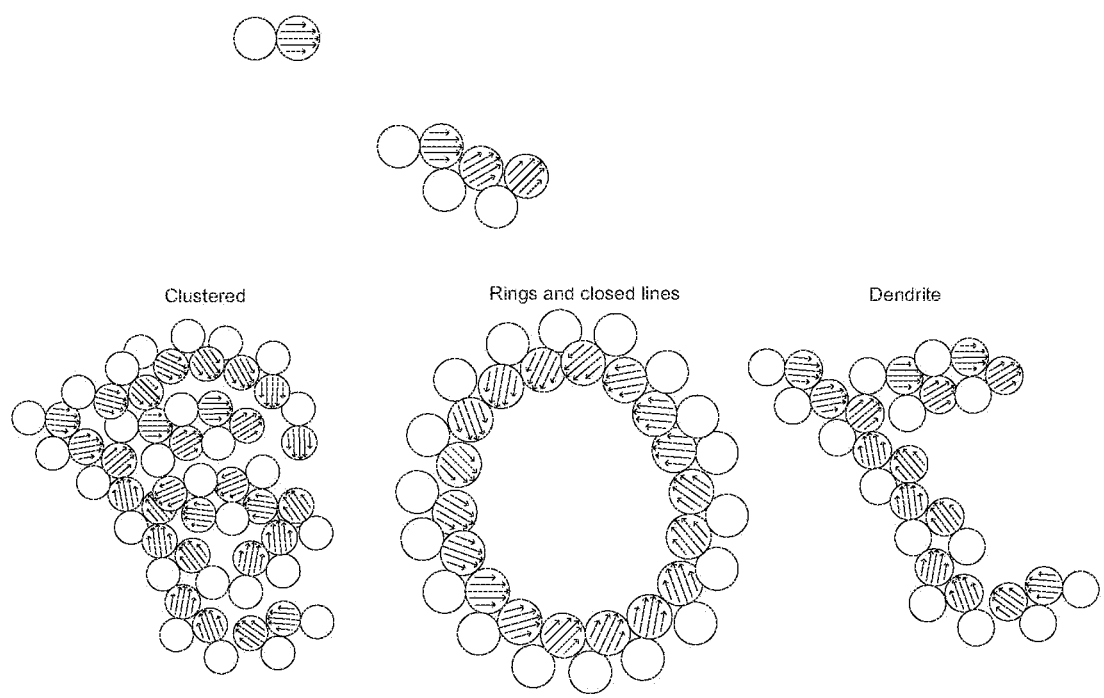
FIG. 17 is a schematic showing that, after joining the particles in a lateral field configuration, the particles would have a tendency to self-assemble in dendrite configurations, clusters and rings.

FIG. 16 is a schematic depicting a situation where, after joining the particles in an orthogonal field configuration, the particles have a tendency to self-assemble in a recto-linear fashion. FIG. 17 is a schematic depicting a situation where, after joining the particles in a lateral field configuration, the particles have a tendency to self-assemble in dendrite configurations, clusters and rings.

The phosphors of this invention are not limited to those described above. Other phosphors are suitable and are applicable for various applications where mixtures of down converters are needed. For example, other down converters known in the art and suitable for this invention include $TiO_2$, ZnO, $Fe_2O_3$, CdTe, CdSe, ZnS, CaS, BaS, SrS and $Y_2O_3$. Other suitable down conversion materials known in the art include zinc sulfide, $ZnS:Mn^{2+}$, ferric oxide, titanium oxide, zinc oxide, zinc oxide containing small amounts of $Al_2O_3$ and AgI nanoclusters encapsulated in zeolite. Other suitable down conversion materials include lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers known in the art are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

In various embodiments of the invention, the following particles can be used similar to that detailed in U.S. Pat. No. 7,090,355, the entire contents of which are incorporated herein by reference. For down-conversion, the following materials can be used: inorganic or ceramic phosphors or nano-particles, including but not limited to metal oxides, metal halides, metal chalcoginides (e.g. metal sulfides), or their hybrids, such as metal oxo-halides, metal oxo-chalcoginides; laser dyes and small organic molecules, and fluorescent organic polymers; semiconductor nano-particles, such as II-VI or III-V compound semiconductors, e.g. fluorescent quantum dots; organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The Garnet series of phosphors can be used: $(Y_mA_{1-m})_3(Al_nB_{1-n})_5O_{12}$, doped with Ce; where $0 \leq m$, $n \leq 1$, where A includes other rare earth elements, B includes B, Ga. In addition, phosphors containing metal silicates, metal borates, metal phosphates, and metal aluminates hosts can be used. In addition, phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used.

Semiconductor nanoparticles can be used. The term "semiconductor nanoparticles," in the art refers to an inorganic crystallite between 1 nm and 1000 nm in diameter, preferably between 2 nm to 50 nm. A semiconductor nanoparticle is capable of emitting electromagnetic radiation upon excitation (i.e., the semiconductor nano-particle is luminescent). The nanoparticle can be either a homogeneous nano-crystal, or comprises multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Other down converters include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties. Examples of doped (or alloyed) glass systems suitable for the invention include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

Alternatively, quantum dots can be used to tailor the down conversion process. As described in U.S. Pat. No. 6,744,960 (the entire contents of which are incorporated by reference), different size quantum dots produce different color emissions. As applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot, may range from about 2 to 10 nm. Since the size of these particles is so small, quantum physics governs many of the electrical and optical properties of the quantum dot. One such result of the application of quantum mechanics to the quantum dot is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 µm. Titanium dioxide $TiO_2$ also emits in this range. The line width of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots, light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm.

The converters in one embodiment can include a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$, alkali lead silicate including compositions of $SiO_2$, $B_2O_3$, $Na_2O$, $K_2O$, PbO, MgO, or Ag, and combinations or alloys or layers thereof.

In other embodiments, a metal coating or a metallic structure can exist inside the dielectric and the relative position of the metal structure to the dielectric structure can enhance plasmonic resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity.

Such nanoparticle structures can exhibit (in certain embodiments) surface plasmonic resonance in the metallic shell to enhance upconversion of light from a first wavelength $\lambda_1$ to a second wavelength $\lambda_2$.

As described above, shell is in particular designed with a layer thickness to enhance the photon upconversion process through plasmonic enhancement. The thickness of the shell is "tuned" in its thickness to the absorption process by having a dimension in which plasmons (i.e., electrons oscillations) in shell have a resonance in frequency which provides spectral overlap with the absorption band of the incident light targeted. Thus, the thickness of the shell is "tuned" in a thickness to where a plasmon resonance resonates at a frequency of interest for stimulating a photoactivatable agent.

Such a plasmon resonating shell can be made of numerous transition metals, including though not limited to gold, silver, platinum, palladium, nickel, ruthenium, rhenium, copper, and cobalt. This capability of matching or tuning of the frequencies provides an enhancement of the absorption which would not be present with a dielectric core alone.

In one embodiment of this invention, the thickness of the metal shell is set depending on the emission frequency to enhance the total efficiency of the emission process. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall conversion process.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient is outside of the shell, the recipient will receive enhanced light $\lambda_2$ by the above-described plasmonic effect than would occur if the shell were absent from the structure.

Accordingly, a plasmonics effect (from plasmonic inducing agents) is advantageous. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy.

Photodynamic Therapy (PDT) with the Energy Modulation Agents of the Invention:

In one embodiment of this invention, the above-described energy modulation agents (phosphors, scintillators, fluorescent materials, up conversion media, down conversion media, and combinations and agglomerations thereof) with or without plasmonic inducing agents can be used in photodynamic therapy for the light source.

PDT involves treatment of diseases such as cancer using light action on a special photoactive class of drugs, by photodynamic action in vivo to destroy or modify tissue PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD).

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

$$PA + h\nu \rightarrow {}^1PA^*(S) \quad \text{Excitation}$$

$${}^1PA^*(S) \rightarrow {}^3PA^*(T) \quad \text{Intersystem crossing for singlet to triplet state}$$

$${}^3PA^*(T) + O_2 \rightarrow {}^1O^*_2 + PA \quad \text{Energy transfer from the drug to singlet oxygen}$$

where PA=photo-active drug at the ground state; ${}^1PA^*(S)$= excited singlet state; ${}^3PA^*(T)$=excited triplet state; ${}^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at ~1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a photosensitizer to be clinically useful. It is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). Toxicity can become an issue if high doses of photosensitizer are necessary in order to obtain a complete response to treatment. An important mechanism associated with PDT drug activity involves apoptosis in cells. Upon absorption of light, the photosensitizer (PS) initiates chemical reactions that lead to the direct or indirect production of cytotoxic species such as radicals and singlet oxygen. The reaction of the cytotoxic species with subcellular organelles and macromolecules (proteins, DNA, etc.) lead to apoptosis and/or necrosis of the cells hosting the PDT drug. The preferential accumulation of PDT drug molecules in cancer cells combined with the localized delivery of light to the tumor, results in the selective destruction of the cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based chlorines, phthalocyanine, and naphthalocyanine have been investigated.

Photoactivation Treatments with the Energy Modulation Agents of the Invention:

For the treatment of cell proliferation disorders, an initiation energy source (e.g., light from the phosphors or scintillators or other down conversion media or up conversion media of the invention) can provide an energy that activates an activatable pharmaceutical agent to treat target cells within a subject. In one embodiment, the energy is applied indirectly to the activatable pharmaceutical agent, preferably in proximity to the target cells.

Within the context of here, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject.

Although not intending to be bound by any particular theory or be otherwise limited in any way, the following theoretical discussion of scientific principles and definitions are provided to help the reader gain an understanding and appreciation of the invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *Staphylococcus aureus* (particularly antibiotic resistant strains such as methicillin resistant *Staphylococcus aureus* or MRSA), and autoimmune disorders.

As used herein, an "activatable agent" is an agent that normally exists in an inactive state in the absence of an activation signal. When the agent is activated by an activation signal under activating conditions, the agent is capable of producing a desired pharmacological, cellular, chemical, electrical, or mechanical effect in a medium (i.e. a predetermined change). For example, when photocatalytic agents are irradiated with visible or UV light, these agents induce polymerization and "curing" of light sensitive adhesives.

Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further require a set of activation conditions. For example, an activatable agent, such as a photosensitizer, may be activated by UV-A radiation (e.g., by UV-A radiation generated internally in the medium). For example, an activatable agent, such as a photosensitizer, may be activated by UV-B or UV-C radiation. Once activated, the agent in its active-state may then directly proceed to produce a predetermined change.

Where activation may further require other conditions, mere delivery of the activation signal may not be sufficient to bring about the predetermined change. For example, a photoactive compound that achieves its effect by binding to certain structure in its active state may require physical proximity to the target structure when the activation signal is delivered. For such activatable agents, delivery of the activation signal under non-activating conditions will not result in the desired effect. Some examples of activating conditions may include, but are not limited to, temperature, pH, location, state of the medium, and the presence or absence of co-factors or conformational changes.

Selection of an activatable agent greatly depends on a number of factors such as the desired change, the desired form of activation, as well as the physical and biochemical constraints that may apply. Exemplary activatable agents may include, but are not limited to agents that may be activated by photonic energy, electromagnetic energy, acoustic energy, chemical or enzymatic reactions, thermal energy, microwave energy, or any other suitable activation mechanisms.

When activated, the activatable agent may effect changes that include, but are not limited to an increase in organism activity, a fermentation, a decrease in organism activity, apoptosis, redirection of metabolic pathways, a sterilization of a medium, a cross polymerization and curing of a medium, or a cold pasteurization of a medium.

As used herein, an "activatable pharmaceutical agent" (alternatively called a "photoactive agent" or PA) is an agent that normally exists in an inactive state in the absence of an activation signal. When the agent is activated by a matching activation signal under activating conditions, it is capable of affecting the desired pharmacological effect on a target cell (i.e. preferably a predetermined cellular change).

A photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated, the activatable pharmaceutical agent may affect cellular changes that include, but are not limited to, apoptosis, redirection of metabolic pathways, up-regulation of certain genes, down-regulation of certain genes, secretion of cytokines, alteration of cytokine receptor responses, production or modulation of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include modulation of or releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondriat at a therapeutically effective amount. In this embodiment, the activatable pharmaceutical agent, preferably a photoactivatable agent, is exposed in situ to an activating energy emitted from an energy modulation agent (e.g., light emitted from a predominantly visible-light emitting phosphor or a mixture of such phosphors).

An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD], alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Additional photoactive agents include, but are not limited to, carbene precursors, nitrene precursors, thio derivatives, benzophenones, and halogenated pyrimidines. Such photochemistries are routinely employed to achieve protein-DNA photocross-links but none has been achieved using an indirect method as presented herein, for example where X-Ray radiation is converted to UV radiation to activate the species and achieve DNA photocross-links.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The nature of the predetermined cellular change will depend on the desired pharmaceutical outcome. Exemplary cellular changes may include, but are not limited to, morphologic changes, apoptosis, necrosis, up-regulation of certain genes, down-regulation of certain genes, modulation of or secretion of cytokines, alteration of cytokine receptor responses, or a combination thereof.

Signals that may be used to activate a corresponding agent may include, but are not limited to, photons of specific wavelengths (e.g. x-rays, or visible light), together with or without electromagnetic energy (e.g. radio or microwave), thermal energy, acoustic energy, or any combination thereof.

Activation of the agent may be as simple as delivering the signal to the agent or may further premise on a set of activation conditions. For example, in the former case, an activatable pharmaceutical agent, such as a photosensitizer, may be activated by UV-A radiation (e.g., UV-A light from the phosphors or scintillators or down conversion or up conversion media of the invention). Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment can be by those methods described in U.S. application Ser. No. 11/935,655, filed Nov. 6, 2007 (the entirety of which is incorporated by reference), or by a modified version of a conventional treatment such as PDT, but using a plasmonics-active agent to enhance the treatment by modifying or enhancing the applied energy or, in the case of using an energy modulation agent, modifying either the applied energy, the emitted energy from the energy modulation agent, or both.

In one embodiment, the activatable pharmaceutical agent is capable of chemically binding to the DNA or mitochondriat a therapeutically effective amount. In this embodiment, the activatable pharmaceutical agent, preferably a photoactivatable agent, is exposed in situ to an activating energy emitted from an energy modulation agent such as the phosphors or scintillators of the invention, which, in turn receives energy from an initiation energy source.

Table 9 below lists some photoactivatable molecules capable of being photoactivated to induce an auto vaccine effect.

TABLE 9

1: SSET and TTET rate constants for bichromophoric peptides

| Compound | $\lambda_{ex}$ (nm) | $E_{SSET}$ | $k_s$ of donor ($s^{-1}$) | $k_{SSET}$ ($s^{-1}$) | $k_{SSET}(s^{-1})$ (Average) | $R_0$ (A) | $R$ (A) | $R_{model}$ (A) (Average) | $E_{TTET}$ | $k_{TTET}$ ($s^{-1}$) |
|---|---|---|---|---|---|---|---|---|---|---|
| 1B | 224 | 96.3 | $9.5 \times 10^6$ | $2.44 \times 10^8$ | $1.87 \times 10^8$ | 14.7 | 9 | 9.5 | | |
| | 266 | 95 | | $1.8 \times 10^8$ | | | | | 2.5 | $5 \times 10^2$ |
| | 280 | 94 | | $1.36 \times 10^8$ | | | | | | |
| 1A | 224 | 80 | $9.5 \times 10^6$ | $3.8 \times 10^7$ | $3.67 \times 10^7$ | 14.7 | 11.8 | 14.1 | | |
| | 266 | 79 | | $3.6 \times 10^7$ | | | | | 2 | $3.6 \times 10^2$ |
| | 280 | 79 | | $3.6 \times 10^7$ | | | | | | |
| 2B | 224 | 77 | $9.5 \times 10^6$ | $3.1 \times 10^7$ | $3.9 \times 10^7$ | 14.7 | 11.9 | 6.5 | | |
| | 266 | 81 | | $3.9 \times 10^7$ | | | | | 32 | $9.4 \times 10^3$ |
| | 280 | 83 | | $4.7 \times 10^7$ | | | | | | |
| 2A | 224 | 69 | $9.5 \times 10^6$ | $2.1 \times 10^7$ | $3 \times 10^7$ | 14.7 | 12.2 | 8.1 | 74.3 | $5.7 \times 10^4$ |
| | 266 | 80 | | $3.7 \times 10^7$ | | | | | | |
| | 280 | 77 | | $3.2 \times 10^7$ | | | | | | |

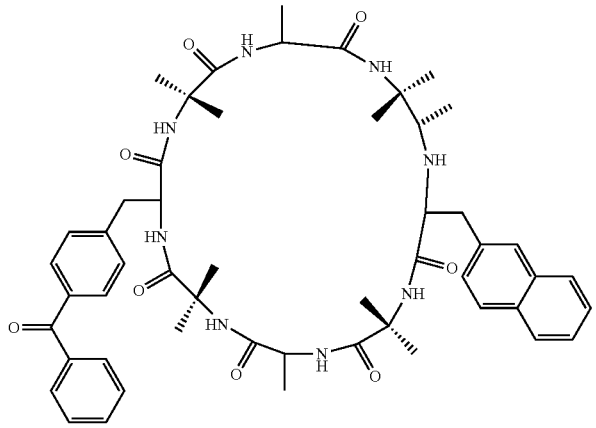

1A

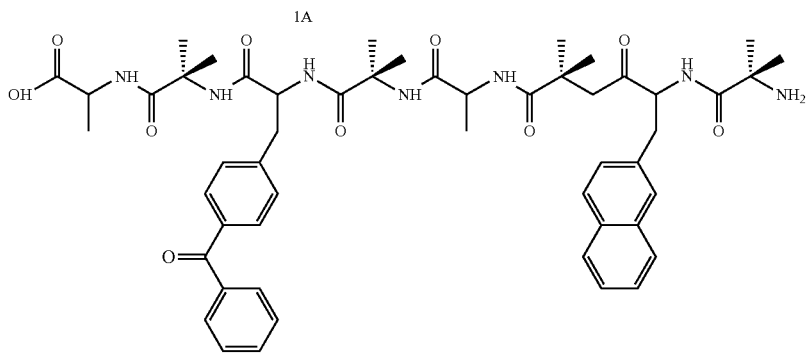

1B

TABLE 9-continued

1: SSET and TTET rate constants for bichromophoric peptides

| Compound | $\lambda_{ex}$ (nm) | $E_{SSET}$ | $k_s$ of donor ($s^{-1}$) | $k_{SSET}$ ($s^{-1}$) | $k_{SSET}(s^{-1})$ (Average) | $R_0$ (A) | R (A) | $R_{model}$ (A) (Average) | $E_{TTET}$ | $k_{TTET}$ ($s^{-1}$) |
|---|---|---|---|---|---|---|---|---|---|---|

2A

2B

Table 10 in FIG. 18 lists some additional endogenous photoactivatable molecules.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

The energy modulation agent may be preferably directed to the desired site (e.g. a tumor) by systemic administration to a subject. For example, a light-emitting energy modulation agent may be concentrated in the tumor site by physical insertion or by conjugating the light emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the light-emitting source in a specific target tumor.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

In a preferred embodiment, the photoactivatable agent, upon activation, binds to DNA or RNA or other structures in a cell. Other means for interaction of the photoactivatable agent with the DNA or RNA are possible, and this invention is not limited to any particular theory of interaction. Regardless, the activated energy state of the photoactivatable agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the invention administers a photoactivatable agent to a patient, stimulates the photoactivatable agent to induce cell damage (or kill), and generates an auto vaccine effect.

Another advantage of using phosphors with visible emissions and mixtures thereof is that side effects of UV induced damage can be greatly reduced by limiting the production of free radicals, singlet oxygen, superoxide, hydroxyl radicals, thiyl radicals, hydrogen peroxide, and other highly reactive groups that are known to damage healthy cells. Furthermore, additional additives, such as antioxidants, may be used to further reduce undesired effects of irradiation.

Energy from light emitted from the phosphors, scintillators, fluorescent materials, and combinations and agglomerations thereof, with or without plasmonic inducing agents, of the invention may be transferred from one molecule to another (intermolecular transfer) or from one part of a molecule to another part of the same molecule (intramolecular transfer). For example, the electromagnetic energy may be converted into thermal energy. Energy transfer processes are also referred to as molecular excitation.

Additionally, energy modulation agents may be included in the medium to be treated. The energy modulation agents may upon receiving of light from the phosphors or scintillators of the invention re-emit a light specific to a desired photo-driven reaction. Energy modulation agents can have a very short energy retention time (on the order of fs-ns, e.g. fluorescent molecules) whereas others may have a very long half-life (on the order of seconds to hours, e.g. luminescent inorganic molecules or phosphorescent molecules). Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent of the invention such as the phosphors, scintillators, fluorescent materials, down conversion or up conversion media and combinations and agglomerations thereof, with or without plasmonic inducing agents may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as an antibody, nucleic acid, peptide, a lipid, chitin or chitin-derivative, a chelate, a surface cell receptor, molecular imprints, aptamers, or other functionalized carrier that is capable of concentrating the UV-A emitting source in a specific target tumor.

Additionally, the energy modulation agent can be used alone or as a series of two or more energy modulation agents wherein the energy modulation agents provide an energy cascade from the light of the phosphors or scintillators. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

In general, photoactivatable agents may be stimulated by light of from the phosphors or scintillators of the invention, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the invention administers a photoactivatable agent to a patient, stimulates the photoactivatable agent by light from the phosphors or scintillators of the invention to induce cell damage, and generates an auto vaccine effect. In one further preferred embodiment, the photoactivatable agent is stimulated via resonance energy transfer.

One advantage is that multiple wavelengths of emitted radiation from the phosphors or scintillators or up conversion or down conversion media of the invention may be used to selectively stimulate one or more photoactivatable agents or energy modulation agents capable of stimulating the one or more photoactivatable agents. The energy modulation agent can be stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

In another embodiment, the invention includes the administration of the activatable pharmaceutical agent, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ via an internal conversion (IC) process. IC processes are transitions between states of the same multiplicity. The molecule subsequently deactivates to the lowest vibronic levels of $S_{n-1}$ via VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of energy needed to induce local damage of the diseased cells, making therapy method less invasive.

Various Light-Activated Pharmaceuticals Activatable with the Energy Modulation Agents of the Invention:

Another object of the invention is to treat a condition, disorder or disease in a subject using an activatable pharmaceutical agent activated using the above-described energy modulation agents (phosphors, scintillators, fluorescent materials, and combinations and agglomerations thereof) with or without plasmonic inducing agents.

In one embodiment, the invention uses ferritin or apoferritin to both encapsulate PA and energy modulation agent-PA systems and also target tumor cells selectively for enhanced drug delivery and subsequent phototherapy. In this case, no additional bioreactors are needed.

The photoactive drug molecules can be given to a patient by oral ingestion, skin application, or by intravenous injection. The photoactive drug molecules drugs travel through the blood stream inside the body towards the targeted tumor (either via passive or active targeting strategies). The invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder can be treated which has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not necessarily have to be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in one embodiment of the invention, it is most preferable to avoid production of an amount of singlet oxygen that would cause cell lysis, due to its indiscriminate nature of attack, lysing both target cells and healthy cells. Accordingly, it is most preferred in the invention that the level of singlet oxygen production caused by the initiation energy used or activatable pharmaceutical agent upon activation be less than level needed to cause cell lysis.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such medical agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions (suitable for injectable use) include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (drug and/or energy modulation agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions of the drug and/or energy modulation agent can generally include an inert diluent or an edible carrier. The oral compositions can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds (drug and/or energy modulation agent) are delivered in the form of an aerosol spray from pressured container or dispenser which contains a suitable propellant, e.g., a gas such as carbon dioxide, or a nebulizer.

Systemic administration of the drug and/or energy modulation agent can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds (drug and/or energy modulation agent) are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds (drug and/or energy modulation agent) are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, the entire contents of which are incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents (drug and/or energy modulation agents) are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located.

It will also be understood that the order of administering the different agents is not particularly limited. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of this approach is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

The methods described here can be used alone or in combination with other therapies for treatment of cell proliferation disorders. Additionally, the methods described can be used, if desired, in conjunction with recent advances in chronomedicine, such as that detailed in Giacchetti et al, *Journal of Clinical Oncology*, Vol 24, No 22 (August 1), 2006: pp. 3562-3569, the entire contents of which are incorporated herein by reference.

In chronomedicine, it has been found that cells suffering from certain types of disorders, such as cancer, respond better at certain times of the day than at others. Thus, chronomedicine could be used in conjunction with the present methods in order to augment the effect of the treatments of the invention.

Photo-Treatment with the Energy Modulation Agents of the Invention

Another object of the invention is to treat a condition, disorder or disease in a subject using an activatable pharmaceutical agent activated using the above-described energy modulation agents (phosphors, scintillators, fluorescent materials, down conversion or up conversion media and/or combinations and agglomerations thereof) with or without plasmonic inducing agents. Exemplary conditions, disorders or diseases may include, but are not limited to, cancer, autoimmune diseases, cardiac ablasion (e.g., cardiac arrhythmiand atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthrisis, joint conditions, lymph node conditions, and cognitive and behavioral conditions.

Accordingly, the invention in one embodiment provides methods utilizing the principle of energy transfer to and among molecular agents to control delivery and activation of pharmaceutically active agents such that delivery of the desired pharmacological effect is more focused, precise, and effective than the conventional techniques. Here, the energy transfer can include light from the phosphors or scintillators.

Although not intending to be bound by any particular theory or be otherwise limited in any way, the following theoretical discussion of scientific principles and definitions are provided to help the reader gain an understanding and appreciation of the invention.

As used here, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division.

As used here, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

As used here, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy which otherwise contributes to heating the environment in vicinity of the light emission. In various embodiments, the energy modulation agents receive higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). The energy modulation agent materials can preferably include any materials that can absorb X ray and emit light in order to excite the PA molecule.

Quantum dots, semiconductor nanostructures and various materials related to quantum dots, semiconductor materials, etc. can be used as energy modulation agents. Scintillator materials can be used as energy modulation agents. Various Suitable energy modulation agents include, but are not limited to, a phosphor, a scintillator, a biocompatible fluorescing metal nanoparticle, fluorescing dye molecule, gold nanoparticle, quantum dots, such as a water soluble quantum dot encapsulated by polyamidoamine dendrimers, a luciferase, a biocompatible phosphorescent molecule, a combined electromagnetic energy harvester molecule, an up-converter, a lanthanide chelate capable of intense luminescence, metals (gold, silver, etc); semiconductor materials; materials that exhibit X-ray excited luminescence (XEOL); organic solids, metal complexes, inorganic solids, crystals, rare earth materials (lanthanides), polymers, and materials that exhibit excitonic properties.

In a preferred embodiment, the energy modulation agents include down converters (such as for example phosphors which can convert x-ray or other high energy photon or particle into visible light. These down converters when used in combination can activate a variety of UV-stimulated photoreactions as well as activate any visible light activated reactions.

Examples of luminescing particles (down converters) can include gold particles (such as for example the nanoparticles of gold), BaFBr:Eu particles, CdSe particles, $Y_2O_3:Eu^{3+}$ particles, and/or other known stimulated luminescent materials such as for example $ZnS: Mn^{2+}$; $ZnS: Mn^{2+},Yb^{3+}$, $Y_2O_3: Eu^{3+}$; $BaFBr:Tb^{3+}$; and $YF_3:Tb^{3+}$. More specific examples of the downconverters include, but are not limited to: $BaFCl:Eu^{2+}$, $BaSO_4:Eu^{2+}$, $LaOBr:Tm^{3+}$, $YTaO_4$, $YTaO_4$: Nb (*), $CaWO_4$, $LaOBr:Tb^{3+}$, $Y_2O_2S:Tb^{3+}$, ZnS:Ag, (Zn, Cd)S:Ag, $Gd_2O_2S:Tb^{3+}$, $La_2O_2S:Tb^{3+}$.

Table 11 shows a listing of normally UV-emitting phosphors and their respective known peak emissions. Combinations of one or more of these phosphors with or without the "visible" phosphors described above can be used in this invention.

TABLE 11

| # | Phosphor | Emission Spectrum Peak Emission (nm) | X-ray Absorption | | | Microstructure | | Hygroscopic |
|---|---|---|---|---|---|---|---|---|
| | | | Emiss Eff (%) | Eff (Z) | K-edge (keV) | Specific Gravity | Crystal Structure | |
| 1 | $BaFCl:Eu^{2+}$ | 380 | 13 | 49.3 | 37.38 | 4.7 | Tetragonal | N |
| 2 | $BaSO_4-:Eu^{2+}$ | 390 | 6 | 45.5 | 37.38 | 4.5 | Rhombic | N |
| 3 | $LaOBr:Tm^{3+}$ | 360, 460 | 14 | 49.3 | 38.92 | 6.3 | Tetragonal | N |
| 4 | $YTaO_4$ | 337 | | 59.8 | 67.42 | 7.5 | Monolithic | N |
| 5 | $YTaO_4:Nb$ (*) | 410 | 11 | 59.8 | 67.42 | 7.5 | Monolithic | N |
| 6 | $CaWO_4$ | 420 | 5 | 61.8 | 69.48 | 6.1 | Tetragonal | N |
| 7 | $LaOBr:Tb^{3+}$ | 420 | 20 | 49.3 | 38.92 | 6.3 | Tetragonal | N |
| 8 | $Y_2O_2S:Tb^{3+}$ | 420 | 18 | 34.9 | 17.04 | 4.9 | Hexgonal | N |
| 9 | ZnS:Ag | 450 | 17 | 26.7 | 9.66 | 3.9 | Hexgonal | N |
| 10 | (Zn, Cd)S:Ag | 530 | 19 | 38.4 | 9.66/26.7 | 4.8 | Hexgonal | N |
| 11 | $Gd_2O_2S:Tb^{3+}$ | 545 | 13 | 59.5 | 50.22 | 7.3 | Hexgonal | N |
| 12 | $La_2O_2S:Tb^{3+}$ | 545 | 12.5 | 52.6 | 38.92 | 6.5 | Hexgonal | N | scintillator materials can be used as energy modulation agents since they absorb X-ray and emit luminescence emission, which can be used to excite the PA system. For example, single crystals of molybdates can be excited by X-ray and emit luminescence around 400 nm [Mirkhin et al, Nuclear Instrum. Meth. In Physics Res. A, 486, 295 (2002, the entire contents of which are incorporated herein by reference]. For example CdS (or CsCl) exhibit luminescence when excited by soft X-ray [Jaegle et al, J. Appl. Phys., 81, 2406, 1997, the entire contents of which are incorporated herein by reference]. XEOL materials such as lanthanides or rare earth materials can be used as energy modulation agents.

In addition to the inorganic compounds described here for down converters, organic compounds can be used to achieve the same purpose described in the current invention. Anthracene and anthracene based compounds can be used to achieve the objective of the invention (curing with no line of sight and thermal energy).

Anthracene exhibits a blue (400-500 nm peak) fluorescence under ultraviolet light. Furthermore, it was found that antharacene exhibits fluorescence under X-Ray energy. Anthracene light output was measured to be 40% to 50% of NaI(Tl).

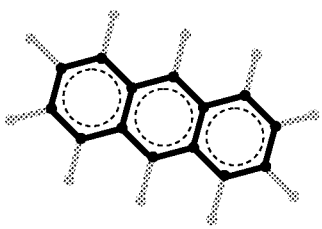

Various plastic scintillators, plastic scintillator fibers and related materials are made of polyvinyltoluene or styrene and fluors. These and other formulations are commercially available, such as from Saint Gobain Crystals, as BC-414, BC-420, BC-422, or BCF-10.

TABLE 12

| Phosphor | Product Reference | Peak Emission (nm) |
|---|---|---|
| Organic | BC-414 | 392 |
| Organic | BC-420 | 391 |
| Organic | BC-422 | 370 |

Other polymers are able to emit in the visible range and these include:

TABLE 13

| Phosphor (Fiber Forms) | Product Reference | Peak Emission (nm) | # of Photons Per MeV |
|---|---|---|---|
| Organic | BCF-10 | 432 | 8000 |
| Organic | BC-420 | 435 | 8000 |
| Organic | BC-422 | 492 | 8000 |

Furthermore, the organic compounds that can convert X-ray to UV energy can be incorporated into synthetic polymer chains. These chains can be used as the base resin system for a cross-linking adhesive; hence leading to the formation of a new set of X-ray activatable resin systems.

A more extensive list of phosphors suitable for this invention is included below in Table 14. Combinations of one or more of these phosphors with or without the "visible" phosphors described above can be used in this invention.

Furthermore, the luminescing particles (down converters, mixtures of down converters, up converters, mixtures of up converters, and combinations thereof) of the invention described here can be coated with insulator materials such as for example silica which will reduce the likelihood of any chemical interaction between the luminescing particles and the medium. For biological applications of inorganic nanoparticles, one of the major limiting factors is their toxicity.

Generally speaking, all semiconductor nanoparticles are more or less toxic. For biomedical applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable energy modulation agents which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, cesium iodide, bismuth germanate, cadmium tungstate, and CsBr doped with divalent Eu.

TABLE 14

| Phosphor | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| Zn3(PO4)2:Tl+ | 310 | | | | | | N |
| BaF2 | 310 | | | | | | Slightly |
| CsI | 315 | | | | | | N |
| Ca3(PO4)2:Tl+ | 330 | | | | | | N |
| YTaO4 | 337 | | 59.8 | 67.42 | 7.5 | Monolithic | N |
| CsI:Na | 338 | | | | | | Y |
| BaSi2O5:Pb2+ | 350 | | | | | | N |
| Borosilicate | 350 | | | | | | N |
| LaCl3(Ce) | 350 | | | | | | Y |
| SrB4O7F:Eu2+ | 360 | | | | | | N |
| RbBr:Tl+ | 360 | | | | | | ? |
| (Ba, Sr, MgMg)3Si2O7:Pb2+ | 370 | | | | | | N |
| YAlO3:Ce3+ | 370 | | | | | | N |
| BC-422 | 370 | | | | | Organic | ? |
| BaFCl:Eu2+ | 380 | 13 | 49.3 | 37.38 | 4.7 | Tetragonal | N |
| BaSO4-:Eu2+ | 390 | 6 | 45.5 | 37.38 | 4.5 | Rhombic | N |
| BaFBr:Eu2+ | 390 | | | | | | ? |
| BC-420 | 391 | | | | | Organic | ? |
| BC-414 | 392 | | | | | Organic | ? |
| SrMgP2O7:Eu2+ | 394 | | | | | | N |
| BaBr2:Eu2+ | 400 | | | | | | N |
| (Sr, Ba)Al2Si2O8:Eu2+ | 400 | | | | | | N |
| YTaO4:Nb (*) | 410 | 11 | 59.8 | 67.42 | 7.5 | Monolithic | N |
| Y2SiO5:Ce3+ | 410 | | | | | | N |
| CaWO4 | 420 | 5 | 61.8 | 69.48 | 6.1 | Tetragonal | N |

TABLE 14-continued

| Phosphor Color | Emission Spectrum Peak Emission (nm) | Emiss Eff (%) | Eff (Z) | X-Ray Absorption K-edge (keV) | Specific Gravity | Crystal Structure | Hygroscopic |
|---|---|---|---|---|---|---|---|
| LaOBr:Tb3+ | 420 | 20 | 49.3 | 38.92 | 6.3 | Tetragonal | N |
| Y2O2S:Tb3+ | 420 | 18 | 34.9 | 17.04 | 4.9 | Hexgonal | N |
| Lu2SiO5:Ce3+ | 420 | | | | | | N |
| Lu1.8Y0.2SiO5:Ce | 420 | | | | | | N |
| ZnS:Ag | 450 | 17 | 26.7 | 9.66 | 3.9 | Hexgonal | N |
| CdWO4 | 475 | | | | | | Slightly |
| Bi4Ge3O12 (BGO) | 480 | | | | | | N |
| (Zn, Cd)S:Ag | 530 | 19 | 38.4 | 9.66/26.7 | 4.8 | Hexgonal | N |
| Gd2SO2S:Tb3+ | 545 | 13 | 59.5 | 50.22 | 7.3 | Hexgonal | N |
| La2O2S:Tb3+ | 545 | 12.5 | 52.6 | 38.92 | 6.5 | Hexgonal | N |
| Y3Al5O12 (Ce) | 550 | | | | | | N |
| LaOBr:Tm3+ | 360, 460 | 14 | 49.3 | 38.92 | 6.3 | Tetragonal | N |
| CaF2(Eu) | 435/300 | | | | | | N |

In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

While many of the energy modulation agents of the invention are down conversion agents (i.e. where higher energy excitation produces lower energy emission), U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 including the ZnS as well as $Er^{3+}$ doped $BaTiO_3$ nanoparticles and $Yb^{3+}$ doped $CsMnCl_3$ are suitable in various embodiments of the invention.

Further, in various embodiments of the invention, up converters can be used in combination with the down converters (or mixtures of down converters) or in combination with various up converters. Various up converters suitable for this invention include CdTe, CdSe, ZnO, CdS, $Y_2O_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}Mn_xSe_y$, $Cd_{1-x}Mn_xTe_y$, $Pb_{1-x}Mn_xS_y$, $Pb_{1-x}Mn_xSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq 1$, and $0<y\leq 1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; $0<x\leq 1$, $0<y\leq 1$, $0<z\leq 1$). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . $0<z\leq 1$, $0<q\leq 1$).

Indeed, some nanoparticles such as $ZnS:Tb^{3+}$, $Er^{3+}$; ZnS: $Tb^{3+}$; $Y_2O_3:Tb^{3+}$; $Y_2O_3:Tb^{3+}$, $Er3+$; $ZnS:Mn^{2+}$; ZnS:Mn, $Er^{3+}$ are known in the art to have two functions, capable of functioning for both down-conversion luminescence and upconversion luminescence.

To reduce the toxicity or to make these nanoparticles bio-inert or biocompatible, one embodiment of the invention described here coats these nanoparticles with silica. Silica is used as a coating material in a wide range of industrial colloid products from paints and magnetic fluids to high-quality paper coatings. Further, silica is both chemically and biologically inert and also is optically transparent. Other coatings suitable for this invention include a polymethyl methacrylate (PMMA) coating and an ethyl-cellulose coating.

Various exemplary uses of energy modulation agents as down converters or up converters or combination of various down converters or combination of various up converters are described below especially with reference to those agents in the medium directly or indirectly activated by light from the energy modulation agents of the invention.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one embodiment, the activatable pharmaceutical agent is capable of chemically binding to the DNA or mitochondria a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

The initiation energy source can be any energy source capable of providing energy at a level sufficient to cause cellular changes directly or via modulation agent which transfer the initiation energy to energy capable of causing the predetermined cellular changes. Also, the initiation energy source can be any energy source capable of providing energy at a level sufficient activate the activatable agent directly, or to provide the energy to a modulation agent with the input needed to emit the activation energy for the activatable agent (indirect activation). In one embodiment, the initiation energy is capable of penetrating completely through the subject. Within the context of the invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, UV light, visible light, IR radiation, x-rays, gamma rays, electron beams, microwaves and radio waves.

An additional embodiment of the invention is to provide a method for treatment of a condition, disease or disorder by the in-situ generation of energy in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to the subject externally, which is converted in-situ to a different energy (of lower or higher energy than that applied), through the use of one or more energy modulation agents.

A further embodiment of the invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying an initiation energy which, directly or indirectly, activates the pharmaceutical agent. As noted elsewhere in this application, this initiation energy can be of any type, so long as it can be converted to an energy suitable for activating the pharmaceutical compound. In addition to applying this initiation energy, in this embodiment of the invention, an energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the invention methods to enhance the onset of apoptosis.

In one embodiment, heat can be generated by any desired manner. Preferably, the heat can be generated using the application of microwaves or NIR energy to the target structure or by the use of use of nanoparticles of metal or having metal shells. Heat can also be generated by the absorption of light from the phosphors or scintillators of the invention. Alternatively, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med. 48(3), 437-444 (2007).)

In another embodiment, the patient's own cells are removed and genetically modified to provide photonic emissions. For example, tumor or healthy cells may be removed, genetically modified to induce bioluminescence and may be reinserted at the site of the disease or condition to be treated. The modified, bioluminescent cells may be further modified to prevent further division of the cells or division of the cells only so long as a regulating agent is present.

In a further embodiment, a biocompatible emitting source, such as a fluorescing metal nanoparticle or fluorescing dye molecule or the phosphors or scintillators of the invention, is selected that emits in the UV-A band. The UV-A emitting source is directed to the site of a disease or condition. The UV-A emitting source may be directed to the site of the disease or condition by systemically administering the UV-A emitting source. Preferably, the UV-A emitting source is concentrated in the target site, such as by physical insertion or by conjugating the UV-A emitting molecule with a specific carrier that is capable of concentrating the UV-A emitting source in a specific target structure, as is known in the art.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into a target site either by systemic administration or direct insertion into the region of the target site. Alternatively, some of these materials can be activated, with the energy being "stored" in the activated material, until emission is stimulated by application of another energy. For example, see the discussion in U.S. Pat. No. 4,705,952 (incorporated by reference in its entirety) regarding infrared-triggered phosphors.

Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference.

In one embodiment, the use of light (e.g. light emitted from the phosphor or scintillator particles or combination thereof) for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence can be used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures (e.g., the gas containing upconverters of the invention) to irradiate the target structure, after exposure to the lanthanide chelate and a photoactive molecule.

In another embodiment, a biocompatible, endogenous fluorophore emitter can be selected to stimulate resonance energy transfer to a photoactivatable molecule. A biocompatible emitter (e.g. the phosphors or scintillators) with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphyrin) is activated by light in the near infrared region (732 nm). Absorption at this wavelength has the advantage of potentially deeper penetration into tissues, compared with the amount of light used to activate other photosensitizers. Lutetium texaphyrin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the inventive approach may be used with any source for the excitation an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Light emission can stimulate the activation of an activatable molecule, such as 8-MOP. In one example, light emission from the phosphors or scintillators of the invention is directed at a solid tumor and stimulates, directly or indirectly, activation of 8-MOP.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the invention.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the invention also provides methods for producing an autovaccine, including: (1) providing a population of targeted cells; (2) treating the cells ex vivo with a psoralen or a derivative thereof; (3) activating the psoralen with an initiation energy source to induce a predetermined change in a target structure in the population of the target cells; and (4) returning the treated cells back to the host to induce an autovaccine effect against the targeted cell, wherein the treated cells cause an autovaccine effect.

Photobiomodulation:

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration and treatment interval is complex and sometimes controversial with different diseases, injuries and dysfunctions needing different treatment parameters and techniques.

In one embodiment of this invention, the above-described energy modulation agents (phosphors, scintillators, fluorescent materials, up conversion and down conversion media, and combinations and/or agglomerations thereof) with or without plasmonic inducing agents provide the light for producing photobiomodulation. Certain wavelengths of light emitted from the phosphor or scintillator configurations of the invention at certain intensities will, for example, aid tissue regeneration, resolve inflammation, relieve pain and boost the immune system. Observed biological and physiological effects to be expected include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). The phosphor or scintillator configurations of the invention can be programmed or instructed to deliver light comparable to that of known photobiomodulation treatments. For example, the phosphor or scintillator configurations of the invention can be programmed or instructed to deliver light with an average power typically in the range of 1-500 mW; or with peak power and short pulse width in the range of 1-100 W with 200 ns pulse widths. In this example, the average beam irradiance would typically be 10 $mW/cm^2$-5 $W/cm^2$. The phosphor or scintillator configurations of the invention can be programmed or instructed to or configured to deliver light at a wavelength typically in the range 600-1000 nm. The red-to-near infrared (NIR) region is preferred for photobiomodulation. Other wavelengths may be also used, e.g., UV light for neurons and green light for prostate tissue. Maximum biological responses have been seen to occur from prior work when the tissues were irradiated at 620, 680, 760, and 820-830 nm (Karu T I, et al., (1998).

In another embodiment, a plurality of sources for supplying electromagnetic radiation energy or energy transfer are provided by one or more molecules administered to a patient. The molecules may emit stimulating radiation in the correct band of wavelength to stimulate the target structure directly or to simulate the photoactivatable agents, or the molecules may transfer energy by a resonance energy transfer or other mechanism directly to the target structure or the photoactivatable agent or indirectly by a cascade effect via other molecular interactions.

The phenomenon of ultra-weak emission from cellular systems has been a topic of various inquiries since the 1900s. In the 1970s, this area of research was investigated by a number of investigators. The presence of biological radiation from a variety of cells was later investigated by several research groups in Europe and Japan using low-noise, sensitive photon-counting detection systems [B. Ruth and F.-A. Popp, "Experimentelle Untersuchungen zur ultraschwachen Photonenemission biologischer Systeme," *Z. Naturforsch., A: Phys. Sci.* 31c, 741-745, 1976; T. I. Quickenden and S. S. Que-Hee, "The spectral distribution of the luminescence emitted during growth of the yeast *Saccharomyces cerevisiae* and its relationship to mitogenetic radiation," *Photochem. Photobiol.* 23, 201-204, 1976; H. Inaba, Y. Shimizu, Y. Tsuji, and A. Yamagishi, "Photon counting spectral analysing system of extra-weak chemi- and bioluminescence for biochemical applications," *Photochem. Photobiol.* 30, 169-175, 1979]. Popp and coworkers suggested the evidence of some 'informational character' associated with the ultra-weak photon emission from biological systems, often referred by Popp as "bio-photons". Other studies reported ultra-weak photon emission from various species including plant, and animals cells [H. J. Niggli, C. Scaletta, Y. Yan, F.-A. Popp, and L. A. Applegate, "Ultraweak photon emission in assessing bone growth factor efficiency using fibroblastic differentiation," *J. Photochem. Photobiol., B*, 64, 62-68, 2001;]. Results of experiments of UV-irradiated skin fibroblasts indicated that repair deficient xeroderma pigmentosum cells show an efficient increase of ultraweak photon emission in contrast to normal cells. [H. J. Niggli, "Artificial sunlight irradiation induces ultraweak photon emission in human skin fibroblasts," *J. Photochem. Photobiol., B* 18, 281-285 (1993)].

A delayed luminescence emission was also observed in biological systems [F.-A. Popp and Y. Yan, "Delayed luminescence of biological systems in terms of coherent states," *Phys. Lett. A* 293, 93-97 (2002); A. Scordino, A. Triglia, F. Musumeci, F. Grasso, and Z. Rajfur, "Influence of the presence of Atrazine in water on in-vivo delayed luminescence of acetabularium acetabulum," *J. Photochem. Photobiol., B*, 32, 11-17 (1996); This delayed luminescence was used in quality control of vegetable products [A. Triglia, G. La Malfa, F. Musumeci, C. Leonardi, and A. Scordino, "Delayed luminescence as an indicator of tomato fruit quality," *J. Food. Sci.* 63, 512-515 (1998)] or for assessing the quality or quality changes of biological tissues [Yu Yan, Fritz-Albert Popp*, Sibylle Sigrist, Daniel Schlesinger, Andreas Dolf, Zhongchen Yan, Sophie Cohen, Amodsen Chotia, "Further analysis of delayed luminescence of plants", *Journal of Photochemistry and Photobiology B*: Biology 78, 235-244 (2005)].

It was reported that UV excitation can further enhance the ultra-weak emission and a method for detecting UV-A-laser-induced ultra-weak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the invention, upon applying an initiation energy from at least one source to a target structure in a subject in need of treatment, the initiation energy contacts the target structure and induces a predetermined change in said target structure in situ, wherein the predetermined change is the enhancement of energy emission from the target, which then mediates, initiates or enhances a biological activity of other target structures in the subject, or of a second type of target structure (e.g., a different cell type).

In another embodiment, the initiation energy can itself be energy emitted by at least one cell excited by metabolic processes or some other internal or external trigger, and said applying is conducted via cell-to-cell energy transfer. There are those that maintain that the health of the body depends on certain bioelectric vibrations that are susceptible to chemical or physical toxic factors. Fröhlich notes that there are coherent electric vibrations in the frequency range 100 GHz to 1 THz, excited in cells by metabolic processes (see Fröhlich H. Coherent electric vibrations in biological systems and the cancer problem, IEEE Transactions on Microwave Theory and Techniques, Vol. MTT-26, No. 8, August, 1978, pp 613-617). This idea is based on observation of the inhibition or stimulation of the growth of yeast and bacteria functions of the applied frequency, showing very stable and repetitive resonances. If such vibrational states are indeed metabolically excited, then they should be manifested in Raman spectroscopy. Actually, their existence has been demonstrated during periods of metabolic activity of lysozyme and *E. coli* (700 GHz to 5 THz). Emissions have also been observed at lower frequencies (150 GHz or less). These vibrations occur in the tissue of higher organisms and they have been hypothesized exercise some control on cellular growth (see also S. J. Webb et al, Nature, Vol. 218, Apr. 27, 1968, pp. 374-375; and S. J. Webb et al et al, Nature Vol. 222, Jun. 21, 1969, pp. 1199-1200). Cancerization could result from a modification of these vibrations by the invasion of foreign molecules, e.g., the presence of free electrons in the condition bands of proteins. There is some evidence for the presence of double spectral lines at 1.5 and 6 THz in breast carcinoma, which may be an indication of an interaction between normal cellular vibrations and free electrons. In such coherent frequency communication between cells, it is believed that the medium through which the communication is transmitted is the water within and around the cells (see Smith, Coherent Frequencies, Consciousness and the Laws of Life, 9$^{th}$ International Conference CASYS '09 on *Computing Anticipatory Systems*, Liege, Belgium, Aug. 3-8, 2009).

Accordingly, in a further embodiment of the invention, the initiation energy is an energy capable of triggering an altered metabolic activity in one or more cells, preferably in the 100 GHz to 10 THz region, and is applied directly to one or more cells, to trigger the cell(s) to undergo altered metabolic activity, and optionally, to further trigger emissions from the cell(s) to thereby cascade the effects of the emissions to other similar or different cell types adjacent thereto, in essentially a triggered entry into the natural emissions process described above, preferably where the medium through which the emissions are communicated is water-based, most preferably where the medium is the water contained within and surrounding the cells.

Indeed, FIG. 5B as described above shows the combination of x-ray and microwave energy (e.g., 100 GHz to 10 THz region) applied to a target site. In this embodiment, the x-ray irradiation triggers light emission from energy modulation agents in the medium (phosphors, scintillators, fluorescent materials, and combinations and agglomerations thereof) with or without plasmonic inducing agents to activate photoactivatable agents in the medium (as discussed above), and the microwave and or RF radiation can cause the alignment of dipoles or alter the mass transport across ionic channels which in turn could trigger the cell(s) to undergo altered metabolic activity, or optionally, to further trigger emissions from the cell(s) to thereby cascade the effects of the emissions to other similar or different cell types adjacent thereto (as described above) to complement the photoactivated photoactivatable agents in the medium.

While not bound to the particular following theory, a photoacceptor first absorbs the light used for the irradiation. After promotion of electronically excited states, primary molecule processes from these states can lead to a measurable biological effect (via secondary biochemical reaction, or photosignal transduction cascade, or cellular signaling) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors. The phosphor configurations of the invention can be programmed or instructed to or configured to deliver light at these wavelengths.

Clinical applications of photobiomodulation include, for example, treating soft tissue and bone injuries, chronic pain, wound healing and nerve and sensory regeneration/restoration, and possibly even resolving viral and bacterial infections, treating neurological and psychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment of inflammation, where the anti-inflammatory effect of location-and-dose-specific laser irradiation produces similar outcomes as NSAIDs, but without the potentially harmful side-effects (Bjordal J M, Couppé C, Chow R T, Tunér J, Ljunggren E A (2003). "A systematic review of low level laser therapy with location-specific doses for pain from chronic joint disorders". The Australian journal of physiotherapy 49(2): 107-16). The phosphor configurations of the invention can be programmed or instructed to or configured to deliver light at the wavelengths and illuminations reported in this work.

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)). The phosphor or scintillator configurations of the invention can be programmed or instructed to or configured to deliver light at these NIR wavelengths.

It has also been shown that light has both inductive and inhibitory effect on cell growth and division in a red tide flagellate, Chattonellantique (Nemote Y., Plant and Cell Physiol., 26(4):669-674 (1985)). The phosphor or scintillator configurations of the invention can be programmed or instructed to or configured to deliver light at these wavelengths.

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells viabsorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)). The phosphor configurations of the invention can be programmed or instructed to or configured to deliver light at these wavelengths.

When photoacceptors absorb photons, electronic excitation followed by photochemical reactions occurring from lower excitation states (first singlet and triplet) takes place. It is also known that electronic excitation of absorbing centers alters their redox properties. Until yet, five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London). The phosphor or scintillator configurations of the invention can be programmed or instructed to or configured to deliver light at these wavelengths.

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes). The phosphor or scintillator configurations of the invention can be programmed or instructed to or configured to deliver light at these wavelengths.

Far red and NIR radiation have been shown to promote wound healing, e.g., infected, ischemic, and hypoxic wounds (Wong-Reley, WTT, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Another clinical application of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vase. Interv. Radiol., 18(6):811 (2007)). When the laser is slowly withdrawn, heat is applied to the vein walls, causing the vein to permanently close and disappear. The phosphor or scintillator configurations of the invention can be programmed or instructed to or configured to deliver light at these wavelengths.

The green light laser is a laser that vaporizes and removes the enlarged prostate tissue (Heinrich E., Eur. Urol., 52(6): 1632-7 (2007)). The significance of the color of the laser light (green) is that this results in absorption by hemoglobin which is contained within red blood cells and not absorbed by water. The procedure may also be known as laser prostatectomy or laser Transurethral resection of the prostate (TURP). The technique involves painting the enlarged prostate with the laser until the capsule of the prostate is reached. By relieving this portion of the prostate, patients are able to void much easier through a wide-open channel in the prostate. The procedure needs to be performed under general or spinal anesthesia. An advantage of the procedure is that even patients taking blood thinners (e.g., aspirin to prevent stroke) can be treated because there is less bleeding compared to a traditional surgery. The phosphor configurations of the invention can be programmed or instructed to or configured to deliver light at these wavelengths.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated, that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations. The phosphor or scintillator configurations of the invention can be programmed or instructed to or configured to deliver light at these wavelengths.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12): 1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE). The phosphor or scintillator configurations of the invention can be programmed or instructed to or configured to deliver light at these wavelengths.

Another type of photobiomodulation methods fall into two general categories: one set of methods uses light to uncage a compound that then becomes biochemically active, binding to a downstream effector; the other set uses light to activate a light-sensitive protein such as rhodopsin (ChR2), which can then excite the cell expressing the opsin. The phosphor or scintillator configurations of the invention can be programmed or instructed to or configured to deliver light for these types of photobiomodulation.

In the first set, this method involves applying "caged" chemicals to a sample and then using light to open the cage to invoke a reaction. Modified glutamate is useful for finding excitatory connections between neurons, since the uncaged glutamate mimics the natural synaptic activity of one neuron impinging upon another. This method is used for elucidation of neuron functions and imaging in brain slices using, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

In the second set which uses light to activate a light-sensitive protein such as rhodopsin (ChR2), which can then excite the cell expressing the opsin, It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulation involves genetic targeting ChR2 to neurons and light pulsing the neurons expressing ChR2 protein. The experiments have been conducted in vitro and in vivo in mice by in vivo deep-brain photostimulation using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulation in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via number of techniques including electroporation, DNA microinjection, viral delivery, liposomal transfection and calcium-phosphate precipitation.

Hence, in one embodiment of the invention, there is provided a system for modulating biological activity within a medium. The system includes a reduced-voltage x-ray source configured to generate x-rays from a peak applied cathode voltage, and a plurality of energy-converting particles in the medium which, upon radiation from the x-ray source, radiate at a lower energy than the x-ray source to alter the biological activity of the medium by photobiomodulation (as discussed above). The ranges of peak applied cathode voltage discussed above are applicable for photobiomodulation. The use of energy-converting particles radiate with an intensity at least 10 times greater than that of $Y_2O_3$, upon exposure of $Y_2O_3$ to the radiation from an initiation source (or with the other greater intensities described above) are applicable for photobiomodulation. The use of first and second energy-converting particles to produce a combination of emission from the first and second plurality of energy-converting particles to produce a spectrum for illumination in the medium (as described above) applicable for direct or indirect (via a photoactivated agent) photobiomodulation.

Photostimulation

A photostimulation technique involves chemical modification of ion channels and receptors to render them light-responsive. The above-described energy modulation agents (phosphors, scintillators, fluorescent materials, up conversion or down conversion and combinations and agglomerations thereof) with or without plasmonic inducing agents can be programmed or instructed to or configured to deliver light for this technique. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself. Here, the phosphor configurations of the invention can be programmed or instructed to or configured to deliver light for direct control of neuronal activity.

In living organisms, scientists have been able to cause worms, C. elegans, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. The mice resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients, but they don't know precisely why. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another potential application is experimenting with simulating neural communications. Because neurons communicate by generating patterns of signals-sometimes on and sometimes off like the 0s and 1s of binary computer code-flashing blue and yellow lights in these patterns could compel neurons to emit messages that correspond to real neural instructions. In the future, this could allow researchers to test and tune sophisticated neuron behaviors. Much farther down the road, the ability to artificially stimulate neural signals, such as movement instructions, could allow doctors to bridge blockages in damaged spinal columns, perhaps restoring some function to the limbs of paralyzed patients.

Finally, the technique could be useful in teasing out the largely unknown functioning of healthy brains. Here, the phosphor or scintillator configurations of the invention can be programmed or instructed to or configured to deliver light for control of these and other neuron activities.

Hence, in one embodiment of the invention, there is provided a system for modulating biological activity within a medium. The system includes a reduced-voltage x-ray source configured to generate x-rays from a peak applied cathode voltage at or below 80 kVp, and a plurality of energy-converting particles in the medium which, upon radiation from the x-ray source, radiate at a lower energy than the x-ray source to alter the biological activity of the medium by photostimulation (as discussed above). The ranges of peak applied cathode voltage discussed above are applicable for photobiomodulation. The use of energy-converting particles radiate with an intensity at least 10 times greater than that of $Y_2O_3$, upon exposure of $Y_2O_3$ to the radiation from an initiation source (or with the other greater intensities described above) are applicable for photostimulation. The use of first and second energy-converting particles to produce a combination of emission from the first and second plurality of energy-converting particles to produce a spectrum for illumination in the medium (as described above) applicable for direct or indirect (via a photoactivated agent) photostimulation.

Photocuring with the Energy Modulation Agents of this Invention:

In this application, the above-described energy modulation agents (phosphors, scintillators, fluorescent materials, up conversion or down conversion media and combinations and/or agglomerations thereof) with or without plasmonic inducing agents are provided and distributed into an uncured polymer based medium for the activation of photosensitive agents in the medium to promote cross-linking and curing of the polymer based medium. For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

In one embodiment, the phosphors or scintillators described above are coupled with the other X-ray down converting particles or other energy modulation agents. In one embodiment, the X-ray down converting particles or other energy modulation agents or metallic structures described herein permit X-ray irradiation to be used alone or in combination with the up converting particles.

Hence, in one embodiment of the invention, there is provided a system for curing a medium. The use of energy-converting particles radiate with an intensity at least 10 times greater than that of $Y_2O_3$, upon exposure of $Y_2O_3$ to the radiation from an initiation source (or with the other greater intensities described above) are applicable for photocuring. The use of first and second energy-converting particles to produce a combination of emission from the first and second plurality of energy-converting particles to produce a spectrum for illumination of the photoactivatable agents in the medium (as described above) are applicable for photocuring.

The photocuring can occur in medical prosthetic or implant devices. Accompanying the photocuring can be the sterilization of the medical prosthetic or implant devices in situ or prior to implantation. Furthermore, once implanted into the patient, the ultraviolet emitting energy modulation agents described above can used to periodically re-sterilize the medical prosthetic or implant device.

Drug Packaging

The reagents and chemicals useful for methods and systems of the invention may be packaged in kits to facilitate application of the invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation or initiation source.

Other Applications

The phosphors, scintillators, fluorescent materials, up conversion or down conversion media and combinations and/or agglomerations thereof with and without plasmonic agents described above can also be used in other applications as described in the related applications to produce desirable changes in the medium in which these energy modulation agents are present. For example, as described in related application U.S. Ser. No. 12/401,478, the phosphors, scintillators, fluorescent materials, and combinations and agglomerations thereof with and without plasmonic agents described above can be used for sterilization and cold pasteurization of fluids, can be used for sterilization of blood products, can be used for waste water detoxification, can be used for photostimulation to alter or change a physical property such as for example, surface modification of biopolymers photografting or photopolymerization or photooxidizing surfaces of the polymers, can be used for photodeactivation of processes such as in cultured food products, and can be used for photoactivated cross-linking and curing of polymers.

In one embodiment, the invention provides a method for producing a change in a medium or body, comprising:

(1) placing in a vicinity of the medium or body at least one energy modulation agent configured to induce change or changes in the modulating medium that in turn induces a change into the medium or body upon interaction with an initiation energy; and (2) applying the initiation energy from an energy source to the medium or body, wherein the energy source is a source of X-rays of 200 kVp or less, wherein the applied initiation energy interacts with the energy modulation agent to directly or indirectly produce the change in the medium or body by said emitted energy.

In a preferred embodiment of the invention, the energy modulation agent can be a single energy modulation agent, or a combination or two or more energy modulation agents. The energy modulation agents of the invention normally convert an incident radiation into a different energy by a variety of pathways. Preferably the conversion of the incident radiation is by upconversion or downconversion to a radiation having lower or higher energy. Each energy modulation agent typically has a predominant emission wavelength.

In a most preferred embodiment, the invention methods apply an initiation energy to these energy modulation agents, which convert the initiation energy to an emitted radiation at a first wavelength range (WR1), which is indicative of the one or more energy modulation agents used. Interestingly, the present inventors have found that it is also possible to use these one or more energy modulation agents to initiate reactions, such as photoreactions, activating photoactivatable agents, curing photocurable media, etc, even when the reactions being initiated are not normally initiated by the first wavelength range (WR1), but are rather normally known to be activated by a second wavelength range (WR2) that is distinct and different from WR1. This is particularly surprising since the energy modulation agents used in this particular embodiment of the invention are not known to emit radiation at any significant extent, intensity, spectral width, etc at the second wavelength range WR2 normally used to activate the reactions of interest.

While the inventors do not wish to be bound to any particular theory or proposed mechanism of action in such cases, it is speculated that the reactions are being activated by a previously unknown pathway, such as the synergistic combination of the emission spectra of the energy modulation agents to generate a wavelength of radiation not normally associated with either energy modulation agent being used, through some form of tunneling effect or photonic coupling (electronic or vibrational) effect to enhance or generate radiation at wavelengths not normally associated with either energy modulation agent, or a pathway not yet understood or known.

One possible mechanism involves the chemical interaction of combinations of phosphor materials in solution and/or under x-ray irradiation. Under x-ray exposure, some of the outer most atomic species of one phosphor might possibly leach into the media and diffuse through it to reach the surface(s) of another phosphor in the mixture. In effect, while the invention is not limited to such an effect, phosphors in a given mixture may ion exchange. In one aspect of this phenomena, the gradient for ion exchange can be enhanced under x-ray exposure. It is known that some phosphors can form solid solutions. It is well known that solid solutions are formed between $Al_2O_3$ and $Cr_2O_3$ where one cation ($Al^{3+}$) in the host lattice can be substituted by another cation ($Cr^{3+}$). The size difference between Cr and Al are known to shift the emission of Ruby ($Al_2O_3$) from red to green.

The leaching of ionic species out and ion exchange between different phosphors would predominantly taking place at the outer most atomic layers with the exchange likely confined to the outer most atomic layers. For this reason, any new emissions (i.e., emissions which do not normally belong to either one of the original phosphors) would be expected to be weak by virtue of the lower number of newly formed emission sites that would be confined to the outer-most atomic layer (the outer surfaces of the particles). Indeed, observations of x-ray induced fluorescence from certain combinations of normally visibly emitting phosphors described herein show the presence of comparatively weak emissions in the UV spectrum.

Regardless of the exact mechanism, the invention provides methods for producing a change in a medium after generation of energy inside the medium. In this method, an initiation energy source provides an initiation energy that penetrates the medium and induces a desired effect in the medium by way of interaction of the initiation energy with energy modulation agents (e.g., phosphors or combination of phosphors).

In one embodiment, the initiation energy source is applied directly or indirectly to the medium. In one embodiment, the initiation energy interacts with a previously supplied energy modulation agent which then activates the activatable agent.

FIG. 18 (as noted above) provides a list of photoactivatable agents that may be used as primary or secondary internal light sources. For example, the photoactivatable agents could be receptors of X-ray induced emissions from nanoparticles (to be discussed later) and which in turn emit a secondary light. In some mediums, it may be that the excitation wavelengths in are transparent to the particular medium and the emission wavelengths are highly absorbent (due to, for example, molecular or solid state band gap transitions). In those cases, the photoreactive agents would be the primary sources for internal light generation.

In various embodiments, the energy modulation agent (down converters, mixtures of down converters, up converters, mixtures of up converters, and combinations thereof) receives energy (from a source and re-emits the energy (e.g. UV-A and/or visible light). Some energy modulation agents may have a very short energy retention time (on the order of femtoseconds (fs), e.g. fluorescent molecules) whereas others may have a very long half-life (on the order of minutes to hours, e.g. luminescent or phosphorescent molecules).

Photoactivatable agents may be stimulated by an energy source through mechanisms such as irradiation, resonance energy transfer, exciton migration, ion-exchange, free radicals, electron injection, or chemical reaction, to an activated energy state that is capable of producing the predetermined change desired. One advantage is that wavelengths of emitted radiation may be used to selectively stimulate one or more photoactivatable agents or energy modulation agents capable of stimulating the one or more photoactivatable agents. The energy modulation agent is suitably stimulated at a wavelength and energy that causes little or no change to the medium.

Yet another example is that nanoparticles or nanoclusters of certain atoms may be introduced such that they are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a medium are capable of stimulating activation of photoactivatable agents disposed in a distant portion of the medium, so long as the distance does not greatly exceed $R_0$. For example, gold nanospheres having a size of 5 atoms of gold have been shown to have an emission band in the ultraviolet range, recently.

In one embodiment of this invention, medical bottle caps which need to be sterilized have under the base cap material a glued seal material which contacts the base of the medical bottle. Because steam autoclaves are insufficient for this purpose, one embodiment of the invention uses luminescing particles included in the adhesive layer when the seal material is applied to the bottle cap. Then, X-ray irradiation becomes capable of curing the adhesive and producing within the adhesive medium radiation for direct sterilization or the production of singlet oxygen and/or ozone for biological germicide.

The activatable agent and derivatives thereof as well as the energy modulation agent, can be incorporated into compositions suitable for delivery to particular mediums. The composition can also include at least one additive having a complementary effect upon the medium, such as a lubricant or a sealant.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Figure 19:
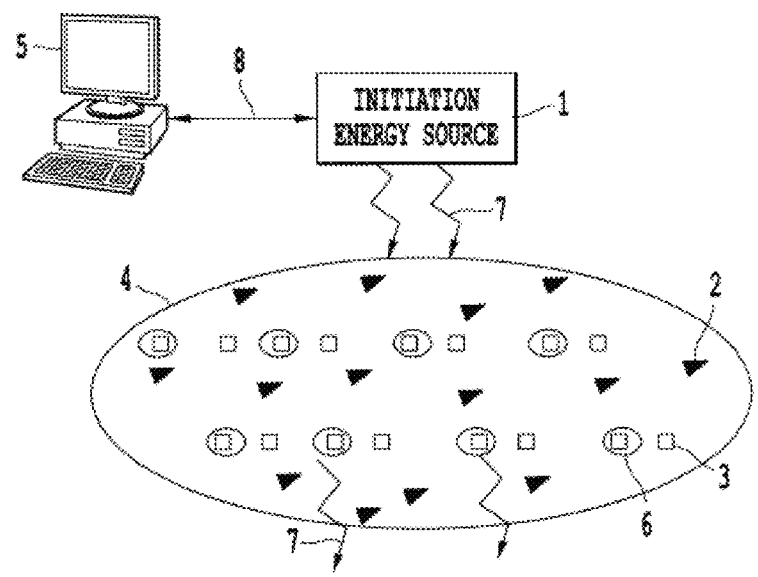
FIG. 19 is a schematic depicting a system according to one embodiment of the invention in which an initiation energy source is directed to a self-contained medium for producing changes in the medium.

Referring to FIG. 19, an exemplary system according to one embodiment of the invention may have an initiation energy source 1 directed at medium 4. Activatable agents 2 and an energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 19 as silica encased energy modulation agents. As shown in FIG. 19, initiation energy 7 in the form of radiation from the initiation energy source 1 permeated throughout the medium 4. The initiation energy source 1 can be an external energy source or an energy source located at least partially in the medium 4. Activatable agents 2 and/or the energy modulation agents 3 can include plasmonics agents which enhance either the applied energy or the energy emitted from the energy modulation agents 3 so as to directly or indirectly produce a change in the medium.

In various embodiments, the initiation energy source 1 may be a linear accelerator equipped with at least kV image guided computer-control capability to deliver a precisely calibrated beam of radiation to a pre-selected coordinate. One example of such linear accelerators is the SMART-BEAM™ IMRT (intensity modulated radiation therapy) system (from Varian Medical Systems, Inc., Palo Alto, Calif.) or Varian OBI technology (OBI stands for "On-board Imaging", and is found on many commercial models of Varian machines). In other embodiments, the initiation energy source 1 may be commercially available components of X-ray machines or non-medical X-ray machines. X-ray machines that produce from 10 to 150 keV X-rays are readily available in the marketplace. For instance, the General Electric DEFINIUM series or the Siemens MULTIX series are two non-limiting examples of typical X-ray machines designed for the medical industry, while the EAGLE PACK series from Smith Detection is an example of a non-medical X-ray machine. Another suitable commercially available device is the SIEMENS DEFINITION FLASH, (a CT system), by Siemens Medical Solutions. As such, the invention is capable of performing its desired function when used in conjunction with commercial X-ray equipment.

According to another embodiment of the invention, energy modulation agents 6 can be placed in the vicinity of a fluid medium 4 (e.g., a liquid or other fluid-like medium) and held inside a container. The container can be made of a material that is "transparent" to the radiation. For example, plastic, quartz, glass, or aluminum containers would be sufficiently transparent to X-rays, while plastic or quartz or glass containers would be transparent to microwave or radio frequency light. The energy modulation agents 6 can be dispersed uniformly throughout the medium or may be segregated in distinct parts of the medium or further separated physically from the medium by encapsulation structures. A supply would provide the medium 4 to the container.

Figure 20:
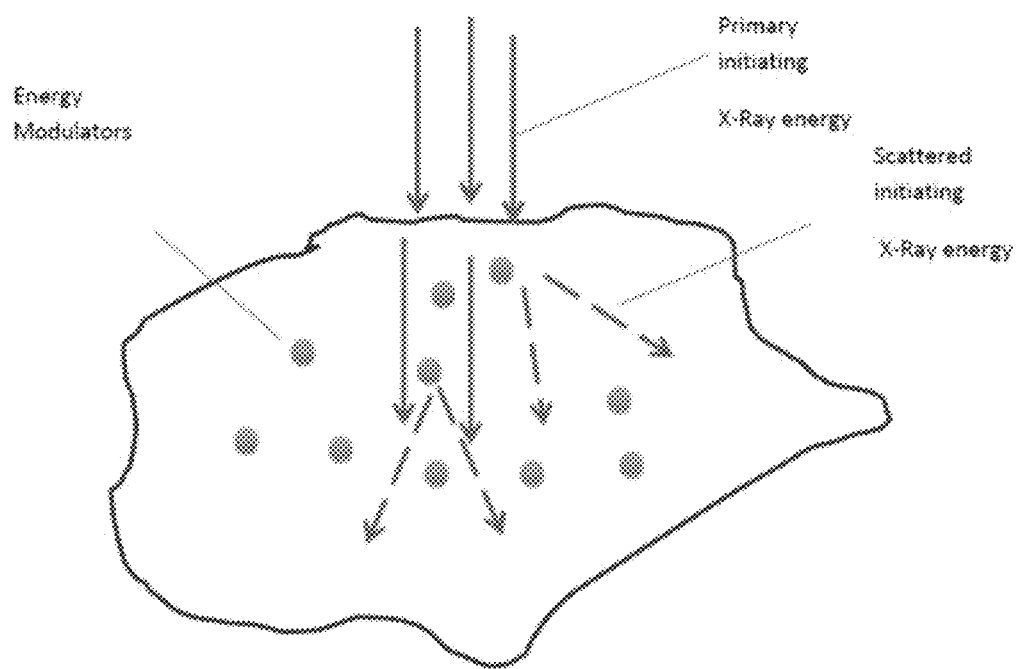
FIG. 20 is a schematic depicting x-ray scattering events and interactions with energy modulation agents in the medium.

FIG. 20 is a schematic depicting x-ray scattering events and interactions with energy modulation agents in the medium. In one embodiment, the effect produced by the interactions of the x-rays and energy modulation agents with the medium occurs by pathways not yet certain where internally produced light (IR, visible, and/or UV) alone or in combination with the x-ray exposure drive a chemical reaction in the medium or to the energy modulation agents themselves. These pathways may be influenced by the generation of free radicals inside the medium. These pathways may alternatively, or in addition, be influenced by the generation of ionized species inside the medium. These pathways include the disassociation of salts that in turn create a desirable chemical reaction. These pathways may be influenced by the scattering of x-rays inside the medium. These pathways may be influenced by the generation of emitted and re-emitted light inside the medium. These pathways may be a combination of these factors.

Further, these pathways may include the in situ generation of singlet oxygen and/or ozone to produce a change in the medium. For example, the photoactivatable agents may be stimulated through mechanisms such as irradiation, resonance energy transfer, exciton migration, ion-exchange, free radicals, electron injection, or chemical reaction to where "activated" agent is capable of producing the predetermined change desired.

In another embodiment, clusters of energy modulations agents (or chemically reactive agents or plasmonic agents) may be provided to a local site where x-ray exposure or internally generated light breaks apart the clusters into a form more useful to treatment at the local site or more useful to generating a local change in the medium nearby where the clusters existed.

Figure 21:
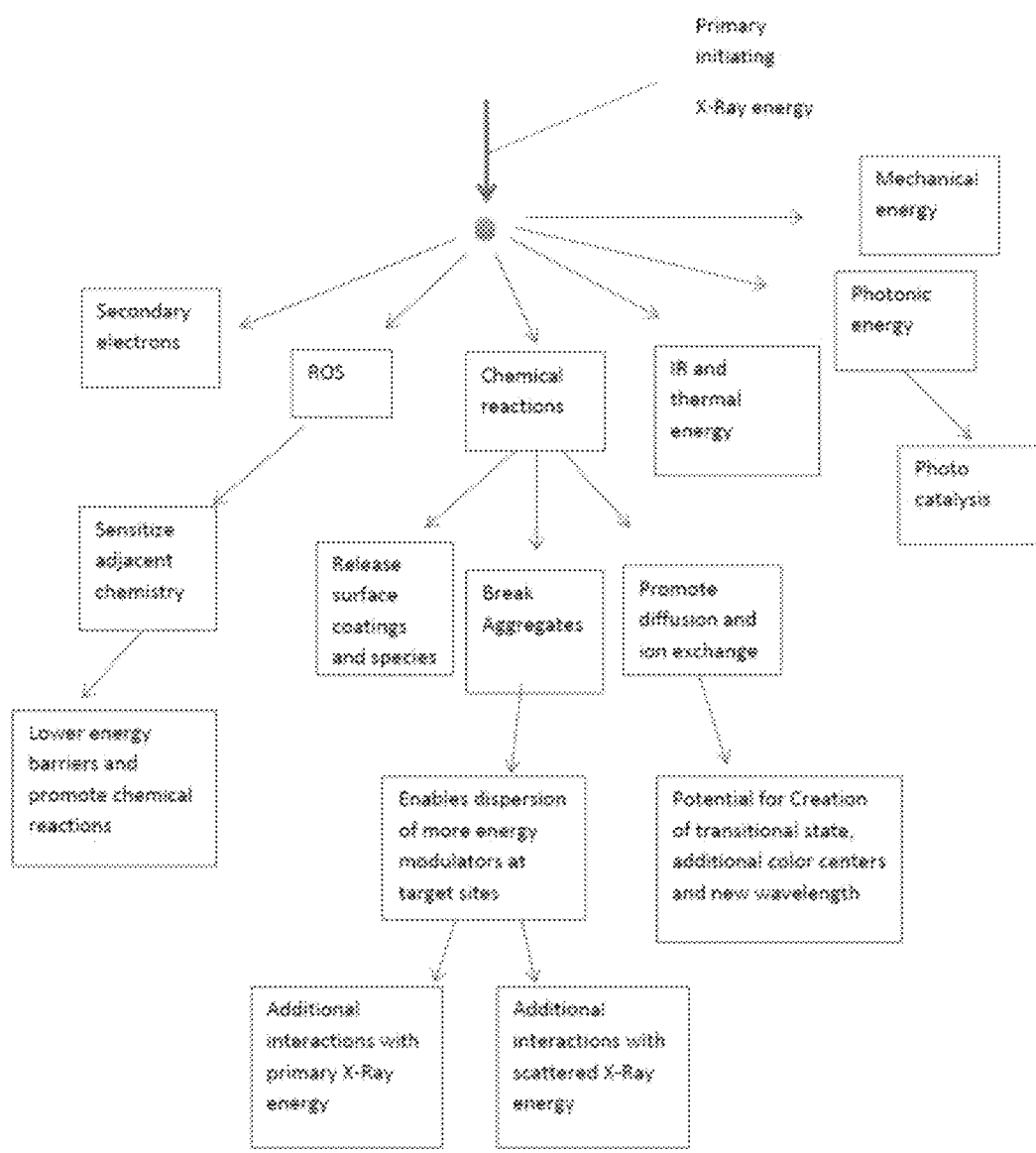
FIG. 21 is a depiction of a cascade of reactions whereby the initiation energy interacts with the energy modulation agents and other constituents in the medium.

FIG. 21 is a depiction of a cascade of reactions whereby the initiation energy interacts with the energy modulation agents and other constituents in the medium to produce a number of primary and secondary reactions. These interactions for example can lead to the production of electrons and/or reactive oxygen species (ROS), can sensitize adjacent chemistry, lower energy barriers and promote chemical reactions, can drive chemical reactions, release surface coatings and species, and/or break aggregates permitting the dispersion of more energy modulators at target sites, can promote additional interactions with primary X-Ray energy, promote additional interactions with scattered X-Ray energy, and/or promote diffusion and ion exchange, can provide a potential for creation of a transitional state and/or provide additional color centers, and can be responsible for emissions at new wavelengths of UV, visible, infrared, or thermal energy not normally present without these interactions. These interactions can result in increased photonic energy, can drive photo catalysis, and can provide mechanical energy to the medium. These interactions can result in disassociation of salts that activate chemical reactions. In turn these salts promote chemical reactions, for example, by cationic (proton generator) mechanisms. Onium salt is an example. Another example is iodonium salt which is in the form of a yellowish liquid in the case of ERGACURE 250 (available from BASF).

The X-ray energy excites the energy modulating media which converts energy (at some quantum yield efficiency) to emit, for example, a suitable UV energy to activate photoinitiators for free radical polymerization and generating reactive chemical intermediates. These include, but are not limited to, homolytic bond cleavage, hydrogen abstraction; or photo-charge transfer as illustrated below.

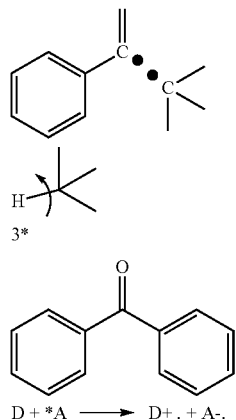

As an illustration of a complex interaction process of this invention, in one embodiment, a coating is applied to an energy modulator. The coating has at least one embedded (not tethered) biotherapeutic agent. The coating is made of chemicals that maintain emissions from the energy modulator (e.g., known visible or UV emissions). The coated energy modulator is delivered to the medium and exposed to x-rays with an intensity that allows the breaking of the coating or the breaking of the outer surfaces of the phosphors (which then releases the biotherapeutic agent). Optionally, the x-ray energy and/or intensity can be lowered to activate photonic emission of the phosphor without necessarily inducing further surface aberration. As a non-limiting example, the coating can be a PMMA coating whereby a high energy of X-Ray can breakdown the coating and a low energy dose of X-Ray can keep the coating intact.

Mass Transport Concept:

A PMMA coating can alternatively be used to isolate the energy modulation agent from the medium within which it is embedded. The PMMA coating can then be rendered semi-permeable upon X-ray exposure using X-rays sufficient to cause some coating breakdown. After X-ray exposure of the coated particle mass transport can then take place between the particle and the medium.

In the invention, energy transfer among molecules may occur in a number of ways. The form of energy may be electronic, thermal, electromagnetic, kinetic, or chemical in nature. The energy can be modulated up to emit higher energy from the energy modulation agent compared to the input initiation energy, or can be modulated down to emit lower energy from the energy modulation agent compared to the input initiation energy. Energy may be transferred from one molecule to another (intermolecular transfer) or from one part of a molecule to another part of the same molecule (intramolecular transfer). For example, a modulation agent may receive electromagnetic energy and re-emit the energy in the form of a different energy. In various preferred embodiments, the energy modulation agents receive higher energy (e.g. x-ray) and re-emits in lower energy (e.g. UV-A, UV-B, UV-C). In other embodiments, different energy modulation agents would receive lower energy (e.g., infrared or near-infrared) and emits in a higher energy (e.g., visible or ultraviolet).

In one embodiment, the energy modulation agent receives x-rays of 200 kVp or less in energy, and then emit lower energy (e.g. UV-A, UV-B, UV-C or combinations thereof), to cause the desired change in the medium or body. A preferred aspect of such embodiments is the use of low energy x-ray generating machines, such as CT scanners and similar medical or non-medical x-ray sources as the source of the initiation energy.

As noted above, the energy modulation agents (some of which are described above as nanoparticles) need not be of nanometer size and can in various embodiments of this invention be of micron-sized proportions. Various exemplary uses of the energy modulation agents of this invention are described.

The modulation agents may further be coupled to a carrier for targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. in close vicinity to a photoactive substance such as for example a photocatalyst or a photo initiator) by pre-distribution of the energy modulation agent into a medium to be exposed to the activation energy. For example, a UV-A emitting energy modulation agent may be concentrated in joints for adhesion of two parts together by physical insertion or by conjugating the UV-A emitting energy modulation agent with a photoactivatable resin.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, a source of x-rays having 200 kVp or less in energy, such as those described above.

In one embodiment of this invention, plasmonic structures can be utilized. The plasmonics-enhanced principle is based in theory on enhancement mechanisms of the electromagnetic field effect. Electromagnetic enhancements are divided into two main classes: a) enhancements that occur only in the presence of a radiation field, and b) enhancements that occur even without a radiation field. The first class of enhancements is further divided into several processes. Plasma resonances on substrate surfaces, also called surface plasmons, provide a significant contribution to electromagnetic enhancement. One effective type of plasmonics-active substrate includes nanostructured metal particles, protrusions, or rough surfaces of metallic materials. Incident light irradiating these surfaces excites conduction electrons in the metal, and induces the excitation of surface plasmons leading to Raman/luminescence enhancement. At a plasmon frequency, metal nanoparticles (or other nanostructured roughened structures) become polarized, resulting in large field-induced polarizations and thus large local fields on the surface. These local fields increase the luminescence/Raman emission intensity, which is proportional to the square of the applied field at the molecule.

As a result, the effective electromagnetic field experienced by an analyte molecule on these surfaces is much larger than the actual applied field. For X-rays and light, this field decreases as $1/r^2$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

Accordingly, plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents thus provides a selective and efficient strategy for the efficient use of internally generated light.

Accordingly, the invention utilizes several important mechanisms:
(A) Increased absorption of the excitation light by the plasmonic metal nanoparticles, resulting in enhanced photoactivation of photoinitiators or photocatalysts;
(B) Increased absorption of the excitation light by the plasmonic metal nanoparticles that serve as more efficient energy modulation agent systems, yielding more light for increased excitation of the photoinitiators or photocatalysts;
(C) Increased absorption of the excitation light by the medium material on or near the plasmonic metal nanoparticles;
(D) Increased light absorption of the energy modulation agent molecules adsorbed on or near the metal nanoparticles;
(E) Amplified light emission from the energy modulation agent molecules adsorbed on or near the metal nanoparticles; and
(F) Increased absorption of emission light emitted from the energy modulation agent by the photoinitiators or photocatalysts.

As discussed above, one of several phenomena that can enhance the efficiency of light emitted (Raman or luminescence) from molecules adsorbed or near a metal nanostructures Raman scatter is the surface-enhanced Raman scattering (SERS) effect. The intensity of the normally weak Raman scattering process is increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

Theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons," and b) an effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface.

A number of the various embodiments of plasmonics-enhanced probe structures (PEPST) can be designed:
(A) Photo-activatable (PA) molecules bound to a metal (e.g., gold) nanoparticle;
(B) Photo-activatable (PA) molecule covered with metal nanoparticles;
(C) Metal nanoparticle covered with PA nanocap;
(D) PA-containing nanoparticle covered with metal nanocap;
(E) Metal nanoparticle covered with PA nanoshell;
(F) PA-containing nanoparticle covered with metal nanoshell; and
(G) PA-containing nanoparticle covered with metal nanoshell with protective coating layer.

A basic embodiment is a PA molecules bound to a metal (e.g., gold) nanoparticle. The plasmonics-enhancement effect as it would be used in this invention would enhance the interaction of the primary excitation light source with energy modulation agents or would enhance the interaction of the secondarily produced light with the medium in effecting a change to the medium. Radiation of suitable energy is used to excite the plasmonic structures which in turn activates for example nearby photoinitiators.

For example, light of a HeNe laser (632.8-nm excitation) can be used for excitation. In this case the metal nanoparticles are designed to exhibit strong plasmon resonance band around 632.8 nm. The surface plasmon resonance effect amplifies the excitation light at the nanoparticles, resulting in an increased photoactivation of a photo-initiator or a photo-catalyst and improved reaction kinetic. Further, for sterilization applications, the effect increases the likelihood for a germicide event in the medium in vicinity of the nanoparticles. While light such as the HeNe laser light might be scattered and absorbed in the medium, the presence of the PEPST structures enhances the interaction of the penetrating light beyond that which would normally be considered useful.

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy, and new photonic devices.

In one embodiment of the invention, the plasmonic structures have a metallic layer over a dielectric core. In one embodiment of the invention, these shells include spheroidal shells, since the plasmon resonances (both longitudinal and transverse modes) are influenced by both shell thickness and aspect ratio. A number of researchers have examined the plasmonic response of the solid spheroidal particle in their analysis of surface-enhanced Raman scattering, although the spheroidal shell appears not to have been investigated. The invention also includes prolate and oblate spheroidal shells, which show some interesting qualitative features in their plasmon resonances. The spheroidal shell presents two degrees of freedom for tuning: the shell thickness and the shell aspect ratio.

Various embodiments of plasmonics-active nanostructures that can be designed, include:

(A) Metal nanoparticle;
(B) Dielectric nanoparticle core covered with metal nanocap;
(C) Spherical metal nanoshell covering dielectric spheroid core;
(D) Oblate metal nanoshell covering dielectric spheroid core;
(E) Metal nanoparticle core covered with dielectric nanoshell;
(F) Metal nanoshell with protective coating layer;
(G) Multi layer metal nanoshells covering dielectric spheroid core;
(H) Multi-nanoparticle structures;
(I) Metal nanocube and nanotriangle/nanoprism; and
(J) Metal cylinder.

In a further embodiment of the invention, the PA molecules can be incorporated into a material (e.g., biocompatible polymer) that can form a nanocap onto the metal (gold) nanoparticles. The material can be a gel or biocompatible polymer that can have long-term continuous release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers.

Other possible plasmonic embodiments of this invention with dielectric down-converting or up-converting material materials in proximity to metal shells or coatings. A plasmonics enhanced effect can occur throughout the electromagnetic region provided suitable nanostructures, nanoscale dimensions, metal types are used.

In various embodiments of this invention, the metal nanoparticles are covered with a layer (1-30 nm) of dielectric material (e.g. silica). The dielectric layer (or nanoshell) is designed to prevent quenching of the luminescence light emitted by the energy modulation agent (also referred to as EEC) molecule(s) due to direct contact of the metal with the energy modulation agent molecules. In yet other alternative embodiments, the energy modulation agent molecules or materials are bound to (or in proximity of) a metal nanoparticle via a spacer (linker). The spacer is designed to prevent quenching of the luminescence light emitted by the energy modulation agent molecules or materials.

In the invention, the experimental parameters including size, shape and metal type of the nano structure can be selected based upon the excitation radiation, the photoactivation radiation, and/or the emission process from the energy modulation agent system.

Combination Emitter Stimulation

As noted above, the invention provides methods for producing a change in a medium or body after generation of radiation inside the medium. In this method, an initiation energy source provides an initiation energy that penetrates the medium and induces internal radiation to produce a desired effect in the medium. In one embodiment of this invention, the effect produced occurs by photostimulation of a chemical reaction driven by a combination of emitters (e.g., down-converters, upconverters, combinations thereof) where the emitted light from each of the emitters individually is nominally not expected to drive the chemical reaction (e.g., a UV-driven reaction stimulated primarily by light emitted in a visible spectrum or a UV-driven reaction stimulated by down-converting phosphors having respective emissions not in the UV range but may exhibit UV emission when combined.)

In one embodiment, the inventors have found that chemical reactions known in the art to be driven by UV radiation in the 300 to 400 nm range can be stimulated from light emitted from energy converters which are considered to nominally have no emission in the 300 to 400 nm range. The exact mechanism of this stimulation is not known at this time. There is optical data evidence showing that the combination of visible emitters produces an emission in the UV range. In other words, the inventors have discovered that combination of visible emitters yields more than the expected summation of the emission peaks. In some cases, new peaks are observed in the UV range. In other cases, prominent peaks in the visible range disappear.

The data in the following figures show this effect.

FIGS. 23-26 show respective x-ray induced optical emission spectra from phosphors having their dominant emissions in the red, green, orange, and yellow parts of the visible spectrum, respectively. The phosphors were obtained from the following sources. "Ruby Red" obtained from Voltarc, Masonlite & Kulka, Orange, Conn., and referred to as "Neo Ruby"; "Flamingo Red" obtained from EGL Lighting, Berkeley Heights, N.J. and referred to as "Flamingo"; "Green" obtained from EGL Lighting, Berkeley Heights, N.J. and referred to as "Tropic Green"; "Orange" obtained from Voltarc, Masonlite & Kulka, Orange, Conn., and referred to as "Majestic Orange"; "Yellow" obtained from Voltarc, Masonlite & Kulka, Orange, Conn., and referred to as "Clear Bright Yellow." The "BP" phosphors are shown in detail below:

TABLE 16

| Code | Phosphor Material Color | Emission Spectrum Peak Emission (nm) | Emiss Eff (%) | Eff (Z) | X-Ray Absorption K-edge (keV) | Density g/cc Specific Gravity | Xtal Crystal Structure | Hygroscopic |
|---|---|---|---|---|---|---|---|---|
| BP1 | CaWO4:Pb | 425 | | | | | | N |
| BP2 | Y2SiO5:Ce | 410 | | | | | | N |

TABLE 16-continued

| Code | Phosphor Material Color | Emission Spectrum Peak Emission (nm) | X-Ray Absorption | | | Density | | | |
|---|---|---|---|---|---|---|---|---|---|
| | | | Emiss Eff (%) | Eff (Z) | K-edge (keV) | g/cc Specific Gravity | Xtal Crystal Structure | Hygroscopic | |
| BP3 | YTaO4 | 337 | 10 | 59.8 | 67.42 | 7.5 | Monolithic | N | |
| BP3-C | YTaO4 | 337 | 10 | 59.8 | 67.42 | 7.5 | Monolithic | N | |
| BP4 | BASF-1 | 460 | | | | | | | |
| BP5 | BASF-2 | 490 | | | | | | | |
| BP6 | YTaO4:Nb (*) | 410 | 11 | 59.8 | 67.42 | 7.5 | Monolithic | N | |
| BP6-C | YTaO4:Nb (*) | | | | | | | | |
| BP7-C | LaOBr:Tm3+ (coated) | 360, 460 | 14 | 49.3 | 38.92 | 6.3 | Tetragonal | N | |
| BP8-C | LaF3:Ce | 280 | | | | | | | |
| BP9 | Y2O3 | 365 | | | | | | | |
| BP-10 | BaSO4-:Eu2+ (coated) | 390 | 6 | 45.5 | 37.38 | 4.5 | Rhombic | N | |
| BP10-C | BaSO4-:Eu2+ (coated) | 390 | 6 | 45.5 | 37.38 | 4.5 | Rhombic | N | |
| BP11 | LaOCl:Tm | | | | | | | | |
| BP12 | Y2O2S:Tm | | | | | | | | |
| BP13 | BaSi2O5:Pb2+ | 350 | | | | | N | | |
| | SrB6O10:Pb | 360 | | | | | | N | |
| | CsI:Na (Coated) | 338 | | | | | | Y | |
| | Gd2O2S:Tm | Blue to Green | | | | | | Y | |

The "BP" phosphors are available from PhosphorTech Corporation of Kennesaw, Ga., from BASF Corporation, or from Phosphor Technology Ltd, Norton Park, Norton Road Stevenage, Herts, SG1 2BB, England.

In general, these phosphors show individually the emission of radiation at wavelengths other than the "primary" color. While these phosphors show little if any indication of emission in the 300 to 400 nm range, the results below show the "UV-activity" of these phosphors once x-ray activated.

When a "photo-caged" luciferin is exposed to UV light in the 300 to 400 nm range, its photocage breaks releasing d-luciferin. Since d-luciferin emits visible light upon reaction with luciferase and appropriate co-factors, exposure of the released d-luciferin to a controlled amount of luciferase provides for visible light production where the amount of visible light produced will be indicative of the amount of d-luciferin uncaged, and evidence of UV activation.

Figure 27:
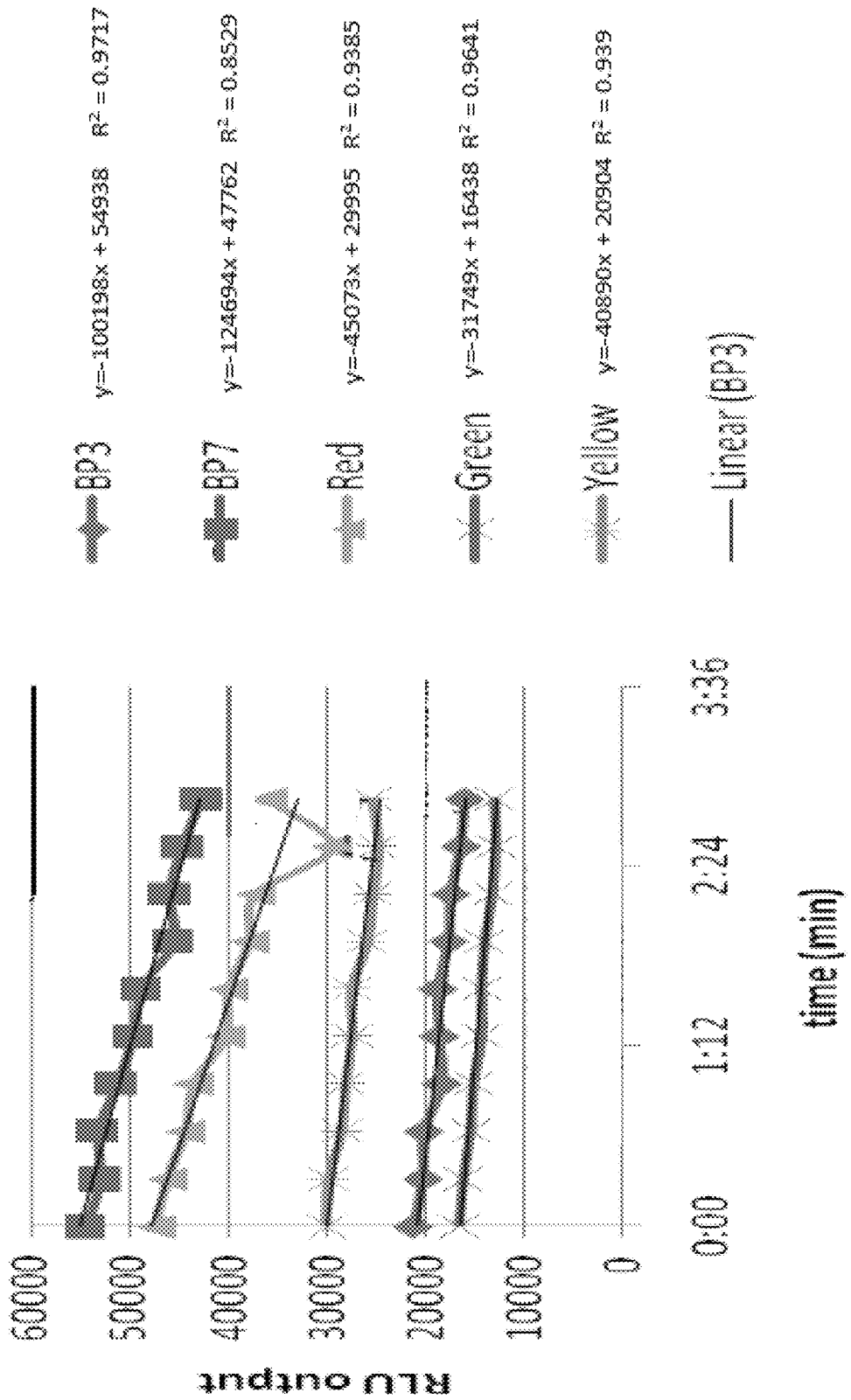
FIG. 27 is a plot of the levels of relative light output for d-luciferin/luciferase reactions obtained over time for individual types of phosphors (i.e., no mixtures) exciting a UV-light severable photocage containing d-luciferin.

FIG. 27 is a plot of the levels of relative light output for d-luciferin/1 luciferase reactions obtained over time for individual types of phosphors (i.e., no mixtures) exciting a UV-light severable photocage containing d-luciferin. The data shows that some light is output which may be due to nucleophilic hydrolysis (i.e. hydroxide ion mediated) of the photocage by the phosphor additions. The plot shows that the level of light output peaks initially and then decays over time.

Figure 28:
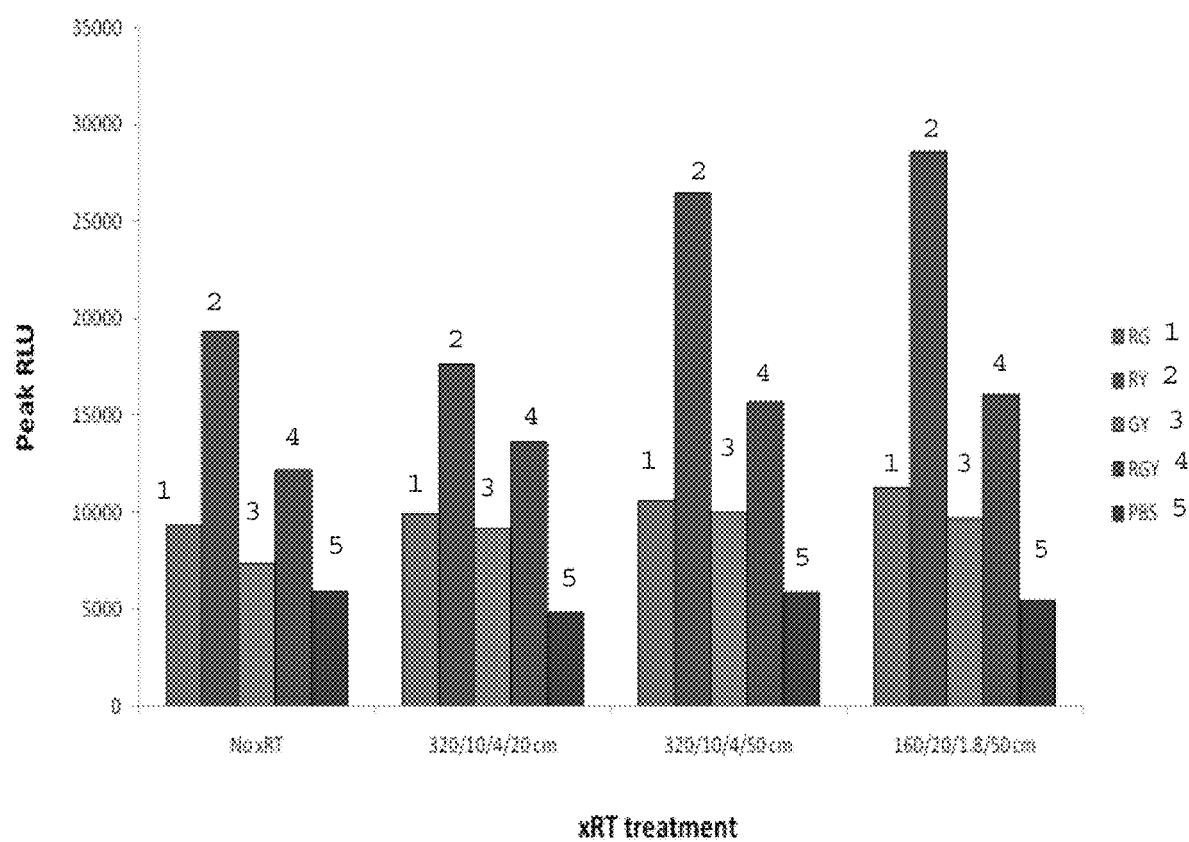
FIG. 28 is a chart comparing peak levels of light output for the for d-luciferin/luciferase reactions from different mixtures (red-green RG, red-yellow RY, green-yellow GY, red-green-yellow RGY exposed to x-ray radiation)

FIG. 28 is a chart comparing peak levels of read-out light from different mixtures (red-green RG, red-yellow RY, green-yellow GY, red-green-yellow RGY). The first data group to the left-most set shows a control with the phosphor combinations not being exposed to x-ray. PBS represents a phosphate buffered saline control for each of the sets. The second data group to the right shows little change in the read-out levels for the x-ray kVp energy/milli-Amps (mA)/x-ray time/x-ray source distance (cm) of 320 kvp/10 mA/4 min/20 cm. However, the third data group to the right and the fourth data group to the right show significant light output when either the x-ray source distance increased or the phosphor loading increased). Of these phosphor combinations, the red yellow RY phosphor combination showed the highest increase.

Figure 29:
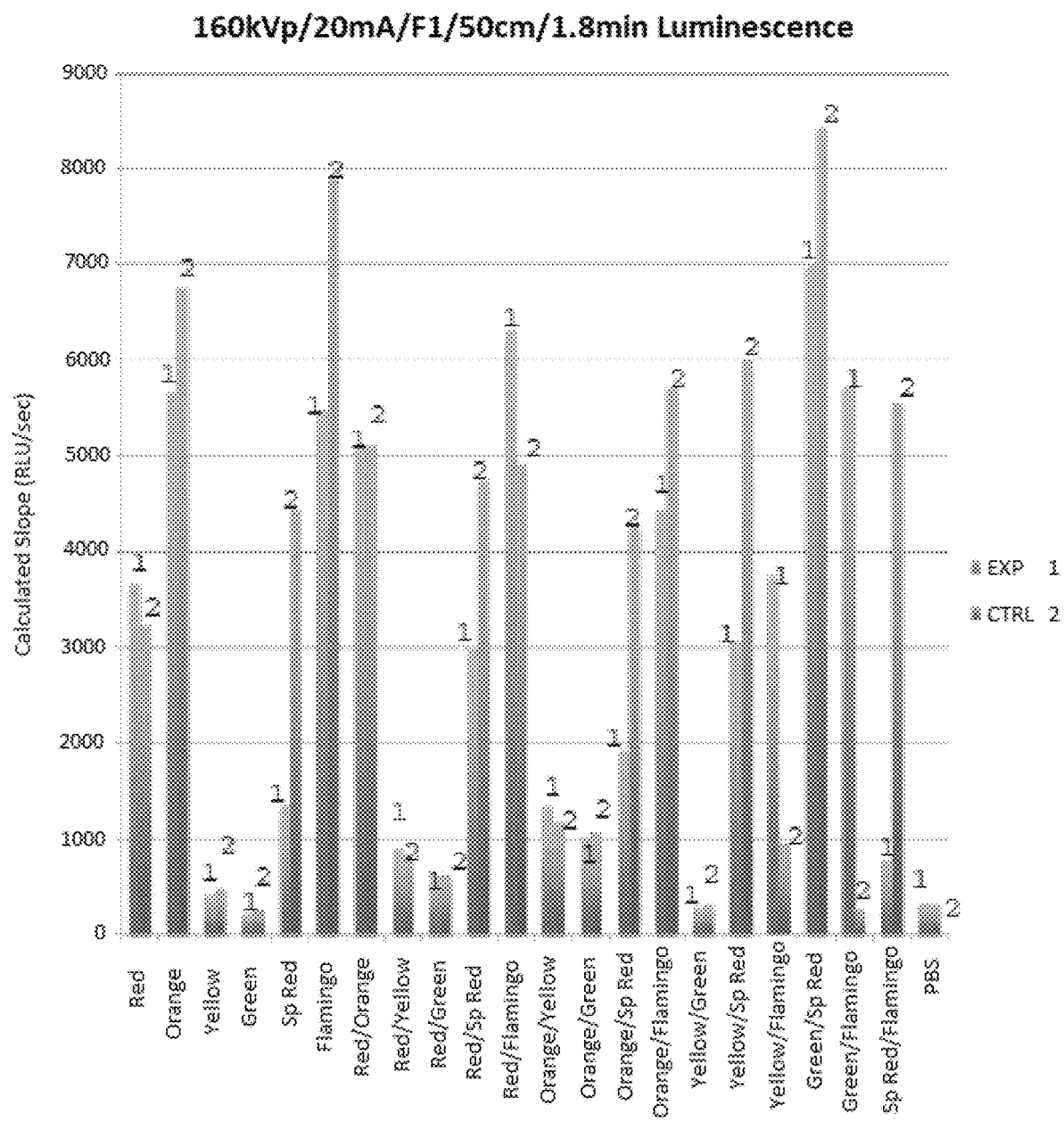
FIG. 29 is plot of a number of different phosphor combinations tested at 160 kVp/20 mA anode current/an aluminum filter in the x-ray beam/50 cm spacing conditions for a 1.8 minute x-ray exposure, except of the phosphor group with no exposure to x-ray radiation (the control set)

FIG. 29 is plot of a number of different phosphor combinations tested at 160 kVp/20 mA anode current/an aluminum filter in the x-ray beam/50 cm spacing conditions for a 1.8 minute x-ray exposure, except of the phosphor group with no exposure to x-ray radiation (the control set marked "CTRL"). FIG. 29 shows that phosphor combinations which showed the highest light output relative to the control were red-flamingo (RF) and green-flamingo (GF). Red-yellow (RY) and orange-yellow (OY) also showed higher light outputs relative to the control.

Figure 30:
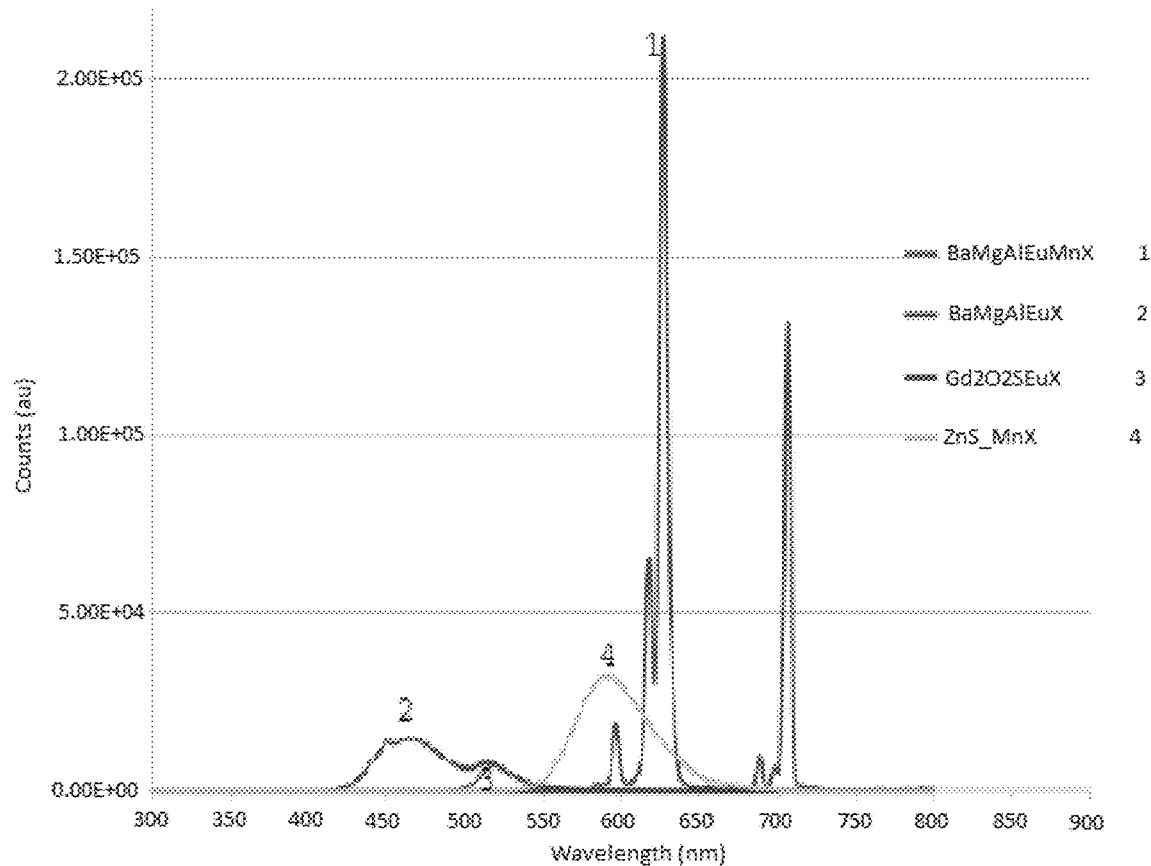
FIG. 30 is a composite of x-ray induced optical emission spectra of various individual visible emitting phosphors overlaid on each other.

FIG. 30 is a composite plot of x-ray induced optical emission spectra of various individual visible emitting phosphors overlaid on each other. The "Gd$_2$O$_2$SEuX" phosphor is the strongest emitter. The "BaMgAlEuX" phosphor has peaks the closest to the UV range. (The "X" here refers to a dopant element present such as for example Tm.)

Yet, when combinations of these phosphors are used as x-ray induced down conversion to drive reactions known to be driven by UV wavelengths in the 300 to 400 nm range, unexpectedly, photoreactions occur.

Figure 31:
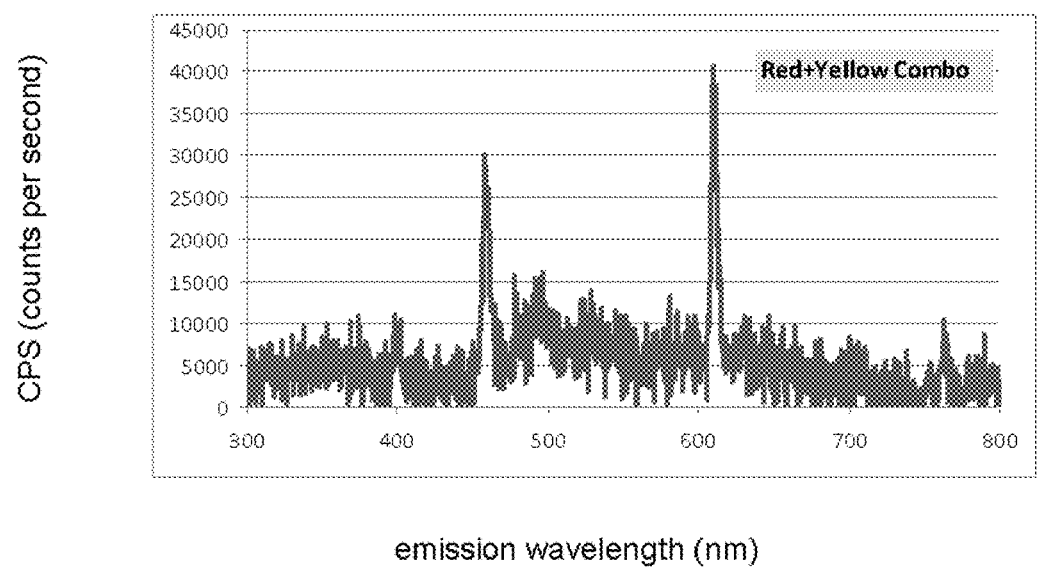
FIG. 31 is a depiction of an x-ray induced optical emission spectrum from a red-yellow RY phosphor combination.

Optically, certain combinations of these phosphors showed more than the normal expected results. FIG. 31 shows the x-ray induced optical emission spectrum from a red-yellow (RY) phosphor combination. As compared to x-ray induced optical emission spectra of FIG. 26 (yellow; Y) and FIG. 23 (red; R), the spectrum of FIG. 31 showed a pronounced reduction in the emission around 500 nm. There also appeared to be the onset of unexpected emissions (although small) in the 300-400 nm wavelength range. These observations seem consistent with the results shown for red-yellow RY in both FIGS. 28 and 29 where substantial UV-driven reactions for red-yellow RY were observed.

Figure 32:
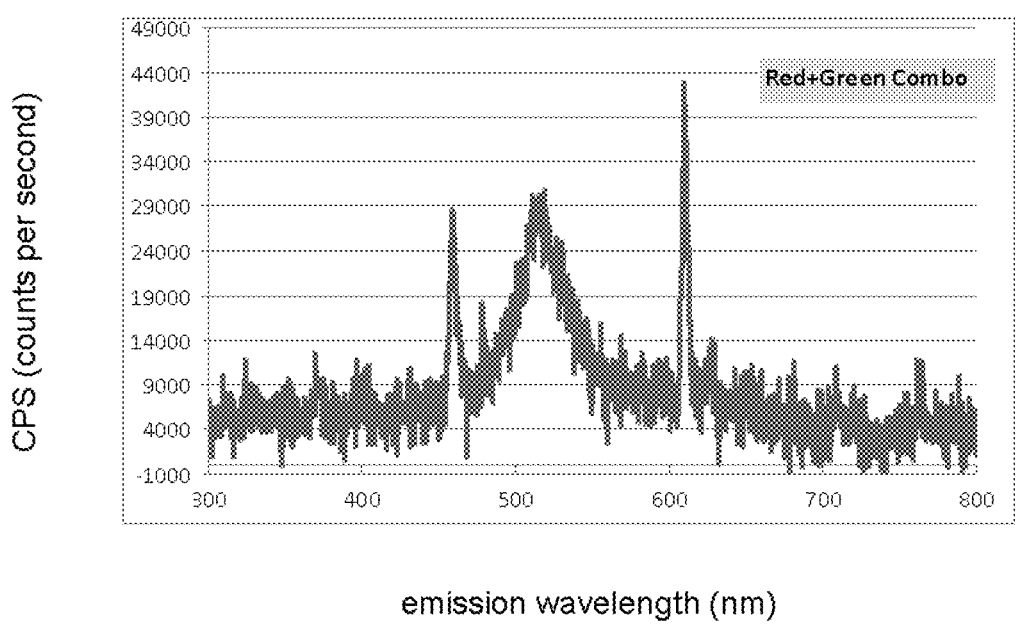
FIG. 32 is a depiction of an x-ray induced optical emission spectrum from a red-green RG phosphor combination.

Meanwhile, FIG. 32 is a depiction of another x-ray induced optical emission spectrum from a red-green RG phosphor combination, showing the onset of a feature around 290 nm. As compared to x-ray induced optical emission spectra of FIG. 24 (green; G) and FIG. 23 (red; R), the spectrum of FIG. 32 shows no unexpected change and does not appear to show the onset of emissions in the 300-400 nm wavelength range. This observation seems consistent with the results shown for red-green RG in FIGS. 14 and 15 where the measured results for UV-driven reactions with red-green RG were not substantially different than the control experiments.

Figure 33:
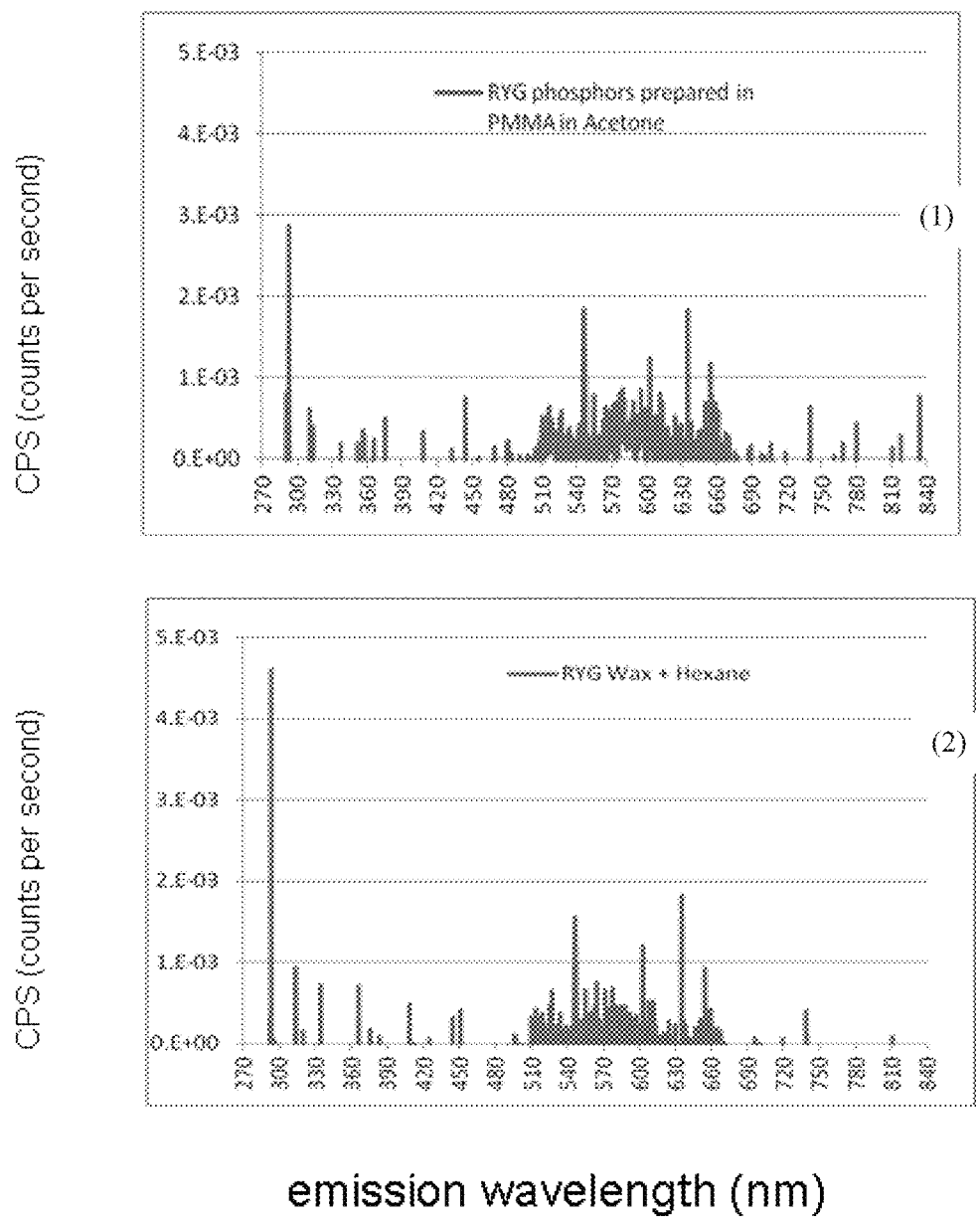
FIG. 33 is a depiction of an x-ray induced optical emission spectrum from a red-yellow-green RYG phosphor combination.

However, some phosphor combinations such as red, yellow, green RYG show a prominent peak in the 280 to 300 nm range which may be contributing to the psoralen activation. FIG. 33 is a depiction of an x-ray induced optical emission spectrum from a red-yellow-green RYG phosphor combination showing a prominent peak in the 280 to 300 nm range for solutions of red-yellow-green phosphors in acetone (1) and in hexane (2).

Medical Applications

Drug Activation

X-ray and other high energy radiation penetrate the human body. Upon their penetration into the body tissue, the energy modulation agents of this invention interact with the incident radiation to generate the secondary light (visible and/or ultraviolet light) as described above. As noted above, the secondary light can activate photoreactive drugs such as psoralen or other types of photoreactive drugs known to be activated by a UV and/or visible light source.

For example, in one embodiment of the invention, a material such as the yttrium oxide (or other phosphors or mixtures of phosphors as described above) is introduced into the body. Yttrium oxide as a host is known to be a down converter from X-ray radiation. In this particular example, X-ray incident radiation on the yttrium oxide will produce UV light which would in turn be used to activate drugs such as psoralen for the treatment of cancer. In this manner, a target organ having inside psoralen or other photoreactive drugs can be treated by irradiation with x-rays or other high energy sources, producing in turn visible and/or ultraviolet light for activation of the photoreactive drug.

Accordingly, in various embodiments, the invention provides methods for the treatment of cell proliferation disorders, in which an initiation energy source (e.g., x-ray or other high energy source) provides an initiation energy that activates an activatable pharmaceutical agent to treat target cells within the subject. In one preferred embodiment, the initiation energy source is applied directly to the energy modulations agents whose light emission in turn activates the activatable pharmaceutical agent, preferably in proximity to the target cells. In one embodiment, the initiation energy source is applied directly to the activatable pharmaceutical agent, preferably in proximity to the target cells. In a particularly preferred embodiment, the initiation energy source is a source of low energy x-rays, of 200 kVp or lower. Suitable such x-ray sources are described above. In this embodiment, the initiation energy source provides low energy x-rays which either directly activate the activatable pharmaceutical agent, or more preferably get converted by the at least one energy modulation agent in situ to an energy capable of activating the activatable pharmaceutical agent.

It is interesting to note that typical x-ray or radiation treatments for medical purposes typically use high energy x-rays, and high x-ray exposures. Often the x-ray source used in such treatments uses x-rays on the order of 1 MV. However, this embodiment of the invention uses x-rays that have much lower energy, of 200 kVp or less. Such x-rays are typically used for imaging or diagnostic purposes, and the invention is believed to be the first use of such low energy x-rays in a therapeutic treatment. Such lower energy photons can provide a more effective activation of phosphors and provide the best balance between UV and light conversion efficiency while at the same time spare the tissue from the non-mitigated unintended effects of radiation.

Within the context of the invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc.

Psoralen Activation

Accordingly, combinations of more than two "visible" phosphors can be used in this invention. Discussed below are x-ray settings and mass ratios for clonogenic cell kill experiments. F1 refers to the insertion of an aluminum filter into the x-ray beam to act as a filter.

TABLE 17

| | XRT settings (kvp/mA) |
|---|---|
| LDLE | 20/20/F1, 30 seconds = 0.1 Gy |
| LDHE | 80/20/F1, 30 seconds = 0.2 Gy |
| HDHE | 80/20/F1, 2.5 minutes = 1.0 Gy |
| HDLE | 20/20/F1, 2.5 minutes = 0.5 Gy |
| | Mass ratio |
| 1a | Red/Yellow/Green (40/40/20) |
| 1b | Red/Yellow/Green (45/45/10) |
| 2a | Flamingo/Yellow/Green (40/40/20) |
| 2b | Flamingo/Yellow/Green (45/45/10) |

Psoralen is known to be activated by UV light in the range from 300 to 400 nm. Thus, a measure of cell kill would normally be assumed to be an indirect measure of the internal generation of UV light.

FIGS. 34A and 34B show cell kill comparisons (shown here as the number of surviving colonies) between B16 cancer cells treated with and without psoralen (i.e., AMT) with different phosphor mixtures, but otherwise being x-ray stimulated and containing the multiple phosphor combinations noted above. On these drawings, LDLE=low xRT dose, low energy; HDHE=high xRT dose, high energy. Regardless of combination, the treatment with psoralen in all cases shows an improved cell kill.

FIGS. 35A and 35B shows a similar comparison as in FIGS. 34A and 34B but at higher kVp x-ray conditions. On these drawings, LDLE=low xRT dose, low energy; HDHE=high xRT dose, high energy. Here, the comparisons of results between FIGS. 19A and 19B does not show an increased kill with psoralen present.

Figure 36:
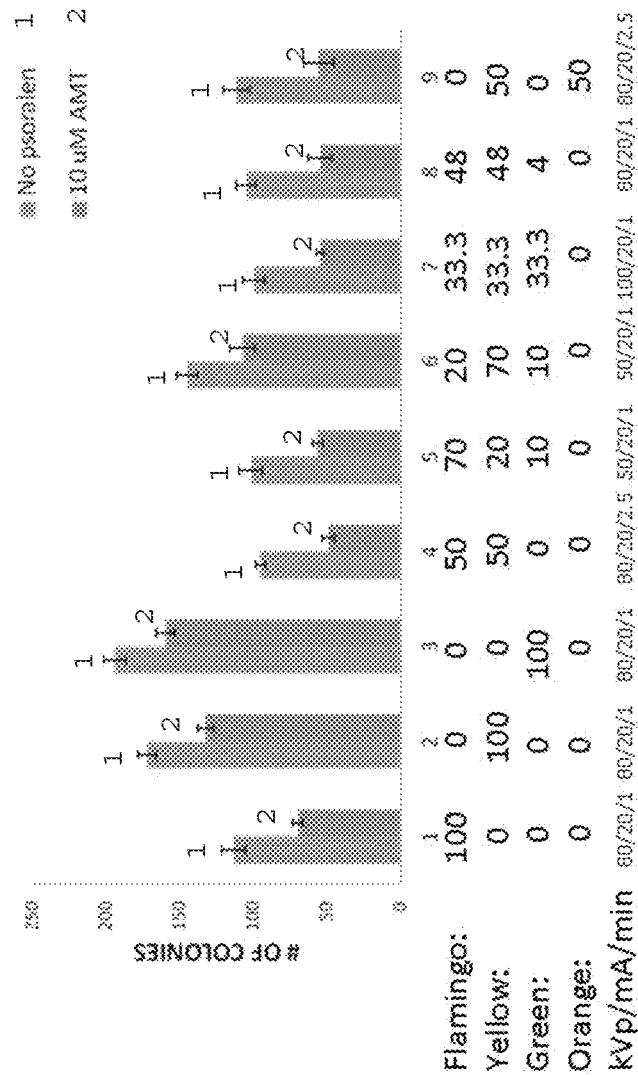
FIG. 36 is a depiction of the results from a clonogenic colony survival assay study utilizing a flamingo, yellow, green FYG phosphor combination in the presence and absence of psoralen (AMT)

FIG. 36 shows a clonogenic study utilizing a flamingo, yellow, green FYG phosphor combination. These results with and without Psoralen (i.e., the AMT) show a pronounced cell kill when the Psoralen is present.

Moreover, HPLC MS/MS analysis of synthetic (i.e. pdAdT) DNA samples after exposure to the x-ray activated multiple visible-light emitting phosphors of this invention showed the presence of mono-adducts of psoralen and in some cases psoralen cross-links with the DNA, consistent with the photoactivation of psoralen The tables below show these results and the capability of energy modulation agents having a normal predominant emission on one wavelength range producing changes in a medium expected to need activation from a different wavelength range.

TABLE 18A

Poly-dAdT crosslinking data using "visible" phosphors

| Sample # | X-Ray Treatment | Time | 150 μL | Diluent | DNA | Mono-Adduct | Cross-link |
|---|---|---|---|---|---|---|---|
| 1 | 160 kvp, 20 mA | 4 min | G + R | PBS | Poly dAdT | 6.13E+03 | — |
| 2 | 160 kvp, 20 mA | 4 min | Y + R | PBS | Poly dAdT | 2.80E+03 | — |
| 3 | 160 kvp, 20 mA | 4 min | Y + R | H2O | Poly dAdT | 4.46E+03 | 1.61E+04 |
| 4 | 160kvp, 20 mA | 4 min | G + R | H2O | Poly dAdT | — | — |

TABLE 18B

Poly-dAdT crosslinking data using "visible" phosphors

| Sample # | X-Ray Treatment | Time | 100 μL | Diluent | DNA | Mono-Adduct | Cross-link |
|---|---|---|---|---|---|---|---|
| 1 | 160 kvp, 20 mA | 4 min | R + G | PBS | Poly dAdT | 1.85E+03 | |
| 2 | 160 kvp, 20 mA | 4 min | R + O | PBS | Poly dAdT | 1.78E+03 | |
| 3 | 160 kvp, 20 mA | 4 min | F + G | PBS | Poly dAdT | 8.75E+02 | |
| 4 | 80 kvp, 20 mA | 4 min | F + G | H2O | Poly dAdT | 6.87E+02. | |

The results with mixtures of two or more of the phosphors show the capacity for "visible emitting" phosphors of this invention to activate UV-sensitive compounds. This capability permits a wider range of phosphor combinations to be used which otherwise would have been dismissed (under conventional practice) as being useless for an UV-activated process.

Photo-Cage Activation

As described above, the energy modulation agents of a preferred embodiment of this invention (upon activation) can produce visible and/or ultraviolet light which (even for predominantly visible light emission) can open photocages designed otherwise for UV severance.

This unique capability permits the use of phosphors such as the red R phosphors or mixtures of the red-green RG, red-yellow RY, green yellow GY, etc to release a chemically active species from a photocage. Moreover, it is known in the art that excessive UV light exposure can degrade properties of the medium, such as UV degradation of the polymers or DNA "light poisoning."

Photocages such as nitrophenyl compounds photolyze with near-UV light centered at 350 nm, which lies in the UVA range (315-400 nm). Unlike UVB (280-315 nm) and UVC (100-280 nm), UVA is not absorbed by DNA appreciably and therefore does not directly cause DNA damage.

A nitrophenyl compound as a photocage for Ca is shown below:

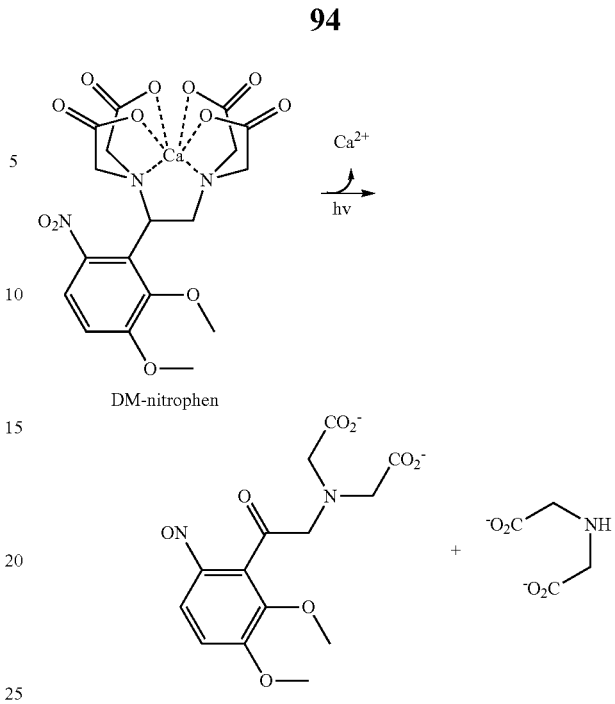

Depending on the intensity of the light source, duration of exposure and cell type, however, UVA light can damage DNA and other cellular components indirectly via the formation of reactive oxygen species. Light toxicity can therefore be a serious limitation of these photocage compounds.

Hence, this embodiment of the invention which activates nominally UV activated photocages with predominantly visible light emitters (or emitters normally expected to have predominantly visible emissions) offers advantages when the medium being treated is particularly suspect to UV degradation.

Moreover, there already exist a number of metal photocages investigated for cancer treatment. Of these, cisplatin has been studied and known for its toxicity to both healthy and cancerous cells. $Pt^{IV}$ complexes are more inert to ligand substitution than their $Pt^{II}$ counterparts, and therefore must be reduced to their active $Pt^{II}$ form by extracellular and/or intracellular agents prior to reaction with DNA.

Workers have reported that, if the rate of reduction of $Pt^{IV}$ to $Pt^{I}$ can be increased at or around a tumor relative to normal tissue, then the effectiveness of the drug could be maximized. The [$PtCl_2I_2$(en)] complex photoreduces with visible light. While the photoproducts were not characterized, the resulting complex was shown to bind DNA. However, the unphotolyzed complex was also able to bind DNA, and there was no difference in cytotoxicity observed for cells kept in the dark as compared to those exposed to light. Accordingly, other Pt photocages were developed.

Cis,trans,cis-[$Pt(N_3)_2(OH)_2(NH_3)_2$] have been found to be stable in the presence of glutathione, and photolyzes into a complex that binds DNA and 5'-GMP. In addition, the photolyzed complex inhibits the growth of human bladder cancer cells as well as cisplatin-resistant cells, while cells treated with the complex and kept in the dark showed very little growth inhibition.

Accordingly, the invention provides a mechanism by which mixtures of predominantly visible light emitters (or emitters normally expected to have predominantly visible emissions) can photoactivate (photolyze) Cis, trans, cis-[$Pt(N_3)_2(OH)_2(NH_3)_2$] without significant degradation and destruction of nearby healthy cells by high UV exposure or singlet oxygen generation.

Photocages for Curing

The discussion above shows that the energy modulation agents of the invention (e.g., phosphors, scintillators, fluorescent materials, up conversion or down conversion media and combinations and/or agglomerations thereof with and without plasmonic agents) can be used to activate a variety of photocages. As discussed above, additives such as salts can be introduced to polymers to activate or promote curing. The salts promote chemical reactions, for example, by cationic (proton generator) mechanisms. Onium salt is an example. Another example is iodonium salt which is in the form of a yellowish liquid in the case of ERGACURE 250 (available from BASF).

Onium salts, namely sulfonium, phosphonium, ammonium, and pyridinium salts containing phenacyl group are photoinitiators appropriate for the polymerization of monomers such as oxiranes and vinyl ethers, which are not polymerizable by a free-radical mechanism. The initiation is accomplished by direct or indirect (sensitized) photolysis of the salts. Depending on the type of the salt, the direct photoinitiation of cationic polymerization involves reversible or irreversible processes. The photolysis of phenacylsulfonium compounds proceeds by a reversible process, while the other types undergo irreversible photolysis leading to complete fragmentation of the photoinitiator. An additionally useful tool, namely photosensitized generation of initiating species enlarges the versatility of these salts as photoinitiators. Photoinitiated free-radical and zwitterionic polymerizations by using phenacyl-type salts are also addressed. Keto-enol tautomerization of phenacyl pyridinium salts is discussed.

Accordingly, in one embodiment of the invention, these salts are released from photocages by light from the energy modulation agents. Thereafter, light preferably from the energy modulation agents (but possibly other external sources) can drive the photolysis of Onium salts.

Photobiomodulation

U.S. Ser. Nos. 12/417,779 and 12/764,184 (the entire contents of which are incorporated herein by reference) describe non-invasive systems and methods for in-situ photobiomodulation. In these different approaches, a condition, disorder or disease in a subject is treated using an initiation energy source to induce a predetermined change in a target structure in a subject in situ to treat the condition, disorder or disease. The initiation energy sources in these applications generate internal light inside the subject to treat the condition, disorder or disease.

In this invention, the combination of energy modulation agents (luminescent particles or down converters, mixtures of down converters, up converters, mixtures of up converters, and combinations thereof as described above for example the mixtures of red, yellow, green, and/or blue phosphors noted above) would be provided inside a subject to be treated, and then activated by x-ray or some other source to generate the photobiomodulation. In one embodiment, the activation produce light in a wavelength range which would be normally expected to not produce a photobiomodulation effect, but now produces a photobiomodulation effect, treating a condition, disorder or disease in the subject and therefore producing a change.

Commercial Applications

In the following commercial applications of the invention described here, the energy modulation agents 3 (e.g., luminescing particles or photon emitters or down conversion media or up conversion media) are provided and distributed into a medium 4 for deactivation or activation of agents in the medium to produce a physical, chemical, or biological change in the medium. In one embodiment, plasmonics agents as described above are added to the medium. The plasmonics agents can enhance both the applied initiation energy such that the enhanced initiation energy activates the at least one activatable agent which produces a change in the medium when activated and can enhance light converted by the energy modulation agents.

In one embodiment of this invention, luminescing particles (down converters, mixtures of down converters, up converters, mixtures of up converters, and combinations thereof) in encapsulated structures could be placed in the vicinity of the medium. In one embodiment for the invention described here, luminescing particles are coated on the interior of quartz or glass tubes and sealed. In another embodiment, luminescing particles could be coated on the surface of spheres or tubes, and afterwards encapsulated with silica (or other suitable passivation layer) using a vapor deposition or sputtering process or spin-on glass process of the solution process described above to make the encapsulation structures which may be part of re-entrant structures extending from walls of a container or which may be part of a fluidized bed structure. In another embodiment, the plasmonics agents are fixed to an outer surface of the glass tubes. External light applied to the tubes and scattered to the outer surfaces is enhanced at the plasmonics agents permitting more efficient treatment of the medium without necessarily having to use energy modulation agents.

Sterilization and Cold Pasteurization of Fluids

It is known that ultraviolet (UV) with a wavelength of 254 nm tends to inactivate most types of microorganisms. The invention described herein provide in one embodiment a configuration where energy modulation agents (such as described above) can be placed inside fixtures such as quartz or glass within the fluid medium (water, fruit juices, dairy products, etc) and irradiated with x-rays (or other penetrating radiation) through for example a plastic or aluminum container to activate the energy modulation agents in the fluid medium with internally generated visible and/or ultraviolet light. As such, the expense and fragility of a conventional sterilization reactor constructed from glass of other similar structure can be avoided.

While discussed with regard to water, fruit juices, dairy products, etc, any other medium to be sterilized including food products, medical products and cosmetic products could be treated using the techniques and energy modulation agents of the invention described herein.

Sterilization of Medical and Pharmaceutical Articles

Gamma irradiation has been used conventionally to sterilize medical bottle caps and other medical, pharmaceutical, and cosmetic articles such as surgical disposables (e.g., surgical bandages, dressings, gauge pads, nappies, delivery kits, and etc.), metallic products (e.g., surgical blades, implants, aluminum caps, containers, etc.), and plastic and rubber Items (e.g., petri-dish, centrifuge tube, blood collection sets, scalp vein sets, shunt valves, rubber gloves, contraceptive devices, gowns, wraps covers, sheets, etc.). The invention would be applicable for the sterilization of any "interior" surfaces of these and other products.

In one embodiment of the invention described herein, luminescent particles (or down converters, mixtures of down converters, up converters, mixtures of up converters, and combinations thereof) would be included in an adhesive layer when the seal material is applied to the bottle cap. X-ray irradiation would then be capable of curing the adhesive (if for example the adhesive were a photosensitive adhesive as discussed below in greater detail) and would produce within the adhesive medium visible and/or ultraviolet radiation for sterilization or for the production of singlet oxygen or ozone for biological germicide. Additionally, plasmonics agents can be included to enhance the effect of the incident radiation or the internally generated (visible and/or ultraviolet) radiation.

While illustrated here with regard to medical bottle caps, other adhesively constructed devices could benefit from these procedures in which the adhesive medium is cured and/or sterilized during activation of the energy modulation agents of the invention.

Sterilization of Blood Products

U.S. Pat. No. 6,087,141 (the entire contents of which are incorporated herein by reference) describes an ultraviolet light activated psoralen process for sterilization of blood transfusion products. Here, this invention can be applied for the treatment of or the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones. These photoactivatable agents are introduced into the blood product (or a patient's blood stream). A penetrating energy is applied to the blood product (or to the patient). The down converters, mixtures of down converters, up converters, mixtures of up converters, and combinations thereof (either included in the blood product) or in encapsulated structures generate secondary light (visible and/or ultraviolet) which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

Low kVp Systems

PCT application PCT/US12/45930 (the entire contents of which are incorporated herein by reference) describes a system for light stimulation within a medium. The system in the '930 application has a reduced-voltage x-ray source configured to generate x-rays from a peak applied cathode voltage at or below 105 kVp, and a first plurality of energy-converting particles in the medium which, upon radiation from the x-ray source, radiate at a first lower energy than the x-ray source to interact with the medium or with at least one photoactivatable agent in the medium.

The x-ray induced emissions noted above represent merely one example of a class where stimulated emission from a combination of energy modulation agents yields unexpected frequencies of emitted light. In one embodiment of this invention, the above-noted energy modulation agents (and combinations thereof) can be used in low kVp systems to activate psoralen and its derivatives.

Additionally, certain phosphors/phosphor combinations may have different excitation optima for emission. Furthermore, certain phosphors/phosphor combinations may show increased emissions or an increased effect when the x-ray energy (kVp) of the beam is lowered.

Sterilization Methods and System Components

Optical techniques have been often used in sterilization procedures to render unwanted or harmful waterborne microorganisms incapable of reproducing using ultraviolet light (specifically the spectral area of UV-C, 200 to 280 nm range). Ultraviolet light in the UV-C is considered the most lethal range as a germicidal disinfectant (capable of altering a living microorganism's DNA, and keeping the microorganism from reproducing). UV-C, with 264 nanometers being the peak germicidal wavelength, is known as the germicidal spectrum. Although the UV-C method is simple and effective, it is not particularly effective in samples (gas, liquids, particulates) enclosed on containers which do not transmit UV light. The invention provides techniques and systems that can use externally applied radiation such as X-ray for sterilization. While illustrated below with respect to X-ray irradiation, and as discussed above, other suitable forms of energy could be used provided the containers and medium to be sterilized was sufficiently transparent for the medium to be thoroughly irradiated. Examples of alternative sources and materials for upconverting luminescence to higher energies have been discussed above. In general, down converters, mixtures of down converters, up converters, mixtures of up converters, and combinations thereof and mixtures thereof with or without plasmonics structures can be used in this invention for sterilization.

Various embodiments of sterilization systems and probes can be used with X ray excitation are described in U.S. Ser. No. 12/401,478 now U.S. Pat. No. 8,376,013, the entire contents of which are incorporated herein by reference. These systems are applicable in a number of the applications discussed above and as well as in other sterilization areas. The systems could thus be used in the waste water detoxification, blood sterilization, cold pasteurization, and photo-deactivation commercial applications discussed in the sections above. These systems show the use of artificial containers in which the medium to be treated is disposed.

One embodiment of a sterilization system of the invention includes: a container and a material containing an X-ray energy converter. The container holds a sample to be sterilized (e.g., liquid, gas, or particulates). X-ray radiation, capable of penetrating the container wall, excites the material containing the X-ray excitation energy converter (EEC), which is configured to emit emission light. The EEC material is selected such that the emitted or luminescence light occurs in a spectral region that can be used for sterilization (e.g., the ultraviolet spectral range).

One embodiment of another sterilization system of the invention utilizes plasmonics and includes: a container, a material containing an X-ray energy converter, a dielectric layer (e.g., silica), and a metal nanostructure (e.g., Au, Ag). The container holds a sample to be sterilized (e.g., liquid, gas, or particulates). X-ray radiation, capable of penetrating the container wall, excites the material containing the X-ray excitation energy converter (EEC), which in turn emits emission light. The EEC material is selected such that the emitted or luminescence light occurs in a spectral region that can be used for sterilization (e.g., an ultraviolet spectral range). The metal nanostructure is designed to amplify the luminescence light due to the plasmonics enhancement effect discussed above. The dielectric layer is designed to separate the material of the X-ray energy converter from the metal nanostructure in order to minimize or prevent possible quenching of the luminescence. The optimal thickness of the dielectric layer is about 1 to 5 nm such that the dielectric layer does not significantly alter the plasmonics effect.

One embodiment of a sterilization probe system of the invention includes a container which can hold the medium to be sterilized and a probe made of material containing an X-ray energy converter. The sample inside the container can be liquid, gas, or particulates. X-ray radiation, capable of penetrating the container wall, excites the probe having the material containing X-ray excitation energy converter (EEC), which in turn emits emission light. The EEC material is selected such that the emitted or luminescence light occurs in a spectral region that can be used for sterilization (e.g., the ultraviolet spectral range). The probe can be removed and reinserted into the container and reused.

In general, without limitation to the sterilization systems discussed above, in one aspect of the invention, there is provided a system for producing a change in a medium disposed in an artificial container. The system includes a mechanism configured to provide to the medium 1) an activatable agent and 2) at least one energy modulation agent, The energy modulation agent is configured to emit light into the medium upon interaction with an initiation energy. The system includes an initiation energy source configured to apply the initiation energy to the medium.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

UV irradiation is known to affect graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hyperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of down converters, mixtures of down converters, up converters, mixtures of up converters, and combinations thereof (serving as energy modulation agents) in dispersion in the fluid medium being used for photostimulation. Additionally, the plasmonics agents can be included to enhance the effect of the incident radiation or the internally generated radiation. In one embodiment, the plasmonics agents are complexed with these energy modulation agents prior to being added to the fluid medium.

Upon irradiation with x-rays (or other penetrating radiation) through for example a plastic or aluminum container, activation of the luminescing particles (i.e., energy modulation agents) would generate visible and/or UV light throughout the volume of the medium (eliminating any shadowing effects) and permitting batch or bulk type processing to occur in parallel throughout the container.

In other examples, the interior generation of light (visible and/or ultraviolet) inside a bulk medium may serve to stimulate a chemical or biological process either by interaction of the light (visible and/or ultraviolet) with activatable agents in the medium or the indirect generation of heat which the invention described here by way of dispersed energy modulation agents would provide a controlled and uniform way to heat a vat of material in a biological or chemical process.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above for liquid pasteurization could be used here. For non-liquid products, energy modulation agents (down converters, mixtures of down converters, up converters, mixtures of up converters, and combinations thereof) with little and preferably no toxicity (e.g. Fe oxides or titanium oxides) could be added. External activation would result in the generation of visible and/or ultraviolet light within the liquid. Here, the concentration of these additives would likely be limited by any unexpected changes in taste.

Photoactivated Cross-Linking and Curing of Polymers

In another embodiment of this invention, a system for curing of a radiation-curable medium includes 1) a mechanism configured to supply an uncured radiation-curable medium including an activatable agent and at least one energy modulation agent into the uncured radiation-curable medium and 2) an initiation energy source configured to apply an initiation energy throughout a region including the uncured radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

In this application, energy modulation agents (down converters, mixtures of down converters, up converters, mixtures of up converters, and combinations thereof) are provided and distributed into an uncured polymer based medium for the activation of photosensitive agents in the medium to promote cross-linking and curing of the polymer based medium. Additionally, the plasmonics agents can be included to enhance the effect of the incident radiation or the internally generated radiation. The plasmonics agents can be complexed with the luminescent particles or other energy modulation agents prior to being added to the polymer.

As noted above, for adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the luminescing particles (or energy modulation agents) are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with for example carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of the invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4, 6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis (.eta..sup.5-2,4-cyclopentadien-1-yl)-bis[2,6-difluoro-3- (1H-pyrrol-1- -yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

It will be appreciated that the most efficient curing system will be one in which the particular photo-initiator is selected based on its absorption, its photo-catalysis sensitivity to the intensity of the incident radiation (i.e.; the efficiency of energy transfer).

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 um. Other Q-CEL products are shown below in tabular form. Another commercially available hollow glass microsphere is sold by Kish under the trade name SPHERICEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCH-LITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, conventional silicone and polymeric adhesive or release or coating compositions are prepared using conventional mixing, heating, and incubation techniques. Included in these conventional compositions are luminescing particles. These luminescing particle containing compositions can then be applied to surfaces of objects to be fixed together or to surfaces where a hard coating is desired or cast in a curable form for the production of molded objects. The luminescing particles in these compositions upon activation will produce radiant light for photoactivated cure of the luminescing particle containing polymer composition. The density of luminescing particles in these compositions will depend on the "light transparency" of the luminescing particle containing composition. Where these compositions contain a significant amount of the inorganic filler as discussed above, the concentration of luminescing particles can be reduced for example as compared to a composition with a black color pigment where the light transparency will be significantly reduced.

One advantage of the invention described here as seen from this example is that color pigments can be included in the light curable resins without significant compromise in the cured product performance. These color pigments may include one or more colored pigments well known to those of ordinary skill in the art. Such pigments are generally metal oxides and include, but are not limited to, titanium dioxide, iron oxides, organic complexes, mica, talc and quartz. One pigment may be used, or a combination of two or more pigments may be utilized. Different colors can be obtained by choosing proper pigments and combining them in a similar fashion as set forth in the following examples with the necessary adjustments, common in the paint industry, being made. Accordingly, in one embodiment of the invention, these color pigments including carbon black may also be included as an optically opaque materials to limit the propagation of internally generated light from the point of generation.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, energy modulation agents (down converters, mixtures of down converters, up converters, mixtures of up converters, and combinations thereof) described above are added to these Bach et al. compositions, optionally including in one embodiment various color pigments. Due to the fact that the exterior energy source penetrates throughout the entirety of the Bach et al. compositions, thicker surface coatings can be realized. Further, the coatings can be applied to intricate surfaces having for example been prepared with recesses or protrusions. Curing with the recesses and around the protrusions without being limited by conventional UV shading will likely provide enhanced adherence of the surface coating to the work piece.

Moreover, in one embodiment of the invention, an external energy source of the initiation energy can be directed to a structural element in which a gap (or crack) therein was filled with an uncured radiation-curable medium (such as those described above). The internally generated light will cure or promote curing of the uncured radiation-curable medium in the gap (or crack) thereby providing a repair to the structure being irradiated.

Presently, there are available commercial epoxy systems which utilize epoxy resin injection for the structural restoration of concrete. Epoxy injection is very often the only alternative to complete replacement of a structure. It therefore results in great cost savings. Besides filling the cracks, epoxy injection is known to protect rebar in the concrete and to stop water leakage. Commercially, the epoxy injection resin provides a system for welding cracks which restores the original strength and loading originally designed into the concrete. Typically, low viscosity resins are pressure injected into the cracks. Often holes are drilled near or into the cracks to provide a conduit for pumping the resin into the cracks.

It, however, takes time for the resin to penetrate into the thinner, even hair line cracks. Unfortunately, time is limited in the present commercial systems due to the fact that the resins are premixed with hardeners whose time to cure sets an upper limit for how long the low viscosity resin can flow into the cracks. Furthermore, time to complete repair is an issue in many industrial repairs as the hardener is usually present in a concentration high enough to have the resin set for example in twenty four (24) hours. Moreover, with traditional resin methods, it is not possible to induce curing at specific regions of interest since all the areas of the resin will be cured.

The invention offers a number of advantages. Firstly, the resin of the invention will be a photoactivated resin which will not substantially cure until the x-ray source generates internal light (visible and/or ultraviolet) to activate the photoinitiators. This provides more flexibility in pumping and waiting for complete crack fill. Secondly, once the photoactivatable resin is in place, its cure is then activated, and the cure occurs at a rate not controlled by the convention hardening reaction. Thirdly, the x-ray penetration through the concrete and the crack region will provide a more uniform mechanism for cure of the resins, with the deep cracks being as likely to fully cure as the narrow cracks which may extend deeper into the material. Furthermore, the invention allows the possibility to cure only the specific areas of interest, i.e., where the X-ray is irradiated.

In another embodiment of the invention, the external energy source can be a directed or focused beam of the initiation energy which cures an uncured radiation-curable medium to produce a patterned element. In this embodiment, the structure holding or at least partially enclosing the uncured radiation-curable medium can be a structure opaque to visible light. In this manner, the uncured radiation-curable medium (which normally would be photoactivated upon exposure to ambient light) can be transported without premature curing. In this embodiment, the curing would be activated for example by directed one or several focused beams of x-rays whose overlap generates regions in the structure holding or at least partially enclosing the uncured radiation-curable medium where the generated UV or visible light from the energy modulation agents in the medium would be of sufficient intensity to activate the photoinitiators.

In this manner, precise three-dimensional and two-dimensional patterning can be performed. In this manner, a number of differently sized and different materials can be adhered to each other.

In general, in this aspect of this invention, a radiation-curable medium can be cured by applying an initiation energy throughout a composition comprising 1) an uncured radiation-curable medium and 2) at least one energy modulation agent. The initiation energy interacts with the energy modulation agent to directly or indirectly cure the uncured medium by polymerization of polymers in the medium. The method includes curing the radiation-curable medium by activating a photoinitiator in the radiation-curable medium. The energy modulation agent has a normal predominant emission of radiation in a first wavelength range (WR1) outside of a second wavelength range (WR2) known to activate the photoinitiator, but under exposure to the applied initiation energy cures the medium.

Thus, in one embodiment, the invention provides a radiation-curable article including a radiation-curable medium and at least one energy modulation agent distributed throughout the medium. The energy modulation agent being a substance which is capable of converting initiation energy to a light capable of curing the radiation-curable medium by polymerization of polymers in the radiation-curable medium.

In one embodiment, the invention permits the adhesively bonded structure to be imaged in order to access the fill and distribution of the adhesive in the joint or seam require holding two articles together or distributing in the gaps in an object. Details of the imaging object provided below.

Working Examples

To demonstrate the invention, an adhesive chemistry was made adding 75% by weight of PUMA 92-056 (from Rahn Corp) to 20% of TriMethyl-Trimethylolpropane-Trimethacrylate (TMPTMA) from BASF and a 5% by weight of photo-initiator Darocur 1173 from BASF. The chemistry was mixed with various phosphors (described below) ranging from 6% by weight to 20% by weight. The mixture was then stirred thoroughly and stored in a light-tight container.

There were three sets of phosphors evaluated. The first set of phosphors included a 50%-50% mixture of the Flamingo-phosphor and the Green-Phosphor. The second set of phosphors consisted of a 50%-50% mixture of the Red-phosphor and the Yellow-Phosphor. The third set of phosphors consisted of a 25% of the Red-phosphor, 25% of the Yellow-phosphor, 25% of the Flamingo-phosphor, 25% of the Green-phosphor.

Furthermore, a fourth set of phosphors included a mixture of 50% of LaOBr and 50% of YTaO4. The fourth set of phosphors were phosphors that emit in the UV regime.

The adhesive/phosphor mixtures (about 0.2 grams) were placed between two glass slides and cured under x-ray exposure. The x-ray energy was set at 160 kVp and 20 mA and the distance from the X-Ray source was set at 10 cm.

The adhesives loaded with the UV emitting phosphors cured in 2 minutes under this x-ray setting. All of the other adhesives loaded 12.5% by weight with the three different set of phosphor combinations cured in 2.5 minutes. The cured adhesive was qualitatively similar regardless of the "visible" or "ultraviolet" phosphors used.

Furthermore, a commercial adhesive system was modified by adding the appropriate amount of phosphor mixtures to ACU-TITE UV106G. This adhesive system contains by weight percent the following components: Acrylate oligomers 30-50%, Acryate esters 40-60%, Substituted acrylate 1-10%, SILICA, AMORPHOUS, FUMED, 0.1-3%, Photoinitiators 1-5% and Adhesion promoter 0.1-1.5%. This adhesive was loaded with the Flamingo-Green phosphor mixture using 12.5% and cured in the x-ray. The cure was under 1 min at 160 kVp, 20 mA when the sample was positioned at a distance of 1 cm.

The UV phosphors have a much higher light intensity output than the "visible" phosphors. Yet the "visible" phosphor mixture cures in about the same amount of time and with approximately the same quality of cure as the UV phosphor-adhesive mixture. Controls with no phosphors of any kind showed no curing under x-ray exposure.

Patterned Element Curing

As an example in another embodiment, a patterned element such as a device (such as plug to close a specific internal hole or path ways) can be fabricated (e.g., cured) inside structures (e.g., building materials, man-made or natural underground storage tank, internal organs of human body, etc) using energy excitation (e.g., X ray) from the outside of such structures. Another application of this technique would involve the fabrication of orthopedic structures inside the body, where the curable resin was introduced locally at the point of the orthopedic structure to be formed and a directed or focused x-ray beam cured the structure.

Accordingly, in another embodiment of the invention, there is provided a method (and associated system) for producing a patterned element inside a structure. The method places inside the structure a radiation curable medium including at least one of a plasmonics agent and an energy modulation agent (down converters, mixtures of down converters, up converters, mixtures of up converters, and combinations thereof). The energy modulation agent is configured to emit light into the medium upon interaction with an initiation energy. The method applies to the medium the initiation energy from a directed or focused energy source. The applied initiation energy interacts with the plasmonics agent or the energy modulation agent to generate light (visible and/or ultraviolet) at local regions inside the structure to cure locally the radiation curable medium.

As noted above, this method can form for the patterned element a plug to close a hole or pathway in the structure such as for example holes or pathways in a building material, a man-made or natural underground storage tank, or an internal organ in a human or animal body. The method can form for the patterned element a prosthetic device at a local point in the body of a human or animal.

The method can further localize the curing by placing in the radiation curable medium optically dense materials (such as the color pigments discussed above) to reduce propagation of the generated light from the point of generation.

Controlled Curing

One issue addressed by this invention is that of curing objects to fix the two objects together. When the objects though which the penetrating radiation must pass causes different attenuations of the penetrating radiation (x-rays, electrons, gammas, infrared, microwave) for one object as opposed to the other or when the adhesive region itself causes significant attenuation of the penetrating radiation, then the curing needs to the controlled in a manner such that one side or one region of the adhesive region does not cure excessively faster than another. With curing comes shrinkage, and the effect of one side or one region of the adhesive region curing excessively faster than another is that of stress induced across the adhesive region.

In one embodiment of the invention, the target workpiece to be cured is rotated in the x-ray beam. In one embodiment of the invention, the x-ray beam is rotated about the object. In one embodiment of the invention, the x-ray beam is delivered from a surrounding or nearly surrounding source.

In one embodiment of the invention, as detailed below in the medical applications, the rotational control can permit depth penetrations without excessive x-ray exposure on the surface. In one embodiment of the invention, a focused beam and a rotating beam uniformly deposit x-ray dose into the adhesive to be cured.

In one embodiment of the invention, the reduction in energy of the x-rays upon transiting the object before entering the adhesive to be cured is accounted for to promote higher phosphor light emission per incident x-ray. Work has shown that there exists a peak in emission intensity as a function of the x-ray kVp range.

For illustration, a peak in light emission was observed for 160 kVp irradiation. The emission reduced at 106 kVp, but surprisingly also decreased at 320 kVp. While the theory explain this effect is not complete, it is believed that the x-ray energy entering the medium causes both photoemission and photoionization which are dependent on the energy of a particular x-ray and the medium absorbing the x-rays. Because of this complex phenomena, in one embodiment of the invention, the x-ray energy is set according to a predetermined range of x-ray energy known (for the construct of the objects being fixed together and the adhesive-type and the phosphor type and phosphor loading) to maximize photoemission.

In one embodiment of the invention, x-ray or ebeam sources can be formed which are conformally shaped to the object or portion of the object to be exposed to high energy x-ray or e-beam radiation for curing. In this manner, the x-ray or e-beam radiation is more directed to the object to be cured as opposed to general irradiation of the entirety of the object. U.S. Pat. No. 7,505,562 (the entire contents of which are incorporated herein by reference) describes discrete x-ray sources made from carbon nanotube x-ray sources. As described in the '562 patent, Zhang et al., A Multi-beam X-ray Imaging System Based on Carbon Nanotube Field Emitters, in Medical Imaging 2006, (Proceedings of SPIE, Vol. 6142, Mar. 2, 2006), the entire contents of which are incorporated herein by reference, reported the fabrication, by Xintek, Inc. of Research Triangle Park, N.C., of a linear array of 5 X-ray sources, each with a focal spot between 200 and 300 µm, based on the use of carbon nanotube (CNT) electrodes. Electron currents in the range of 0.1-1 mA were reported at an accelerating voltage of 40-60 kVp. The lifetime of the cold cathode was estimated to exceed 2000 hours. For an accelerating voltage of 200 kV, a beam current of 13 mA has been measured. Devices with 1000 pixels per meter and pulse repetition rates on 10 MHz can be envisioned with technology within the current state of the art.

In an x-ray source, a cathode assembly generates an electron beam which is directed to an x-ray generating target, by an electric field established by an anode and grid. The target in turn emits x-ray radiation in response to the incident electron beam. The radiation absorbed by a patient generally is that which is transmitted from the target in the x-ray tube through a window in the tube, taking into account transmission losses. This window typically is a thin section of beryllium, or other suitable material. In an ebeam source, the accelerated electrons pass through an electron beam window (e.g., titanium or mylar) without interacting with an x-ray generating target.

In one embodiment of the invention, x-ray or ebeam sources of the invention can include a shell or capsule which encloses a cathode and a target element (or electron window). The capsule therefore encloses the x-ray or ebeam source 20 and defines a substantially evacuated interior region. The inner surface of the capsule can be lined with an electrical insulator, while the external surface of the capsule may be electrically conductive.

In one embodiment of the invention, the target element is preferably spaced apart from and opposite an electron emissive surface of the cathode. In one embodiment, the target element can be a small beryllium (Be) substrate, coated on the side exposed to the incident electron beam with a thin film or layer of a high-Z material, such as tungsten (W), uranium (U) or gold (Au). As the atomic number of the x-ray emissive material increases, the peak output in the spectral distribution curve of the emitted x-rays, and the characteristic spectral lines of the x-rays, shift to higher energies. The efficiency of x-ray generation is highly dependent on the acceleration voltage provided. The x-rays are then directed outward through an x-ray transmissive window onto a desired region-to-be-treated.

Similar to the '562 patent, but different, in one embodiment of the invention, x-ray or ebeam sources made for example from carbon nanotube arrays could be configured in a linear or two-dimensional array or a three-dimensional array and triggered in parallel or sequentially of in a phased manner. While other procedures could be used, the fabrication procedures of the '562 patent could be used in the present invention to produce a contoured or shaped x-ray or ebeam source including linear or two-dimensional array or a three-dimensional array of electron emitters formed on a shaped base which would conform to the shape of the object to be irradiated. The use of 'conformal" x-ray or ebeam source arrays of this type may be particularly advantageous for the following reasons:

The x-ray source could be very compact, especially in the dimension along the line of x-ray emission.

Use of a contoured array of x-ray beams could advantageously reduce overexposure of outside-target regions not associated with the curing.

Parallel processing could be used to fabricate stacks of objects.

Sequential processing for different components at different geometries or material constructions could be accomplished efficiently by "custom" sources for each adhesive joint assembly.

In one embodiment of the invention, the x-ray or ebeam sources are part of an overall assembly line completing the construction of an object. In one embodiment, there are multiple of the x-ray or ebeam sources disposed at different "positions" along an assembly with each source designed to cure a particular element of the object.

For example, in the fabrication of a household glass window, a first x-ray or ebeam source could be a linear array disposed in the horizontal direction with a second x-ray or ebeam source disposed in the vertical direction. A window panel with the glass panes in place would pass by the horizontal linear array stopping at two points to form the adhesive seal along the two horizontal extending sides of the glass pane. The window panel would then pass by the vertical linear array stopping at two points to form the adhesive seal along the two vertical extending sides of the glass pane. At that point, the window panel could have handles placed on the wooden frames with adhesive layer between the handles and the wood frame. The window panel would then transit to a third x-ray or ebeam source having a contoured array of xray or ebeam emitters designed to emit xrays or electrons preferentially to the adhesive layer adhesive layer between one of the handles and the wood frame. The window panel would be positioned relative to the third x-ray or ebeam source sequentially so that multiple exposures would adhere all the handles to the wood.

In another example, sewing remains a fairly intensive component of apparel construction. Pockets, belt loops, hems, seams, and collars are typically sewn in order to complete the article of apparel. Moreover, the conventional sewing process (while subject to automation) nevertheless requires the sewing of one article at a time. With the materials of apparel being light weight (low in atomic number and mostly carbon), in one embodiment of the invention, the shaped x-ray or ebeam source described herein could be stationed above a stack of apparel and above for example the pocket region and shaped to the outline of the pocket. In this manner, exposure from the pocket-shaped x-ray or ebeam source would adhere the entire stack of shirts (e.g., 20-50 or 200 to 500) in one step. Similar to that described above for the glass panel, the stack of shirts could then be moved to a second shaped x-ray or ebeam source (in this case a linear shaped x-ray or ebeam source) where the seams of the shirt (along the line of buttons or the button holes) could be adhered instead of sewing. In this manner, the stack of shirts could all be processed in parallel.

While described above with regard to the fabrication of a window pane and clothing apparel, the same sequence of using shaped x-ray or ebeam sources at different "points" in an assembly process could be used in various embodiments of the invention to adhesively assemble a wide variety of products including but not limited to plastic products, wood products, aluminum products, glass products, textile products, apparel products (e.g., shoes, dresses, pants, coats, outer wear, gloves, etc.).

Moreover, there is discussion and development of light weight "natural" products for automotive and other bodies to reduce weight. One such company FlexFrom Technologies, Indiana, makes environmentally friendly composite materials using customizable blends of sustainable natural fibers (such as kenaf, jute and hemp) and fiberized thermoplastic polymers to create materials that are moldable, strong, lightweight, shatter resistant, appealing in look and feel, noise reducing, recyclable and cost effective. The FlexForm materials provide moldable substrates for numerous important applications, such as interior panels, load floors and underbody shields for cars and trucks, workspace panels and furnishings for offices and homes, containers for shipping and storage, structural support for agricultural seedlings, and many other applications. For automotive applications, FlexForm materials reduce vehicle weight and fuel consumption, and increase safety by their resistance to shattering on impact.

As such the attachment of fixtures to the molded parts or the adhesion of one pre-molded part to another could be accomplished in one embodiment of the invention by utilization of the shaped x-ray or ebeam sources. By having a reliable way to adhere multiple pre-molded components together, the assembly can be accelerated without having to drill holes and add fastening attachments.

U.S. Pat. No. 8,022,610 (the entire contents of which are incorporated herein by reference) describes a way of making an electron beam source from array of carbon nanotubes. The '610 patent describes a carbon nanotube device applicable to an electron source, an STM (scanning type tunnel microscope) probe, or an ATM (atomic force microscope) probe. While other procedures could be used, the '610 patent describes fabrication procedures which could be used in the present invention to produce a contoured or shaped x-ray or ebeam source including linear or two-dimensional array or a three-dimensional array of electron emitters formed on a shaped base.

Accordingly, one example of how to form the present x-ray source or ebeam source with an array of carbon nanotubes would include forming an aluminum thin film on a shaped or contoured conductive surface, then anodically oxidizing the aluminum thin film. This process would be applicable to an aluminum film on insulator or glass substrates which provides the present invention a wide latitude in shapes and/or patterns that can be used. For example, a relatively large substrate can have a patterned layer of aluminum present initially or formed by way of selective chemical etching after fabrication. Carbon nanotubes 24 would then be grown from the conductive surface in narrow holes formed in the Al anodic oxidized film (alumina film). The conductive surface 21 could include a layer containing at least one element selected from the group consisting of titanium (Ti), zirconium (Zr), niobium (Nb), tantalum (Ta), molybdenum (Mo), copper (Cu) and zinc (Zn), or more preferably, layer comprising Nb. That is, when the conductive surface is formed from such a material, the narrow holes formed in the alumina film never disappear, and anodic oxidation of Al never peels off the alumina film from the conductive surface. When the conductive surface is formed of such a material, it is possible to form a bridge-shaped path containing the material composing the conductive surface, connecting the narrow hole bottom and the conductive surface, in the alumina film present between the narrow hole and the layer composing the conductive surface, by continuing anodic oxidation even after the completion of oxidation of the Al film.

Anodic treatment of Si can be carried out by using a Si support as an anode and platinum as a cathode in a fluoric acid solution and feeding a current of several tens of mA/cm$^2$. This method makes it possible to form a plurality of narrow holes isolated from each other by silicon or silicon oxide on the Si support surface. It is therefore possible to obtain a carbon nanotube device of the invention by preparing a conductive silicon support (p-type Si or the like) as a support, anodizing the surface of the conductive silicon support to form narrow holes isolated by silicon or silicon oxide, and causing carbon nanotubes to grow from the bottom of the narrow holes.

When forming a carbon nanotube in the narrow hole resultant from Al anodic oxidation or anoxidation of Si as described above, it is recommendable to form a catalytic fine particle on the narrow hole bottom, i.e., on the conductive surface, and to cause the carbon nanotube to grow from the surface of this catalytic fine particle 23. Applicable catalyst materials include, for example, iron (Fe), cobalt (co) and nickel (Ni).

The catalytic super-fine particle should preferably have a particle diameter within a range of from 1 to 10 nm, or more preferably, from 2 to 50 nm. A catalyst of such a material having such a size can efficiently cause a carbon nanotube to grow and achieve a size excellent in electron emitting efficiency.

For depositing such a catalytic particle into the narrow hole, for example, the AC electro-deposition process is effectively applicable.

When preparing a Co super-fine particle, for example, it suffices to impress an AC (50 Hz) voltage of about 15 V to a space between the conductive surface 21 and the opposed electrode in an aqueous solution of $CoSO_4.7H_2O$=5% and $H_3BO_3$=2%. This method permits introduction of the catalytic super-fine particle 23 even into the slightest narrow hole 53 formed by, for example, the Al anodic oxidation.

Another method for introducing the catalytic particle into the narrow hole comprises vapor-depositing Fe, Co or Ni onto the conductive surface having a narrow hole and a side wall, and thermally aggregating this vapor-deposited film.

An effective method for causing a carbon nanotube to grow on the conductive surface provided with the catalyst comprises, for example, thermally treating the support in a gas atmosphere containing not only the raw material gas, but also added with a diluent gas or a growth accelerator gas. Many gases containing carbon are applicable as a raw material gas.

Examples of the raw material gas include gases comprising only carbon and hydrogen, such as methane, ethane, propane, butane, pentane, hexane, ethylene, acetylene, benzene, toluene and cyclohexane, and gases comprising carbon, hydrogen and other elements, such as benzonitrile, acetone, ethyl alcohol, methyl alcohol and carbon monoxide.

Preferable raw materials from among these applicable ones, somewhat varying with the kind of the support, the composition of the growth nucleus, growing temperature and pressure, are ones comprising carbon, hydrogen and oxygen, which make it difficult for impurities to come in.

For low temperature growth of the carbon nanotube 24, ethylene, acetylene and carbon monoxide are preferable. Hydrogen is preferable as a growing or growth accelerating gas. However, because effectiveness of hydrogen depends upon the raw material gas, the reaction temperature, and the composition of the growth nucleus, hydrogen is not an essential requirement.

In one example, a contoured or shaped support having the catalytic particles can placed in the reactor, and hydrogen in an amount of 10 sccm introduced at a pressure of 500 Pa. The support temperature can be brought to between 400 and 800° C. by turning on an infrared lamp or other heater.

After temperature stabilization, a raw material gas such as methane, ethylene, acetylene, carbon monoxide or benzene was introduced in an amount of 10 sccm from a raw material gas tube 44, and the pressure in the reactor of 1000 Pa was kept for 20 minutes.

In another example, a Si wafer or silicon on insulator SOI substrate cut or diced to a desired shape serves as the support, and a Co film having a thickness of 0.1 μm can be formed on this support by the RF sputtering process. Then, an Al film can be continuously formed to a thickness of 0.2 μm to form an Al/Co layered film by sputtering.

This support was immersed in a 0.3 M oxalic acid solution, and the Al film was anodically oxidized by using support as an anode and Pt as a cathode and impressing 40 V while keeping a temperature of 17° C. As a result of voltage impression, the Al surface will be oxidized, leading to the formation of narrow holes. Upon the completion of oxidation of the Al film, the narrow hole would have reached the undercoat Co, and the anodic oxidation discontinued.

To widen the bore of the narrow holes, the support can be immersed in a phosphoric acid solution of about 5 wt. % for 40 minutes and taken out. As a result of this treatment, the undercoat Co surface is exposed on the bottom of the narrow holes and could be used as a catalyst portion. This process is also applicable to amorphous or microcrystalline silicon on insulator or glass substrates which provides the present invention a wide latitude in shapes and/or patterns that can be used. For example, a relatively large substrate can have patterned layer of silicon present initially or formed by way of selective chemical etching after fabrication.

Regardless, the support can be placed in a reactor, and hydrogen gas was introduced in an amount of 20 sccm at a pressure in the reactor of 500 Pa. The support temperature can be increased to 600° C. by turning on an infrared lamp. After stabilization of temperature, ethylene diluted with nitrogen to 10% can be introduced in an amount of 20 sccm to bring pressure in the reactor to 1,000 Pa which was kept for 20 minutes.

Once the carbon nanotubes are in place on the shaped or contoured support, electrodes are formed to make contact with the carbon nanotubes. Conventional photolithography and etching can be used prior to carbon nanotube formation to form contact pads connecting to the aluminum or cobalt deposits noted above. After carbon nanotube formation, an insulating layer and a top electrode can be formed on the shaped or contoured support over regions of the carbon nanotubes not to be utilized. After carbon nanotube formation, electrical contact to the contact pads can be made to permit voltage application to the carbon nanotubes in contact with each pad.

At this point, the ebeam source has been fabricated on the contoured or shaped support. The support in whole or in part can now be included with conventional elements of an ebeam source (e.g., acceleration grids and transparent window) and/or with conventional elements of a x-ray source (e.g., acceleration grids, target for x-ray production) and transparent x-ray window).

This construction would follow similar procedures as set forth in U.S. Pat. No. 5,548,185 (the entire contents of which are incorporated herein by reference) in order to establish a matrix addressable xray or ebeam source, that is a matrix addressable field emission type grid having a triode (three terminal) structure. These procedures are known in the art and omitted from this detailed discussion. The matrix addressable xray or ebeam source would have a plurality of carbon nanotubes or other field-emission cathodes including a low work function material and a grid assembly positioned between corresponding anodes and cathodes to thereby control emission levels to the anodes (the xray target material or electron transmission window. Besides carbon nanotubes, the layer of low work function material could be an amorphic diamond film. The grid assembly includes a conductive layer deposited between the plurality of anodes and cathodes and over interstices between the cathodes, the conductive layer having apertures therein, the cathodes aligned with, and of the same size as, the apertures.

In other words, the matrix addressable xray or ebeam source is of a field emission type using a triode (three terminal) pixel structure. The matrix addressable xray or ebeam source is matrix-addressable by using grid and cathode assemblies arranged in strips in a perpendicular relationship whereby each grid strip and each cathode strip can be individually addressable by grid and cathode voltage drivers, respectively. Effectively, a "pixel" is formed at each intersection of a grid strip and a cathode strip. The result is that each pixel within the matrix addressable xray or ebeam source may be individually illuminated.

Since the substrates noted above can be silicon on insulator or aluminum on insulator, thin panels of the carbon nanotubes can be formed with thin glass panels and the substrate containing the carbon naonotubes or low work function material can be encased with a thin glass panel opposing the carbon nanotubes and forming the electron optics and target material for the x-ray or the transmission window for the electrons.

The thin panels are flexible and can be shaped after fabrication to conform to the object to be treated.

Computer-Assisted Control

In one embodiment of the invention, there is provided a computer implemented system for designing and selecting suitable combinations of initiation energy source, energy modulation agent, and activatable agent. For example, the computer system 5 shown in FIG. 1 can include a central processing unit (CPU) having a storage medium on which is provided: a database of excitable compounds, a first computation module for a photoactivatable agent or energy transfer agent, and a second computation module predicting the requisite energy flux needed to sufficiently activate the energy transfer agent or photoactivatable agent.

Figure 22:
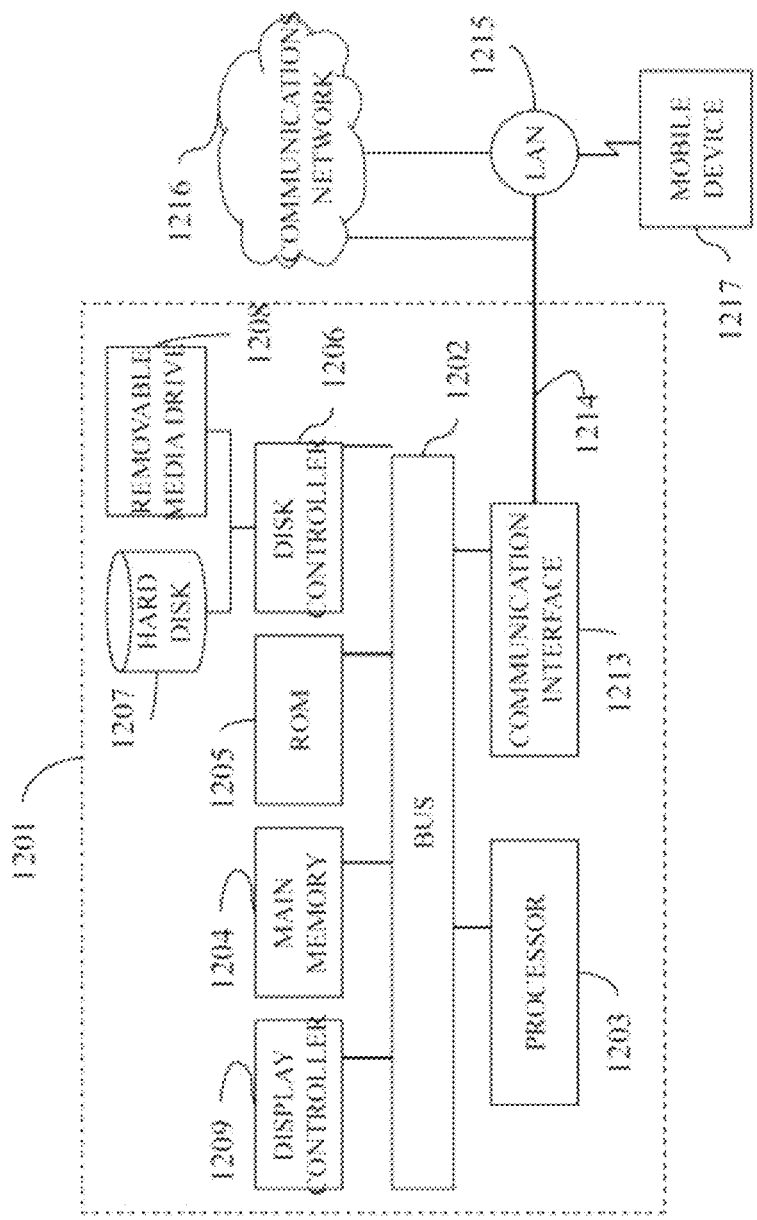
FIG. 22 is a schematic of an exemplary computer system for implementing various embodiments of the invention.
Figure 23:
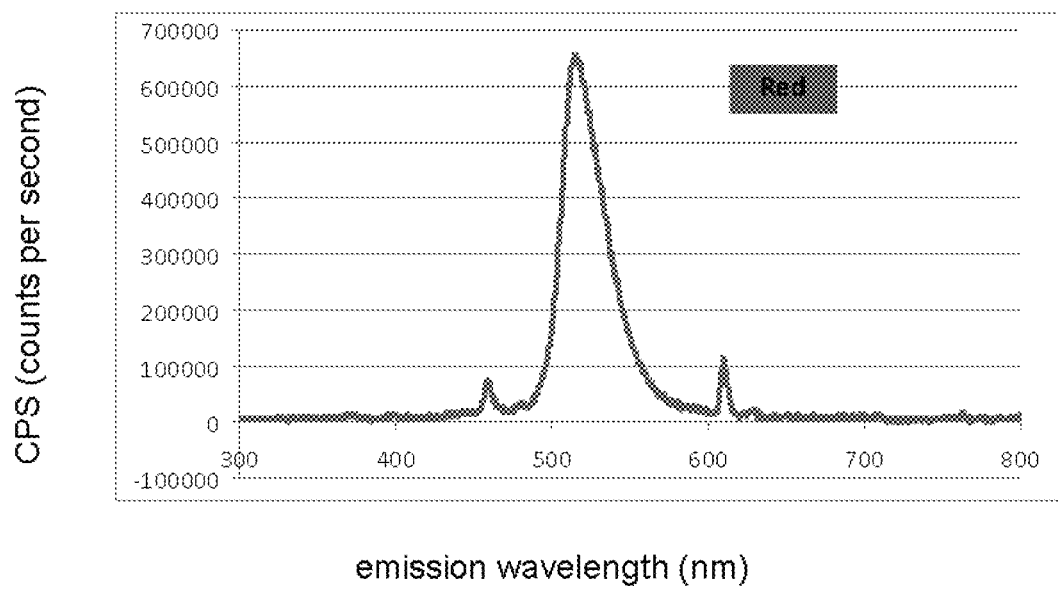
FIG. 23 is a depiction of an x-ray induced optical emission spectra from a red (R) phosphor.
Figure 24:
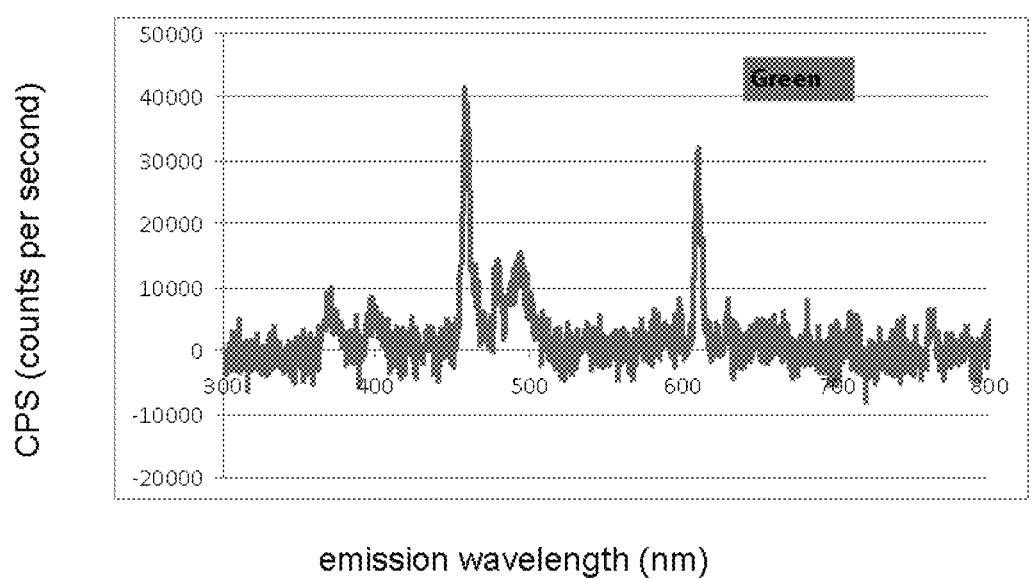
FIG. 24 is a depiction of an x-ray induced optical emission spectra from a green (G) phosphor.
Figure 25:
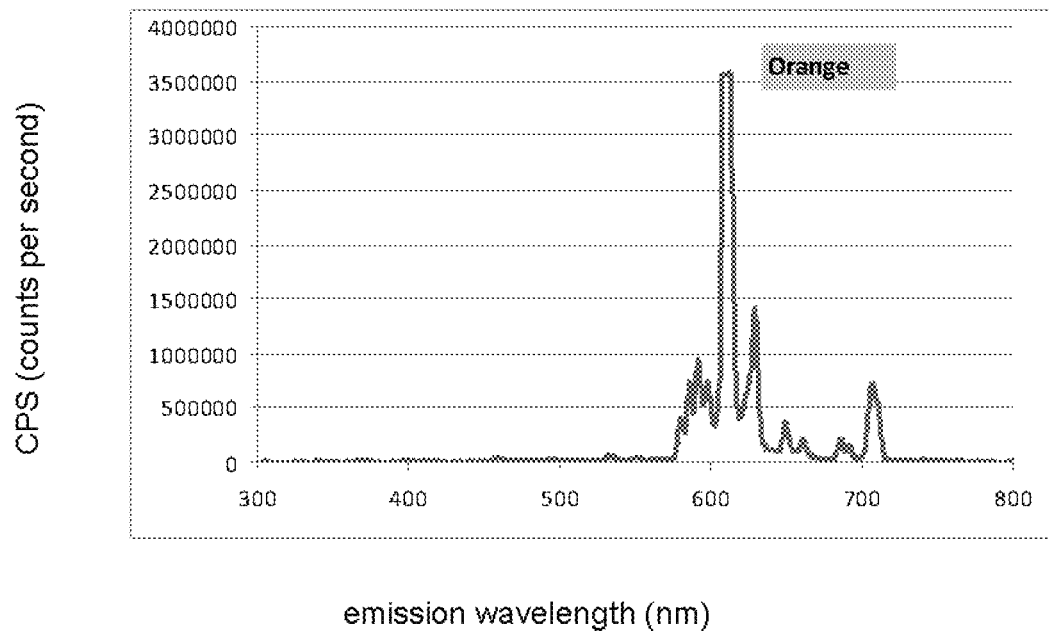
FIG. 25 is a depiction of an x-ray induced optical emission spectra from an orange (O) phosphor.
Figure 26:
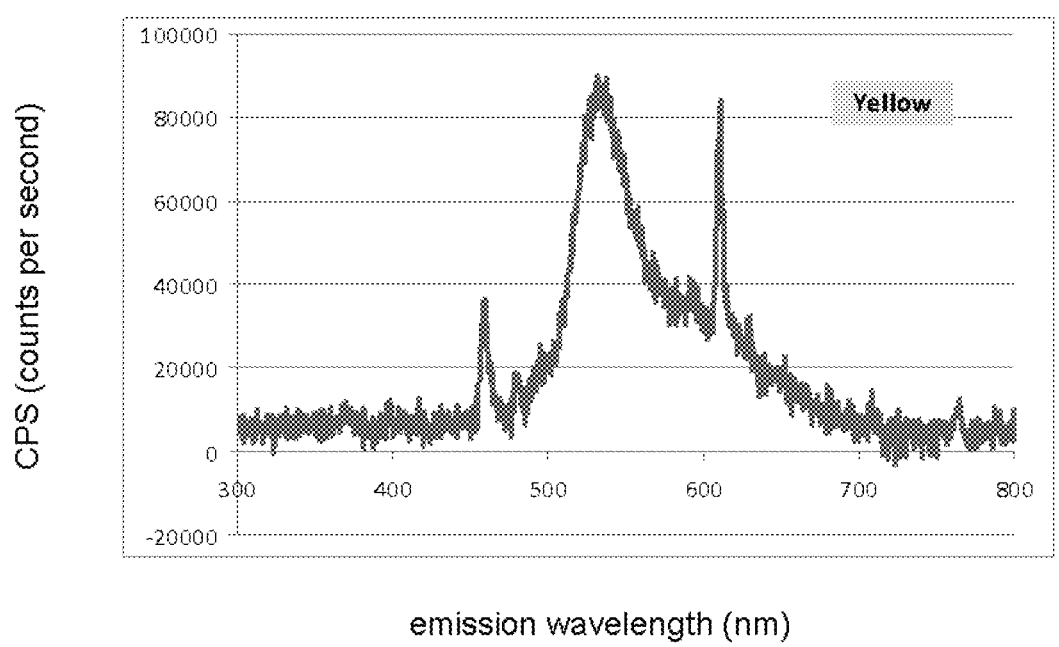
FIG. 26 is a depiction of an x-ray induced optical emission spectra from a yellow (Y) phosphor.

FIG. 22 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps (or functions) of this invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The reagents and chemicals useful for methods and systems of the invention may be packaged in kits to facilitate application of the invention. In one exemplary embodiment, a kit would comprise at least one activatable agent capable of producing a predetermined cellular change, at least one energy modulation agent capable of activating the at least one activatable agent when energized, optionally at least one plasmonics agent that can enhance applied initiation energy such that the enhanced initiation energy activates the at least one activatable agent which produces a change in the medium when activated, and containers suitable for storing the various agents in stable form, and further comprising instructions for administering the at least one activatable agent and/or at least one energy modulation agent to a medium, and for applying an initiation energy from an initiation energy source to activate the activatable agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

System Implementation

In one embodiment, there is a system for imaging or treating a tumor in a human or animal body. The system includes a pharmaceutical carrier including phosphors which are capable of emitting radiation into the tumor or the body upon interaction and which provide x-ray contrast, one or more devices which infuse the tumor with a photoactivatable drug and the pharmaceutical carrier, an x-ray or high energy electron source, and a processor programmed to at least one of 1) produce images of the tumor or 2) control a dose of x-rays or electrons to the tumor for production of light inside the tumor to activate the photoactivatable drug.

In one embodiment, there is a method for imaging or treating a tumor in a human or animal body. The method includes injecting into a vicinity of and inside the tumor a pharmaceutical carrier including phosphors which are capable of emitting radiation into the tumor or the body upon interaction and which provide x-ray contrast, infusing the tumor with a photoactivatable drug and the pharmaceutical carrier, applying x-ray or high energy electrons to the tumor, and at least one of obtaining images of the tumor and producing light inside the tumor to activate the photoactivatable drug.

In one embodiment of the invention, there is a system for producing a change in a medium (which may or may not to be disposed in an artificial container). The first system includes a mechanism configured to supply in the medium at least one of a plasmonics agent and an energy modulation agent (down converters, mixtures of down converters, up converters, mixtures of up converters, and combinations thereof). The plasmonics agent enhances or modifies energy in a vicinity of itself. In one example, the plasmonics agent enhances or modifies the applied initiation energy such that the enhanced initiation energy produces directly or indirectly the change in the medium. The system includes an initiation energy source configured to apply an initiation energy through the artificial container to the medium to activate the at least one activatable agent in the medium.

In one embodiment, the applied initiation energy interacts with the energy modulation agent to directly or indirectly produce the change in the medium by emitted light (UV and/or visible light). The energy modulation agent predominantly emits light in a visible wavelength range to activate a normally ultraviolet activated photoreaction to produce said change.

As used herein, "normal predominant emission" means the emission that an energy modulation agent is normally expected to emit upon application of an initiation energy.

In one embodiment, the energy modulation agent converts the applied initiation energy and produces light (UV and/or visible light) at an energy different from the applied initiation energy. The plasmonics agent (if present) can enhance the light from the at least one energy modulation agent. In one embodiment, the applied initiation energy source is an external initiation energy source. In one embodiment, the applied initiation energy source is a source that is at least partially in a container holding the medium.

The medium in one embodiment is substantially transparent to the initiation energy. For example, if the medium is a liquid or fluid food product such as orange juice which has a substantial amount of suspended solids, then UV light for example as described above and even visible light will be substantially absorbed and/or scattered by the orange juice medium. Furthermore, microwave energy will likewise be absorbed by this medium. However, an initiation energy source such as an X-ray source will essentially transmit entirely through for example an orange juice medium. The effect is the medium can now be totally illuminated with the external initiation energy source.

The activatable agents can be photoactivatable agents such as the photocages (described elsewhere) such that upon exposure to the initiation energy source, the photocage disassociates rendering an active agent available.

The activatable agents can include agents such as those recited above. The activatable agents can alternatively include photocatalysts such as $TiO_2$, $ZnO$, $CdS$, $CdSe$, $SnO_2$, $SrTiO_3$, $WO_3$, $Fe_2O_3$, and $Ta_2O_5$ particles.

The systems described herein can include a mechanism configured to provide in the medium energy modulation agents (down converters, mixtures of down converters, up converters, mixtures of up converters, and/or combinations thereof) which converts the initiation energy to an activation energy for activation of the activatable agent(s). Phosphorescent compounds, chemiluminescent compounds, and bioluminescent compounds can be included in a photocage. The energy modulation agent(s) can be up conversion or down conversion agents or combinations thereof. The energy modulation agent(s) can be luminescent particles which emit light upon exposure to said initiation energy. The luminescent particles can be nanoparticles of semiconducting or metallic materials. The luminescent particles can be chemiluminescent particles which show enhanced chemiluminescence upon exposure to microwaves.

The systems described herein can include a mechanism configured to provide in the medium plasmonics-agents including metal nanostructures such as for example nanospheres, nanorods, nanocubes, nanopyramids, nanoshells, multi-layer nanoshells, and combinations thereof. The form and structure of these plasmonics-agents can vary as shown in the figure above.

Depending on the initiation energy source, the system can include a container for the medium that is permeable to the applied initiation energy. For example, for an X-ray source, the container can be made of aluminum, quartz, glass, or plastic. Furthermore, the container can be a container which receives and transmits the initiation energy to fluid products to pasteurize the fluid products, or can be a container which receives and transmits the initiation energy to fluid products to remediate contaminants in the fluid products.

In another embodiment of the invention, there is provided a system for curing a radiation-curable medium. This system includes a mechanism configured to supply an uncured radiation-curable medium including at least one plasmonics agent, energy modulation agents (down converters, mixtures of down converters, up converters, mixtures of up converters, and/or combinations thereof), and at least one activatable agent which produces a change in the radiation-curable medium when activated, and further includes an applied initiation energy source configured to apply initiation energy to a composition including the uncured radiation-curable medium, optionally the plasmonics agent, and the energy modulation agent. The energy modulation agents as described above absorb the initiation energy and convert the initiation energy to an activation energy capable of curing the uncured medium (i.e., promoting polymerization of polymers in the uncured medium). The plasmonics agent if present enhances the applied initiation energy such that the enhanced initiation energy directly or indirectly cures the medium by polymerization of polymers in the medium. For example, the plasmonics agent can enhance the activation energy light such that enhanced light activates the at least one photoactivatable agent to polymerize polymers in the medium. In another example, activation of the energy modulation agent produces radiation (such as, for example, UV and/or visible light) which activates the at least one photoactivatable agent to polymerize polymers in the medium.

The systems described herein can further permit the at least one activatable agent to include a photoinitiator such as one of benzoin, substituted benzoins, alkyl ester substituted benzoins, Michler's ketone, dialkoxyacetophenones, diethoxyacetophenone, benzophenone, substituted benzophenones, acetophenone, substituted acetophenones, xanthone, substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators, non-fluorene-carboxylic acid peroxyesters and mixtures thereof.

The systems described herein can also include a mechanism configured to provide in the medium plasmonics-agents including metal nanostructures such as for example nanospheres, nanorods, nanocubes, nanopyramids, nanoshells, multi-layer nanoshells, and combinations thereof.

The systems described herein can include a container for the uncured radiation-curable medium that is permeable to the applied initiation energy. The container can be configured to contain the uncured radiation-curable medium or to hold a mold of the uncured radiation-curable medium. The container as before can be an aluminum container, a quartz container, a glass container, or a plastic container, depending on the applied initiation energy.

In one embodiment, an energy source (e.g., an external energy source) is configured to irradiate the uncured radiation-curable medium in a joint region (or regions) adhering one region of a utensil to another region of the utensil. In another embodiment, the energy source is configured to irradiate the joint regions and thereby induce sterilization of the joint regions due to the production of internal radiation (UV and/or visible light) inside the joint regions. In another embodiment, the energy source is configured to irradiate a surface coating. In another embodiment, the energy source is configured to irradiate a mold of the radiation-curable medium.

The radiation-curable medium in the surface coating or in the mold or in other medium can include color pigments to add color to a finished cured product. The radiation-curable medium in the surface coating or in the mold or in another medium can include fumed silica to promote strength and enhance distribution of the internally generated radiation (UV and/or visible light). The radiation-curable medium in the surface coating or in the mold or in another medium can include a moisture cure promoter to supplement the cure.

The systems described herein can provide one mechanism for production of novel radiation-cured articles, which include a radiation-cured medium, optionally at least one plasmonics agent, and at least one energy modulation agent distributed throughout the medium. The energy modulation agents (down converters, mixtures of down converters, up converters, mixtures of up converters, and/or combinations thereof) being substances which is capable of converting an applied energy to a radiation (UV and/or visible light) capable of producing a cure for the radiation-cured medium. The plasmonics agent enhances the applied initiation energy such that the enhanced initiation energy activates the energy modulation agents.

Radiation produced from the energy modulation agent can also be enhanced by the plasmonics agents in the medium. The article can include luminescent particles such as for example nanotubes, nanoparticles, chemiluminescent particles, and bioluminescent particles, and mixtures thereof. The article can include nanoparticles of semiconducting or metallic materials. The article can include chemiluminescent particles. The article can include color pigments or fumed silica. The article can include plasmonics-agents including metal nanostructures such as for example nanospheres, nanorods, nanocubes, nanopyramids, nanoshells, multi-layer nanoshells, and combinations thereof. The form and structure of these plasmonics-agents can include the probe structures detailed above.

In another embodiment of the invention, there is provided a system for producing a change in a medium disposed in an artificial container. This system includes a mechanism configured to provide to the medium 1) an activatable agent and 2) at least one of a plasmonics agent and various energy modulation agents (down converters, mixtures of down converters, up converters, mixtures of up converters, and combinations thereof). The energy modulation agent converts an initiation energy to an activation energy (UV and/or visible light) which then activates the at least one activatable agent. This system further includes an applied initiation energy source configured to apply the initiation energy through the artificial container to activate the at least one activatable agent in the medium. The plasmonics agent if present enhances or modifies an energy in a vicinity of itself. In one example, the plasmonics agent enhances or modifies the applied initiation energy such that the enhanced initiation energy produces directly or indirectly the change in the medium.

The systems described herein can include encapsulated structures including at least one of the energy modulation agents and the plasmonics agents. The encapsulated structures can include nanoparticles of the energy modulation agents (down converters, mixtures of down converters, up converters, mixtures of up converters, and combinations thereof) encapsulated with a passivation layer or can include sealed quartz or glass tubes having the energy modulation agent inside. The encapsulated structures can include sealed tubes having the plasmonics agent disposed on an outside of the sealed tube (which may or may not be exposed directly to the medium).

In another embodiment of the invention, there is provided a system for producing a photo-stimulated change in a medium disposed in an artificial container. This system includes a mechanism configured to provide in the medium at least one of a plasmonics agent and various energy modulation agents (down converters, mixtures of down converters, up converters, mixtures of up converters, and/or combinations thereof). The energy modulation agents convert an initiation energy to an activation energy (UV and/or visible light) which then produces the photo-stimulated change. The fourth system further includes an initiation energy source configured to apply the initiation energy to the medium to activate the at least one energy modulation agent in the medium. The plasmonics agent enhances or modifies an energy in a vicinity of itself. In one example, the plasmonics agent enhances or modifies the applied initiation energy such that the enhanced initiation energy produces directly or indirectly the change in the medium. As above, this system can include encapsulated structures including therein the energy modulation agents (down converters, mixtures of down converters, up converters, mixtures of up converters, and/or combinations thereof). The encapsulated structures can include nanoparticles of the energy modulation agent encapsulated with a passivation layer. The encapsulated structures can include sealed tubes having the plasmonics agent disposed on an outside of the sealed tube (which may or may not be exposed directly to the medium).

The systems described herein an include a container which receives and transmits the initiation energy to products within the medium. The products can include plastics, where the activation energy alters the surface structure of the plastics. The products can include polylactic acid (PLA) plastics and polyhydroxyalkanoates (PHA) plastics. In this embodiment, the activation energy can photo-graft a molecular species onto a surface of the plastics.

Treatment of Cell-Proliferation Disorders

Conventional radiation treatment for cell proliferation disorders such as cancer typically involve subjecting the patient to high doses of x-rays (1 MV or more), while attempting to focus the x-rays on the sites of tumors. This type of exposure, however, causes significant negative side-effects, such as killing of healthy cells in the path of the x-rays, as well as often causing significant burns, both external and internal, in the patient's tissues. In a preferred embodiment of the invention, a subject is administered an activatable pharmaceutical agent, optionally along with at least one energy modulation agent capable of converting x-rays into a wavelength that will activate the activatable pharmaceutical agent. The subject is then placed into a source of low energy x-rays, such as a CT scanner, and subjected to the low energy x-rays. CT scanners typically use low dose x-rays on the order of 200 kVp or less, and provide significantly lower exposures for the patient. As an added embodiment, since low energy x-rays are typically used for imaging and diagnostic purposes, the low energy x-ray source can be used to simultaneously, or in rapid succession, image the site of tumors, and treat the tumors in a single session.

Having generally described this invention, a further understanding can be obtained by reference to certain specific examples which are provided herein for purposes of illustration only and are not intended to be limiting unless otherwise specified.

In order to show that a low energy x-ray source such as a CT scanner can activate a pharmaceutical agent and kill cancer cells, the following tests were performed:

Cell cultures of BT474 and 4T1/HER2 cancer cell lines were grown in separate containers. The samples were then treated using a CT scanner under the following conditions, using UVADEX (8-MOP or 8-methoxypsoralen) as pharmaceutical agent, and as the energy modulation agent, a combination of 2 phosphors NP200 and GTP4300 (both phosphors commercially available from Voltarc) in a 33:67 wt % ratio respectively, and placed in sample containers as follows:

1. Control (cell line only; no pharmaceutical agent; no energy modulation agent; no x-ray)
2. UVADEX only (1:10)
3. NP200/GTP4300 (200 μg/mL)
4. UVADEX+NP200/GTP4300 (200 μg/mL)
5. NP200/GTP4300 (50 μg/mL)
6. UVADEX+NP200/GTP4300 (50 μg/mL)

These samples were each tested under three CT scanner settings:

1. no CT
2. 80 kV/160 mA/8 min
3. 100 kV/130 mA/8 min

The two energy modulation agents have elemental compositions as follows:

GTP 4300=Ca, F, Cl, PO4, (96-99%)
Mn (1-3%) Sb (<1%)
NP200=LaPO4; Ce, Tb (doped)

(Another purchased nominally "NP200" phosphor was determined to elementally contain Zn, Si, O, Mn via XPS, EDS and ICP-MS. XRD suggests an amorphous crystal phase with some indication of a Willemite (Trigonal Rhombohedral) type structure present. The molecular composition is likely to be Zn2SiO4:Mn with Mn doped between 0.05-10%.)

TABLE 19

| | | % Viability (1-Toxicity) | Psoralen & Phosphor | Fractional Kill |
|---|---|---|---|---|
| NP200 | LaPO4: $Ce^{3+}$, $Tb^{3+}$ | 75% | 0.51 | 32.0% |
| GTP 4300 | $3Ca_3(PO4)_2 \cdot Ca(Fl,Cl)_2$: $Sb^{3+}$, $Mn^{2+}$ | 70% | 0.54 | 22.9% |

Figure 39:
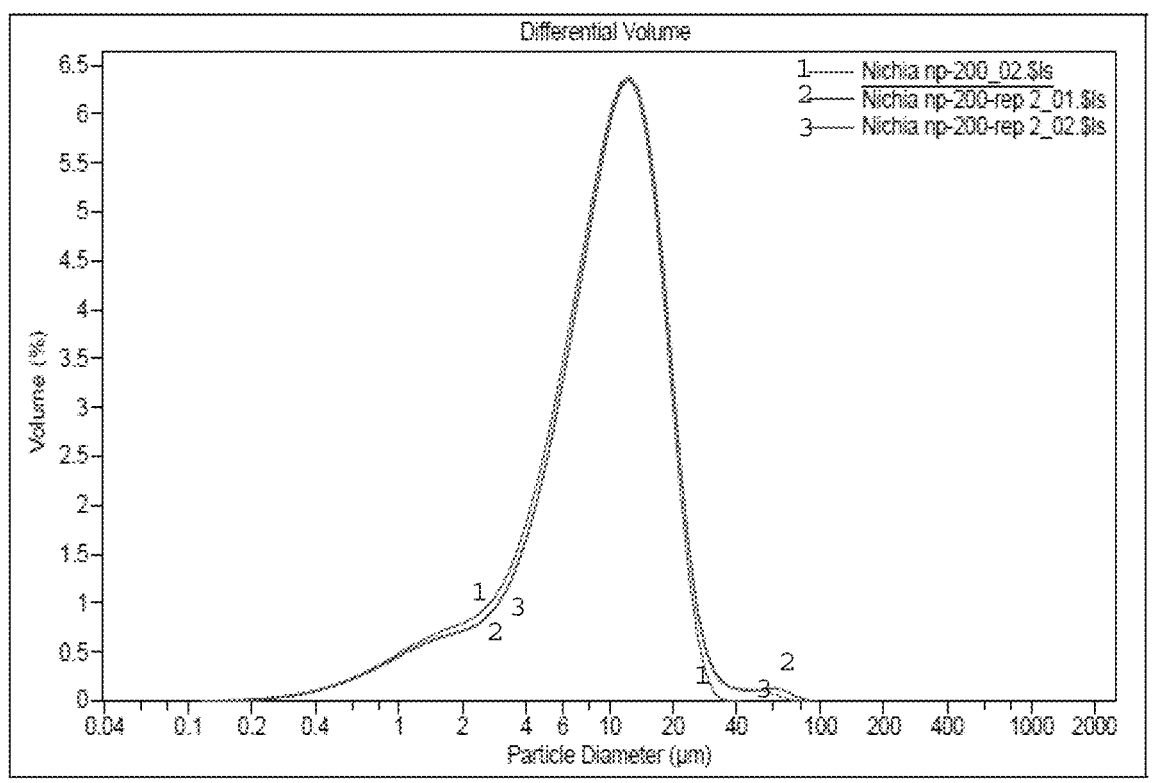
FIG. 39 is a schematic depicting a preferred particle size distribution of one preferred phosphor of interest: NP 200.
Figure 40:
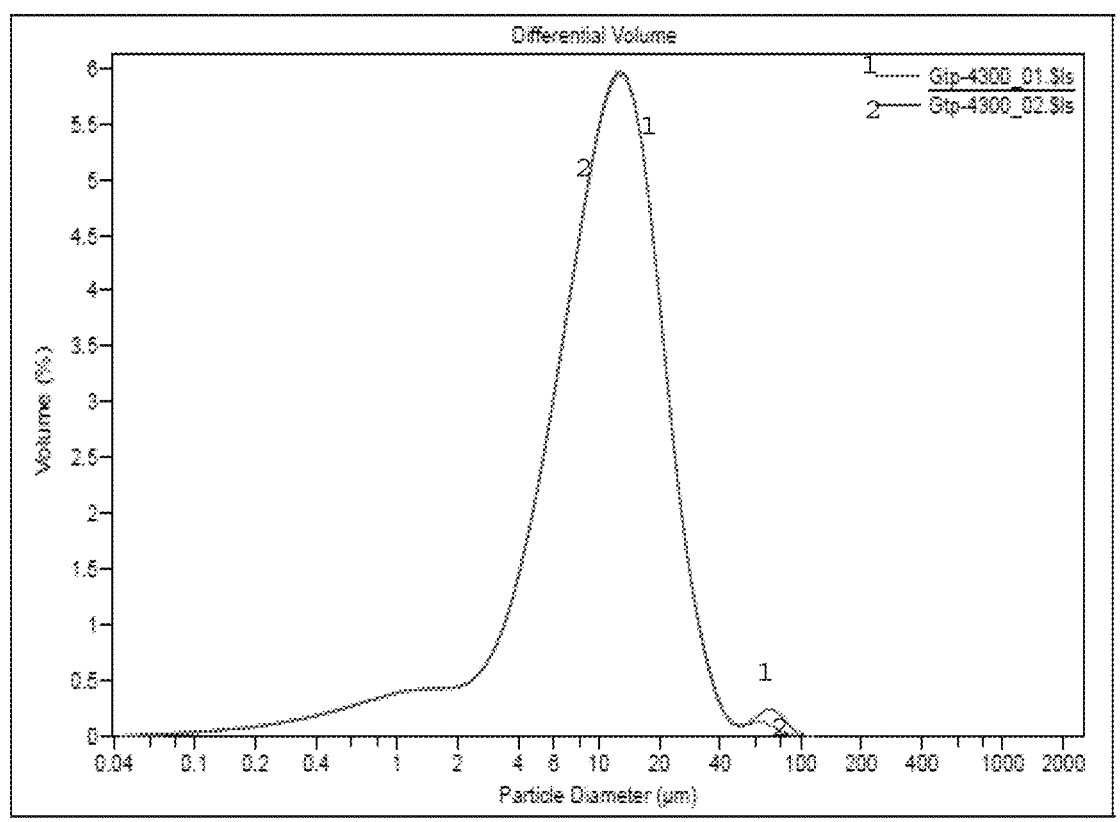
FIG. 40 is a schematic depicting a preferred particle size distribution of another preferred phosphor of interest: GTP 4300.
Figure 41:
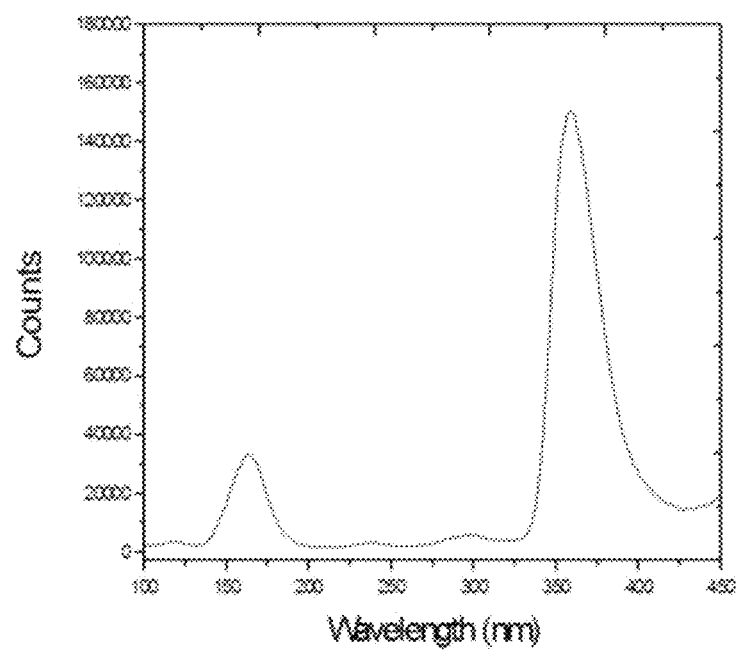
FIG. 41 is a plot of an emission spectrum of $LaPO_4$: $Ce^{3+}$, $Tb^{3+}$.
Figure 42:
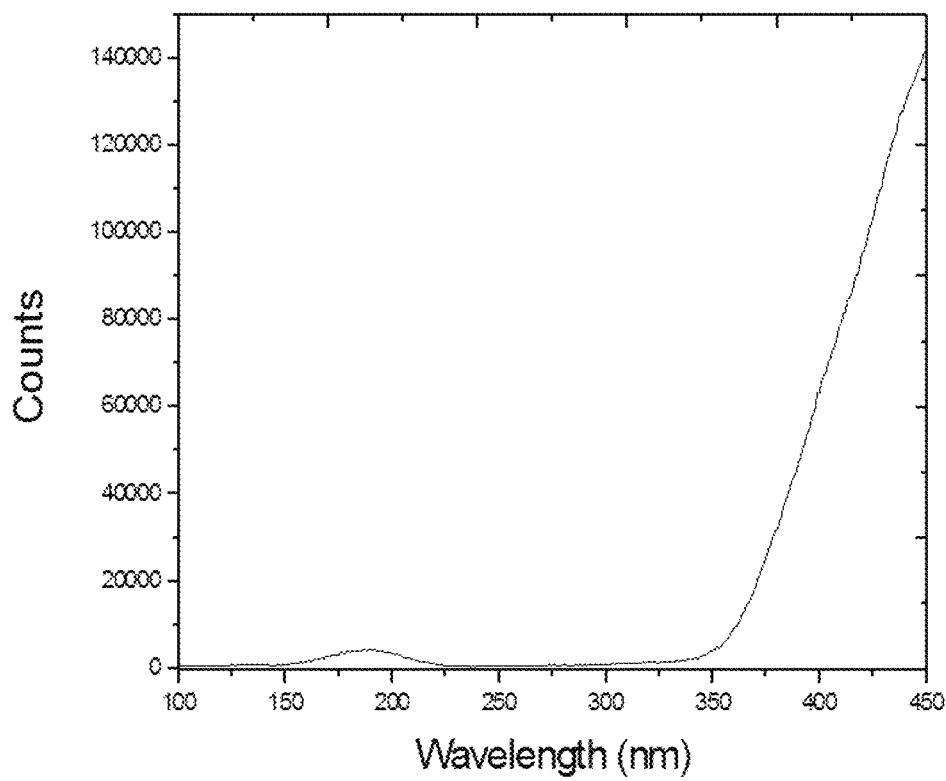
FIG. 42 is a plot of emission spectra of $3Ca_3(PO4)_2.Ca(Fl,Cl)_2$: $Sb^{3+}.Mn^{2+}$.
Figure 43:
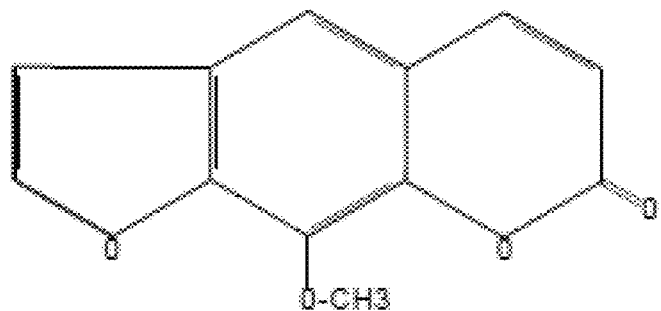
FIG. 43 is a schematic depicting the chemical structure of 9-methoxy-7Hfuro[3,2-g][1]-benzopyran-7-one (also known as methoxsalen, 8-methoxypsoralen, or 8-MOP)
Figure 44:
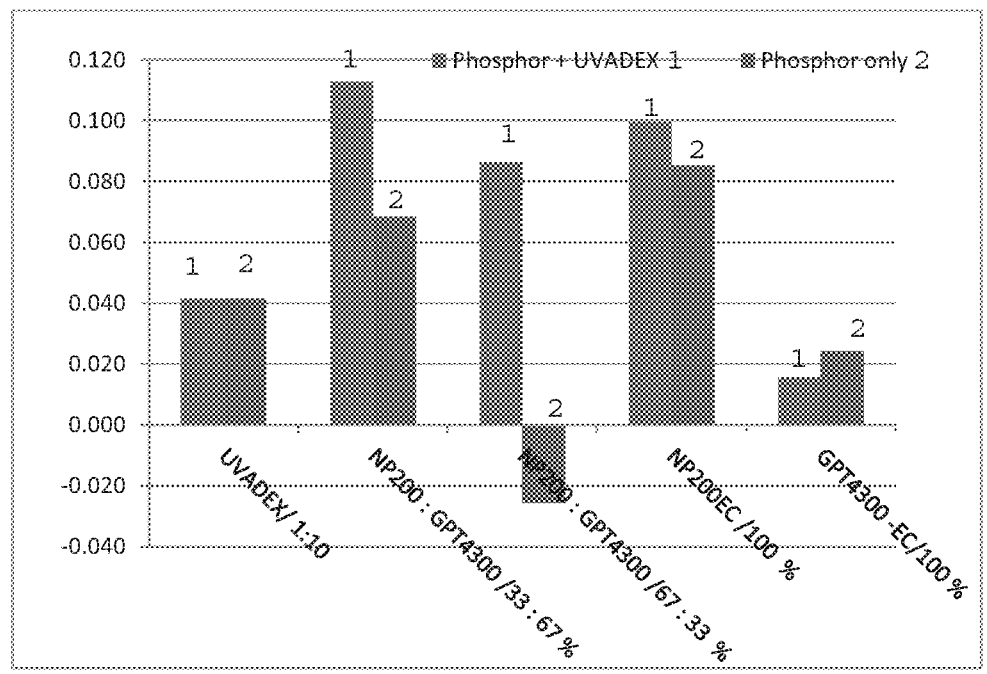
FIG. 44 is a schematic depicting cell kill results under various combinations of phosphor and UVADEX with X-ray.
Figure 45:
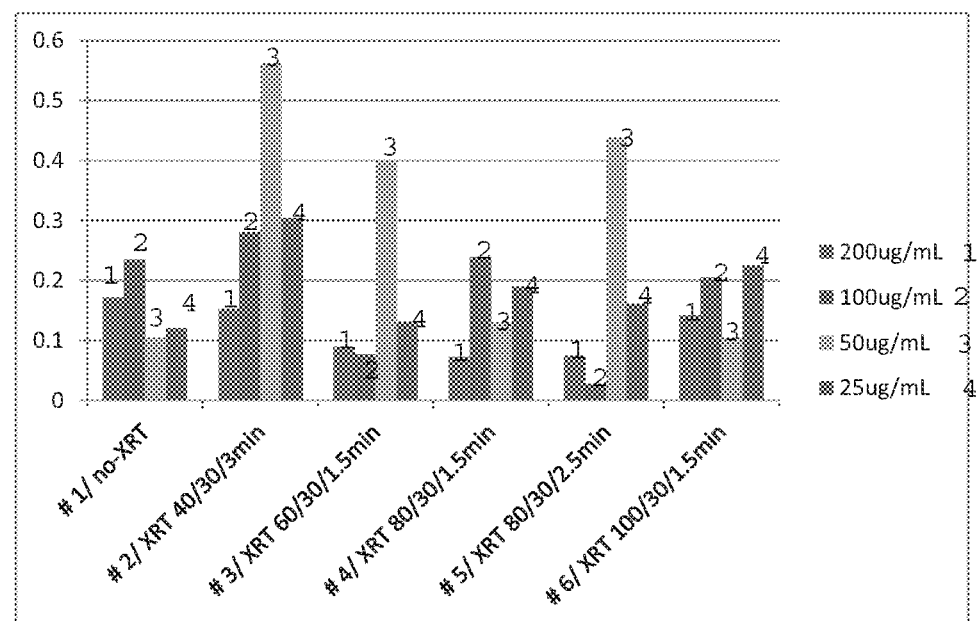
FIG. 45 is a schematic depicting a summary of the results carried out using different X-Ray conditions from an Ortho-voltage X-Ray source and using varying concentration of phosphors and UVADEX from 200 micrograms to 25 micrograms.

Fraction kill: Added cell kill by the combination of Psoralen and phosphor and X-Ray (See FIG. 39 and FIG. 40 for the particle size distribution of two preferred phosphors of interest: NP 200 and GTP 4300.)

Figure 37:
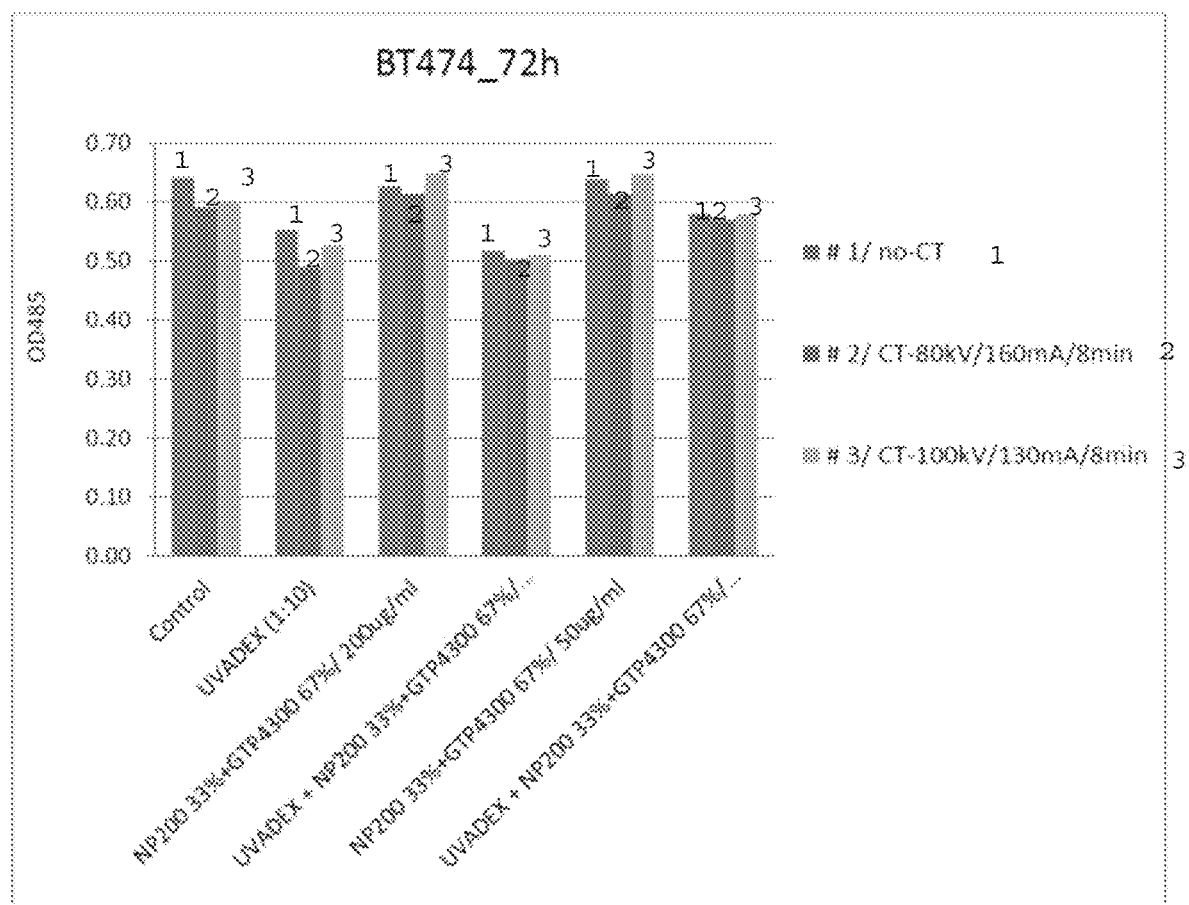
FIG. 37 is a graphical representation of the treatment results for the BT474 cancer cell line using a CT scanner as initiation energy source.
Figure 38:
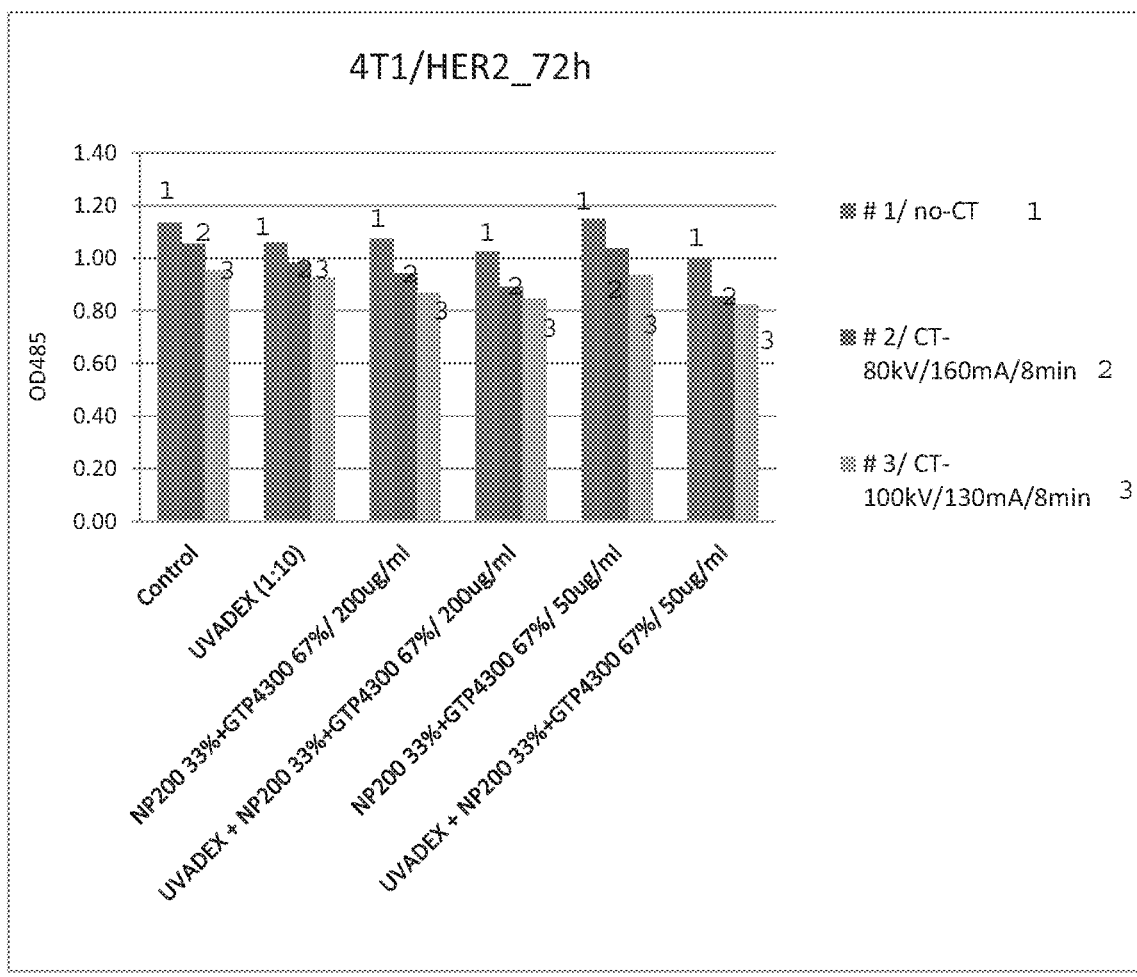
FIG. 38 is a graphical representation of the treatment results for the 4T1/HER2 cancer cell line using a CT scanner as initiation energy source.

FIGS. 37 and 38 graphically show the results of these tests. Each of these figures show cell kill as measured by optical density at 485 nm. FIG. 37 shows the treatment results for the BT474 cancer cell line and FIG. 38 shows the treatment results for the 4T1/HER2 cancer cell line. In each case, treatment with UVADEX and CT x-rays, with or without the energy modulation agents, gave significant improvements in cell kill, relative to the Control, and relative to those examples having no UVADEX present. Particularly of interest was the finding that significant improvements were found at both CT energy levels.

Some of the phosphors used for Psoralen activation have a high atomic mass with a high probability of interaction with the X-Ray photons. As a result, the phosphors used for activating bio-therapeutic compounds are also very good X-Ray contrasting agents. An image can be derived through X-Ray imaging and can be used to pin-point the location of the tumor, to insure that the down converting media is correctly distributed at the tumor site.

The biotherapeutic agent can be delivered systemically. Through the use of existing administration protocols, UVADEX can be administered to a patient and carried through the blood stream to tumor sites. The phosphors that best activate UVADEX can be injected directly in the tumor site. This injection can be done ahead or subsequent to the administration of UVADEX. The phosphors are prepared using an Ethyl cellulose coating and mixed with a saline solution. It is also possible to inject a mixture of both UVADEX and a saline solution containing coated phosphors into the tumor site. Various modalities of administration are possible.

The particle size distribution of the phosphors varies from nano-meter size particles to micro-meter size particles. The particle size distribution of these phosphors is exemplified in FIG. 39. It recognized that the micro-meter particles will reside inside the tumorous tissue and may be less prone to mass transport due to blood flow. On the other hand, nano-meter particles can be easily carried out in the blood stream into various cells in the tumor region. Particles in the size range of 35 nm can in fact enter the cell's nucleus.

Particles in the size range of 50 nm can enter the cell wall but not the cell nucleus. Particles in the size range of 100 nm can stay lodged interstitially between cells. Particles that are in the 1000 nm size and above can stay between cells.

For best results, a distribution of particle size is used. It is believed that each of the particle size ranges by virtue of their proximity to specific reactive site can activate the biotherapeutic to react with DNA and various proteins present in the nucleus and or cell wall membranes. The photo-catalysis makes the bio-therapeutic active, and the activity leads to chemical reactions with various molecules that can react with the biotherapeutic agent. DNA-DNA cross-linking and DNA-protein cross-linking occurs between 300 nm and 365 nm. DNA-DNA cross-linking and DNA-protein cross-linking are a two-photon processes. Absorption of the first photon forms a 4',5'-adduct with DNA. The absorption of the second photon leads to cross-linking to protein. We have observed reactions below the 300 nm range and we have observed reactions and activity when a mixture of phosphors is used.

The emission spectra of $LaPO_4$: $Ce^{3+}$, $Tb^{3+}$ is shown in FIG. 41. In this case the $LaPO_4$: $Ce^{3+}$, $Tb^{3+}$ was measure in terms of emission under an electron beam. The emission spans UVA, UVB and UVC. The emission spectra of $3Ca_3(PO4)_2.Ca(Fl,Cl)_2$: $Sb^{3+}$, $Mn^{2+}$ is shown in FIG. 42. In this case the $3Ca_3(PO4)_2.Ca(Fl,Cl)_2$: $Sb^{3+}$, $Mn^{2+}$ was measure in terms of emission under an electron beam. The emission spans UVA, UVB and UVC. The emissions under X-Ray and e-beam are exactly the same. This is so because of the underlying mechanism is one and the same. For this reason, the activation of bio-therapeutic agent using an e-beam or an X-Ray beam are equally viable. However, the depth of penetration depth of X-Ray may be greater than that possible with e-beam which has practical advantages for both medical and non-medical applications.

It was surprising to find that the two materials in combination with one another lead to a better results than when either material was used alone. The results were done using UVADEX a commercial product as the source of psoralen. Methoxsalen is a naturally occurring photoactive substance found in the seeds of the Ammi majus (Umbelliferae) plant. The chemical name of methoxsalen is 9-methoxy-7Hfuro[3, 2-g][1]-benzopyran-7-one; it has the structure depicted in FIG. 43. Each mL of UVADEX® (methoxsalen, 8 methoxypsoralen) Sterile Solution contains methoxsalen 20 mcg, propylene glycol 50 mg, sodium chloride 8 mg, sodium acetate 1.75 mg, ethanol 0.05 mL, glacial acetic acid 0.0012 mL, and Water for Injection q.s. to 1.0 mL. UVADEX® is used in combination with the UVAR® or UVAR® XTS™ Photopheresis System to extracorporeally treat leukocyte enriched buffy coat.

The percent cell kill due to phosphor only and phosphor plus UVADEX was measured using a proliferation assay. The UVADEX was diluted 10:1 concentration to minimize its toxicity. The materials $LaPO_4$: $Ce^{3+}$, $Tb^{3+}$ and $3Ca_3(PO4)_2.Ca(Fl,Cl)_2$: $Sb^{3+}$, $Mn^{2+}$ were used alone or in combination with one another. The cell kill using 4T1-HER2 cell line incubated for 48 hours prepared in cell media, various well plates were prepared. The proliferation assay that resolves the surviving cell fraction was used to compare the various results. The cell kill, defined as an aberration of cell colonies above and beyond a control group, was measured for various phosphor mixtures. As can be seen from FIG. 44, the results show that the combination of phosphor and UVADEX under suitable X-Ray conditions is better that the cell kill results from either the dark toxicity of the UVADEX or the phosphors by themselves. Furthermore, the combination of phosphors yields a better result than the single phosphor chemistry by itself. This is a surprising result. This may be due to the coordination of one phosphor around another to satisfy their charge neutrality and hence the minimization of the dark toxicity. It could also be due to the combination of overlapping UV energy that is favorable to constructive cell kill. It could also be due to the creation of wavelengths that neither phosphorous material emits by itself. It could be due to other unknown mechanisms. But mechanistic explanation aside, we find that the combination is better for the purpose of targeting cancerous cell to yield an effective targeted therapy for cancer. It was also found that the best combination reacted better when delivered in the cell well plate using a given dose and at a given mass.

FIG. 45 provides a summary of the results carried out using different X-ray conditions from an Orthovoltage X-ray source and using varying concentration of phosphors and UVADEX from 200 micrograms to 25 micrograms. In this in-vitro runs, the results show better results when using 50 micrograms and when using between 40 kVp and 80 kVp. The beam hardening in this case was done using an Aluminum filter of 2 mm thickness.

Principle elements in a radiographic imaging using X-Ray are illustrated in FIG. 46. These elements include an X-ray source and a power supply, A beam collimator along with a beam filter or filters (as the case may require), a set of apertures that can be adjusted to obtain the desirable X-ray beam projection to minimize skin dose, such as done in dynamic conformal arc therapy, an X-ray detector and computer with a GUI interface (or equivalent thereof) to get close loop feedback to the operation of the system.

X-ray imaging from analogue to digital methods can be useful to provide feedback. For obvious reasons digital radiographic systems would more useful. Digital radiographic detectors can be of different kinds. The objective of using X-Ray imaging is however independent with respect to the detection technology method being used and more focus around the method of use to derive real time (or close to real time) feedback as to the distribution of the phosphors in the tumor and ensuring that the patient is treated at the right time when the phosphors and the biotherapeutic agent are both present with the right concentrations. The sharpness of a medical imaging is directly related to resolution and the higher resolution is better with focus on the ability to distinguish and resolve the presence of the phosphors in the target area prior to irradiating. There are various manufacturers of digital radiography imaging systems and these include Lumisys, Inc, Sunnyvale, Calif., Eastman Kodak Health Imaging, Rochester, N.Y., Agfa Medical Systems, Fuji Medical Systems, Konica Imaging Systems, Varian medical, Siemens, General Electric, Philips. The use of newer technologies such as CdZTe (man-made crystals) is quite attractive and may lead to imaging resolutions far surpassing conventional technologies.

One particularly suitable x-ray source is manufactured by XinRay Systems Inc (Research Triangle Park, N.C. 27709). This source uses carbon nanotube (CNT) field emission technology. This system is configured as rotating x-ray source and detector to provide x-ray exposure and imaging. In this commercial system, the anode voltage of x-ray source is variable 10-50 kV; the anode material is tungsten; the peak power is 100 W with an anode current of 2.0 mA. In this commercial system, there are two choices of focal spot size of 100 μm and 65 μm. The source can contain three focal spots spaced 5 mm apart that can be controlled simultaneously and independently permitting tomography in the same machine. The carbon nanotubes (CNT) make for "cold", field emission cathodes which produce electrons at room temperature and which do not require heating or cooling. Additionally, in this commercial system, the pulse width of the x-ray can be controlled as short as 0.1 ms and synchronized with regular or irregular trigger signals.

In one embodiment of the invention, the trigger signal system is modified to provide even shorter gating signals to the CNT array such that variable, short x-ray pulses can be produced from the μsecond to millisecond range. Accordingly, in one embodiment of the invention, the energy modulation agents can be activated with extremely short pulses of x-rays.

Other suitable x-ray sources are available from XinRay Systems Inc. include their micro-CT system (designed for small animal imaging). The system utilizes a single CNT based X-ray source. Due to the unique nature of CNT X-ray sources, the system is capable of instantaneous X-ray firing. This allows for simultaneous physiological gating to the cardiac and respiratory cycle of a free-breathing patient. This system is capable of "microbeam" radiation which, in this invention, would result in targeted exposures of phosphors in the patient without as much collateral damage to nearby healthy tissues.

Furthermore, XinRay produces an Image Guided Radiation Therapy (IGRT) system suitable for the imaging and treatment protocols of this invention. IGRT permits accurate patient positioning and precise dose delivery to the target. According to XinRay, their IGRT system provides three-dimensional image guidance allows precise dose delivery to tumors and reduces the exposure of healthy tissues to unplanned radiation. Tomosynthesis-based 3D image guidance provides in-plane resolution as good as CT and excellent in-depth information with dose levels comparable to a 2D radiograph. Tomosynthesis imaging requires projection images from different viewing angles. According to XinRay, conventional systems use a moving X-ray source to acquire the individual projections. Using the XinRayMBFEX technology with the number of beams that equals the number of required projections, this can be achieved without any mechanical motion. Advantages are a faster image acquisition speed, higher spatial and temporal resolution and simple system design. These advantages would be effective also in this invention, with higher spatial and temporal resolution of the phosphors in the patient during the imaging resulting in less damage to nearby healthy tissue.

Additionally, U.S. Pat. No. 8,488,737 (the entire contents of which are incorporated herein by reference) describes a medical X-ray imaging system, having a flat, planar X-ray source having a surface with X-ray focal points arranged adjacent to one another and an X-ray detector with a sensor surface. The X-ray source has a plurality of field emission guns with at least one field emission cathode and the surface with focal points of the X-ray source is larger in size than the sensor surface of the X-ray detector.

U.S. Pat. No. 8,428,221 (the entire contents of which are incorporated herein by reference) describes a medical x-ray acquisition system having an x-ray source and an x-ray detector. The x-ray source has at least one field emission radiator with at least one field emission cathode. The field emission cathode can be formed by a nanostructured material with carbon nanotubes.

As described therein, one, two or more field emission radiators can be provided in a medical x-ray acquisition system, wherein a single field emission radiator generally exhibits a higher power and a lower power per radiator can also be provided given a number of field emission radiators. Multiple field emission radiators can be arranged as what is known as an array along a circle segment of a C-arm, for example, wherein all field emission radiators are aligned toward the x-ray detector. Such an arrangement can be flat or can also be fashioned directly adapted to the curvature of the C-arm. For example, an array can extend over an angle range of the curvature of the C-arm, for example of 5° or 10° or 20° or 40°.

Mechanical movements of the C-arm can be replaced or assisted by sequential operation of different field emission radiators by means of the arrangement of an array along a circle segment of the C-arm. Instead of a rotation of the C-arm in its circumferential direction around an examination subject, given a linear arrangement, the field emission radiators can be activated in sequence to emit radiation, and a series of projection exposures are thereby acquired at different angle positions. For example, a first field emission radiator arranged at the edge of the array is activated to emit radiation and a first projection image is acquired; a second field emission radiator arranged next to the first field emission radiator is subsequently activated and a second projection image is acquired. This sequence is continued until the opposite end of the array, for example, until a plurality of projection images has been acquired. These projection images can subsequently be reconstructed into a volume image and replace a mechanical rotation of the C-arm. Only individual field emission radiators from the array can also be activated if, for example, only two projection images at two different angulations are necessary.

Angulations of more than 40° (for example 60°) can also be covered by means of an array (which covers an angle range of 40°, for example) if an activation of different field emission radiators is combined with mechanical displacement. In such a case only a mechanical panning of 20° is then necessary; the change from one angulation to a second angulation is achieved via combination of mechanical displacement and selection of a different field emission radiator. In the case of 3D acquisitions in which a fast panning over large angle ranges (of 200°, for example) is necessary, mechanical panning and electronic through-switching can likewise be combined in order to achieve a higher acquisition speed.

U.S. Pat. Appl. Publ. No. 20040114721 (the entire contents of which are incorporated herein by reference) also describes an x-ray generating device includes at least one field-emission cathode having a substrate and incorporating nanostructure-containing material including carbon nanotubes.

These above-noted x-ray systems (along with the systems described below) would be suitable for the invention in providing x-ray radiation for either a radiation therapy treatment or for radiation imaging, both as discussed elsewhere.

Figure 47:
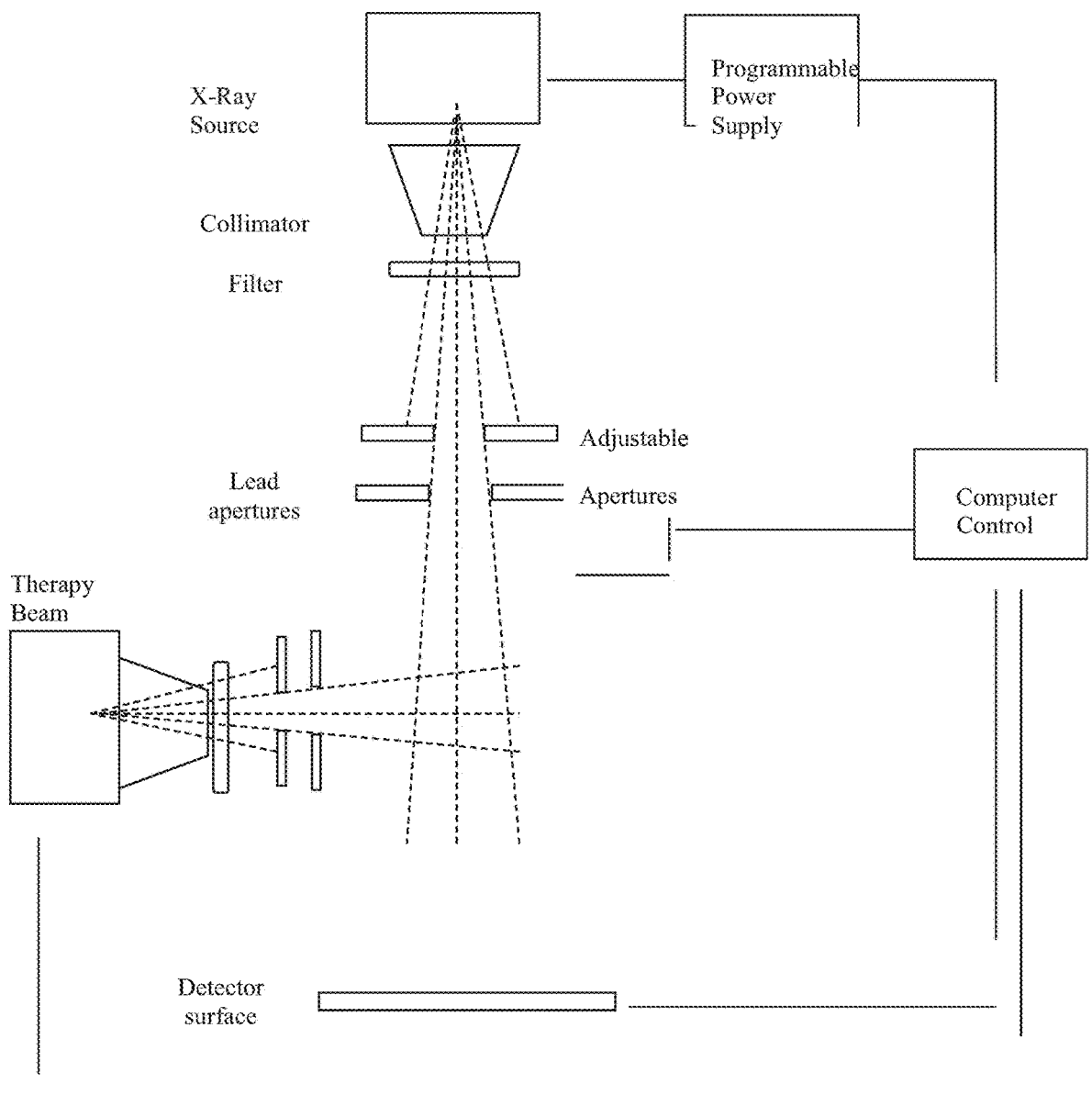
FIG. 47 is a schematic depicting principle elements in a therapy beam based on either X-Ray or electron beam.

In general, an x-ray imaging system of the invention in one embodiment can be used be used along with a therapy beam. The principle elements in a therapy beam based on either x-ray or electron beam are illustrated in FIG. 47. These elements include an x-ray or an electron beam source, a power supply, a beam collimator along with a beam filter or filters (as the case may require), a set of apertures that can be adjusted to obtain the desirable x-ray or electron beam projection, an x-ray detector and computer with a graphical user interface (GUI) or equivalent thereof to get closed loop feedback to the operation of the system. The imaging and the therapy beams can be operated at the same time or sequentially. The use of a system with the dual imaging and therapy beam is compatible with the invention.

In one embodiment of the invention, a processor associated with the x-ray source is configured and programmed to assemble the images of the target (e.g., a tumor) into tomographic views of the tumor. Capturing of x-ray images and assembly into tomographic views is known in the art. As the art developed, a sectional image through a body was made by moving an X-ray source and the image detector in opposite directions during the exposure. Consequently, structures in the focal plane appear sharper, while structures in other planes appear blurred. By modifying the direction and extent of the movement, different focal planes which contain the structures of interest become manifest in the image plane. Modem machines gather projection data from multiple directions and feed the data into a tomographic reconstruction software algorithm which are processed to form the images typically viewed as two-dimensional slices. Different types of signal acquisition can be used in similar calculation algorithms in order to create tomographic images, including x-rays, gamma, electrons, radio frequency waves, muons. The sources in the invention can use one or more of the sources for imaging in addition to the x-ray or gamma or electrons for radiation therapy activating the energy modulation agents inside the medium being treated regardless of whether the medium is that of a patient, an adhesive medium, a medium being sterilized, a medium being photografted or any of the other treated mediums described herein.

Besides the practical advantages of digital technology, including electronic image transmission, file recordation, time stamped imaging, data sharing and post-processing, the advantage of real time imaging can be used to determine the correct time (perhaps the optimum time) for a patient to receive the x-ray therapy beam or the particle beam as the case may apply. The advances of x-ray imaging or computerized radiography would make it possible to make better judgment for the targeted therapy. Advances in the field are on-going to obtain better modulation transfer functions, noise power spectrums, detective quantum efficiency, higher pixilation with tighter pitch area array detectors. Tagging chemistry applied to the bio-therapeutic agent may permit visualization of the permeation of the tumorous tissue with the bio-therapeutic agent, prior to applying the main x-ray therapy beam.

The typical tube voltage for radiography is typically in the range of 60-120 kV. The x-ray beam is then passed through filtration achieved by interposing various metal filters in the x-ray path. The metals that are used include Aluminum (Al) and Copper (Cu). The filtration of the beam eliminates noise and results in a cleaner output beam, preferentially removing softer photons. This leads to a cleaner spectrum and systems from different vendors would result in having substantially the same output spectrum. After filtration the beam is passed through a collimator. X-ray radiation can be collimated into a fan-shaped beam. The beam is passed through an adjustable aperture. Lead (Pb) plates of about 2 mm in thickness can be used to block the beam and limit the exposure of x-ray to the tumor area.

The 60-120 kV beam can be sufficient to activate the bio-therapeutic agent via the energy modulating media described in the invention.

Methods for inspecting the delivery of the converting media can be done using the commercial equipment noted above or other x-ray and CT scanning equipment with control of the x-ray dose intensity and period. For instance, some equipment is designed to take a series of pictures (using pulses of x-ray with a duration of 6 micro-seconds), while the activation of the bio-therapeutic may be done in a continuous mode for one minute to one and half minutes. In this case, an x-ray protocol may be necessary to program the correct modality. Regardless of which specific safety function needs to be overridden, the common feature to the preferred recipe (best mode) would include steps of delivering the converting media along with the bio-therapeutic agent, imaging, applying the correct dose, optionally imaging and then saving the data with a time stamp.

Figure 48A:
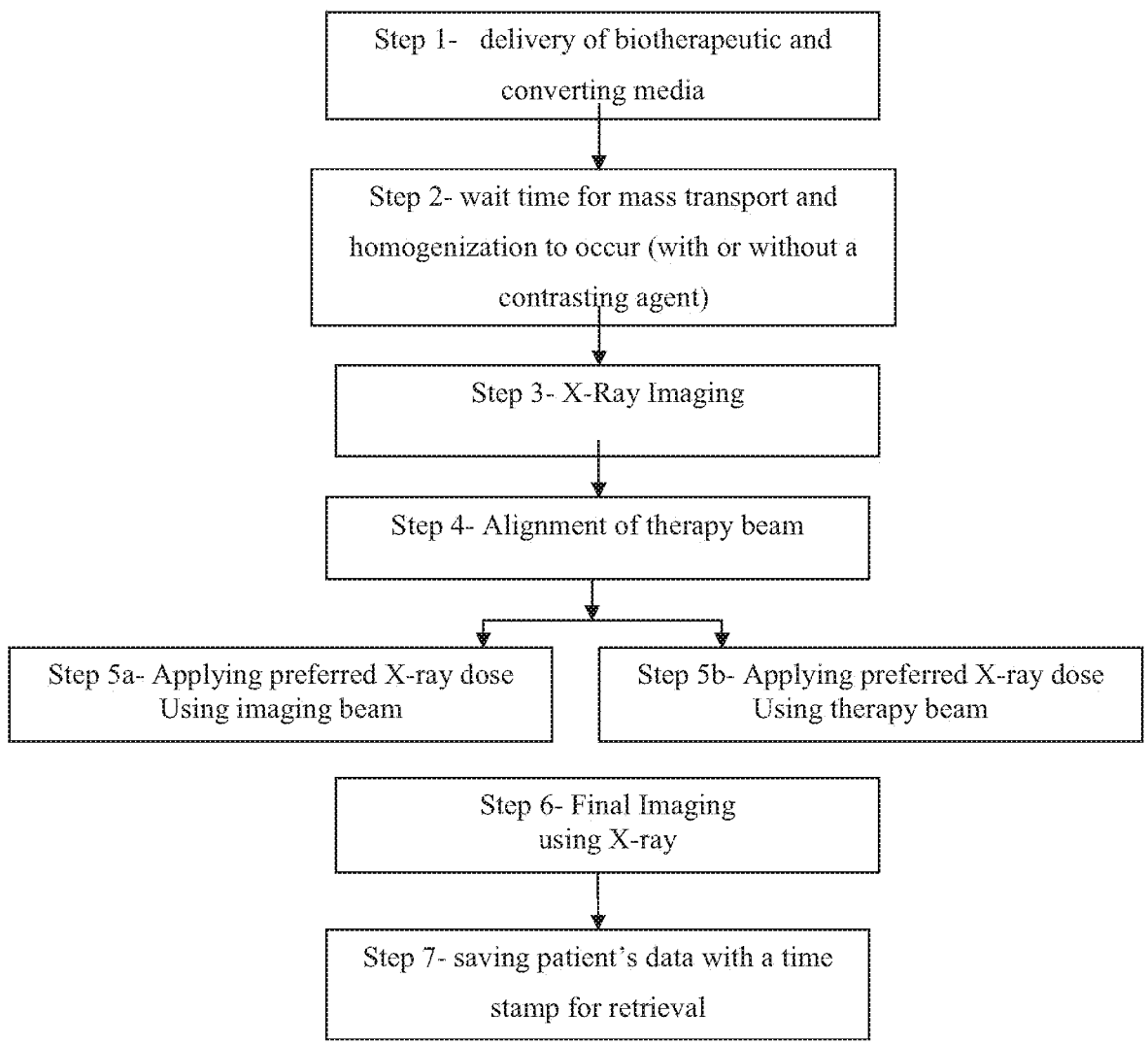
FIG. 48A is a schematic depicting sequential steps used in an embodiment of activation of a bio-therapeutic agent using X-Ray to UV modulating media using steps of delivery, imaging, activations and quality control and data documentation.

FIG. 48A illustrates sequential steps used in the activation of a bio-therapeutic agent using x-ray to UV modulating media using steps of delivery, imaging, activations and quality control and data documentation. In one sequence, the x-ray activation includes an imaging beam with a contrast agent to maximally determine the morphology of the tumor and ensure the media has been delivered. Subsequently, the therapy beam delivers an adequate x-ray dose for that particular set of phosphors used for activating the UVADEX. The therapy beam can use x-ray energy or electron beam energy.

Step 1. delivery of light modulating media with a bio-therapeutic agent—there are some options that can be exercised such delivering both the drug and the media at the tumor site or delivering the drug systemically while delivering the media at the tumor site (both of these modalities are acceptable). Additionally a contrast agent can be added to the mix to enhance imaging. This contrast agent however should not interfere with the constructive reaction taking place between the media and the bio-therapeutic agent and between the therapeutic agent and DNA or proteins of interest at the tumor site.

Figure 46:
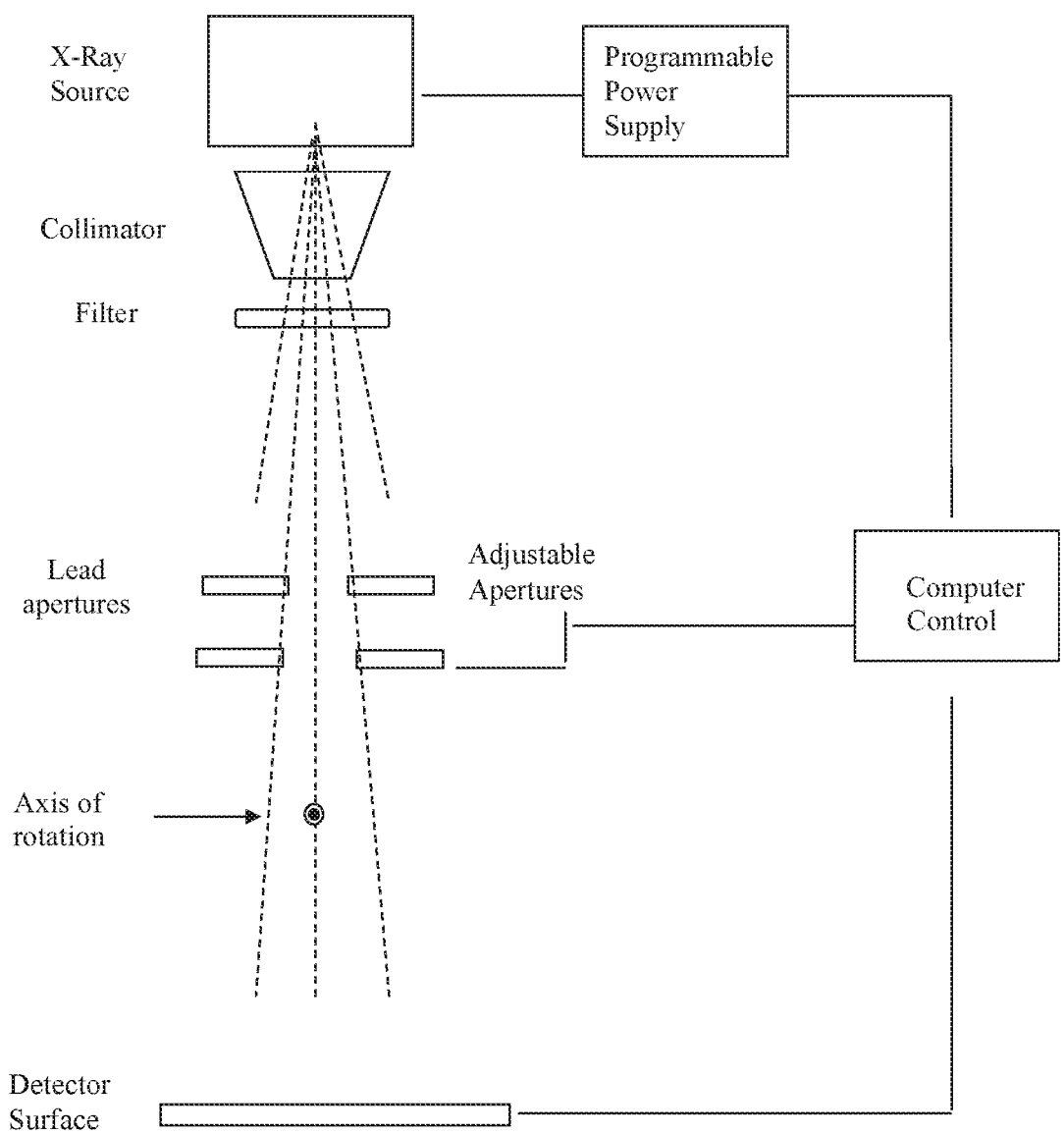
FIG. 46 is a schematic depicting principle elements in an exemplary radiographic imaging using X-Ray.

Step 2. waiting for a time period for profusion and mass transport to take place. when the homogenization of the bio-therapeutic agent along with the modulating media has been achieved, an X-Ray imaging step is performed Step 3. Imaging can be done using a system having the fundamental elements described in FIG. 46.

Step 4. The apertures are opened appropriately in the X-axis and in the Y-axis to ensure the optimal positions are programmed. This limits the beam to the tumor area and minimizes skin dose.

Step 5. The X-Ray beam (either therapy of imaging beam) applies the correct energy dose of X-Ray.

Step 6. An optional step is to take another image after the treatment has been done.

Step 7. The data is saved under digital formats that enable image processing and patient's information documentation.

Figure 48B:
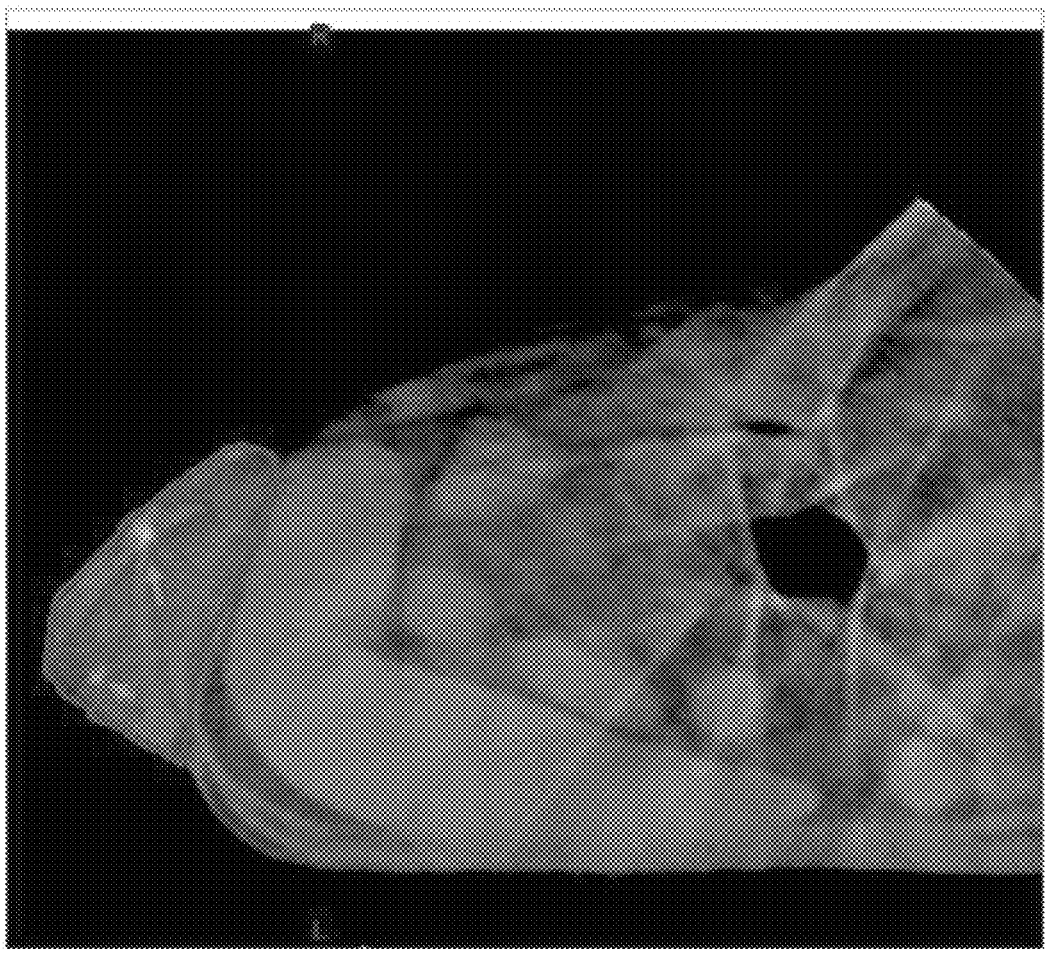
FIG. 48B is an image of a tumor in a canine with illuminated phosphor contrast regions denoted by arrows.

The imaging system along with the therapy beam enables the obtainment of optimized location and intensity modulated dose delivery. The patients benefit from a fully integrated treatment whereby imaging and therapy for tumor growth retardation are done in the same machine and at the same time. FIG. 48B is an image of a tumor in a canine with illuminated phosphor contrast regions denoted by arrows.

Contrast Agents:

Contrast agents can be used along with the energy modulating media to further enhance the image. Such chemistries include, but are not limited to, iodine containing contrast agents which are used in the medical practice.

X-Ray Dose Optimization

The radiation therapy of this invention in one embodiment permits the lowering of the overall x-ray dose required to lead to shrink the tumor, to cause tumor growth retardation, to cause tumor cell death via apoptosis and perhaps to engender an immune response.

For this reason, a selection of the x-ray kV is important once the depth and the size of the tumor is identified. Estimation can be based on the center of the tumor or on the surface of the tumor.

X-ray radiation is a deeply penetrating radiation. When a flux of x-rays is directed into an object, some of the photons are absorbed and some are partially absorbed and scattered, and yet others can penetrate the object with no to limited interaction. It is useful to express the penetration of the radiation as the fraction of radiation passing through the object. The more penetration typically means less attenuation, and penetration is generally the inverse of attenuation. The penetration depends on the photonic energy of the individual photons and certain characteristic of the object being exposed including the atomic number, the density, and the thickness of the object.

Different kV have different penetration depth of different half value layer. As can be seen from the following graph, different kv have different depth of penetration. The quality of the x-ray beam depends on the degree of filtration used to harden the beam. The more filtered beams typically would have deeper penetration into matter (including tissue). The lower energy photons are therefore subject to being absorbed more easily than those photons having more photonic energy and therefore higher depth of penetration. For this reason, the position of a deep seated tumor can define the choice of a kV used in the x-ray beam. The selection criteria can be simplified to: 1—the beam has to have enough photonic energy to reach the center of the tumor, 2—the photonic energy of the photons should not be so high as to bypass (penetrate without depositing energy) the tumor site. In effect, to maximize the X-Ray interaction with the phosphors that are mixed with the biotherapeutic agent and delivered to the deeply seated tumor site.

TABLE 20

| X-Ray kv | HVL (mm) 30 keV | HVL (mm) 60 keV | HVL (mm) 120 keV |
|---|---|---|---|
| Tissue | 20 | 35 | 45 |

Reference: Physical Principles Of Medical Imaging, Perry Sprawls; Ph.D.

Figure 49:
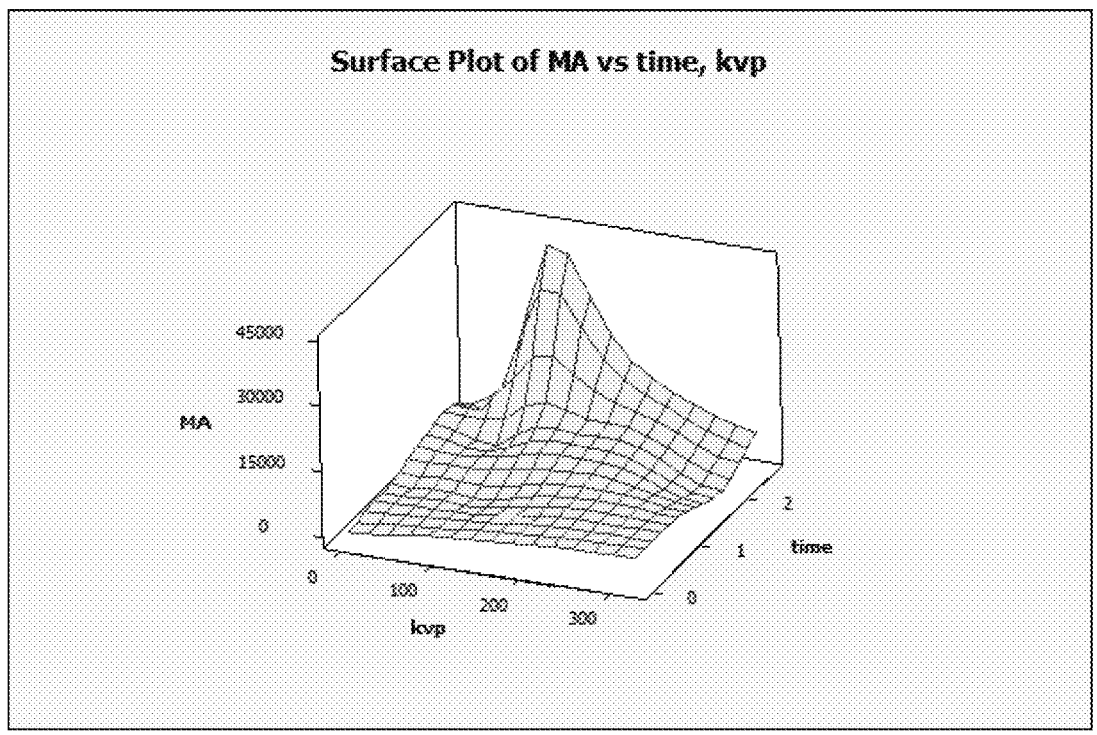
FIG. 49 is a schematic depicting Mono-Adduct formation in Poly-dAdT using an embodiment of the invention using AMT as the bio-therapeutic agent.
Figure 50:
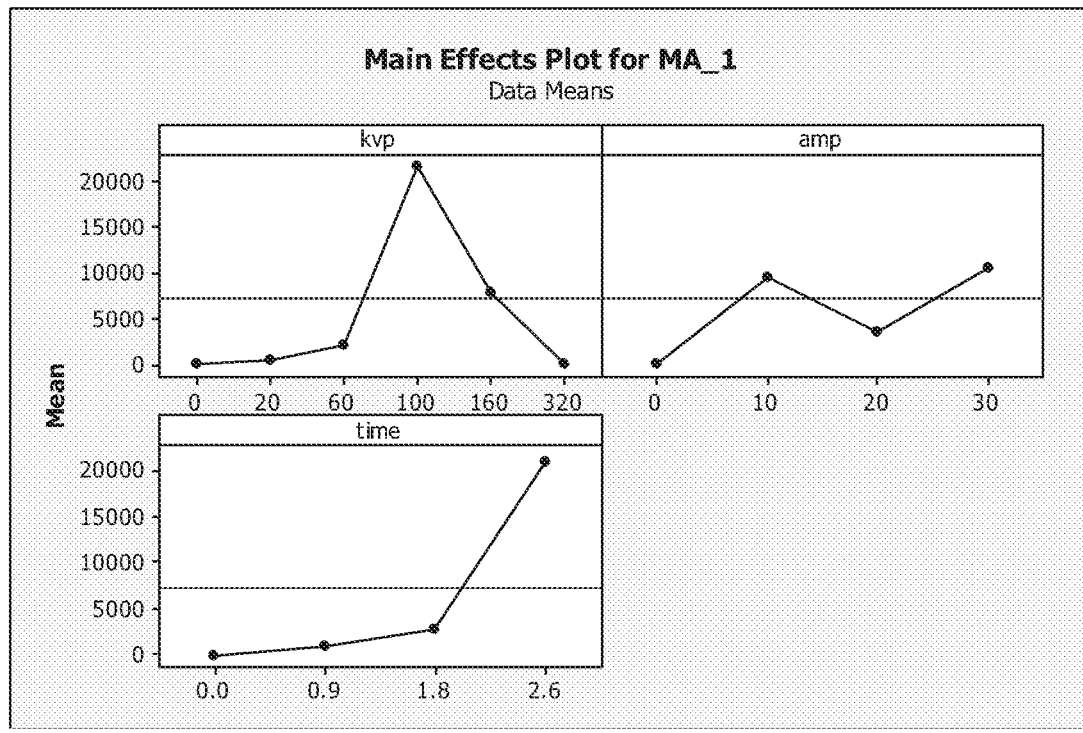
FIG. 50 is a schematic depicting an embodiment wherein Mono-adduct formation goes through a local optimum around 100 kVp.

One example according to one embodiment of the invention is the combination of YTaO4 and LaOBr:Tm using a mixed ratio of 2:1 by weight. With this phosphor system using AMT as the bio-therapeutic agent it was found that the x-ray dose required achieving Mono-Adduct formation in Poly-dAdT followed a particular pattern described in FIG. 49. As illustrated in FIG. 50. For BP3:BP7 (combo 2:1), the Mono-adduct formation goes through a local optima around 100 kVp. Time becomes critical in advancing the reaction. The reaction is derailed at higher kVp values (due to unknown mechanisms). It is believed that higher x-ray energy imparts damage onto the phosphor particles or the surrounding medium.

Figure 51:
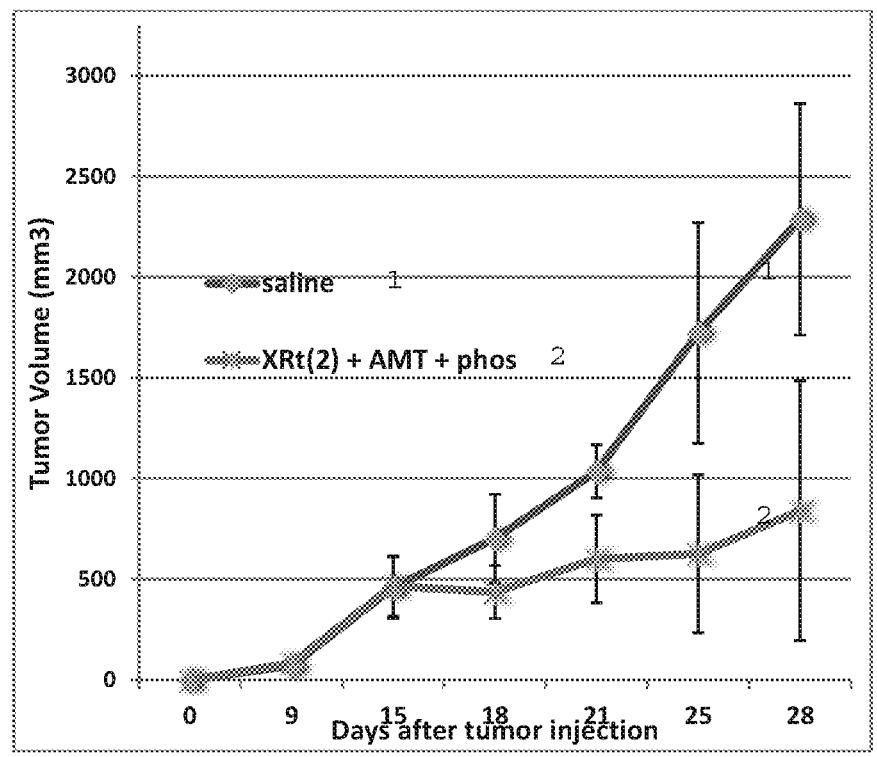
FIG. 51 is a schematic depicting tumor growth delay in a first animal study.
Figure 52:
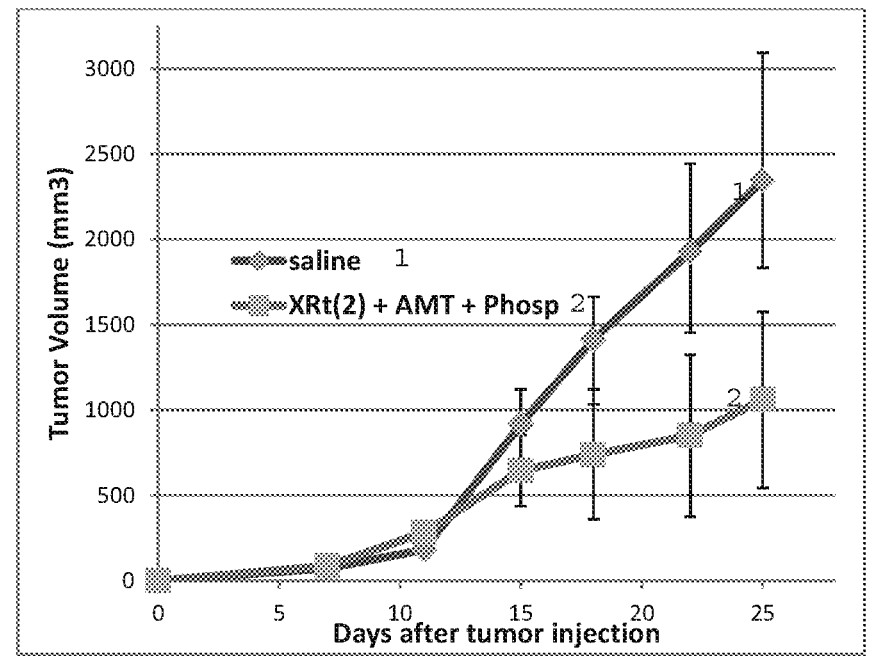
FIG. 52 is a schematic depicting tumor growth delay in a second animal study.

Animal Study:

A phosphor system containing the following phosphor combination: LaPO4:Ce3+, Tb3+, 3Ca3(PO4)2.Ca(Fl,Cl)2: Sb3+, Mn2+, ZrO6–: Pr,Si, CaSiO3:Mn,Pb was used in an animal study based on a Rodent Syngeneic Model. In this animal study, a 50-100 uL intra-tumoral injection three times per week using 100 ug phosphor and 5 uM psoralen (AMT) and exposed to X-Ray dose of 75 kVp using 30 mA for a duration of 3 min. The groups of mice in this study consisted of eight BALB/c female mice. The tumor growth delay was contrasted against a group of eight mice that had only a saline treatment. The results are shown in FIG. 51. The animal study was then repeated and did yield the same results of tumor growth delay as is illustrated in FIG. 52.

Van Hoof et al *Development and validation of a treatment planning system for small animal radiotherapy*: Smart-Plan, Stefan J. van Hoof, Patrick V. Granton, Frank Verhaegen; Radiotherapy and Oncology 109 (2013) 361-366; (the entire contents of which are hereby incorporated by reference) describe one system for the use of image-guided equipment for the precision irradiation of small animals that can be used in the invention for the development of treatment regimens, and development of pre-clinical and clinical studies.

Pulsing of Initiation Energy Source to Maximize Reaction while Minimizing Side-Effects In a further embodiment of the invention, it has been found that one can apply the initiation energy source in a predetermined sequence of pulses in order to advance reaction by the energy modulation agent and activatable pharmaceutical agent (or the energy modulation agent and other activatable agent), while minimizing the potential detrimental effects of the initiation energy source itself upon the subject. The energy modulation agents for use in this embodiment can be any of those noted above, and preferably are one or more phosphors optionally coated with diamond or diamond-like coating, or with ethyl cellulose.

The diamond-like coating can be deposited in a physical vapor deposition (PVD) system under conditions well known to those that practice the art. Carbon can form various phases each with a specific microstructure. The various forms include diamondlike carbon (DLC) which is of interest. DLC can be amorphous carbon (a-C) or hydrogenated amorphous carbon (a-C:H), including a hybridized network of $sp^3$ and $sp^2$ co-ordinations. DLC can be deposited at low temperature which makes it an attractive coating compatible with a variety of substrates (especially those that cannot withstand temperature). DLC coatings have attractive properties such biocompatibility, chemical inertness; wear resistance, high hardness, high thermal conductivity, and optical properties. Two characteristics for this embodiment of the invention include biocompatibility and UV transparency. The hydrogenated amorphous carbons (a-C:H) include a small C—C sp3 content. DLC's with higher sp3 content are termed tetrahedral amorphous carbon (ta-C) and its hydrogenated analog ta-C:H. Amorphous carbons with the same sp3 and H content show different optical, electronic, and mechanical properties according to the clustering of the sp2 phases. It was found the a-C:H films had better UV transparency than (ta-C). For this reason, one embodiment of the invention uses hydrogenated amorphous carbons (a-C:H). However other DLC films also work for the purpose of the invention including those having a high $sp^3$ content.

Different DLC Coating:

Various DLC films were made some of which are sp3 rich, some were sp2 rich and some were hydrogenated. Various coatings were tested including: a 100 nm Ethyl cellulose coating, a DLC film with 50 nm coating that is rich in $sp^2$ bonding, a hydrogenated aC:H having a 100 nm film thickness. This film was further autoclaved for the biological application considered in the invention.

TABLE 21

| Coatings tested |
|---|
| EC |
| SP2 coating |

TABLE 21-continued

Coatings tested

H100
H100 - Autoclave

TABLE 22

(X-Ray and Ebeam exposure conditions)
Processing Conditions

E-Beam/125 MU/12 MeV/100 mm SSD/20 mm × 20 mm
X-Ray/40 KV, 80 mA/32 mSec/16 min total/8 exposures/70 mm SSD Under similar experimental exposure, the reaction extent advances better with some coatings and not others. The $sp^2$ rich coating seems to work and is effective at inducing cell kill, but it is not as effective as the H100 film. The hydrogenated DLC film (100 nm hydrogenated film) is better than the other coatings for the illustrated experimental conditions, shown in FIG. 56.

Figure 56:
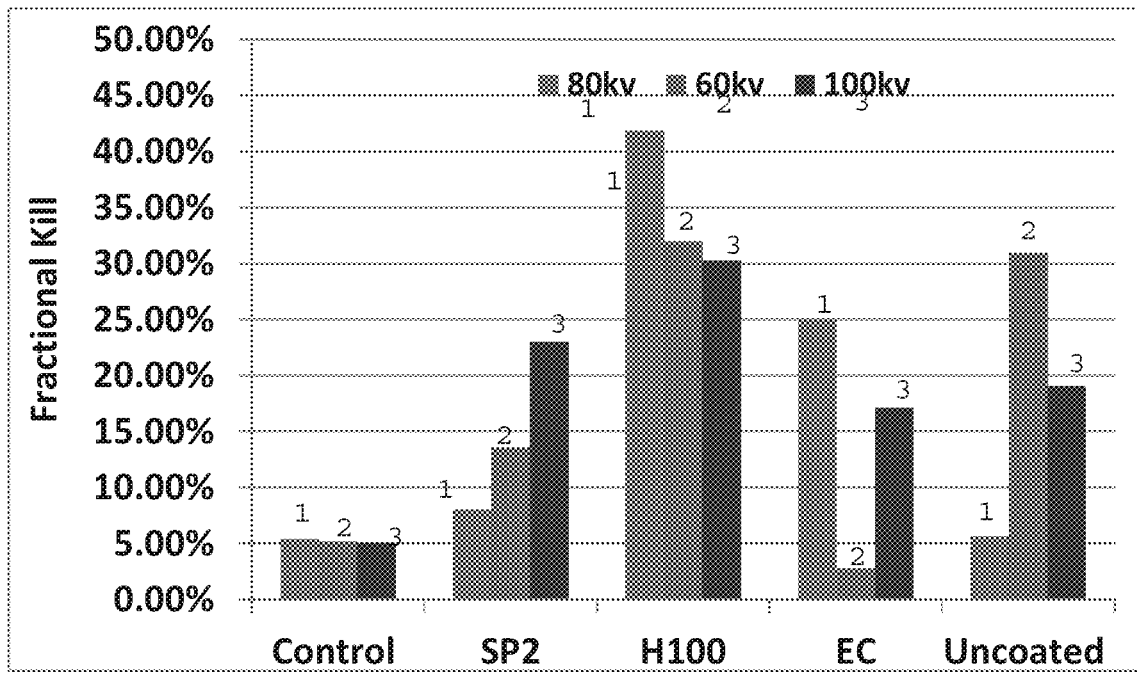
FIG. 56 is a schematic depicting cell kill in a further WST1 assay evaluating the effect of coating type and kVp.

As illustrated in FIG. 56 both of the coating as well as the kv used to deliver the X-Ray dose have an effect on the extent of the desirable reaction.

Figure 57:
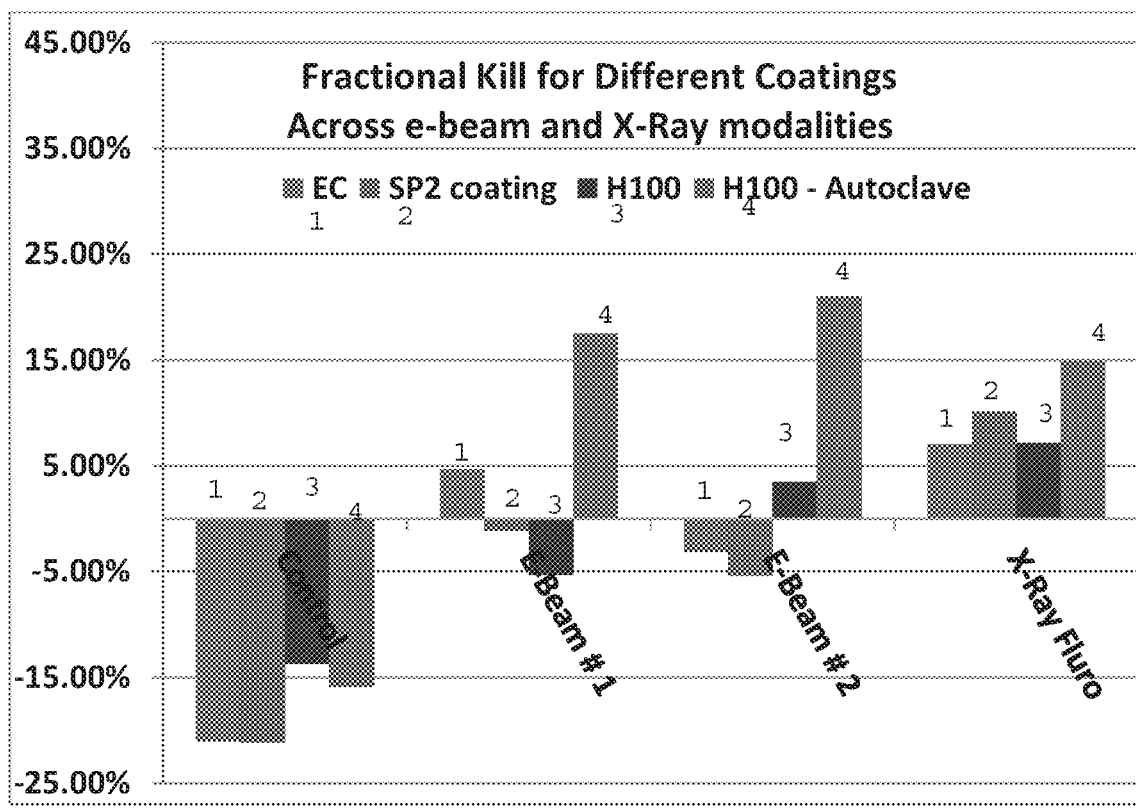
FIG. 57 is a schematic depicting cell kill in a further WST1 assay evaluating the effect of coating type and kVp and e-beam.

Furthermore, a particle beam was used to study the extent to which the reaction can advance. In this experiment the H100 coating was autoclaved. The electron beam was demonstrated to be effective at activating the phosphor and that the reaction can proceed using either X-Ray or e-beam energy exposure, as illustrated in FIG. 57. The DLC coating can be further modified by formation in an atmosphere containing elements such as argon or hydrogen (such as 9 atomic % argon or 40 atomic % hydrogen, in a carbon plasma).

The initiation energy source can be any desired initiation energy source that works with the selected energy modulation agent to provide initiation energy which is converted by the energy modulation agent to an energy sufficient to activate an activatable agent in the system. In preferred embodiments, the energy modulation agent is one of the above noted phosphors which converts the ionizing initiation energy source, such as x-rays or e-beam, into UV or visible radiation, which then activates an activatable pharmaceutical agent, such as a psoralen derivative.

While not wishing to be bound by any particular theory of mechanism of action, it is believed that upon application of an ionizing radiation such as x-ray or e-beam, electrons within the phosphor are energized and move to a higher energy orbital in the phosphor, forming electron/hole pairs (e/h pairs). This pair formation can be thought of as charging up the phosphor. Once a saturation level has been reached (and even prior to saturation), the electron that has been moved to higher energy can then relax back to its original orbital by electron-hole recombination, emitting UV/vis radiation in the process. The net fluency of the UV/vis output of the phosphor then depends on the number of recombination events occurring per unit time. With ionizing radiation sources, one can reach a saturation point, beyond which the continued application of the ionizing radiation source will not increase the energy output of the phosphor. However, when the ionizing radiation source is removed, electron-hole recombination will continue to occur at the same inherent recombination rate until decay of the signal starts to occur. Once the signal decays too far, the fluency of output energy is too low to drive any further reaction.

Figure 53:
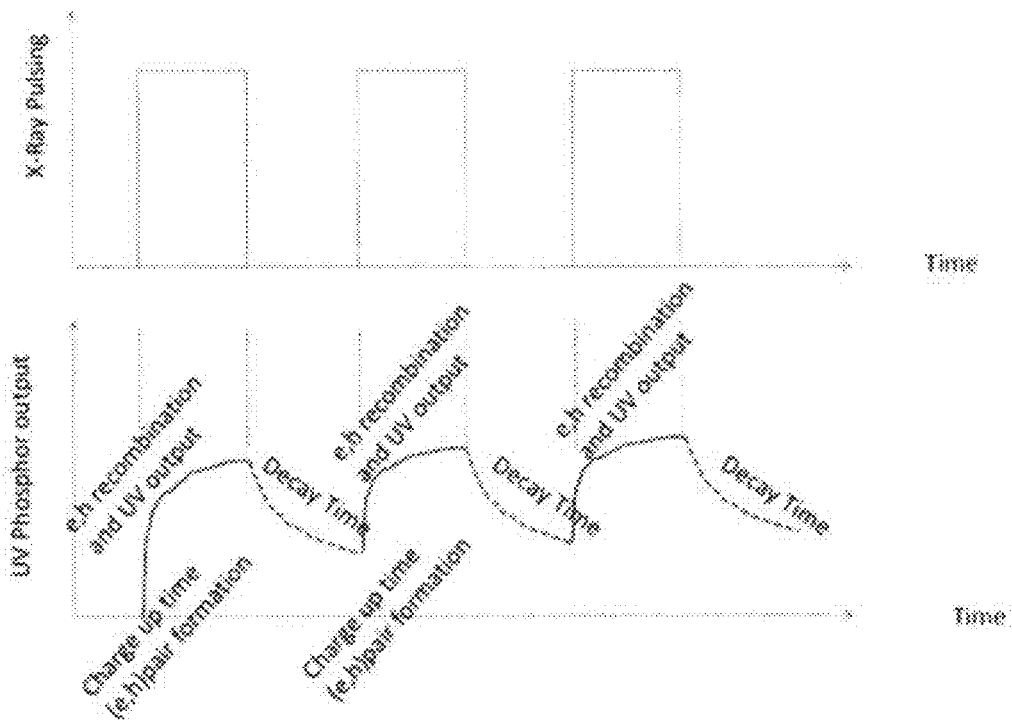
FIG. 53 is a schematic representing a pulsing embodiment according to the invention, with the top figure showing the "on-off" pulse sequence of the initiation energy source, and the bottom figure showing the charging of the phosphor by the initiation energy source during the "on" periods, to maximum intensity followed by decay during the "off" periods.

Applicants have found however, that by pulsing the initiation energy source such that the pulse width (i.e., time for which the initiation energy source is "on") is sufficient to fully charge the energy modulation agent, and to reach maximum energy output from the energy modulation agent, then the initiation energy source is turned "off" after which the energy output from the energy modulation agent continues, but ultimately begins to decay. This is shown schematically in FIG. 53, with the top figure showing the "on-off" pulse sequence of the initiation energy source, and the bottom figure showing the charging of the phosphor by the initiation energy source during the "on" periods, to maximum intensity followed by decay during the "off" periods.

By determining the decay time for the particular energy modulation agent, which can be performed by one of ordinary skill in the art using conventional spectrometric equipment, the sequence of "on" and "off" events can then be determined to provide the maximum energy output for the energy modulation agent, while minimizing the time and/or amount of initiation energy source energy that must be applied. Particularly when the initiation energy source is an ionizing radiation such as x-rays or e-beams, this reduction in the time and/or exposure of the subject to the ionizing radiation can significantly reduce the detrimental effects of the ionizing radiation.

For example, using x-rays as the initiation energy source, it is possible to stimulate and to advance a reaction between the energy modulation agent, activatable pharmaceutical agent, and the target cells to be treated by turning the x-ray source on continuously for 1.5 minutes. However, in doing so, the amount of collateral damage (i.e. killing of cells, both target cells and healthy non-target cells, by the x-rays alone) is quite significant. However, by pulsing the x-rays such that the same level of cumulative radiation is applied, but with intermittent "off" periods when the x-ray source is not being applied, but in which the phosphor is still emitting UV/vis radiation sufficient to activate the activatable pharmaceutical agent and treat target cells, the level of collateral damage can be dramatically decreased, while maintaining the same or even better treatment of target cells.

Accordingly, in one embodiment of the invention, a pulsing configuration is determined and used to charge the energy modulation agent (such as one or more phosphors), wherein the charging time (or "on" time) can be any desired value, the "off" time can be any desired value to permit the energy modulation agent to undergo the decay cycle to any desired level, at which the initiation energy is reapplied in an "on" cycle, wherein the decay can be to any desired level relative to maximum charging, even to the point of fully discharging the energy modulation agent. The desired pulsing cycle can be readily determined by one of ordinary skill in the art, based upon the exemplary embodiments described herein. In one exemplary embodiment, x-ray pulse sequences were set according to the following table:

TABLE 23

|  | kv | mA | cycle | pulse width ms | Pulses |
|---|---|---|---|---|---|
| Plate 1 | 80 | 200 | 10 | 800 | 21 |
| Plate 2 | 80 | 200 | 5.3 | 800 | 21 |
| Plate 3 | 80 | 200 | 20 | 800 | 21 |
| Plate 4 | 100 | 200 | 10 | 800 | 14 |

Equipment Examples

In this test, the radiographic mode of an imaging beam in Varian Medical oncology equipment was used, which has software tools for managing the x-ray exposure in terms of dose delivery, treatment planning, dosimetry verification, and quality assurance. The Acuity and the Trilogy Varian products were used during testing. However, the process described here is applicable to other radiation oncology products from various Original Equipment Manufacturers. These include for example the ARIA, Eclipse, Clinac, Trilogy, TrueBeam, Edge System from Varian Medical. Other oncology product equipment examples include the Revolution EVO, Revolution CT, Revolution GSI, Revolution HD from GE health care. Yet other examples of oncology equipment would include by way of illustration, the SOMATOM CT family, the SOMATOM particle therapy from Siemens oncology equipment offering.

Embodiments of the X-Ray On Cycle are shown below in Table 24.

TABLE 24

|  | kv | mA | Pulse | # Pulses | Gy |
|---|---|---|---|---|---|
| plate 1 | 80 | 200 | 300 ms | 51 | 1 |
| plate 2 | 80 | 200 | 500 ms | 33 | 1 |
| plate 3 | 80 | 200 | 800 ms | 21 | 1 |
| plate 4 | 80 | 200 | 1000 ms | 16 | 1 |

Various pulse widths were programmed in milliseconds ranging from 300 ms to 1000 ms. In other words, during the on cycle for the X-Ray, a pulsing rate of 300 ms, 500 ms, 800 ms and 1000 ms was used. The number of pulses for each of the tested conditions was changed to deliver a constant X-Ray dose of 1 Gy. The off-cycle time between the X-Ray pulses remained constant at 10 sec. This time is referred to as the off time between on cycle when the X-Ray is turned off. The results show that modulating the pulsing of the X-Ray impacts the extent to which the reaction takes place. In this case, using a mixture of NP200 and GTP 4300 phosphors at a ratio of 2:1, and having a coating of 100 nm of Hydrogenated DLC film, it was found that a pulse of 800 ms was best. This would be unexpected since a dose of X-Ray is believed to be the only important factor in play regardless on how it is delivered. The results showed, however, that in fact a 1 Gy dose delivered in different conditions yield different results. In this case the pulsing of X-Ray during the on-cycle was simulated.

The results (according to a WST1 assay) are summarized in the following table 25:

TABLE 25

| WST1 | 300 ms | 500 ms | 800 ms | 1000 ms |
|---|---|---|---|---|
| Ctrl | −0.03 | 0.10 | 0.07 | 0.08 |
| H100 | 0.07 | 0.26 | 0.29 | 0.20 |
| EC | 0.20 | 0.32 | 0.28 | 0.21 |

Embodiments of the X-Ray Off Cycle are shown below as the off cycle time was manually changed according to the following Table 26:

TABLE 26

|  | kv | mA | Off-cycle | pulse width ms | Pulses |
|---|---|---|---|---|---|
| Plate 1 | 80 | 200 | 10 | 800 | 21 |
| Plate 2 | 80 | 200 | 5.3 | 800 | 21 |
| Plate 3 | 80 | 200 | 20 | 800 | 21 |
| Plate 4 | 100 | 200 | 10 | 800 | 14 |

The X-Ray off cycle was changed from 5.3 sec to 20 sec. Unexpectedly, the reaction extent was higher for some X-Ray off cycle times than others. This implies the effective time for a reaction to advance with minimal radiation toxicity (or collateral damage) depends on both the pulsing used during the X-Ray-on-cycle time as well as the duration of the X-Ray off cycle time, with particularly preferred results being at 800 ms pulsing and an X-Ray-off-cycle time in the range of 5.3 seconds.

The tabulated results of Table 27 are shown below.

TABLE 27

|  | 1Gy-5.3 s cycle-800 ms- −80 kv | 1Gy-10 s cycle-800 ms- −80 kv | 1Gy-20 s cycle-800 ms- −80 kv | 1Gy-10 s cycle-800 ms- −100 kv |
|---|---|---|---|---|
| CTRL | −0.002 | −0.016 | 0.008 | 0.005 |
| H100 | 0.270 | 0.293 | 0.371 | 0.330 |
| EC | 0.676 | 0.727 | 0.725 | 0.595 |

Embodiments of the KV setting are shown below in Table 28.

TABLE 28

| WST1 | | | | |
|---|---|---|---|---|
|  | 1Gy-5.3 s cycle-800 ms--80 kv | 1Gy-10 s cycle-800 ms- −80 kv | 1Gy-20 s cycle-800 ms- −80 kv | 1Gy-10 s cycle-800 ms- −100 kv |
| CTRL | 0.0733 | −0.0163 | 0.1020 | 0.1729 |
| H100 | 0.2418 | 0.2696 | 0.2413 | 0.1814 |
| EC | 0.4266 | 0.2847 | 0.1827 | 0.3159 |

Various embodiments of the kV of the x-ray from the imaging beam were further determined using a voltage of 80 kV and 100 kV. The results showed that using 80 kV to produce the x-ray is better than using 100 kV for the specific in vitro conditions that were tested. The particular level of kV to be used would depend on the particular treatment being performed, and would be readily determined by one of ordinary skill in the art.

Minimization of Radiation Induced Toxicity:

Using UVADEX (8-methoxypsoralen) as the activatable pharmaceutical agent (using concentrations in the range of 10 ug/mL to 50 ug/ml), and using either H100 (diamond coating formed in the presence of 40 atomic % hydrogen) or EC (ethyl cellulose coating) with the central phosphor being a 2:1 mixture of NP200 and GTP 4300, the following cell kill results were obtained.

Figure 54:
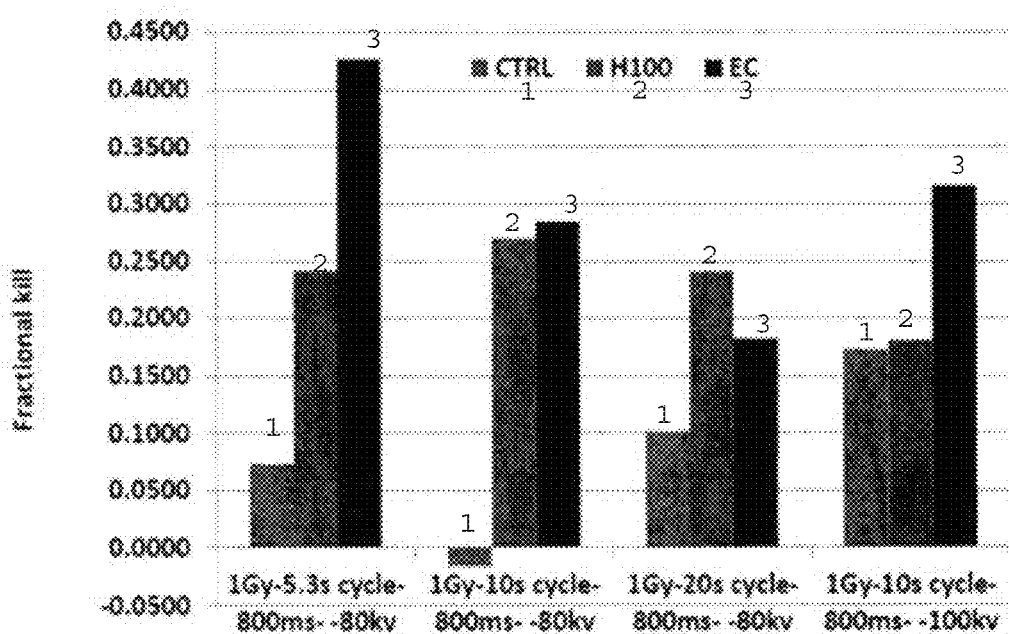
FIG. 54 is a schematic showing cell kill in a WST1 assay, using UVADEX (8-methoxypsoralen) as the activatable pharmaceutical agent (using concentrations in the range of 10 ug/mL to 50 ug/ml), and using either H100 (diamond coating formed in the presence of 40 atomic % hydrogen) or EC (ethyl cellulose coating) with the central phosphor being a 2:1 mixture of NP200 and GTP 4300.

These are graphically shown in FIG. 54. Several things can be seen in these results. The level of cell kill occurring due to x-ray alone depends on the pulse width (time period the pulse is "on" for each pulse) and the cycle delay (time period the pulse is "off" in each sequence between pulses). As shown in the results above, the best results with respect to minimizing collateral damage occurred for this particular test using an 800 ms pulse at 80 kv at either a 5.3 or 10 second cycle time. It is important to note that the total applied x-ray dosage was the same in each test, at 1 Gy. Optimum cell kill at the 80 kV strength also occurred at the 5.3 and 10 second cycle time. While the 100 kV x-ray source provided significantly higher cell kill for the EC coated phosphor at a 10 s delay, the collateral damage was significantly higher as well.

In a further WST1 assay, using the same UVADEX activatable pharmaceutical agent, and the same H100 and EC coated phosphors, with a 5 s cycle time between pulses for the 80 kv sequence, and a 10 s cycle time between pulses for the 100 kv sequences, the following cell kill results were obtained as shown in Table 29.

TABLE 29

WST1

|  | 1Gy-800 ms-80 kv | 1Gy-500 ms-100 kv | 1Gy-800 ms-100 kv | 1Gy-1600 ms-100 kv |
| --- | --- | --- | --- | --- |
| CTRL | 0.036 | 0.018 | 0.025 | 0.101 |
| H100 | 0.269 | 0.280 | 0.320 | 0.149 |
| EC | 0.223 | 0.227 | 0.432 | 0.300 |

Figure 55:
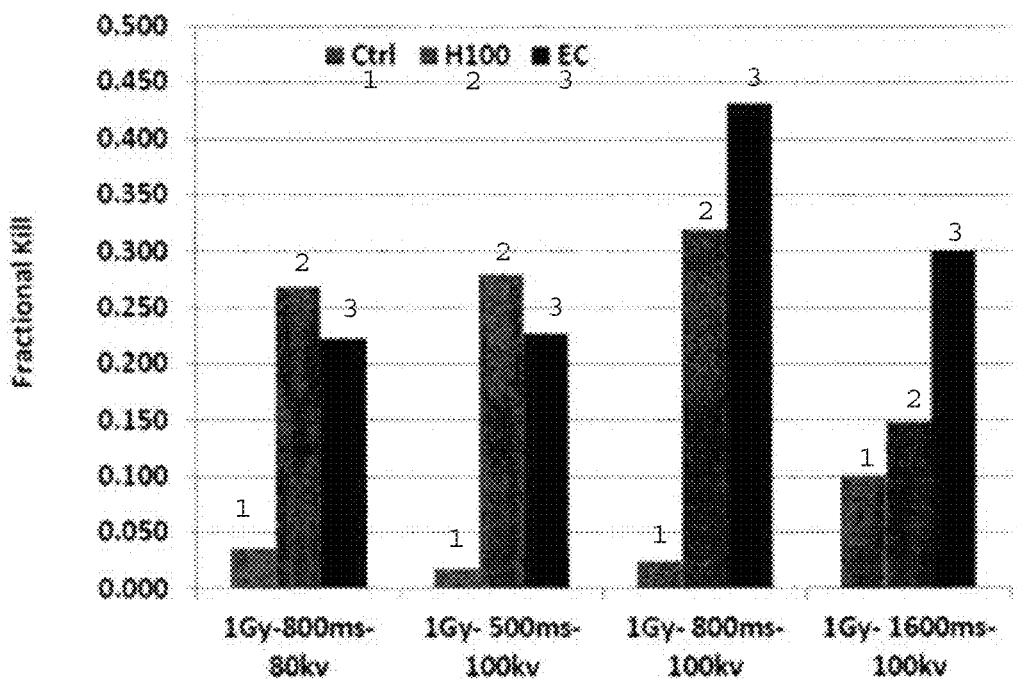
FIG. 55 is a schematic showing cell kill in a further WST1 assay, using the same UVADEX activatable pharmaceutical agent, and the same H100 and EC coated phosphors, with a 5 s cycle time between pulses for the 80 kv sequence, and a 10 s cycle time between pulses for the 100 kv sequences.

These results are graphically depicted in FIG. 55. The results showed that the pulse width also displays a "sweet spot" for maximizing cell kill while minimizing collateral damage. In this instance, the best pulse sequence with respect to maximizing cell kill while minimizing collateral cell damage was at 100 kV for 500 ms and 800 ms pulses, with a 10 s delay between pulses.

Accordingly, in this embodiment of the invention, based on a particular combination of energy modulation agent and coating on the energy modulation agent, once can readily determine the best combination of pulse width (time the initiation energy is applied) and pulse cycle (time between pulses of initiation energy) to gain maximum reaction and cell kill of target cells, while minimizing collateral damage to healthy cells due to the initiation energy itself. This is particularly important when using ionizing radiation as the initiation energy source, such as x-rays or e-beam, as these are known to inflict such collateral damage indiscriminately otherwise.

Embodiments for Pulsing based on kv are shown below in Table 30. Based on the choice of the kV, a pulsing sequence was determined with a x-ray beam of 100 kV and using a Nexin-V assay.

TABLE 30

|  | 1Gy-500 ms-100 kv | 1Gy-800 ms-100 kv | 1Gy-1600 ms-100 kv |
| --- | --- | --- | --- |
| Ctrl | −0.003 | −0.003 | 0.002 |
| H100 | 0.528 | 0.438 | 0.385 |
| EC | 0.592 | 0.562 | 0.474 |

Figure 58:
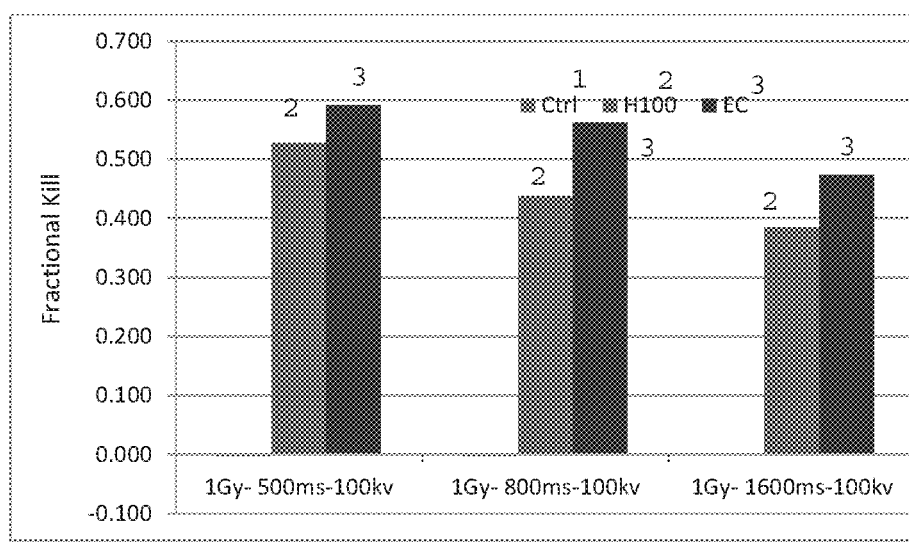
FIG. 58 is a schematic depicting cell kill in a further WST1 assay evaluating the effect of coating type and current (x-ray flux level)

The graph of these results is given in FIG. 58. As can be seen, a higher kV most likely require faster pulsing cycle to minimize toxicity and to maximize the beneficial activation of the biotherapeutic agent.

Figure 59:
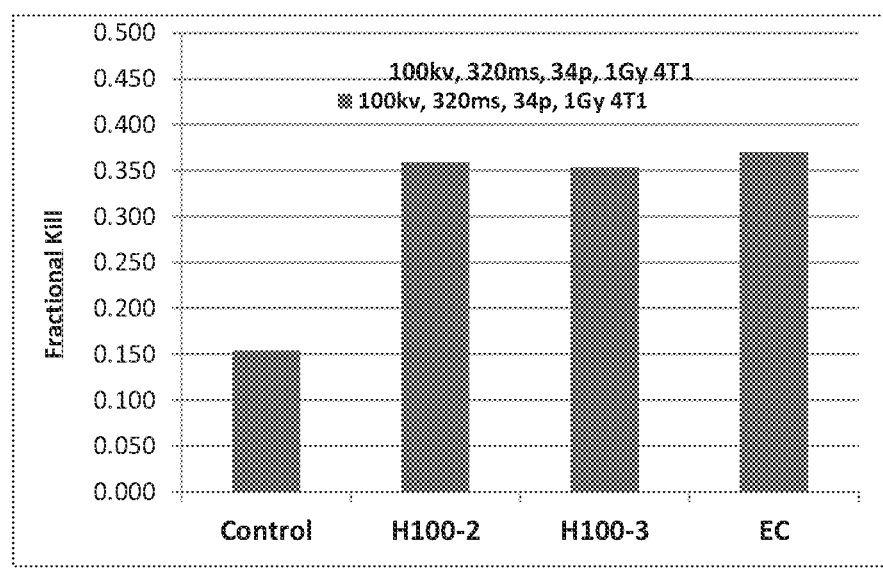
FIG. 59 is a schematic depicting cell kill in a further WST1 assay evaluating the effect of pulsing rate and different coatings.

Another test was conducted at a pulsing rate of 300 ms that compared 2 different batches of the H100 coating and contrasted with the Ethyl Cellulose coating. The results shown in FIG. 59 were based on a WST1 assay which yielded a higher level of cell kill at the control level than the Nexin V assay.

Equipment Control:

Given the various factors that can influence the efficacy of the treatment, a treatment regimen would be programmed to permit an operator to select machine output factors associated with information pertaining to the measure tumor depth and size (type, number of pretreatments, etc.), to be further refined through the selection of a predetermined pulsing sequence based on the phosphor/coating selected. The procedures would be programmed to maximized apoptosis while minimizing detrimental coupling to normal tissue. The following sequence is provided for the purpose of illustration not limitation of the invention.

Step 1: The Choice of the kV Based on the Depth of the Tumor:

A tumor that is seated 1 cm from the skin could be treated using 80 kV. A tumor that is seated 4 cm from the skin surface would be treated at 100 kv. Deeper seated tumors would preferably use higher kV beams.

Step 2—The Choice of the kV Influences the Choice of the Pulsing Sequence:

For a given set of phosphors and coating, the pulsing can be selected depending on the choice of the kv used. For 80 kV, a pulse of 800 ms is selected. For 100 kv, a pulse of 300 ms is selected.

Step 3—The Choice of the kv and the Pulsing Influences the Choice of the x-Ray Off Cycle:

The X-Ray off cycle can be affected by the decay time of the phosphors and by the recombination rate induced by the kV level selected to carry out the exposure. The higher kV levels may lead to electron hole pair creation where the electrons are created with enough kinetic energy to travel farther than the lattice from which they were excited from. The recombination is therefore gated by the diffusion of the electrons to recombine with the various holes. The higher photonic energy of the X-ray results in higher electron with higher kinetic energy, which in turn may result in longer the decay time; and, lastly longer time for the X-Ray off cycle.

Step 4-Treatment of Deep-Seated Targets

The on-board imaging (OBI) system of a Novalis Tx radiosurgery platform or mounted on a medical linear accelerator (Varian Trilogy) was used to deliver a prescribed dose (0.6 Gy) in an in-vivo setting using 80 and 100 kVp. A collimated rotational delivery of the penetrating x-rays was used as a strategy to minimize skin dose for deep seated targets.

Dose calculations with homogeneous cylindrical phantoms confirmed this approach. Indeed, dosimetric measurements included kVp, HVL, depth dose, backscatter factors, collimator and phantom scatter factors, field size factors, and blade leakage have been used. Absolute dosimetry was performed following AAPM TG61 recommendations and verified with an independent kV dose meter. The results of this approach shoed that heat loading was tolerable; using a 50 cm SSD, 0.5 Gy delivered to a 5 cm depth using an 80 kVp beam before the anode reaches 75% heat capacity. This analysis indicated that a tolerable skin dose of approximately 75% of mean target dose for an 80 kVp collimated rotational delivery to a 3 cm diameter target within a 20 cm diameter phantom.

Figure 63:
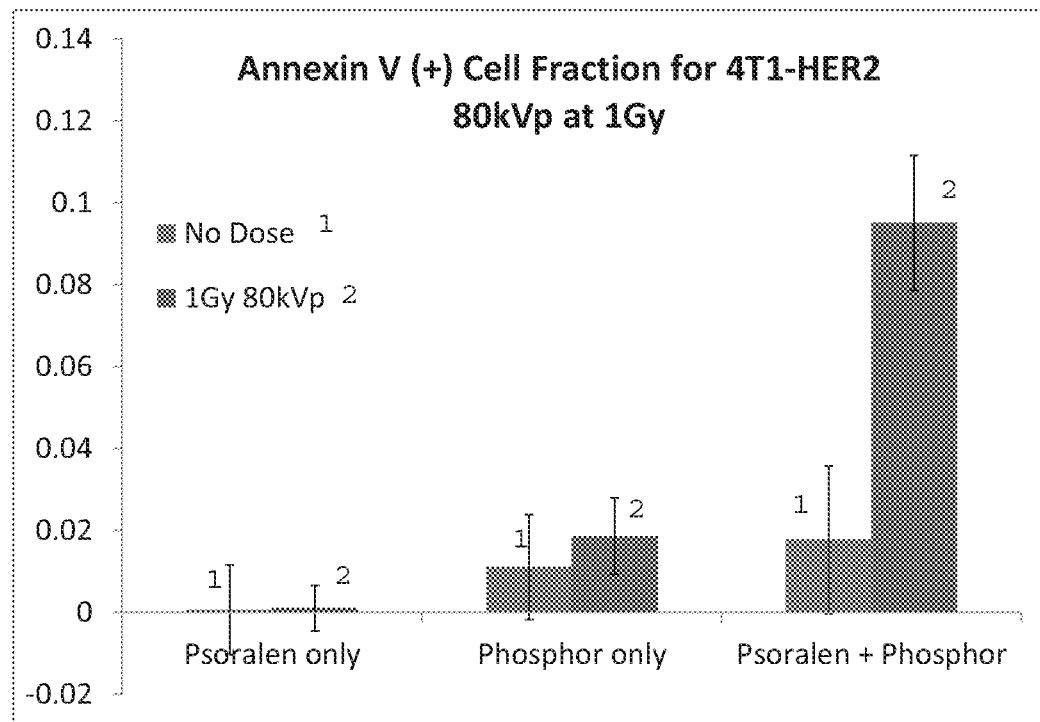
FIG. 63 is a schematic depicting cell kill comparison showing that rotational low kVp x-ray dose (1 Gy, 80 kVp) in combination with psoralen and phosphors are effective for cell kill.
Figure 64A:
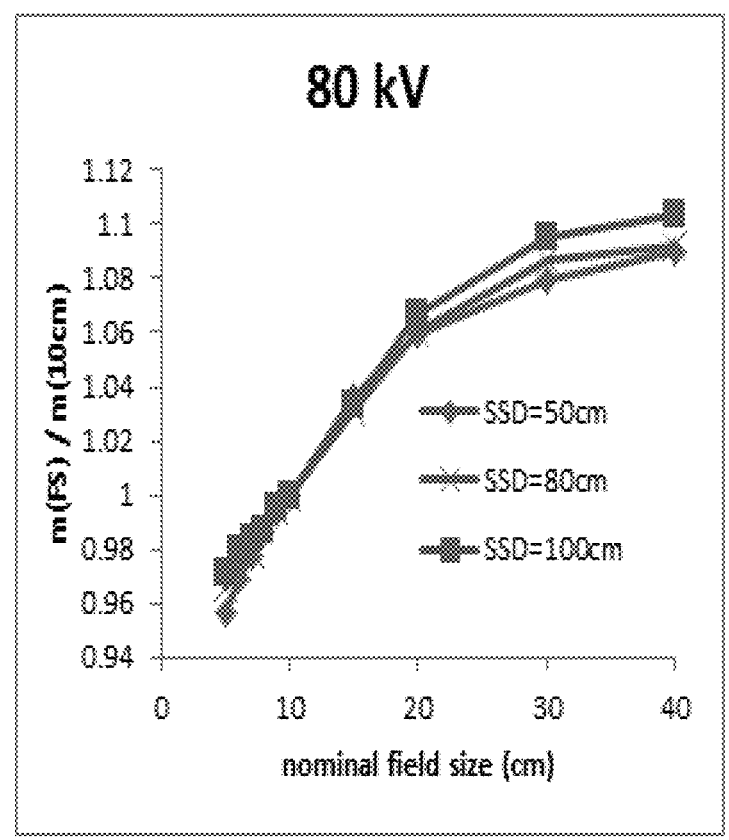
FIGS. 64A, 64B, and 64C are plots showing the field size output factors, backscatter factors, and percent depth dose measured for 80 kVp.
Figure 64B:
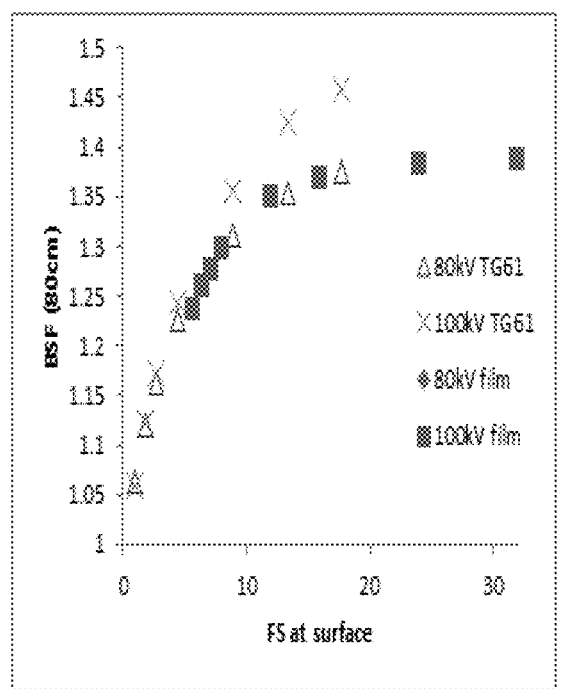
Figure 64C:
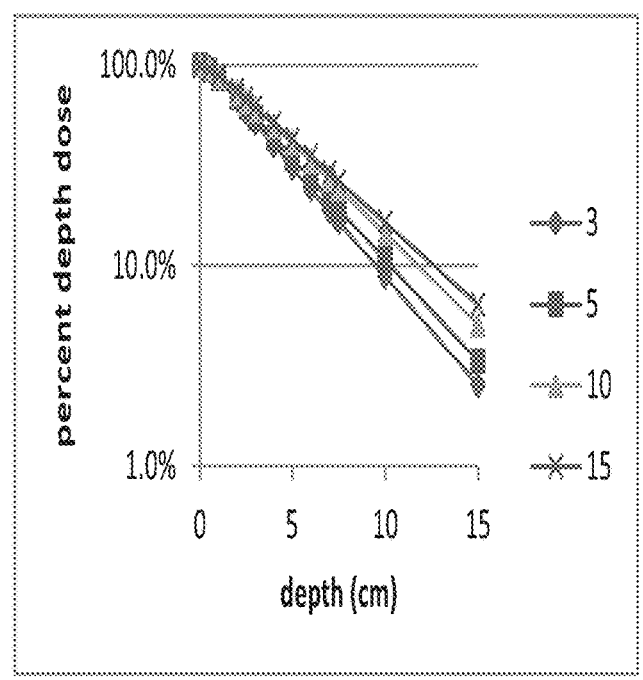
Figure 65:
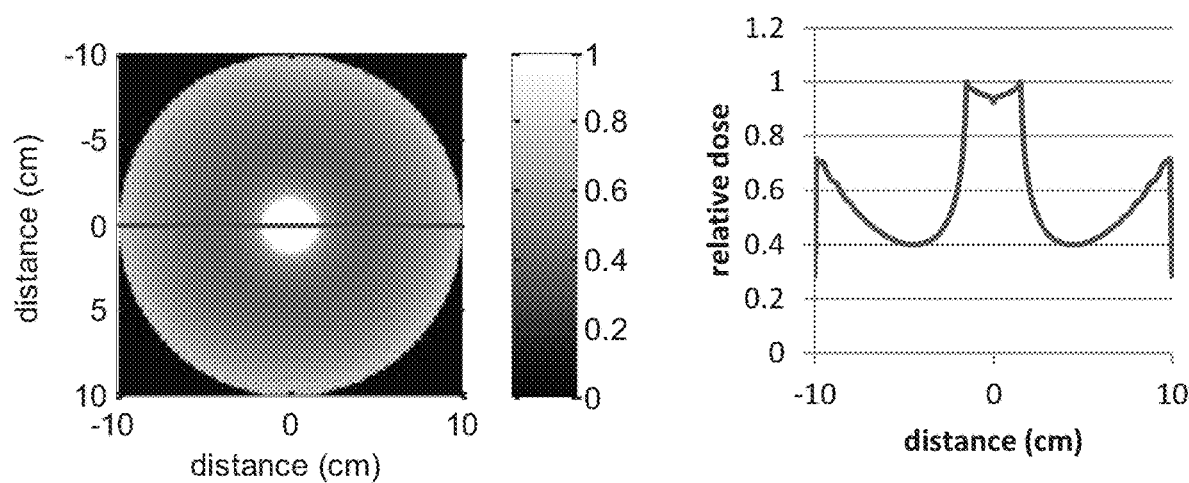
FIG. 65 is a schematic representation depicting the x-ray penetration.

FIG. 63 is a cell kill comparison showing that rotational low kVp x-ray dose (I Gy, 80 kVp) in combination with psoralen and phosphors are effective for cell kill. FIG. 63 shows specifically that psoralen activated by kV x-rays induces apoptosis as determined by Guava flow cytometry. Annexin V+cell fractions per sample were normalized by subtracting "background" Annexin V signals from control cells from the same plate. Substantial apoptosis was observed in cells that receive kV x-rays, phosphors, and psoralen combined. Error bars indicate one standard deviation. FIGS. 64A, 64B, and 64C are schematic representations depicting the x-ray penetration. FIG. 65 are plots showing the field size output factors, backscatter factors, and percent depth dose measured for 80 kVp. It shows that a tolerable skin dose can be achieved for a low dose kV therapy technique. Shown is the primary beam contribution for an 80 kV collimated rotational delivery to a 3 cm diameter target within a 20 cm diameter water equivalent phantom. Skin dose in this demonstration is 75% of mean target dose.

Software Subroutine

A software subroutine controls the level of reaction leading to minimal collateral damage to normal tissue and maximum interaction with the phosphor responsible for UV generation in-vivo. A first step comprises determining the size and location of the tumor, which information is stored and reviewed. A second beam (used for the purpose of therapy) is then applied using a predetermined specification including:

a—The kV beam based on tumor depth
b—The X-Ray dose
c—The pulse during the X-Ray on cycle
d—The X-Ray off cycle A hardware controller box can be adapted to automate the on/off switch cycle to activate the x-ray systems when operating in a radiographic mode. Alternatively, one can control the on/off cycle manually.

The controller box adapter can be adapted to existing equipment without having to decommission the system for rewiring and testing.

In one embodiment, the invention offers therapy from x-ray systems that do not have a pulsing capability. For such a system (which include an orthovoltage), an x-ray shutter scheme is designed to enable the electron beam to remain on and the x-ray flood beam to be gated through a shutter that results in effectively limiting the x-ray beam on and off resulting in pulsation. A representative design is described below and shown in FIG. 69.

An exemplary multi-aperture shutter with an actuating arm is shown in the figure. The actuating arm can translate back and forth resulting in an effective pulsing of a constant incident beam. In a similar way, the multi-aperture shutter can be made by creating a disk that has the ability to block x-ray and hollowing out certain sites that allow passage of the energy. This design allows a rotational movement to create an effective pulsing of the X-Ray beam.

Figure 61:
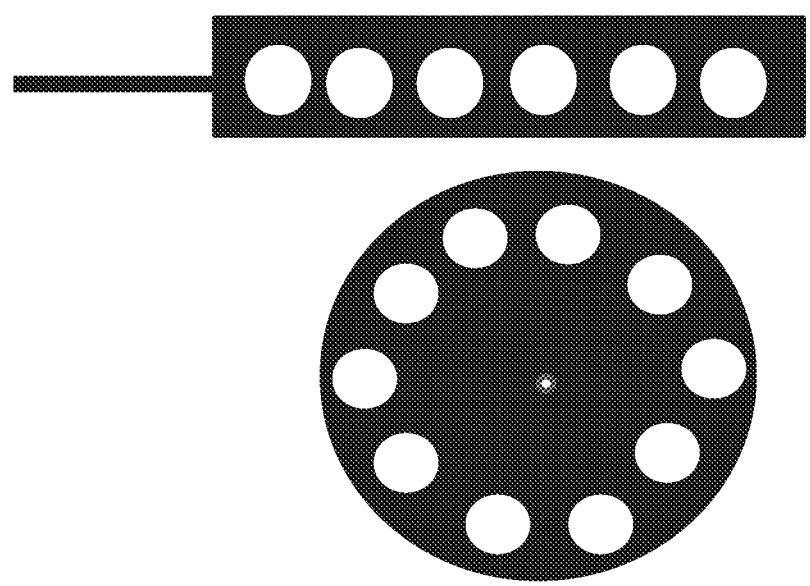
FIG. 61 is a schematic showing linear and circular aperture plate arrangements for use in an X-ray system.
Figure 60:
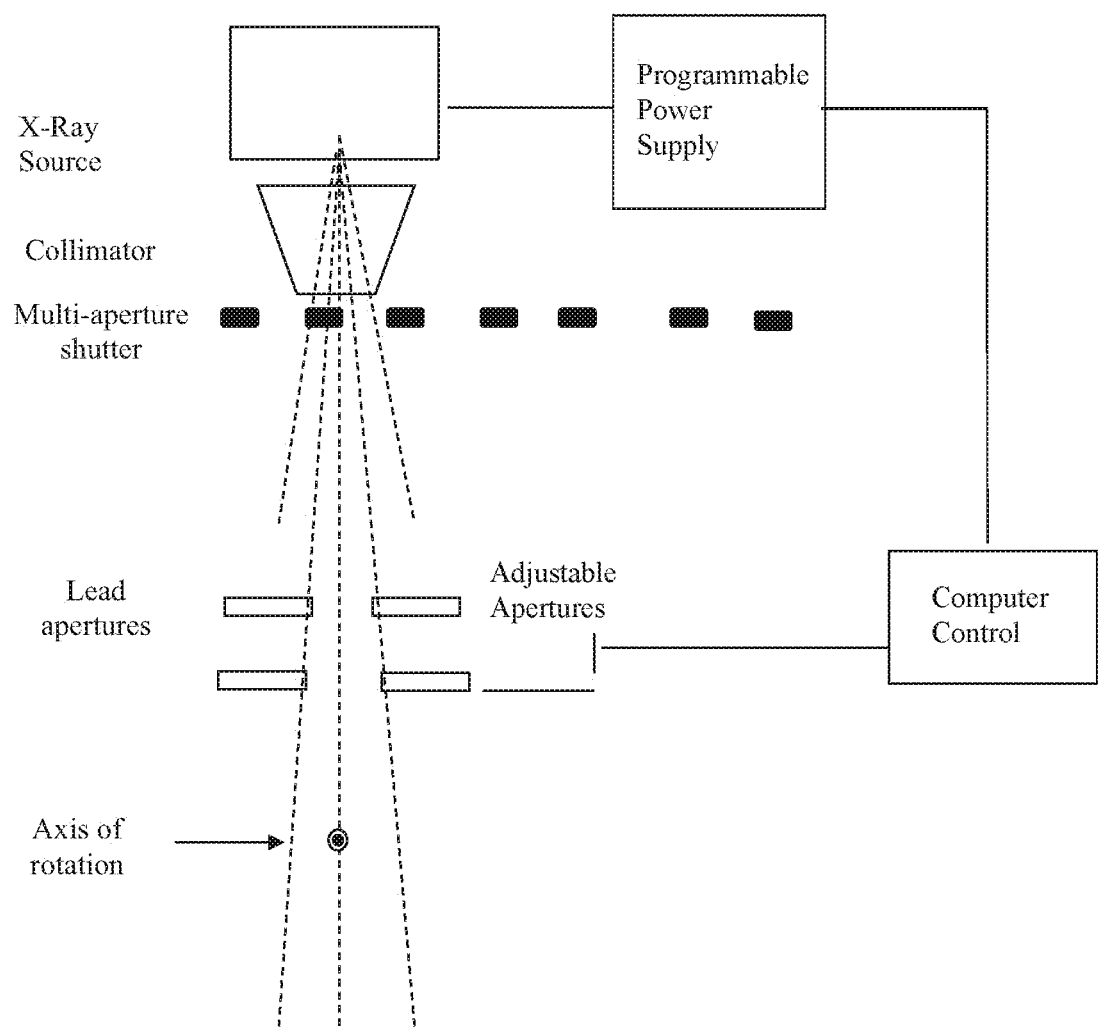
FIG. 60 is a schematic showing an X-ray system.

Exemplary designs of various apertures and one with a center of rotation are illustrated in FIG. 61.

Conformal Sources for Minimization of Collateral Radiation Exposure

The above noted shaped or conformal xray or ebeam sources are applicable here as a way to minimize collateral radiation exposure. Here, the target site to be treated is exposed to xrays or electrons form the conformal or shaped sources noted above. In this way, 1) the x-ray or ebeam source is placed proximate to the patient or 2) as detailed below the x-ray or ebeam source is inserted into the patient to be adjacent the tumor or diseased site to be treated.

As noted above, since the substrates can be silicon on insulator or aluminum on insulator, thin panels of the carbon nanotubes can be formed with thin glass panels and the substrate containing the carbon naonotubes can be encased with a thin glass panel opposing the carbon nanotubes and forming the electron optics and target material for the x-ray or the transmission window for the electrons.

The thin panels are flexible and can be shaped after fabrication to conform to the tumor or target site to be treated. This capability permits the invention in one embodiment to utilize miniaturized flexible x-ray or ebeam sources for bodily insertion. These sources would be conformal to the target site and as noted above could be inserted nest to the tumor or diseased site to be treated.

Furthermore, the nature of the array of carbon nanotubes and the patterning to collect electrically to selected groups of the nanotubes means that the tumor site can receive x-ray or electron dose from all of the nanotubes at once (for example concentrating the dose at a focal-type point) or in a programmed progressive manner which distributes in time the total x-ray dose from different sections of the conformal xray or ebeam source that preferably would not overheat or radiation damage the collateral tissue.

In one embodiment of the invention, if the miniaturized conformal source is surgically implanted, the source could remain in the patient for subsequent treatments or for palliative radiation doses following the treatment. (Subsequent treatments including booster treatments and palliative radiation treatments are discussed in more detail elsewhere.) Since the intensity of the radiation from a source decreases uniformly with approximately the square of the distance (R) from the source (i. e., $1/R^2$), a local source of radiation at the target site will utilize more effectively the generated radiation. By having an array of sources programmable and selectable for on/off and duration and intensity, a more uniform dose of radiation to the target site can be obtained than from a point source.

International Publication WO 92/04727 (the entire contents of which is incorporated herein by reference) and International Publication WO 03/061763 (the entire contents of which is incorporated herein by reference) describe surgically inserted x-ray sources. These sources could be used in one embodiment of this invention to provide radiation to the target site in the patient.

Moreover, the '727 publication describes a method of treating malignant cells, such as found in tumors, in vivo, utilizing the apparatus described above. The '727 method involved a low-power electron beam source and a selectively shaped x-ray radiation pattern generating target and shield assembly that were positioned proximate to the malignant cells. X-rays emitted from the target and shield assembly are introduced into the malignant cells for selective destruction of the cells. In the '727 method, the target and shield assembly geometry and materials were shaped and selected in accordance with the characteristics of the malignant cells. These methods are applicable in various embodiments of this invention. As in the '727 method, in various embodiments of this invention, a programmable power supply can be provided, which may be used to vary the voltage, current, and duration of the electron beam source to establish a desired electron beam which is directed to the target.

The '763 publication describes a controller having functions suitable for at least one embodiment of the invention. In the present invention, a controller in various embodiments can provide for selective and independent control each of a plurality of therapeutic radiation sources (i.e., the linear or two-dimensional array or a three-dimensional array, noted above). The controller would be programmed to selectively generate therapeutic radiation at selected time intervals and at selected intensities. The controller could include intensity control circuitry for controlling the intensity of the therapeutic radiation generated by each therapeutic radiation source. The controller could also include duration control circuitry for controlling the duration of the therapeutic radiation generated by each therapeutic radiation source. The controller may also control an introduction mechanism for inserting the therapeutic array into a treatment region, and for withdrawing the array from the treatment region.

Similar to the '763 publication, this invention in various embodiments can utilize an elongated cylindrical probe can have a hollow tube for electron acceleration to an x-ray generating target. Parts of the probe may be selectively shielded to control the spatial distribution of x-rays. In addition, the probe may be magnetically shielded to prevent external magnetic fields from deflecting the electron beam away from the x-ray generating target.

An electron beam generator in the probe may include a tungsten filament thermionic electron emitter or a low work function electron emitting source such as the carbon nanotubes describes above. The electron emitter is driven preferably by a floating low voltage power supply or the electron emitter could be a photocathode irradiated by an LED or laser source. In one embodiment, a high voltage power supply establishes an acceleration potential difference between a cathode and a grounded anode so that an electron beam is established along the hollow axis of the probe.

In one embodiment, the probe is a hollow, evacuated beryllium (Be), tantalum (Ta) or stainless steel cylinder e.g., 15 cm long, with an interior diameter of 2 mm, and an exterior diameter of 3 mm. The x-ray generating target can include a target assembly having a beryllium (Be) disc, coated on the side exposed to the incident electron beam with a thin film or layer of tungsten (W). In this example, with electrons accelerated to 30 keV, a 2.2 micron thick tungsten film absorbs substantially all the incident electrons, while transmitting approximately 95% of any 30 keV, 88% of any 20 keV- and 83% of any 10 keV x-rays generated in that layer.

Treatment Assessment

As noted above, this invention utilizes in various embodiments the presence of (i) x-ray, (ii) energy modulation agents (down converter, up converters, or mixtures of each or combinations thereof), and (iii) psoralen to induce apoptotic cell death. Well plates of 4T1-Her2 breast cancer cells and radiation-resistant sarcoma cell lines KP1408 and KP1619 were prepared. Cells in each well were either exposed to no reagents (controls), psoralen only, energy modulation agents only, or psoralen and energy modulation agents combined. The plates were then irradiated with 1 Gy of 80 kVp x-ray beam from a clinical CBCT (as described above) at various tube currents either delivered continuously or in multiple intermittent pulses (fractions). An identical plate was prepared but was not irradiated as "no-CT" control. Apoptotic cell fractions were determined from annexing V Flow cytometry assay.

The results of this work showed that a 1 Gy x-ray treatment at 80 kVp itself does not induce significant apoptosis in 4T1-Her2 cells. Yet a statistically significant ($p<0.001$) increase in apoptosis results when cells with both energy modulation agents and psoralen undergo x-ray irradiation. Two sarcoma cell lines, KP1408 and KP1619, also exhibited high apoptosis when psoralen, phosphor (e.g., an energy modulation agent), and x-ray were present. Data suggest that apoptotic fraction in 4T1-Her2 can vary from 4% to 12% even at a constant radiation dose of 1 Gy at 80 kVp depending on irradiation condition.

Figure 66:
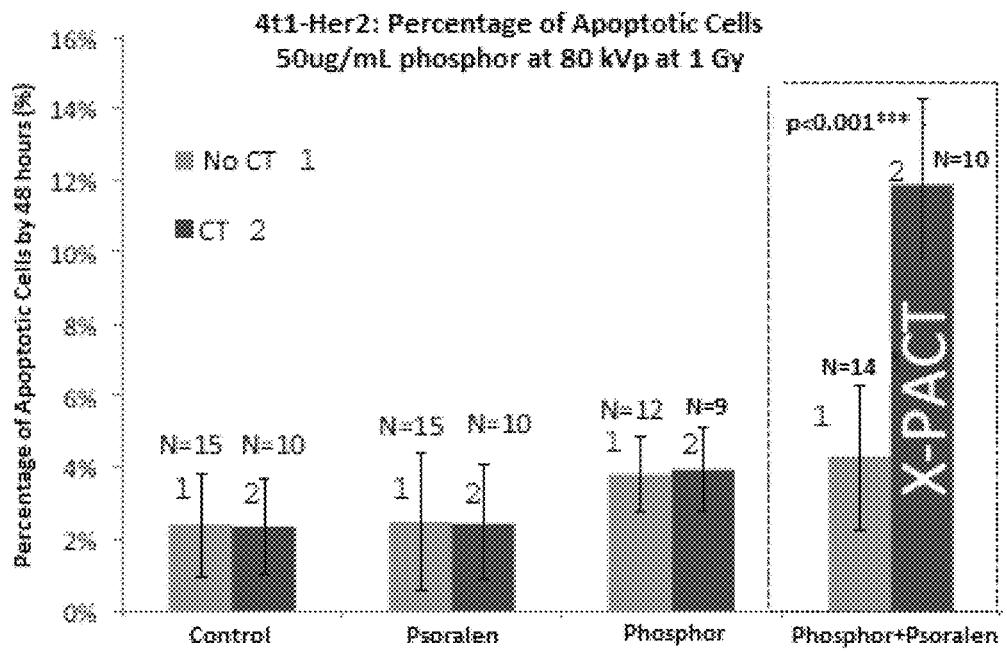
FIG. 66 is a plot of cell kill for the Her2 cell line.
Figure 67:
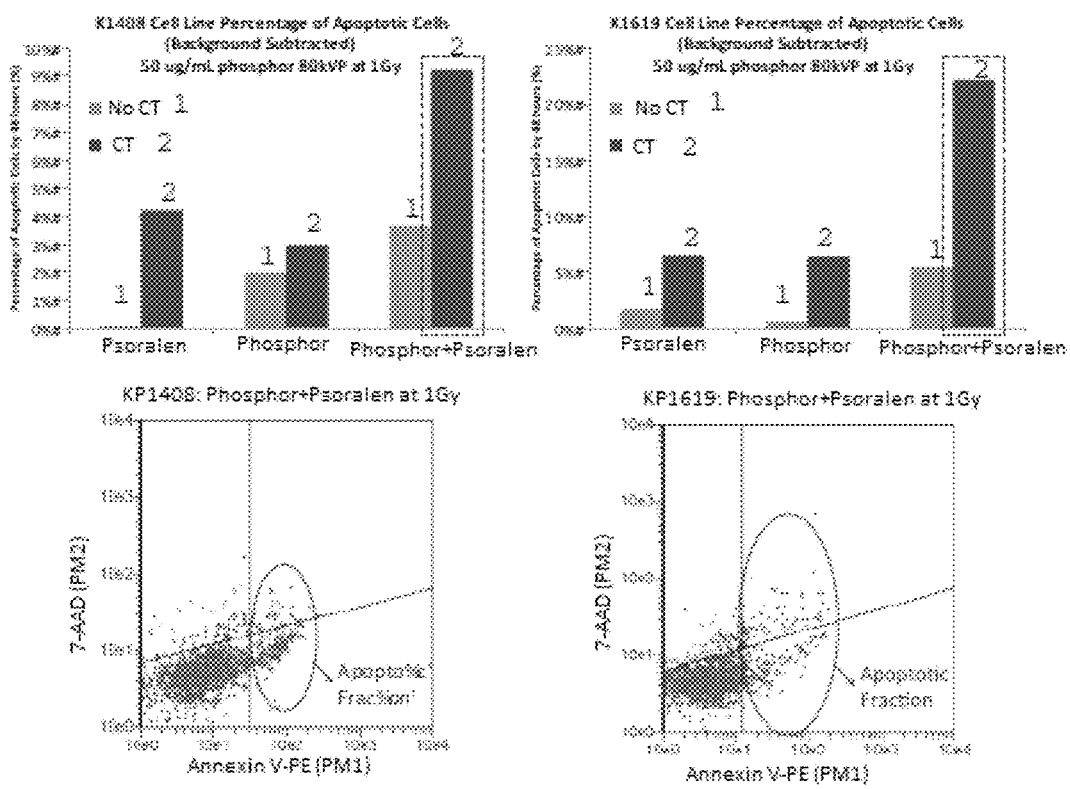
FIG. 67 is a plot of cell kill of the KP1408 and KP1619 cell lines.

FIG. 66 is a plot of cell kill for the Her2 cell line. It shows that, when phosphor, psoralen, and 1 Gy of x-ray were simultaneously present, induction of apoptosis was greatly enhanced, due to UV light activation of psoralen. Actual fractional cell kill was also increased. FIG. 67 is a plot of cell kill of the KP1408 and KP1619 cell lines. It shows that cell line data showing sarcoma lines KP1408 and KP1618 undergoing X-PACT therapy experience apoptosis. Raw cell cytometry data for X-PACT shows distinct apoptotic cell fractions in these cells.

Figure 68:
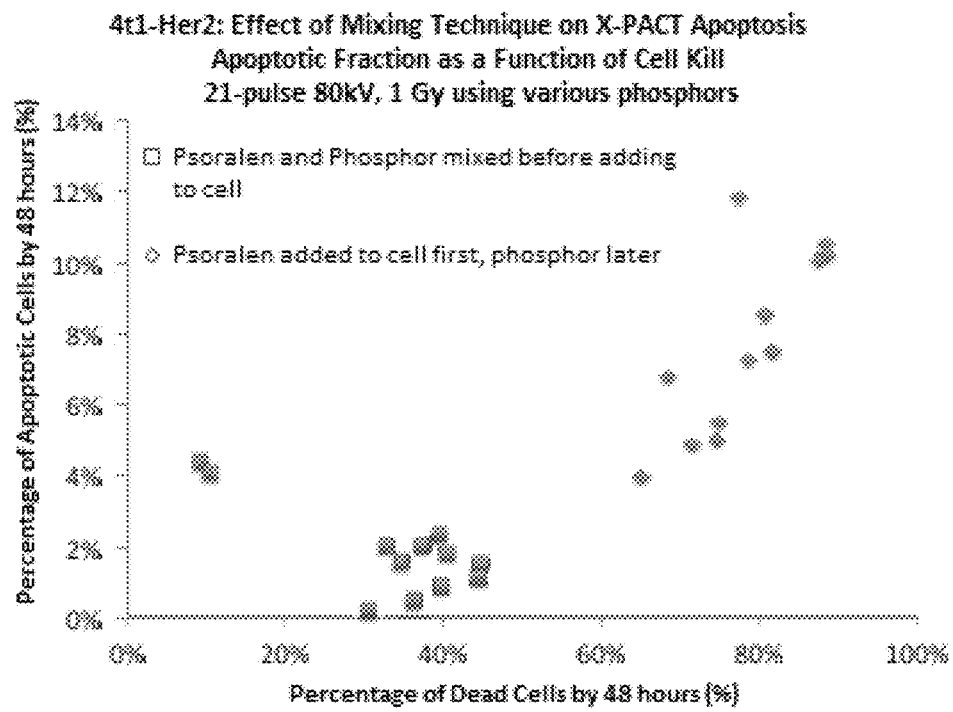
FIG. 68 is a plot of cell kill for the Her2 cell line as a function of the mixing procedure.

FIG. 68 is a plot of cell kill for the Her2 cell line as a function of the mixing procedure. It shows specifically that the effect of two different mixing techniques at same exact phosphor concentration, psoralen concentration, and irradiation condition with 80 kVp at 1 Gy on the outcome of X-PACT. Upon irradiation, both actual cell death and fraction of apoptotic cells were increased when psoralen is added to cells first before adding phosphor. Accordingly, the results showed that mixing psoralen with cells first before adding phosphors increases both cell kill and apoptosis, despite all other conditions being equal. Nevertheless, the invention permits any order of processing in order to in vivo expose the psoralen (or other photoactivatable) to activation light.

Treatment Protocol

The following protocols and variations thereof are utilized with the invention in order to visualize and/or treat malignancies in animals or human patients.

Protocol Summary:

Without limiting the invention, the following describes nine (9) repeated sessions including tumor measurements, visualizations, and treatments. More or less than nine sessions can be used depending on the state of the malignancy. Indeed, a treatment with 3 5 sessions might useful in situations where the tumor is near surface and thorough exposure of the tumor is likely at each session. Alternatively, a treatment with 12-15 sessions might useful in situations where the tumor is within a human organ inside the musculoskeletal system exposure of the tumor is limited to the radiation exposure dose. Moreover, while described below with emphasis on canine treatments, the invention is not limited to the use of these protocols to canines as other animal and human patients could benefit.

While other measurements, evaluations, and treatments for the malignancies can occur, each session typically includes: tumor measurements, toxicity scoring, labwork (collected—at treatments #2, 3, 6 and 9), intratumoral injections of drug and energy modulator substances (preferably while anesthetized), and radiation treatment (RT) with for example radiation of 1 Gy via 80 kVp X-rays. Following the nine sessions, there are follow-up weekly evaluations 3 and 6 weeks after completing the last RT. The follow-up weekly evaluations a) evaluate acute local and systemic toxicity via physical examination and routine labwork, and b) estimate the tumor volume. Following the nine sessions, there are follow-up monthly evaluations at 3, 6, 9 and 12 months after completing the last RT. The follow-up monthly evaluations a) evaluate delayed local toxicity via physical examination, and b) describe duration of local tumor in enrolled cases.

Protocol Entry Assessment for Animals (with Emphasis on Canine Treatment):

The procedures are open to any breed of dog more than 1 year old and having a body weight greater than 5 kg. In one branch of this protocol, the treatment addresses peripheral malignancies accessible for repeated intratumoral injections that have mot metastasized. In one branch of this protocol, the tumor lesion size is larger than 2 cm or 8 cm³ (whichever is smaller). Additionally, the tumor lesion size is smaller than 6 cm. Tumor volume is estimated by multiplying the product of 3 orthogonal diameters by $\pi/6$.

Protocol Baseline Evaluation:

Prior to entering the treatment sessions noted above, patients undergo the following: 1) complete medical history and physical examination including 3-dimensional caliper measurements of the target lesion, 2) complete blood count, 3) serum biochemical profile, 4) urinalysis—free-catch is acceptable—, 5) three-dimensional thoracic radiographs, and 6) abdominal ultrasound.

Treatment and Imaging:

As noted above, subjects in the protocol are planned to anesthetized nine (9) times over 3 weeks. The treatment includes intratumoral injections of a slurry containing a commercially-produced pharmaceutical grade psoralen and a pre-selected phosphor or other energy modulation agent. During the radiation treatment, the tumor is imaged preferably using a cone-beam CT technology. The imaging may provide an indication of the localization of phosphors and there distribution throughout the volume of the tumor. As detailed below, visible or infrared emissions from the phosphors or other energy modulation agents in the near-surface region of tumor can provide information about the uniformity of the exposure of the tumor volume (under the premise that surface emissions are as equally occluded as emissions inside the mass of the tumor.

During the treatment and imaging, the patients are anesthetized for approximately 45 minutes per treatment session. All anesthetic protocols are devised/approved by the anesthesiologists, and tailored to the specific medical needs of each individual subject.

The following is a summary of the drugs, doses, routes, frequency of administration, and anticipated duration of therapeutic effect: While the description below references "phosphors," the protocol can include at least one of down conversion or up conversion media, and combinations and agglomerations thereof with or without plasmonic agents.

Intratumoral Injections:
1. 3-dimensional caliper measurements of the tumor.
2. Tumor volume will be estimated by multiplying the product of 3 orthogonal diameters by it/6.
3. The total volume to be injected into each tumor follows the regiment outlined below using vials of sterilized phosphor to be mixed UVADEX™ (100 µg/mL 8-MOP) as the sole diluent

TABLE 32

| Tumor volume | mL of slurry per cm³ tumor | | milligrams of phosphor per cm³ of tumor | | Total volume injected |
|---|---|---|---|---|---|
| | Min | Max | Min | Max | |
| 8-15 cubic centimeters | 0.034 | 0.063 | 0.333 | 0.625 | 0.5 mL |
| 15-29.9 cubic centimeters | 0.033 | 0.067 | 0.334 | 0.667 | 1 mL |
| 30-49.9 cubic centimeters | 0.040 | 0.067 | 0.401 | 0.67 | 2 mL |
| 50-74.9 cubic centimeters | 0.040 | 0.060 | 0.401 | 0.600 | 3 mL |
| 75-99.9 cubic centimeters | 0.040 | 0.053 | 0.400 | 0.533 | 4 mL |
| >100 cubic centimeters | 0.044 | 0.050 | 0.435 | 0.500 | 5 mL |

Especially for the canine treatments, but also for other patients, the fur/hair will be clipped to improve visibility of the tumor. The tumor skin overlying the tumor will be prepared via three (3) alternating scrubs of alcohol (or sterile saline) and chlorohexidine (or iodine).

A grid (e.g., of 1 cm squares) may be placed over the tumor. Each week, the center and corners is marked (e.g., with a permanent or paint marker) in blue at the first of that week's treatments, green at the second treatment and white at the 3rd treatment The grid serves as a template for free-hand injection of the psoralen/phosphor slurry. The grid is rotated (in the same plane, pivoting about the center) 0.25 cm per day.

An appropriate amount of individual, coated phosphors were weighed into a glass crimp top vial, fitted with a Teflon septum top and an aluminum crimp ring, sealed via a crimp tool and autoclaved on a dry goods cycle (250×C, 30 minutes) and immediately removed from the autoclave, allowing to cool to room temperature. The sterilized materials were stored at room temperature, protected from light until use.

TABLE 31

| Species | Procedure or condition | Agent* | Dosage, route | Frequency | Duration |
|---|---|---|---|---|---|
| Canine | Pre-anesthetic sedation | Butorphanol | 0.2-0.4 mg/kg IM | Once per anesthetic | 1-3 hrs |
| Canine | Induction of anesthesia for CT | Propofol | 4-6 mg/kg1V (to-effect) | Once per anesthetic | ~20 min |
| Canine | Maintenance of anesthesia | Isoflurane in oxygen | 0.5-4% as needed for | Throughout anesthetic | <3 hr |
| Canine | Post anesthetic sedation | Acepromazine | 0.005-0.02 mg/kg IV | Once per anesthetic if | 4-6 hr |
| Canine | Hypotension during anesthesia | Dopamine | 2-8 µg/kg/min | CRI if needed during anesthesia | <3 hr |
| Canine | Bradycardia during anesthesia | Glycopyrrolate | 0.01 mg/kg IM or IV | Once per anesthetic | 2-4 br |
| Canine | Fluid therapy | Lactated Ringers Solution LRS | 5 ml/kg/hr | Throughout anesthetic | <3 hr |

In one example, approximately 30 minutes prior to injection, sterilized phosphors in sealed, crimp top vials were rehydrated with the indicated volume of UVADEX via a sterile needle through a septum cap. Post addition of UVADEX, the entire mixture was continuously vortexed (using a laboratory grade vortex mixer set to the highest setting) for approximately 2 minutes. The mixed sample was introduced into a sterile syringe and sealed with a luer lok cap. Syringes were delivered to the treatment room and immediately prior to intratumoral injection, the sealed syringed was mixed via vortex for approximately 30 sec followed by injection into the desired subject site.

A 20-25 gauge sterile hypodermic needle can be used to make free-hand injections at the corner of each square on the grid. (Changing the size of the needle or syringe can be used to optimize the injection distribution.) The total volume to be injected is divided evenly. Injections are preferably made into palpable tumor, but not adjacent normal tissues. The plunger will be depressed as the needle is withdrawn from the tumor, to maximize the distribution of phosphors and psoralen.

In one embodiment, tumors on or near the surface can be palpated to facilitate delivery of the phosphors. Typically, multiple injections are made to help distribute the phosphors throughout the tumor mass. For deeper treatment areas where the tumor cannot be palpated, ultrasound guidance can be employed. Additionally, ultrasound can be used to assist in the dispersion of the phosphors after the phosphors are delivered to the treatment site.

This protocol uses UVADEX (8-methoxypsoralen) as the activatable pharmaceutical agent (using concentrations in the range of 10 µg/mL to 50 µg/ml), and uses either H100 (diamond coating formed in the presence of 40 atomic % hydrogen) or EC (ethyl cellulose coating) or both with the combination phosphor being a 2:1 mixture of NP200 ($LaPO4:Ce^{3+}, Tb^{3+}$) and GTP 4300 ($3Ca_3(PO_4)_2.Ca(Fl, Cl)_2: Sb^{3+}, Mn^{2+}$). Other protective coatings and ratios of the NP200 and GTP 4300 can be used in the invention.

Following injection of the phosphors and psoralen, the resultant distribution of the phosphor within the tumor was retrospectively evaluated on each cone-beam computed tomography (CBCT). If the grid pattern of injection does not result in even distribution of the phosphor within the tumor, a free-hand approach may be taken instead, such that injections are made every 0.5 to 2.0 cm, and in orthogonal planes.
Radiation Therapy:

0.6-1 Gy of radiation is delivered per treatment session using 80-100 kVp X-rays from the on board imaging (OBI) device of a Novalis Tx radiosurgery platform. (Besides the OBI device of a Varian linear accelerator, a Trilogy, iX, TruBeam, etc. could be used with appropriate adjustment of x-ray dose and energy). With regard to the Novalis Tx platform, this platform includes three imaging modalities for pinpointing a tumor and positioning the patient with high precision. The OBI may be programmed to provide continual imaging during treatment to detect movement and support robotic adjustments in patient positioning in six dimensions (although image quality during treatment will not be optimum). The patient disposed on the Novalis Tx platform is positioned above the concentric imaging position of the x-ray source at a distance of 50 to 70 cm from the x-ray anode.

Subjects can be positioned on a linear accelerator's treatment couch (with the gantry at zero degrees) with the tumor centered at the isocenter of the linear accelerator (centering accomplished using visual inspection and lasers from the linear accelerator); the subject can then be vertically raised to a position with a source to surface distance SSD of 70-90 cm, per the optical distance indicator. This corresponds to a source to surface distance of 50-70 cm when the kilovoltage X-ray source (in the on-board imaging system) is moved to zero degrees for irradiation. Subjects with small body size are elevated on a riser which sits atop the 1 linear accelerator's couch, to facilitate a terminal SSD of 50-70 cm; the goal is always to make the terminal SSD (from the kV source) as close to 50 cm as possible, to minimize treatment times.

Immediately following the final intratumoral injection (preferably within several minutes) alignment radiation from the x-ray source (fluoroscopy and/or planar radiographs) confirms that the source is properly positioned to deliver x-rays to the tumor site by imaging of fiducial markers around the tumor. Then, within several or 5 minutes of the final injection, x-rays from the 80 kVp source pulsing for 800 microsecond pulses can be delivered to the target site. In one example, the flux of x-rays is interrupted periodically and restarted until a dose of 0.5 to 1.0 Gy has been delivered in total. As an example, multiple pulses can be used with each pulse is set for 80 Kv, 200 mA, 800 milliseconds. The total dose (in Gy) delivered is determined by the number of pulses delivered. The number of pulses delivered to achieve the therapeutic dose is a function of the depth and location of the tumor. Bone mass in the exposure region should be accounted for. For example, a radiation therapy typically is designed for a maximum estimated fractional bone dose of 3 Gy per fraction.

After, this therapeutic radiation treatment (preferably less than 30 minutes, more preferably less than 20 minutes), the region of interest will be exposed to the kilovoltage radiation using the Varian Novalis OBI (on bard imaging system). At least one rotational kilovoltage CBCT is typically scheduled such that images can be stored for evaluation. Additional beam angles collimated per the recommendations can be used.

Patient data is uploaded into the record such that the images stored can be used to review e.g., tumor volumes (contoured to determine volume estimates) and phosphor distribution within the tumor).
Sample Collection Blood samples are collected via peripheral venipuncture, or from a sampling catheter. Free-catch urine samples are collected for urinalyses.

TABLE 33

| Assay | Fluid | Volume per sample | Number of samples (per dog) | Time of sample collection |
|---|---|---|---|---|
| Complete blood count | Whole blood (in EDTA) | 1 mL | 7 | Baseline, day 3, week 1, 2, 3, 6 and |
| Chemistry profile | Serum | 1 mL | 7 | Baseline, day 3, week 1, 2, 3, 6 and |

TABLE 33-continued

| Assay | Fluid | Volume per sample | Number of samples (per dog) | Time of sample collection |
|---|---|---|---|---|
| Urinalysis | Urine | 1 mL | 7 | Baseline, day 3, week 1, 2, 3, 6 and |
| PK-Day 1 (psoralen) | Plasma | 0.5 mL | 8 | Baseline, 10, 30 minutes, 1, 1.5, 3, |
| PK-Day 9 (psoralen) | Plasma | 0.5 mL | 4 | Baseline, 30 minutes, 1.5 and 6 |
| Elemental analysis (phosphor) | Plasma | 0.5 mL | 10 | Baseline, 30 minutes, 1.5 hours, 6 hours, 12 hours, 3 days, 1, 3, 6 and |
| Stored sample (for future analyses of immune and/or inflammatory mediators) | Plasma | 0.5 mL | 10 | Baseline, 30 minutes, 1.5 hours, 6 hours, 12 hours, 3 days, 1, 3, 6 and 9 weeks |

Pharmacokinetic samples are frozen and stored. The pharmacokinetic study determines whether enough psoralen is absorbed systemically to create concern regarding systemic exposure and toxicity.

Blood and urine samples for elemental analysis are frozen and stored. Additional plasma samples are collected and stored.

The preceding treatment may be further supplemented with a "booster" treatment, that is, the initial treatment considered a "priming treatment" with an additional treatment used to "boost" the initial treatment response. A "booster treatment" in one embodiment could involve re-injecting the tumor with psoralen (or other photoactivatable drug) and radiating the tumor site again. A "booster treatment" in another embodiment could involve re-injecting the tumor with psoralen (or other photoactivatable drug) and an energy modulation agent and radiating the tumor site again. A "booster treatment" in another embodiment could involve radiating the tumor site again, but at a radiation level considered to be at either a palliative or therapeutic level. The purpose of these "booster" treatments is to activate the immune response initially or originally generated within the patient during the initial treatments.

In one embodiment of the booster treatment, the phosphor concentration is increased to 20 mg/mL, the amount of UVADEX is increased 2-4 times, and the treatment frequency is increased to five (5) treatments in five (5) consecutive days. Furthermore, the timing between the prime (initial treatment sessions such as the nine treatments described above) and the booster treatment is set to allow for an initial humoral or cellular immune response, followed by a period of homeostasis, most typically weeks or months after the initial priming treatment.

In another embodiment, particularly for more aggressive cancers, an intervening treatment between the prime and boost stages can be provided to stunt the growth of the tumor while the immune system develops a response. The intervening treatment can take the form of palliative radiation, or other treatments known to those skilled in the art.

The invention utilizes a booster treatment in a manner similar to that described by Jeffrey C. Nolz and John T. Harty in their Chapter 7 entitled "Strategies and Implications for Prime-BoostVaccination to Generate Memory CD8 T Cells" in the book *Advances in Experimental Medicine and Biology* 780, DOI 10.1007/978-1-4419-5632-3_7, © Springer Science+Business Media, LLC 2011 (the entire contents of which are incorporated herein by reference). The invention utilizes the booster treatment in a manner similar to that described by David L. Woodland in their paper in TRENDS in Immunology Vol. 25 No. 2 Feb. 2004, entitled "Jump-Starting the Immune System: Prime-Boosting Comes of Age" (the entire contents of which are incorporated herein by reference). The basic prime-boost strategy involves priming the immune system to a target antigen, or a plurality of antigens created by the drug and/or radiation induced cell kill and then selectively boosting this immunity by re-exposing the antigen or plurality of antigens in the boost treatment. As described in the literature, one key strength of this strategy is that greater levels of immunity are established by heterologous prime-boost than can be attained by a single vaccine administration or homologous boost strategies. For example, the initial priming events elicited by a first exposure to an antigen or a plurality of antigens appear to be imprinted on the immune system. This phenomenon is particularly strong in T cells and is exploited in prime-boost strategies to selectively increase the numbers of memory T cells specific for a shared antigen in the prime and boost vaccines. As described in the literature, these increased numbers of T cells 'push' the cellular immune response over certain thresholds that are required to fight specific pathogens or cells containing tumor specific antigens. Furthermore, the general avidity of the boosted T-cell response is enhanced, which presumably increases the efficacy of the treatment.

Here, in this invention and without limitation as to the details but rather for the purpose of explanation, the initial treatment protocol develops antibodies or cellular immune responses to the psoralen-modified or X-ray modified cancer cells. These "initial" responses can then be stimulated by the occurrence of a large number of newly created psoralen-modified or X-ray modified cancer cells. As such, the patient's immune system would mount a more robust response against the cancer than would be realized in a single treatment series.

In one embodiment of the invention, prior to the initial treatment or prior to booster treatments, the immune system of the subject could be further stimulated by injection of a more conventional vaccine such as for example a tetanus vaccine. Prior work has shown the efficacy of a tetanus booster to bolster the immune system's attack on the tumor by helping cancer vaccines present in the subject migrate to the lymph nodes, activating an immune response. Here, in this invention, the autovaccines generated internally from the treatments described above could also benefit from this effect.

Treatment of Non-Adherent or Liquid Tumors

The invention also has utility in treating non-adherent (liquid) tumors, such as lymphoma. Instead of injecting the phosphors and drug into the solid tumor, the phosphor and drug combination can be injected into a lymph node, preferably the draining lymph node distal to a lymphoma tumor, or any lymph node with disease involvement. Alternatively, treating any area with a lymphoma infiltration is acceptable.

Debris from dead and dying tumor cells would be transported to regional lymph nodes where immune activation would occur and tumor specific immune cells would then recirculate and begin to destroy tumor cells at multiple sites. This killing of tumor cells in the lymph or any organ with a lymphoma infiltrate creates more immune stimuli for activation in the regional lymph nodes and further re-circulation, making repeat treatments beneficial.

In one embodiment of the invention, as noted above, the treatments for the non-adherent or liquid tumors can be given once, or periodically (such as 3 to 5 times a week), or intermittently, such as 3 to 5 times a week, followed by a period of no treatment, typically one to two weeks, followed by another treatment period of 3 to 5 times a week.

Additionally, a prime-boost strategy can be employed, such as is described herein for the treatment of solid tumors. The prime phase can be a single treatment, periodic treatment or intermittent treatment, followed by a period of no treatment, typically 6-12 weeks, followed by a booster treatment. The booster treatment can be the same duration and frequency as the prime treatment, or can be accelerated or shortened.

In one embodiment of the invention, intervening treatments to control the growth or spread of the lymphoma while the immune system activates can also be added. These treatments can include palliative x-ray, enzyme treatments such as asparginase, chemotherapy, or surgery.

Other Visualization Techniques

As noted above, the tumor site of a patient is infused with a combination of a photoreactive drug and an energy modulation agent such as a phosphor which generates specific wavelength or wavelengths of light for activation of the photoreactive drug. The phosphor may also acts as a contrast agent for the above noted cone-beam computed tomography (CBCT) images. The phosphor in general is capable of emitting under x-ray exposure ultraviolet, visible and near infrared light. For phosphors deposited at the near tumor skin surface, these emissions can escape the tumor and serve a diagnostic imaging purpose.

In one embodiment of the invention, the distribution of light emitted from the near tumor skin surface is a metric of how uniformly the tumor is being exposed to the specific wavelength or wavelengths of light for activation of the photoreactive drug. The premise here is that the surface emission is indicative of emissions throughout the mass of the tumor.

In one embodiment of the invention, the distribution of light emitted from the near tumor skin surface can be affected by absorption bands of the psoralen. It is expected that UV absorption edge of psoralen when present in the tumor would result in the phosphor emission in those bands being absorbed. Similarly, visible and infrared absorptions of psoralen could be monitored provided that there were phosphors administered into the tumor which would emit about those bands. Infrared emissions in particular have less "natural" absorption in the bodily fluids and thus would be more likely to probe a greater depth of the mass of the tumor.

In another embodiment of the invention, the paramagnetic properties of the phosphors can be utilized to image the tumor via commercially available magnetic resonance imaging (MRI) systems.

Figure 62:
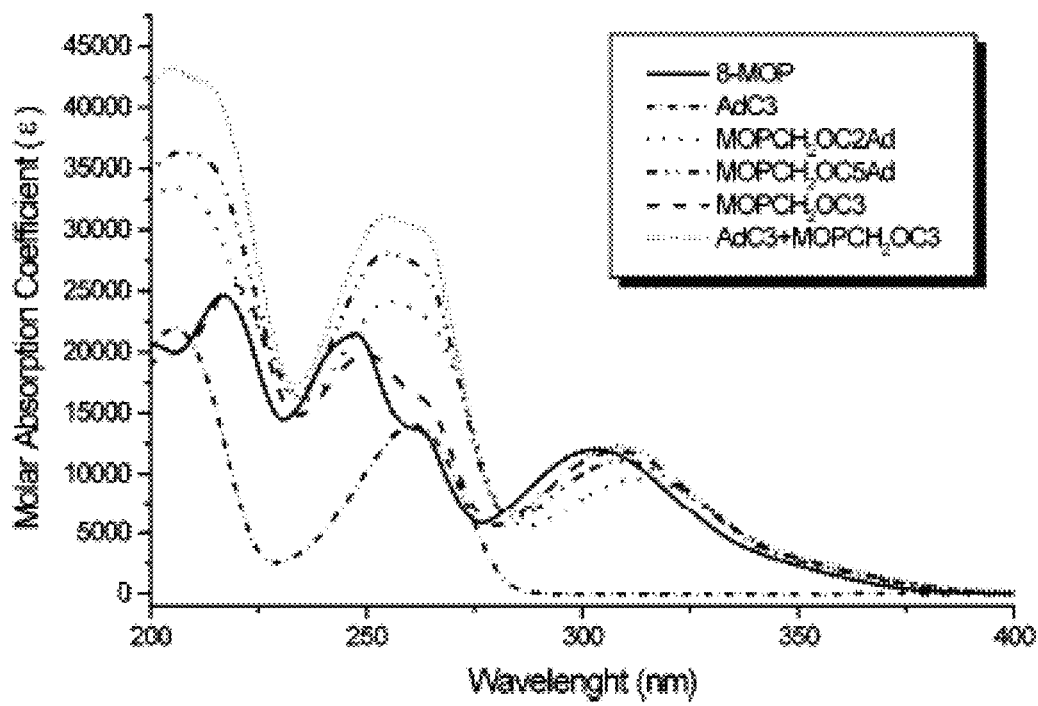
FIG. 62 is a plot of specific absorption bands of psoralen.

Shown in FIG. 62 are specific absorption bands of psoralen (occluding the expected emission) could be used in one embodiment of the invention as a visual monitor of the presence of psoralen in the tumor. Accordingly, in one embodiment of the invention, the sources of radiation shown in FIGS. 3, 4, 5A, and 5B comprise a source of diagnostic radiation analyzing the tumor.

Area Array Electrodes

Pulsing

In one embodiment of the invention, an X-Ray system has the capability of pulsing the X-Ray output through the control of the source for obtaining high pulse rates. The high pulse rate in this case would refer to pulsing frequencies in the range of GHz, MHz, KHz and below. These in turn correspond to pulse widths of nano-seconds, micro-seconds, milli-seconds, and down to $\frac{1}{10}$ of a second.

Many conventional X-Ray sources utilize electron beam generation through a filament based technology; however, those X-Ray sources may be inherently limited to slow pulse rates (and limited operational life time). On the other hand, X-Ray sources may generate electron emission and beams through the excitation of point sources, points of electron emissions, attached to an electrode or to multiple electrodes. As discussed above, carbon nanotubes, amorphic diamond, low work function materials, or photo-induced emission can be used for such sources. X-Ray systems based on these materials and/or based on point sources of electron emission can lead to high pulse rate.

Field Emission

Figure 69:
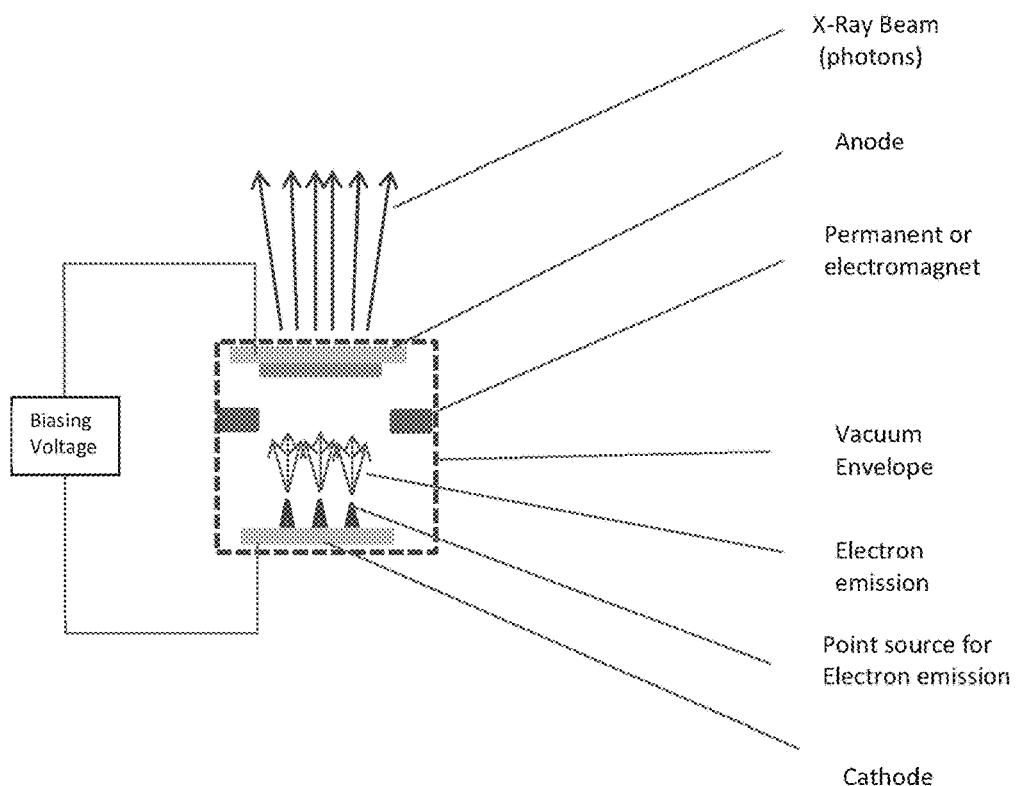
FIG. 69 is a schematic depicting an X-Ray source based on a single electrode configuration and capable of high pulse rate.

FIG. 69 is a schematic depicting an X-Ray source based on a single electrode configuration and capable of high pulse rate. The field emission portion of the x-ray device has an electrode and various point sources enabling electronic mission. The point sources have to be in electrical continuity with the electrode. The point sources preferably possess high current carrying capability. Another component is an anode upon which a voltage bias is applied. Another component is a vacuum envelope so that the electrons emitted are accelerated through a voltage gradient field (i.e. an electric field) without impinging on air atoms and other gaseous element that would break their acceleration. Another component is the target that the electron beam would impinge upon to create x-rays. Another component is a magnetic field device (either a permanent magnet or an electro-magnet) which collimates the electron beam toward the target.

Figure 70:
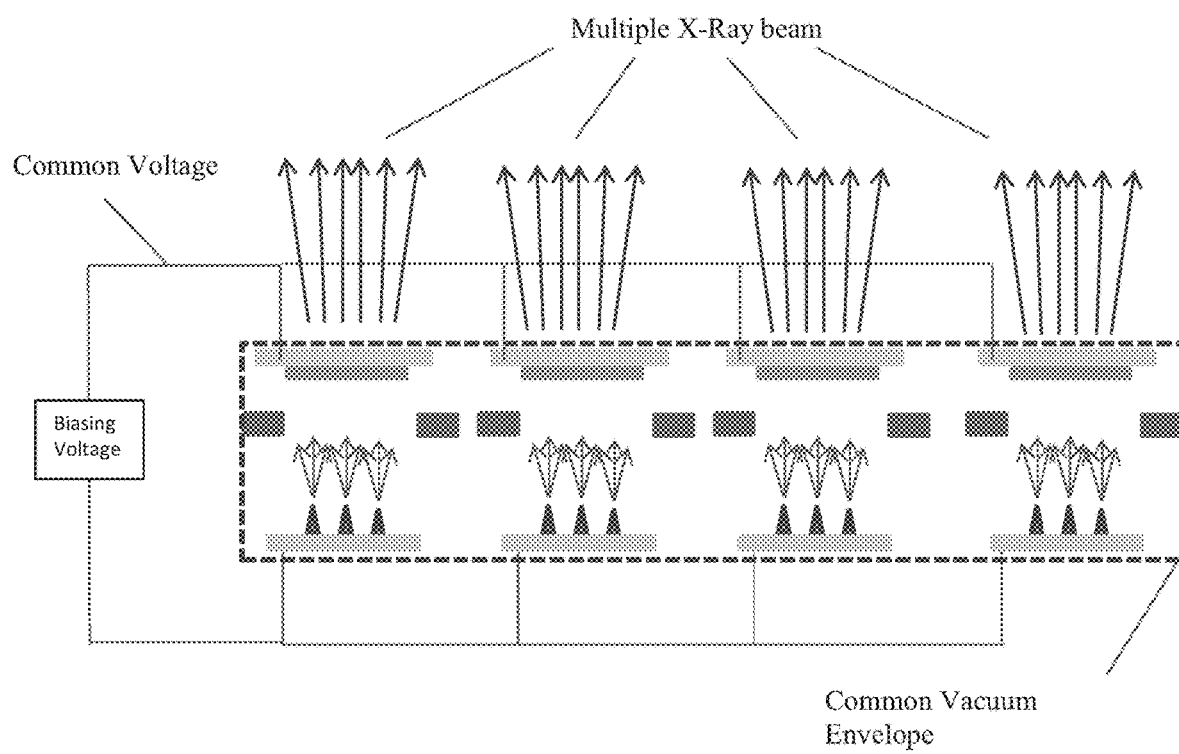
FIG. 70 is a schematic illustration of an X-Ray source based on a multiple electrode configuration and capable of high pulse rate.

X-Ray System with Multiple Electrodes:

FIG. 70 is a schematic illustration of an X-Ray source based on a multiple electrode configuration and capable of high pulse rate. From an economy of scale, it is preferable to have a common vacuum envelope that hosts the x-ray generation devices. Such X-Ray systems possessing at least two electrodes can be pulsed by gating the voltage between the electrode and the anode. High pulse rates can be achieved depending on the power supply. The power supply can interface with multiple electrodes to energize and pulse the electron emission across multiple electrodes at once. The voltage from the power supply can be applied to a single electrode at a time or to a multitude of electrodes at time; and, in some preferred cases, the voltage can be applied in a controllable manner to a single electrode at a time in a sequential manner across the available electrodes.

In one embodiment of the invention, multiple electrodes and multiple anodes and multiple targets are placed under a common envelope and a common voltage. In one embodiment, a small number of paired electrode anode and targets are placed under the manifold of a vacuum envelope. For illustration purposes four such electrodes are enclosed inside the vacuum envelope shown in FIG. 70.

X-Ray System with Multiple Vacuum Envelops

Figure 71:
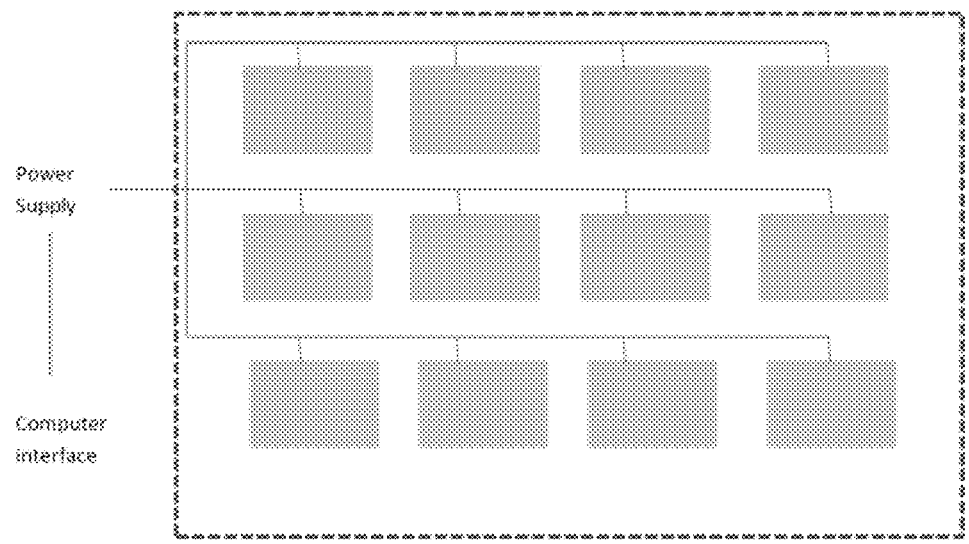
FIG. 71 is a schematic showing a top view of a common vacuum envelope with an array of electrodes.

FIG. 71. is a schematic showing a top view of a common vacuum envelope with an array of electrodes. In the case of multiple electrodes per envelope, the controllable sequence for energizing multiple electrodes in this case is designed to suite the need of the intended application. In other words, a programmable software interface can control the array of available electrodes and turn the electrodes one a time in a well-defined series. The order by which a partial number of electrodes (out of the entire number of available electrodes) are sequentially activated can be different and various permutations and combinations become possible through the control interface.

The array of electrodes can be present in a large area coverage leading to maximized flexibility in delivering X-Ray energy. This can be done by having a large vacuum envelope with multiple electrodes in a array configuration as illustrated through FIG. 71.

Figure 72:
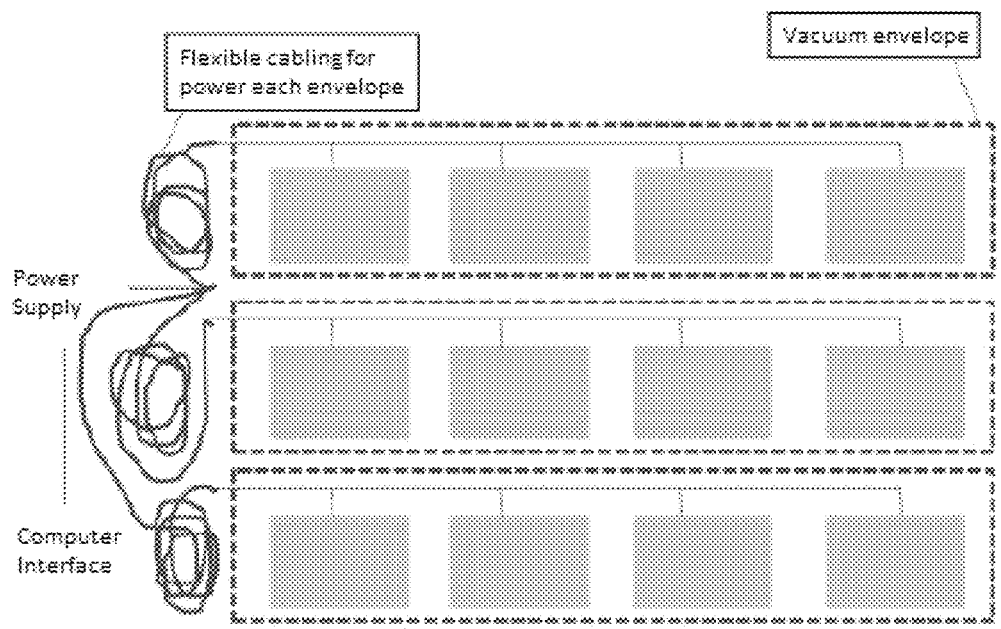
FIG. 72 is a schematic illustrating an array like configuration achieved through multiple vacuum envelopes.

Alternatively, multiple vacuum envelopes each containing multiple electrodes can be developed to lead to area array coverage. The advantage of having multiple envelopes is that the field servicing of such systems could be easier. A set of electrodes that have gone defective can be replaced without having to discard the entire array. Rather, the specific vacuum envelope containing the defective electrodes can be replaced. FIG. 72 is a schematic illustrating an array like configuration achieved through multiple vacuum envelopes. The multiple vacuum envelopes each contain multiple electrodes to permit a large area array coverage of X-Ray. In one embodiment, flexible cabling leads permits positioning the vacuum envelopes apart.

Figure 73:
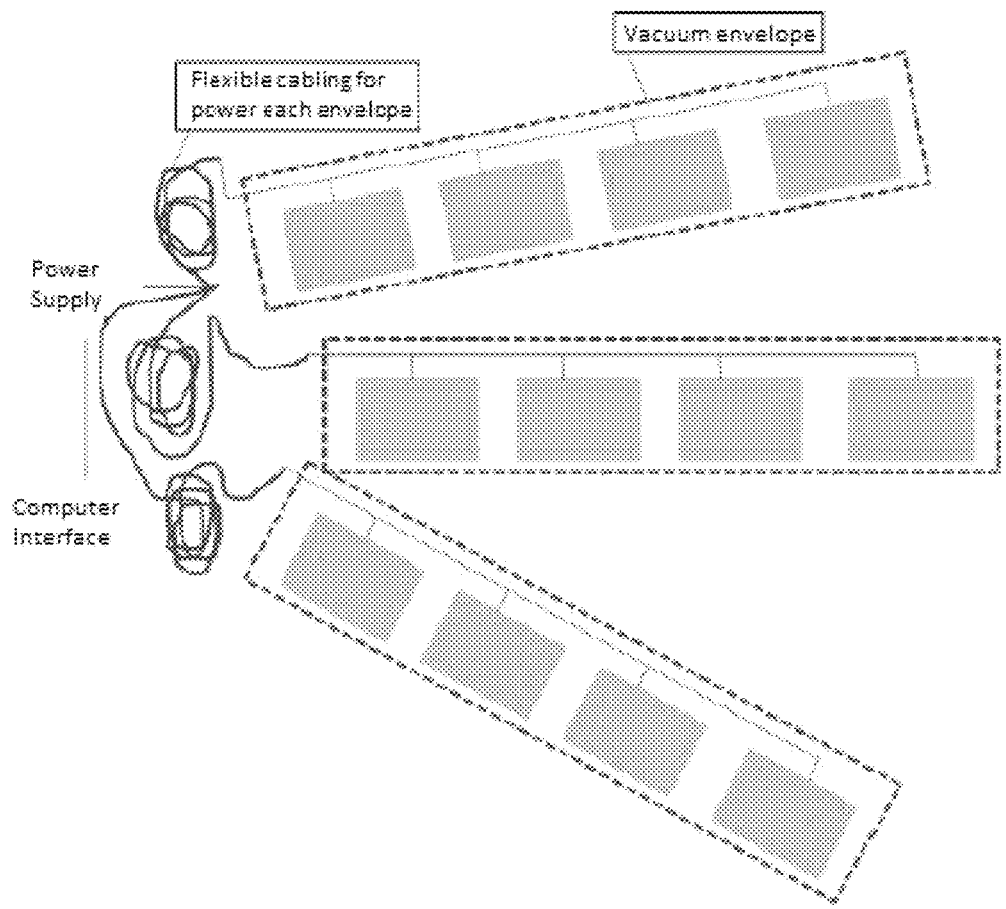
FIG. 73 is a schematic illustrating a top view of multiple vacuum envelopes, each containing multiple electrodes to permit a large area array coverage of X-Ray.

FIG. 73 is a schematic illustrating a top view of multiple vacuum envelopes, each containing multiple electrodes to permit a large area array coverage of X-Ray and having flexible cabling leads to adjust the positioning of the vacuum envelopes apart to process a particular material geometry.

Figure 74:
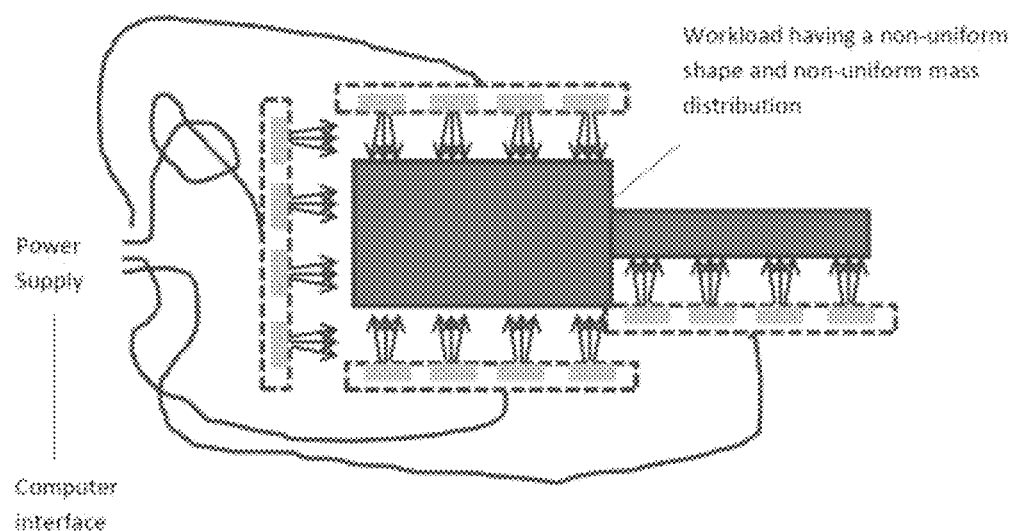
FIG. 74 is a schematic showing multiple vacuum envelope containing X-Ray generating electrodes positioned in a flexible configuration around a complex shaped workload or work piece.

X-Ray System for Complex Geometry Workloads:

The array of electrodes can be positioned around a workload in a configuration that is best suitable for imparting energy to the material to be processed such as illustrated in FIG. 74. FIG. 74 is a schematic showing multiple vacuum envelope containing X-Ray generating electrodes positioned in a flexible configuration around a complex shaped workload or work piece.

This figure illustrates that multiple sources can be complementary in the area of the workload or that multiple sources may not need too much energy and can be redundant and supplementary in the area where more X-Ray is needed.

The smaller vacuum envelopes would be powered through a common power supply and the leads that would be used to apply voltage to each of the vacuum envelopes are made flexible. In such a case all four electrodes with flexible electrical cables reside inside a lead chamber for containing the x-rays. The number of vacuum envelopes can be configured according to the workload topology i.e. shape thickness and volume.

This figure illustrates the configurable x-ray system that adapts the delivery of photonic energy accordingly to the need of the workload. Furthermore, different workloads may require a different configuration of the various vacuum envelopes each containing a number of electrodes. Each electrode within a given vacuum envelope is independently controlled. As such, the sequence of photonic energy delivery is greatly flexible and modulated through a software interface that allows the operator to deliver the right amount of energy to the specific portion of the workload.

Figure 75:
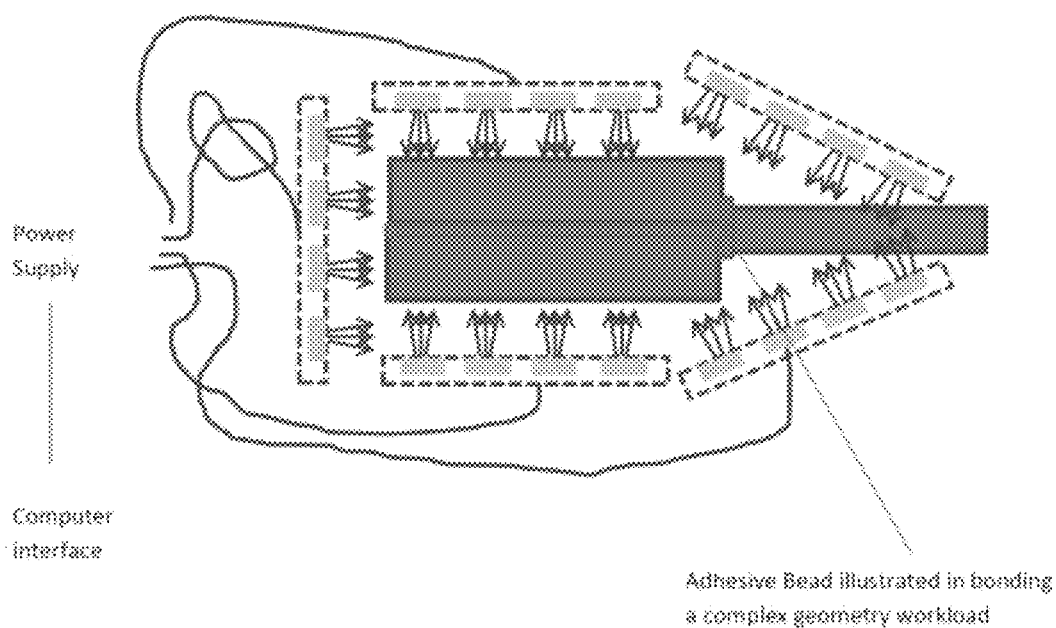
FIG. 75 is a schematic depicting a multiple vacuum envelope construction containing X-Ray generating electrodes positioned in a flexible configuration around a complex shaped workload.

For further illustration, FIG. 75 is a schematic depicting a multiple vacuum envelope construction containing X-Ray generating electrodes positioned in a flexible configuration around a complex shaped workload to cure an adhesive bead disposed at the interface of various sub-parts. In particular, five vacuum envelopes each containing four electrodes are shown disposed around the sample to be processed for x-ray exposure to activate an adhesive for example.

Figure 76:
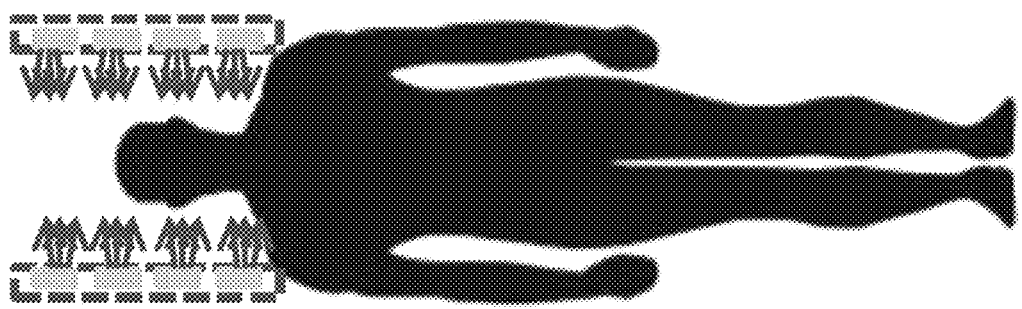
FIG. 76 is a schematic depicting a multiple vacuum envelope construction containing X-Ray generating electrodes positioned in a flexible configuration around the head of a patient.

FIG. 76 is a schematic depicting a multiple vacuum envelope construction containing X-Ray generating electrodes positioned in a flexible configuration around the head of a patient being treated for Glioblastoma (GBM) (as an example) having been injected with a phosphorous material emitting UV light under X-Ray. In this embodiment, a phosphor (introduced to the patient) would be capable of activating a bio-therapeutic agent such as Psoralen delivered to a tumor area.

Figure 77:
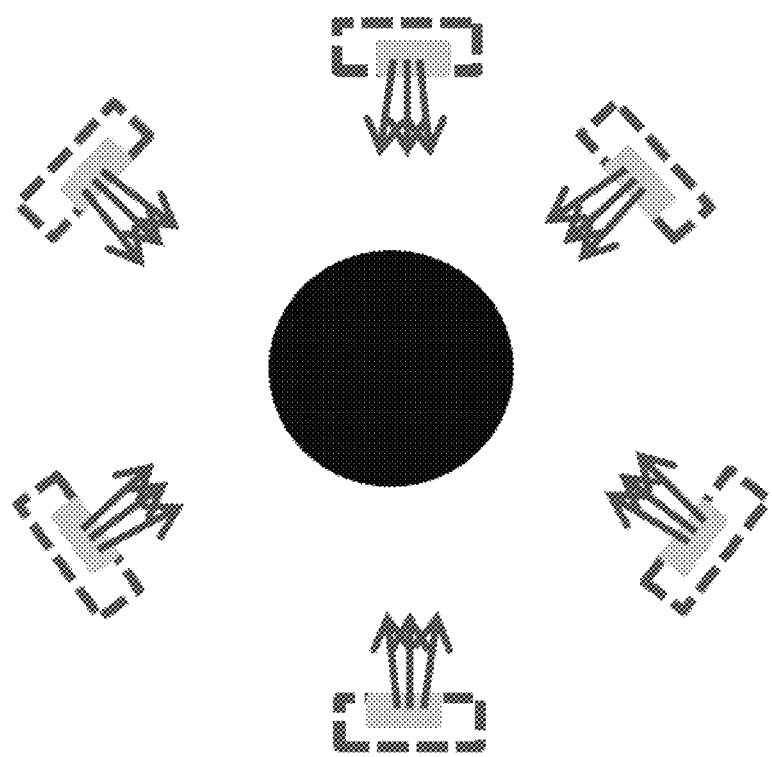
FIG. 77 is a schematic depicting a multiple vacuum envelope construction containing X-Ray generating electrodes positioned in a pentagonal, hexagonal or octagonal configuration around the head of a patient.

FIG. 77 is a schematic depicting a multiple vacuum envelope construction containing X-Ray generating electrodes positioned in a pentagonal, hexagonal or octagonal configuration around the head of a patient being treated for GBM (as an example) having been injected with a phosphorous material emitting UV light under X-Ray, whereby, the phosphor is capable of activating a bio-therapeutic agent such as Psoralen delivered to the tumor area. Each X-Ray vacuum envelope can be activated a time independently or in conjunction with other ones. Indeed, one or more X-Ray electrodes can be activated at a time to deliver a prescribed regiment of X-Ray energy suitable for activating the phosphor which in turn activates the bio-therapeutic agent.

Time Resolve Measurements

Figure 78:
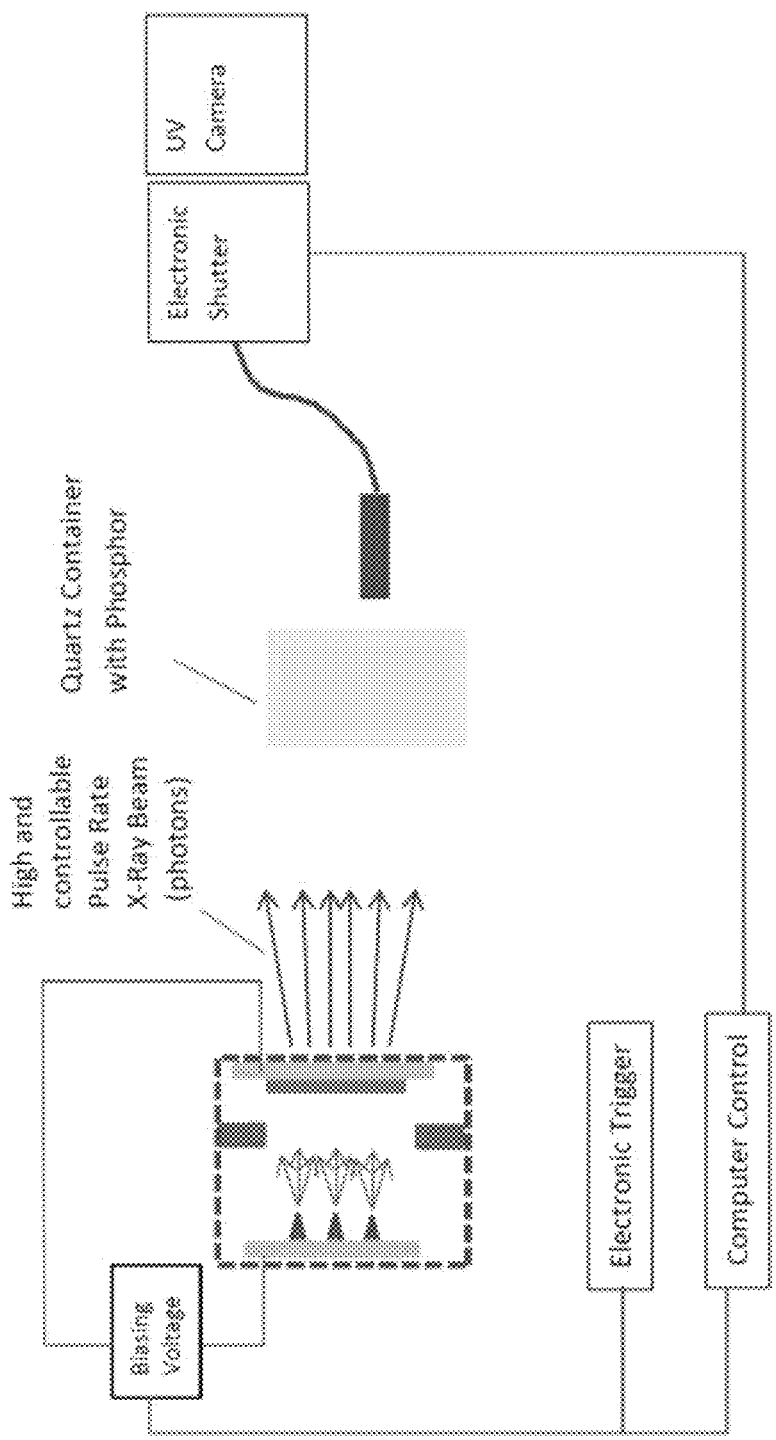
FIG. 78 is a schematic illustrating an X-Ray apparatus for life time measurements of excited energy states triggered by controlled X-Ray pulsing.

FIG. 78 is a schematic illustrating an X-Ray apparatus for life time measurements of excited energy states triggered by controlled X-Ray pulsing and measured in the UV and the visible range using a photodetector having a controlled electronic shuttering system for resolving the measurements. The UV light emitted can be revealing about the nature of a processes during the electron hole pair generation that takes place under X-Ray absorption and/or exposure. A manifold of excited states can be created.

Excited states and life time measurement are commonly done under UV energy using a LASER or an Arc lamp to excite a phosphor and then to measure the half life of these excited states using a UV or visible camera. Heretofore, no such apparatus exists for X-Ray induced phosphor emission analysis.

This apparatus of FIG. 78 has the capability to control the voltage applied to the electrode to generate an X-Ray beam. This controlled pulsing of the X-Ray energy is synchronized with the measurements of the UV emissions in such a way that time resolve measurements of excited lifetimes becomes possible.

At this point, time resolved measurements of the above-noted NP200 and GTP 4300 phosphors were measured under the excitation of an e-beam in the case of cathode-luminescence and under a time resolve set up. The measurements under the cathode-luminescence as illustrated in FIGS. 79 and 80 for both these phosphors. FIG. 79 is a plot of cathode luminescence for phosphor NP200. FIG. 80 is a plot of cathode luminescence for phosphor GTP 4300.

Figure 81:
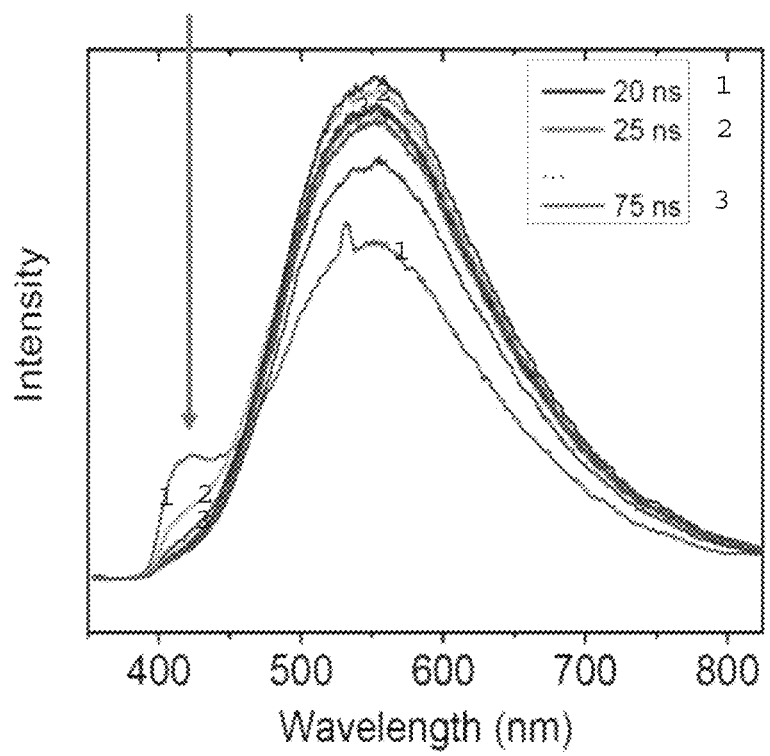

FIG. 81 is a transient PL Spectra-GTP 4300 using a 365 nm LASER as an excitation source. It shows a short lived peak at 420 nm which disappears in ~40 ns. This result illustrates the presence and rapid decay of rapidly excited and decaying peaks. FIG. 82 shows that after ~40 μs, the broad peak starts to turn into two sharper peaks at 480 and 585 nm.

FIG. 83 shows transient PL spectra for phosphor NP200. In the case of NP 200, from 5-30 μs, a rapidly decaying transition is observable (shoulder, emission at λ>600 nm). Strongest emission at 530 nm decays much more slowly. These features cannot be identified until such a time that time resolve measurements are performed.

In one embodiment of the invention, X-Ray pulsing with camera detection in a rapid and synchronized manner will permit a better understanding of the emitted wavelengths generated inside a patient or workpiece whereby phosphors can be better designed for activation of a photoactivatable agent inside a medium or a drug photoactivatable agent inside a patient.

Moreover, the spectral emission of light from the near surface of the object or patient being treated may serve as a diagnostic tool indicating the light was generated internally in the patient or object to be treated. As noted above, specific absorption bands of psoralen (occluding the expected emission) could be used in one embodiment of the invention as a visual monitor of the presence of psoralen in the tumor.

Numerous modifications and variations of the invention are possible in light of the above teachings. It is therefore to be understood that within the scope of the appended claims, the invention may be practiced otherwise than as specifically described herein. All of the publications, references, patents, patent applications, and other documents identified above are incorporated by reference herein in their entirety.

The invention claimed is:

1. A method for imaging and treating a disease in a human or animal body, comprising:
   infusing a diseased site with a photoactivatable drug and a pharmaceutical carrier including one or more phosphors which are capable of emitting ultraviolet or visible light into the body and which provide x-ray contrast;
   irradiating the diseased site with at least one of x-rays, gamma rays, or electrons to thereby initiate emission of said ultraviolet or visible light into the body; and
   producing images of the diseased site and controlling a dose of said x-rays, gamma rays, or electrons to the diseased site for production of said ultraviolet or visible light at the diseased site thus activating the photoactivatable drug.

2. The method of claim 1, wherein irradiating comprises irradiating with x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

3. The method of claim 1, wherein the phosphors comprise:
   a first plurality of energy-converting particles in the medium which, upon radiation from the x-ray source, radiate at a first energy lower than the x-ray source; and
   a second plurality of energy-converting particles which, upon radiation from the x-ray source, radiate at a second energy lower than the x-ray source.

4. The method of claim 3, wherein
   a combination of the first and second plurality of energy-converting particles comprises a weighted composition, and emission from the weighted composition activates the photoactivatable drug.

5. The method of claim 4, wherein emission overlaps an absorption spectrum of the photoactivatable drug.

6. The method of claim 1, wherein infusing comprises injecting the phosphors nearby the diseased site for illumination of the photoactivatable drug to treat the diseased site.

7. The method of claim 6, wherein the phosphors injected nearby the diseased site comprise a mixture of micron-size and nanometer-size particles.

8. The method of claim 1, further comprising:
   externally applying an electric field or a magnetic field distribution which concentrates the phosphors at the diseased site.

9. The method of claim 1, wherein the irradiating comprises irradiating with an x-ray or high energy electron source utilizing carbon nanotubes as a source of electrons.

10. The method of claim 1, further comprising assembling said images of the diseased site into tomographic views of the diseased site.

11. The method of claim 10, wherein assembling comprises assembling images of a tumor or a malignancy.

12. The method of claim 1, wherein the phosphors comprise at least one of:
   phosphor particles;
   ionic doped phosphor particles;
   single crystal or poly-crystalline powders;
   single crystal or poly-crystalline monoliths;
   scintillator particles;
   a metallic shell encapsulating at least a fraction of a surface of the phosphors;
   a semiconductor shell encapsulating at least a fraction of a surface of the phosphors; and
   an insulator shell encapsulating at least a fraction of a surface of the phosphors; and
   phosphors of a distributed particle size.

13. The method of claim 12, wherein the metallic shell comprises a plasmonic shell configured to enhance at least one of said absorption or said emission.

14. The method of claim 1, wherein the phosphors comprise particles having a dielectric core.

15. The method of claim 14, wherein the phosphors comprise a metallic shell at least partially covering said dielectric core and comprises at least one of Au, Ag, Cu, Ni, Pt, Pd, Co, Ru, Rh, or a combination thereof.

16. The method of claim 1, wherein the phosphors comprise at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn, $Er^{3+}$; $CaWO_4$, $YaTO_4$, $YaTO_4$:Nb, $BaSO_4$:Eu, $La_2O_2S$:Tb, $BaSi_2O_5$:Pb, NaI(Tl), CsI(Tl), CsI(Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), BGO bismuth germanate, GSO gadolinium oxyorthosilicate, LSO lutetium oxyorthosilicate, $LaCl_3$(Ce), $LaBr_3$(Ce), $LaPO_4$; Ce, Tb (doped), and $Zn_2SiO_4$:Mn with Mn doped between 0.05-10%.

17. The method of claim 1, wherein the phosphors comprise at least one of down conversion or up conversion media, and combinations and agglomerations thereof with or without plasmonic agents.

18. The method of claim 1, wherein infusing comprises administering the photoactivatable drug in accordance with a volume of the diseased site.

19. The method of claim 18, wherein
an amount of the phosphors in the pharmaceutical carrier ranges from 0.1 to 0.66 milligrams of phosphor per cm$^3$ of the volume of the diseased site, and
a concentration of the photoactivatable drug in the pharmaceutical carrier ranges from 10 μg/mL to 50 μg/mL.

20. The method of claim 1, wherein the photoactivatable drug comprises a psoralen compound mixed with the phosphors.

21. The method of claim 1, wherein the photoactivatable drug is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

22. The method of claim 1, wherein the photoactivatable drug comprises a psoralen, a coumarin, a porphyrin or a derivative thereof.

23. The method of claim 1, wherein the photoactivatable drug comprises s 8-MOP, TMP, or AMT.

24. The method of claim 1, wherein the photoactivatable drug comprises one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

25. The method of claim 1, wherein the photoactivatable drug is coupled to a carrier that is capable of binding to a receptor at the diseased site.

26. The method of claim 25, wherein the carrier is one selected from insulin, interleukin, thymopoietin or transferrin.

27. The method of claim 25, wherein the receptor is one selected from nucleic acids of nucleated cells, antigenic sites on nucleated cells, or epitopes.

28. The method of claim 1, wherein the photoactivatable drug has an affinity for a tumor at the diseased site.

29. The system of claim 28, wherein the photoactivatable drug is capable of being absorbed by a tumor at the diseased site.

30. The method of claim 29, wherein the photoactivatable drug is a DNA intercalator or a halogenated derivative thereof.

31. The method of claim 1, wherein irradiating comprises delivering a controlled radiation dose to the phosphors for activation of the photoactivatable drug.

32. The method of claim 31, wherein the controlled radiation dose causes an auto-vaccine effect in the human or animal body.

33. The method of claim 1, further comprising controlling the x-ray or high energy source during a booster treatment repeated on a periodic basis after an initial treatment of the diseased site.

34. The method of claim 33, wherein, in the booster treatment, at least one of phosphor concentration, photoactivatable drug concentration, and the radiation dose is increased by a factor of at least two times, five times, or ten times respective initial values.

35. The method of claim 33, wherein the booster treatment produces psoralen-modified cancer cells or X-ray modified cancer cells.

36. The method of claim 33, wherein the booster treatment produces radiation damaged cancer cells.

37. The method of claim 33, wherein a period between booster treatments is delayed according to a tolerance level of the human or animal body for radiation-modified cells generated during the booster treatment.

38. The method of claim 37, wherein the period between booster treatments is delayed such that no tolerance is developed for the radiation-modified cells.

39. The method of claim 1, further comprising at least one of:
simultaneously providing 1) a controlled radiation dose for activation of the photoactivatable drug and 2) an image-forming beam; or
rotationally directing the controlled radiation dose about a rotational axis to minimize radiation loading at a surface of the human or animal body.

40. The method of claim 1, further comprising:
infusing up-conversion phosphors into the diseased site, and
irradiating the diseased site with infrared radiation to produce from the up-conversion phosphors at least one of visible or ultraviolet light.

41. The method of claim 1, further comprising irradiating the diseased site with at least one of visible light, infrared light, or microwave radiation.

42. The method of claim 41, wherein said irradiating with the visible light, infrared light, or microwave radiation mediates, initiates or enhances treatment of the diseased site or provides diagnostic radiation for analysis the diseased site.

43. The method of claim 1, wherein irradiating comprises directing radiation to at least one of a tumor or a malignancy.

44. The method of claim 1, wherein irradiating comprises directing radiation to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

45. The method of claim 1, wherein irradiating comprises directing radiation to the diseased site in a pulsed manner having an on and off time.

46. The method of claim 45, wherein irradiating comprises directing said radiation to a tumor or a malignancy in a pulsed manner having an on and off time.

47. The method of claim 46, wherein irradiating comprises directing said radiation to the diseased site such that the on time activates the phosphor and the off time is long enough for decay of phosphor light emission.

48. The method of claim 1, wherein irradiating comprises directing said radiation to the diseased site according to a predetermined radiation protocol such that a predetermined change occurs in the diseased site.

49. The method of claim 48, wherein
said predetermined change at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

50. The method of claim 1, further comprising controlling the penetrating radiation during a booster treatment repeated on a periodic basis after an initial treatment of the diseased site.

51. The method of claim 50, wherein, in the booster treatment, at least one of phosphor concentration, photoactivatable drug concentration, and the radiation dose is increased by a factor of at least two times, five times, or ten times respective initial values.

52. The method of claim 50, wherein the booster treatment produces psoralen-modified cancer cells or X-ray modified cancer cells.

53. The method of claim 50, wherein the booster treatment produces radiation damaged cancer cells.

54. The method of claim 50, wherein a period between booster treatments is delayed according to a tolerance level of the human or animal body for radiation-modified cells generated during the booster treatment.

55. The method of claim 54, wherein the period between booster treatments is delayed such that no tolerance is developed for the radiation-modified cells.

56. A method for at least one of imaging and treating a disease in a human or animal body, comprising:
  infusing a diseased site with a photoactivatable drug and a pharmaceutical carrier including one or more phosphors which are capable of emitting ultraviolet or visible light into the body and which provide x-ray contrast wherein infusing comprises injecting the phosphors nearby the diseased site for illumination of the photoactivatable drug to treat the diseased site; wherein the phosphors comprise a mixture of micron-size and nanometer-size particles;
  irradiating the diseased site with at least one of x-rays, gamma rays, or electrons to thereby initiate emission of said ultraviolet or visible light into the body; and
  producing images of the diseased site and controlling a dose of said x-rays, gamma rays, or electrons to the diseased site for production of said ultraviolet or visible light at the diseased site to activate the photoactivatable drug.

57. The method of claim 56, wherein irradiating comprises irradiating with x-rays from a peak applied cathode voltage at or below 300 kVp, at or below 200 kVp, at or below 120 kVp, at or below 105 kVp, at or below 80 kVp, at or below 70 kVp, at or below 60 kVp, at or below 50 kVp, at or below 40 kVp, at or below 30 kVp, at or below 20 kVp, at or below 10 kVp, or at or below 5 kVp.

58. The method of claim 56, wherein the phosphors comprise:
  a first plurality of energy-converting particles in the medium which, upon radiation from the x-ray source, radiate at a first energy lower than the x-ray source; and
  a second plurality of energy-converting particles which, upon radiation from the x-ray source, radiate at a second energy lower than the x-ray source.

59. The method of claim 58, wherein
  a combination of the first and second plurality of energy-converting particles comprises a weighted composition, and
  emission from the weighted composition activates the photoactivatable drug.

60. The method of claim 59, wherein emission overlaps an absorption spectrum of the photoactivatable drug.

61. The method of claim 56, further comprising:
  externally applying an electric field or a magnetic field distribution which concentrates the phosphors at the diseased site.

62. The method of claim 56, wherein the irradiating comprises irradiating with an x-ray or high energy electron source utilizing carbon nanotubes as a source of electrons.

63. The method of claim 56, further comprising assembling said images of the diseased site into tomographic views of the diseased site.

64. The method of claim 63, wherein assembling comprises assembling images of a tumor or a malignancy.

65. The method of claim 56, wherein the phosphors comprise at least one of:
  phosphor particles;
  ionic doped phosphor particles;
  single crystal or poly-crystalline powders;
  single crystal or poly-crystalline monoliths;
  scintillator particles;
  a metallic shell encapsulating at least a fraction of a surface of the phosphors;
  a semiconductor shell encapsulating at least a fraction of a surface of the phosphors; and
  an insulator shell encapsulating at least a fraction of a surface of the phosphors; and
  phosphors of a distributed particle size.

66. The method of claim 65, wherein the metallic shell comprises a plasmonic shell configured to enhance at least one of said absorption or said emission.

67. The method of claim 56, wherein the phosphors comprise particles having a dielectric core.

68. The method of claim 67, wherein the phosphors comprise a metallic shell at least partially covering said dielectric core and comprises at least one of Au, Ag, Cu, Ni, Pt, Pd, Co, Ru, Rh, or a combination thereof.

69. The method of claim 56, wherein the phosphors comprise at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, Er3+; ZnS:$Mn^{2+}$; ZnS:Mn,$Er^{3+}$; $CaWO_4$, $YaTO_4$, $YaTO_4$:Nb, $BaSO_4$:Eu, $La_2O_2S$:Tb, $BaSi_2O_5$:Pb, NaI(Tl), CsI(Tl), CsI(Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), BGO bismuth germanate, GSO gadolinium oxyorthosilicate, LSO lutetium oxyorthosilicate, $LaCl_3$(Ce), $LaBr_3$(Ce), $LaPO_4$; Ce, Tb (doped), and $Zn_2SiO_4$:Mn with Mn doped between 0.05-10%.

70. The method of claim 56, wherein the phosphors comprise at least one of down conversion or up conversion media, and combinations and agglomerations thereof with or without plasmonic agents.

71. The method of claim 56, wherein infusing comprises administering the photoactivatable drug in accordance with a volume of the diseased site.

72. The method of claim 71, wherein
  an amount of the phosphors in the pharmaceutical carrier ranges from 0.1 to 0.66 milligrams of phosphor per $cm^3$ of the volume of the diseased site, and
  a concentration of the photoactivatable drug in the pharmaceutical carrier ranges from 10 µg/mL to 50 µg/mL.

73. The method of claim 56, wherein the photoactivatable drug comprises a psoralen compound mixed with the phosphors.

74. The method of claim 56, wherein the photoactivatable drug is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

75. The method of claim 56, wherein the photoactivatable drug comprises a psoralen, a coumarin, a porphyrin or a derivative thereof.

76. The method of claim 56, wherein the photoactivatable drug comprises s 8-MOP, TMP, or AMT.

77. The method of claim 56, wherein the photoactivatable drug comprises one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

78. The method of claim 56, wherein the photoactivatable drug is coupled to a carrier that is capable of binding to a receptor at the diseased site.

79. The method of claim 78, wherein the carrier is one selected from insulin, interleukin, thymopoietin or transferrin.

80. The method of claim 78, wherein the receptor is one selected from nucleic acids of nucleated cells, antigenic sites on nucleated cells, or epitopes.

81. The method of claim 56, wherein the photoactivatable drug has an affinity for a tumor at the diseased site.

82. The system of claim 81, wherein the photoactivatable drug is capable of being absorbed by a tumor at the diseased site.

83. The method of claim 82, wherein the photoactivatable drug is a DNA intercalator or a halogenated derivative thereof.

84. The method of claim 56, wherein irradiating comprises delivering a controlled radiation dose to the phosphors for activation of the photoactivatable drug.

85. The method of claim 84, wherein the controlled radiation dose causes an auto-vaccine effect in the human or animal body.

86. The method of claim 56, further comprising controlling the x-ray or high energy source during a booster treatment repeated on a periodic basis after an initial treatment of the diseased site.

87. The method of claim 86, wherein, in the booster treatment, at least one of phosphor concentration, photoactivatable drug concentration, and the radiation dose is increased by a factor of at least two times, five times, or ten times respective initial values.

88. The method of claim 86, wherein the booster treatment produces psoralen-modified cancer cells or X-ray modified cancer cells.

89. The method of claim 86, wherein the booster treatment produces radiation damaged cancer cells.

90. The method of claim 86, wherein a period between booster treatments is delayed according to a tolerance level of the human or animal body for radiation-modified cells generated during the booster treatment.

91. The method of claim 90, wherein the period between booster treatments is delayed such that no tolerance is developed for the radiation-modified cells.

92. The method of claim 56, further comprising at least one of:
simultaneously providing 1) a controlled radiation dose for activation of the photoactivatable drug and 2) an image-forming beam; or
rotationally directing the controlled radiation dose about a rotational axis to minimize radiation loading at a surface of the human or animal body.

93. The method of claim 56, further comprising:
infusing up-conversion phosphors into the diseased site, and
irradiating the diseased site with infrared radiation to produce from the up-conversion phosphors at least one of visible or ultraviolet light.

94. The method of claim 56, further comprising irradiating the diseased site with at least one of visible light, infrared light, or microwave radiation.

95. The method of claim 94, wherein said irradiating with the visible light, infrared light, or microwave radiation mediates, initiates or enhances treatment of the diseased site or provides diagnostic radiation for analysis the diseased site.

96. The method of claim 56, wherein irradiating comprises directing radiation to at least one of a tumor or a malignancy.

97. The method of claim 56, wherein irradiating comprises directing radiation to at least one of a eukaryotic cell, a prokaryotic cell, a subcellular structure, an extracellular structure, a virus or prion, a cellular tissue, a cell membrane, a nuclear membrane, cell nucleus, nucleic acid, mitochondria, ribosome, or other cellular organelle.

98. The method of claim 56, wherein irradiating comprises directing radiation to the diseased site in a pulsed manner having an on and off time.

99. The method of claim 98, wherein irradiating comprises directing said radiation to a tumor or a malignancy in a pulsed manner having an on and off time.

100. The method of claim 99, wherein irradiating comprises directing said radiation to the diseased site such that the on time activates the phosphor and the off time is long enough for decay of phosphor light emission.

101. The method of claim 56, wherein irradiating comprises directing said radiation to the diseased site according to a predetermined radiation protocol such that a predetermined change occurs in the diseased site.

102. The method of claim 101, wherein
said predetermined change at least one of 1) affects a prion, viral, bacterial, fungal, or parasitic infection, 2) comprises at least one of one of tissue regeneration, inflammation relief, pain relief, immune system fortification, or 3) comprises at least changes in cell membrane permeability, up-regulation and down-regulation of adenosine triphosphate and nitric oxide.

103. The method of claim 56, further comprising controlling the penetrating radiation during a booster treatment repeated on a periodic basis after an initial treatment of the diseased site.

104. The method of claim 103, wherein, in the booster treatment, at least one of phosphor concentration, photoactivatable drug concentration, and the radiation dose is increased by a factor of at least two times, five times, or ten times respective initial values.

105. The method of claim 103, wherein the booster treatment produces psoralen-modified cancer cells or X-ray modified cancer cells.

106. The method of claim 103, wherein the booster treatment produces radiation damaged cancer cells.

107. The method of claim 103, wherein a period between booster treatments is delayed according to a tolerance level of the human or animal body for radiation-modified cells generated during the booster treatment.

108. The method of claim 107, wherein the period between booster treatments is delayed such that no tolerance is developed for the radiation-modified cells.

* * * * *

UNITED STATES PATENT AND TRADEMARK OFFICE
CERTIFICATE OF CORRECTION

| | |
|---|---|
| PATENT NO. | : 10,596,387 B2 |
| APPLICATION NO. | : 15/307766 |
| DATED | : March 24, 2020 |
| INVENTOR(S) | : Harold Walder et al. |

It is certified that error appears in the above-identified patent and that said Letters Patent is hereby corrected as shown below:

On the Title Page

On page 2, in Column 2, item (56), Other Publications, Line 1, ""Opical fiber" should read --"Optical Fiber--

In the Specification

Column 3, Line 49, "Er3+;" should read --$Er^{3+}$;--

Column 4, Line 57, "Tm3+" should read --$Tm^{3+}$--

Column 5, Line 7, "BaSO4:" should read --$BaSO_4$:--

Column 6, Line 2, "CaWO4" should read --$CaWO_4$--

Column 7, Line 36, "(PO4)2·" should read --$(PO_4)_2$·--

Column 14, Line 18, "phtoactivatable" should read --photoactivatable--

Column 14, Line 23, "particles" should read --particles.--

Column 14, Line 62, "phtoactivatable" should read --photoactivatable--

Column 20, Line 46, "YTaO4," should read --$YTaO_4$,--

Column 22, table 6, Line 11 (approx.), "Hexgonal" should read --Hexagonal--

Column 22, table 6, Line 12 (approx.), "Hexgonal" should read --Hexagonal--

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

Column 22, table 6, Line 13 (approx.), "Hexgonal" should read --Hexagonal--

Column 22, table 6, Line 14 (approx.), "Hexgonal" should read --Hexagonal--

Column 22, table 6, Line 15 (approx.), "Hexgonal" should read --Hexagonal--

Column 25, Line 2, "Tm$_3$+" should read --Tm$^{3+}$--

Column 25, Line 30, "LaF3:" should read --LaF$_3$:--

Column 25, Line 33, "Tm$_3$+" should read --Tm$^{3+}$--

Column 25, Line 36, "CaWO4" should read --CaWO$_4$--

Column 27-28, table 7-continued, Line 11 (approx.), "Hexgonal" should read --Hexagonal--

Column 27-28, table 7-continued, Line 14 (approx.), "Hexgonal" should read --Hexagonal--

Column 27-28, table 7-continued, Line 17 (approx.), "Hexgonal" should read --Hexagonal--

Column 27-28, table 7-continued, Line 18 (approx.), "Hexgonal" should read --Hexagonal--

Column 27-28, table 7-continued, Line 19 (approx.), "Hexgonal" should read --Hexagonal--

Column 31, Line 32, "Coluny Counter." should read --Colony Counter.--

Column 33, Line 32, "BaSi$_1$O$_5$:" should read --BaSi$_2$O$_5$:--

Column 34, Line 41, "YTaO:" should read --YTaO$_4$:--

Column 34, Line 59, "YTaO4," should read --YTaO$_4$,--

Column 37, Line 36, "Y$_2$ O$_3$." should read --Y$_2$O$_3$.--

Column 37, Line 60, "chalcoginides" should read --chalcogenides--

Column 37, Lines 61-62, "chalcoginides" should read --chalcogenides--

Column 39, Line 16, "Er3+;" should read --Er$^{3+}$;--

Column 40, Line 43, "oxygen" should read --oxygen.--

Column 40, Line 44, "lifetime" should read --life time--

Column 41, Line 64, "Sjogrens syndrome," should read --Sjogren's syndrome,--

Column 43, Line 33, "mitochondriat" should read --mitochondria--

Column 43, Line 66, "anthroquinones," should read --anthraquinone,--

Column 46, Lines 5-6, "mitochondriat" should read --mitochondria at--

Column 56, Line 19, "ablasion" should read --ablation--

Column 56, Line 20, "arrhythmiand" should read --arrhythmia and--

Column 56, Line 21, "restinosis)," should read --restenosis),--

Column 56, Line 24, "arthrisis," should read --arthritis,--

Column 58, Lines 24-25, "Y$_2$ O$_3$:" should read --Y$_2$O$_3$:--

Columns 57-58, table 11, Line 12 (approx.), "Hexgonal" should read --Hexagonal--

Columns 57-58, table 11, Line 13 (approx.), "Hexgonal" should read --Hexagonal--

Columns 57-58, table 11, Line 14 (approx.), "Hexgonal" should read --Hexagonal--

Columns 57-58, table 11, Line 15 (approx.), "Hexgonal" should read --Hexagonal--

Columns 57-58, table 11, Line 16 (approx.), "Hexgonal" should read --Hexagonal--

Column 58, Line 65, "antharacene" should read --anthracene--

Column 60, Lines 24-25, "Y$_2$ O$_3$" should read --Y$_2$O$_3$--

Columns 61-62, table 14-continued, Line 4 (approx.), "Hexgonal" should read --Hexagonal--

Columns 61-62, table 14-continued, Line 5 (approx.), "Hexgonal" should read --Hexagonal--

Columns 61-62, table 14-continued, Line 6 (approx.), "Hexgonal" should read --Hexagonal--

Columns 61-62, table 14-continued, Line 7 (approx.), "Hexgonal" should read --Hexagonal--

Columns 61-62, table 14-continued, Line 8 (approx.), "Hexgonal" should read --Hexagonal--

Column 62, Line 20, "Er3+;" should read --Er$^{3+}$;--

Column 63, Lines 5-6, "mitochondriat" should read --mitochondria at--

Column 64, Line 21, "thermoablative" should read --thermoablation--

CERTIFICATE OF CORRECTION (continued)

U.S. Pat. No. 10,596,387 B2

Column 65, Lines 64-65, "electrophysipologically" should read --electrophysiologically--

Column 66, Lines 25-26, "aminoinethyltrimethylpsoralen" should read --aminoethyltrimethylpsoralen--

Column 67, Line 47, "photophoresis." should read --photopheresis.--

Column 71, Line 9, "and or" should read --and/or--

Column 72, Line 11, "cardiomyocites)" should read --cardiomyocytes)--

Column 72, Line 19, "viabsorption" should read --via absorption--

Column 84, Line 26, "nanometer size" should read --nanometer-size--

Column 89, Line 45, "d-luciferin/l" should read --d-luciferin/--

Column 97, Line 27, "porphorinporphyrins," should read --porphyrinporphyrins,--

Column 97, Line 29, "anthroquinones." should read --anthraquinones.--

Column 99, Line 21, "agent," should read --agent.--

Column 102, Line 22, "diethoxyxanthone," should read --methoxyxanthone,--

Column 102, Line 59, "Tetraisopropoxytitanate" should read --Tetraisopropyltitanate--

Column 102, Lines 59-60, "tetrabutoxytitanate" should read --tetrabutyltitanate--

Column 106, Line 42, "YTaO4." should read --YTaO$_4$.--

Column 106, Line 58, "Acryate" should read --Acrylate--

Column 110, Line 26, "FlexFrom" should read --FlexForm--

Column 110, Line 32, "FlexFrom" should read --FlexForm--

Column 111, Line 37, "anoxidation" should read --an oxidation--

Column 113, Line 51, "naonotubes" should read --nanotubes--

Column 119, Line 18, "diethoxyxanthone," should read --methoxyxanthone,--

Column 122, Line 3, "PO4," should read --PO$_4$,--

Column 122, Line 5, "LaPO4;" should read --LaPO$_4$;--

Column 122, Line 12, "Zn2SiO4:" should read --Zn$_2$SiO$_4$:--

Column 123, Line 9, "and or" should read --and/or--

Column 123, Line 25, "(PO4)$_2$." should read --(PO$_4$)$_2$.--

Column 123, Line 26, "(PO4)$_2$." should read --(PO$_4$)$_2$.--

Column 123, Line 56, "(PO4)$_2$." should read --(PO$_4$)$_2$.--

Column 125, Line 20, "of"microbeam"" should read --of "microbeam"--

Column 127, Line 13, "Modem" should read --Modern--

Column 128, Line 36, "performed" should read --performed.--

Column 129, Lines 59-60, "LaPO4:Ce3+, Tb3+, 3Ca3(PO4)2.Ca(Fl,Cl)2:Sb3+, Mn2+, ZrO6-: Pr,Si, CaSiO3:" should read --LaPO$_4$:Ce$^{3+}$, Tb$^{3+}$, 3Ca$_3$(PO$_4$)$_2$.Ca(Fl,Cl)$_2$:Sb$^{3+}$, Mn$^{2+}$, ZrO$_6$-: Pr,Si, CaSiO$_3$:--

Column 130, Line 42, "sp3" should read --sp$^3$--

Column 130, Line 45, "sp3" should read --sp$^3$--

Column 130, Line 47, "sp2" should read --sp$^2$--

Column 130, Line 54, "sp3" should read --sp$^3$--

Column 130, Line 55, "sp2" should read --sp$^2$--

Column 137, Line 64, "naonotubes" should read --nanotubes--

Column 138, Line 25, "(i. e.," should read --(i.e.,--

Column 142, Line 4, "it/6." should read --$\pi$/6.--

Column 143, Line 8, "lok" should read --lock--

Column 143, Line 36, "PO4:" should read --PO$_4$:--

Column 143, Line 36, "(PO4)$_2$." should read --(PO$_4$)$_2$.--

Column 143, Line 51, "Trubeam," should read --Truebeam,--

Column 147, Line 37, "asparginase," should read --asparaginase,--

Column 150, Line 47, "half life" should read --half-life--

In the Claims

Column 152, Line 52, Claim 16, "Er3+;" should read --$Er^{3+}$;--

Column 153, Line 19, Claim 21, "porphorinporphyrins," should read --porphyrinoporphyrins,--

Column 153, Line 21, Claim 21, "anthroquinones." should read --anthraquinones.--

Column 153, Line 26, Claim 23, "s 8-" should read --8- --

Column 153, Lines 31-32, Claim 24, "tetrasulonate," should read --tetrasulfonate,--

Column 153, Line 32, Claim 24, "hematophorphyrin," should read --hematoporphyrin,--

Column 153, Line 32, Claim 24, "phthadocyanine." should read --phthalocyanine.--

Column 154, Line 57, Claim 49, "one of one of" should read --one of--

Column 156, Line 31, Claim 69, "Er3+;" should read --$Er^{3+}$;--

Column 156, Line 65, Claim 74, "porphorinporphyrins," should read --porphyrinoporphyrins,--

Column 156, Line 67, Claim 74, "anthroquinones." should read --anthraquinones.--

Column 157, Line 5, Claim 76, "s 8-" should read --8- --

Column 157, Lines 10-11, Claim 77, "tetrasulonate," should read --tetrasulfonate,--

Column 157, Line 11, Claim 77, "hematophorphyrin," should read --hematoporphyrin,--

Column 157, Line 11, Claim 77, "phthadocyanine." should read --phthalocyanine.--

Column 158, Line 40, Claim 102, "one of one of" should read --one of--